US008535673B2

(12) United States Patent
Schenk

(10) Patent No.: US 8,535,673 B2
(45) Date of Patent: Sep. 17, 2013

(54) PREVENTION AND TREATMENT OF AMYLOIDOGENIC DISEASE

(75) Inventor: Dale B. Schenk, Burlingame, CA (US)

(73) Assignee: Janssen Alzheimer Immunotherapy (IE)

(*) Notice: Subject to any disclaimer, the term of this patent is extended or adjusted under 35 U.S.C. 154(b) by 300 days.

(21) Appl. No.: 10/923,471

(22) Filed: Aug. 20, 2004

(65) Prior Publication Data
US 2005/0013815 A1 Jan. 20, 2005

Related U.S. Application Data

(60) Division of application No. 09/724,319, filed on Nov. 27, 2000, now abandoned, which is a continuation of application No. 09/322,289, filed on May 28, 1999, now Pat. No. 7,964,192, which is a continuation-in-part of application No. 09/201,430, filed on Nov. 30, 1998, now Pat. No. 6,787,523.

(60) Provisional application No. 60/080,970, filed on Apr. 7, 1998, provisional application No. 60/067,740, filed on Dec. 2, 1997.

(51) Int. Cl.
A61K 39/395 (2006.01)

(52) U.S. Cl.
USPC ...................................... 424/145.1

(58) Field of Classification Search
USPC ................... 530/387.1, 387.3, 388.1, 388.15
See application file for complete search history.

(56) References Cited

U.S. PATENT DOCUMENTS

| 4,666,829 | A | 5/1987 | Glenner et al. |
|---|---|---|---|
| 4,713,366 | A | 12/1987 | Stevens |
| 4,816,397 | A | 3/1989 | Boss et al. |
| 4,816,567 | A | 3/1989 | Cabilly et al. |
| 4,879,213 | A | 11/1989 | Fox et al. |
| 4,883,666 | A | 11/1989 | Sabel et al. |
| 4,912,206 | A | 3/1990 | Goldgaber et al. |
| 4,966,753 | A | 10/1990 | McMichael |
| 5,004,697 | A | 4/1991 | Pardridge |
| 5,057,540 | A | 10/1991 | Kensil et al. |
| 5,096,706 | A | 3/1992 | Flint |
| 5,187,153 | A | 2/1993 | Cordell et al. |
| 5,192,753 | A | 3/1993 | McGeer et al. |
| 5,208,036 | A | 5/1993 | Eppstein et al. |
| 5,220,013 | A | 6/1993 | Ponte et al. |
| 5,225,539 | A | 7/1993 | Winter |
| 5,227,159 | A | 7/1993 | Miller |
| 5,231,000 | A | 7/1993 | Majocha et al. |
| 5,231,170 | A | 7/1993 | Averback |
| 5,245,015 | A | 9/1993 | Fung et al. |
| 5,258,498 | A | 11/1993 | Huston et al. |
| 5,262,332 | A | 11/1993 | Selkoe |
| 5,270,165 | A | 12/1993 | Van Nostrand et al. |
| 5,278,049 | A | 1/1994 | Baker et al. |
| 5,358,708 | A | 10/1994 | Patel |
| 5,385,887 | A | 1/1995 | Yim et al. |
| 5,387,742 | A | 2/1995 | Cordell |
| 5,417,986 | A | 5/1995 | Reid et al. |
| 5,434,170 | A | 7/1995 | Andrulis, Jr. |
| 5,441,870 | A | 8/1995 | Seubert et al. |
| 5,464,823 | A | 11/1995 | Lehrer et al. |
| 5,470,951 | A | 11/1995 | Roberts |
| 5,472,693 | A | * 12/1995 | Gourlie et al. ............. 424/133.1 |
| 5,514,548 | A | 5/1996 | Krebber et al. |
| 5,530,101 | A | * 6/1996 | Queen et al. ............... 530/387.3 |
| 5,571,499 | A | 11/1996 | Hafler et al. |
| 5,571,500 | A | 11/1996 | Hafler et al. |
| 5,576,184 | A | 11/1996 | Better et al. |
| 5,583,112 | A | 12/1996 | Kensil et al. |
| 5,585,089 | A | 12/1996 | Queen et al. |
| 5,585,100 | A | 12/1996 | Mond et al. |
| 5,589,154 | A | 12/1996 | Anderson |
| 5,593,846 | A | 1/1997 | Schenk et al. |
| 5,601,827 | A | 2/1997 | Collier et al. |
| 5,605,811 | A | 2/1997 | Seubert et al. |
| 5,612,486 | A | 3/1997 | McConlogue et al. |
| 5,618,920 | A | 4/1997 | Robinson et al. |
| 5,620,844 | A | 4/1997 | Neurath et al. |
| 5,622,701 | A | 4/1997 | Berg |
| 5,624,821 | A | 4/1997 | Winter et al. |
| 5,624,937 | A | 4/1997 | Reel et al. |
| 5,641,473 | A | 6/1997 | Hafler et al. |
| 5,641,474 | A | 6/1997 | Hafler et al. |
| 5,645,820 | A | 7/1997 | Hafler et al. |
| 5,648,260 | A | 7/1997 | Winter et al. |

(Continued)

FOREIGN PATENT DOCUMENTS

| AU | 192870091 | 7/1999 |
|---|---|---|
| EP | 285 159 A1 | 10/1988 |

(Continued)

OTHER PUBLICATIONS

Johnson-Wood et al., 1997, PNAS, 94:1550-1555.*
Seubert et al., 1992, Nature, 359:325-327.*
Research Corporation Technologies, News, Nov. 11, 2002.*
Chemicon International, Inc., Chemicon Catalog. Data sheet for catalog #: MAB1561.*
Bard et al., 2003, PNAS, 100:2023-2028.*
Jung et al., J Neurosci Res., Nov. 1, 1996, 46(3):336-48.*
Lambert et al., Journal of Neurochemistry, 2001, 79:595-605.*
Racke et al., Journal of Neuroscience, 2005, 25(3):629-636.*
Broadwell et al. Serum proteins bypass the blood-brain fluid barriers for extracellular entry to the central nervous system. Exp Neurol. Apr. 1993;120(2):245-63.*
Khatoon et al. Levels of normal and abnormally phosphorylated tau in different cellular and regional compartments of Alzheimer disease and control brains. FEBS Lett. Aug. 29, 1994;351(1):80-4.*

(Continued)

Primary Examiner — Gregory S Emch
(74) Attorney, Agent, or Firm — Alston & Bird LLP

(57) ABSTRACT

The invention provides compositions and methods for treatment of amyloidogenic diseases. Such methods entail administering an agent that induces a beneficial immune response against an amyloid deposit in the patient. The methods are particularly useful for prophylactic and therapeutic treatment of Alzheimer's disease. In such methods, a suitable agent is Aβ peptide, active fragments thereof or an antibody thereto.

11 Claims, 16 Drawing Sheets

(56) References Cited

U.S. PATENT DOCUMENTS

| | | |
|---|---|---|
| 5,652,334 A | 7/1997 | Roberts |
| 5,677,425 A | 10/1997 | Bodmer et al. |
| 5,679,348 A | 10/1997 | Nesburn et al. |
| 5,688,651 A | 11/1997 | Solomon |
| 5,693,761 A | 12/1997 | Queen et al. |
| 5,693,762 A | 12/1997 | Queen et al. |
| 5,702,906 A | 12/1997 | Rosenthal |
| 5,721,130 A | 2/1998 | Seubert et al. |
| 5,723,130 A | 3/1998 | Hancock et al. |
| 5,731,284 A | 3/1998 | Williams |
| 5,733,547 A | 3/1998 | Weiner et al. |
| 5,733,548 A | 3/1998 | Restifo et al. |
| 5,736,142 A | 4/1998 | Sette et al. |
| 5,744,132 A | 4/1998 | Warne et al. |
| 5,744,368 A | 4/1998 | Goldgaber et al. |
| 5,750,349 A | 5/1998 | Suzuki et al. |
| 5,750,361 A | 5/1998 | Prusiner et al. |
| 5,753,624 A | 5/1998 | McMichael et al. |
| 5,766,846 A | 6/1998 | Schlossmacher et al. |
| 5,770,700 A | 6/1998 | Webb et al. |
| 5,773,007 A | 6/1998 | Penney et al. |
| 5,776,468 A | 7/1998 | Hauser et al. |
| 5,780,587 A | 7/1998 | Potter |
| 5,786,180 A | 7/1998 | Konig et al. |
| 5,798,102 A | 8/1998 | McMichael et al. |
| 5,817,626 A | 10/1998 | Findeis et al. |
| 5,824,322 A | 10/1998 | Balasubramanian |
| 5,837,268 A | 11/1998 | Potter et al. |
| 5,837,473 A | 11/1998 | Maggio et al. |
| 5,837,672 A | 11/1998 | Schenk et al. |
| 5,846,533 A | 12/1998 | Prusiner |
| 5,849,298 A | 12/1998 | Weiner et al. |
| 5,851,996 A | 12/1998 | Kline |
| 5,854,204 A | 12/1998 | Findeis et al. |
| 5,854,215 A | 12/1998 | Findeis et al. |
| 5,858,981 A | 1/1999 | Schreiber et al. |
| 5,859,205 A | 1/1999 | Adair et al. |
| 5,866,129 A | 2/1999 | Chang et al. |
| 5,869,046 A | 2/1999 | Presta et al. |
| 5,869,054 A | 2/1999 | Weiner et al. |
| 5,869,093 A | 2/1999 | Weiner et al. |
| 5,877,399 A | 3/1999 | Hsiao et al. |
| 5,891,991 A | 4/1999 | Wasco et al. |
| 5,895,654 A | 4/1999 | Hartford et al. |
| 5,910,427 A | 6/1999 | Mikayama et al. |
| 5,935,927 A | 8/1999 | Vitek et al. |
| 5,955,079 A | 9/1999 | Mond et al. |
| 5,955,317 A | 9/1999 | Suzuki et al. |
| 5,958,883 A | 9/1999 | Snow |
| 5,985,242 A | 11/1999 | Findeis et al. |
| 5,989,566 A | 11/1999 | Cobb et al. |
| 5,994,083 A | 11/1999 | Felici et al. |
| 6,015,662 A | 1/2000 | Hackett et al. |
| 6,022,859 A | 2/2000 | Kiessling et al. |
| 6,054,297 A | 4/2000 | Carter et al. |
| 6,057,098 A | 5/2000 | Buechler et al. |
| 6,057,367 A | 5/2000 | Stamler et al. |
| 6,096,318 A | 8/2000 | Stevens et al. |
| 6,114,133 A | 9/2000 | Seubert et al. |
| 6,121,022 A | 9/2000 | Presta et al. |
| 6,150,091 A | 11/2000 | Pandolfo et al. |
| 6,165,745 A | 12/2000 | Ward et al. |
| 6,175,057 B1 | 1/2001 | Mucke et al. |
| 6,180,370 B1 | 1/2001 | Queen et al. |
| 6,194,551 B1 | 2/2001 | Idusogie et al. |
| 6,210,671 B1 | 4/2001 | Co |
| 6,218,506 B1 | 4/2001 | Krafft et al. |
| 6,261,569 B1 | 7/2001 | Comis et al. |
| 6,262,335 B1 | 7/2001 | Hsiao et al. |
| 6,267,958 B1 | 7/2001 | Andya et al. |
| 6,270,757 B1 | 8/2001 | Warne |
| 6,277,375 B1 | 8/2001 | Ward |
| 6,284,221 B1 | 9/2001 | Schenk et al. |
| 6,284,533 B1 | 9/2001 | Thomas |
| 6,294,171 B2 | 9/2001 | McMichael |
| 6,303,567 B1 | 10/2001 | Findeis et al. |
| 6,331,440 B1 | 12/2001 | Nordstedt et al. |
| 6,339,068 B1 | 1/2002 | Krieg et al. |
| 6,372,716 B1 | 4/2002 | Bush et al. |
| 6,399,314 B1 | 6/2002 | Krishnamurthy |
| 6,407,213 B1 | 6/2002 | Carter et al. |
| 6,417,178 B1 | 7/2002 | Klunk et al. |
| 6,432,710 B1 | 8/2002 | Boss, Jr. et al. |
| 6,528,624 B1 | 3/2003 | Idusogie et al. |
| 6,538,124 B1 | 3/2003 | Idusogie et al. |
| 6,548,640 B1 | 4/2003 | Winter |
| 6,562,341 B2 | 5/2003 | Prusiner et al. |
| 6,582,945 B1 | 6/2003 | Raso |
| 6,610,493 B1 | 8/2003 | Citron et al. |
| 6,632,927 B2 | 10/2003 | Adair et al. |
| 6,639,055 B1 | 10/2003 | Carter et al. |
| 6,710,226 B1 | 3/2004 | Schenk |
| 6,713,450 B2 | 3/2004 | Frangione et al. |
| 6,727,349 B1 | 4/2004 | LaRosa et al. |
| 6,743,427 B1 | 6/2004 | Schenk |
| 6,750,324 B1 | 6/2004 | Schenk et al. |
| 6,761,888 B1 | 7/2004 | Schenk |
| 6,787,129 B1 | 9/2004 | Klein et al. |
| 6,787,138 B1 | 9/2004 | Schenk |
| 6,787,139 B1 | 9/2004 | Schenk |
| 6,787,140 B1 | 9/2004 | Schenk |
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk et al. |
| 6,808,712 B2 | 10/2004 | Schenk |
| 6,818,218 B2 | 11/2004 | Schenk |
| 6,824,780 B1 | 11/2004 | Devaux et al. |
| 6,866,849 B2 | 3/2005 | Schenk |
| 6,866,850 B2 | 3/2005 | Schenk |
| 6,875,434 B1 | 4/2005 | Schenk |
| 6,890,535 B1 | 5/2005 | Schenk |
| 6,905,686 B1 | 6/2005 | Schenk |
| 6,913,745 B1 | 7/2005 | Schenk |
| 6,923,964 B1 | 8/2005 | Schenk |
| 6,933,368 B2 | 8/2005 | Co et al. |
| 6,936,698 B2 | 8/2005 | Taylor |
| 6,946,135 B2 | 9/2005 | Schenk |
| 6,962,707 B2 | 11/2005 | Schenk |
| 6,962,984 B2 | 11/2005 | Ishiwata et al. |
| 6,972,127 B2 | 12/2005 | Schenk |
| 6,982,084 B2 | 1/2006 | Schenk |
| 7,014,855 B2 | 3/2006 | Schenk |
| 7,112,661 B1 | 9/2006 | Miller |
| 7,147,851 B1 | 12/2006 | Ponath et al. |
| 7,179,892 B2 | 2/2007 | Basi et al. |
| 7,189,819 B2 | 3/2007 | Basi et al. |
| 7,195,761 B2 | 3/2007 | Holtzman et al. |
| 7,256,273 B2 | 8/2007 | Basi et al. |
| 7,582,733 B2 | 9/2009 | Basi et al. |
| 7,625,560 B2 | 12/2009 | Basi et al. |
| 7,790,856 B2 | 9/2010 | Schenk |
| 7,871,615 B2 | 1/2011 | Basi et al. |
| 7,893,214 B2 | 2/2011 | Schenk |
| 7,906,626 B2 | 3/2011 | Raso |
| 7,928,203 B2 | 4/2011 | Schenk et al. |
| 2001/0018053 A1 | 8/2001 | McMichael |
| 2001/0021769 A1 | 9/2001 | Prusiner |
| 2002/0009445 A1 | 1/2002 | Du et al. |
| 2002/0058267 A1 | 5/2002 | Ozenberger et al. |
| 2002/0077288 A1 | 6/2002 | Frangione |
| 2002/0086847 A1 | 7/2002 | Chain |
| 2002/0094335 A1 | 7/2002 | Chalifour et al. |
| 2002/0102261 A1 | 8/2002 | Raso |
| 2002/0132268 A1 | 9/2002 | Chang et al. |
| 2002/0133001 A1 | 9/2002 | Gefter et al. |
| 2002/0136718 A1 | 9/2002 | Raso |
| 2002/0160394 A1 | 10/2002 | Wu |
| 2002/0162129 A1 | 10/2002 | Lannfelt |
| 2002/0168377 A1 | 11/2002 | Schaetzl |
| 2002/0187157 A1 | 12/2002 | Jensen et al. |
| 2002/0197258 A1 | 12/2002 | Ghanbari et al. |
| 2003/0009104 A1 | 1/2003 | Hyman et al. |
| 2003/0039645 A1 | 2/2003 | Adair et al. |

| | | |
|---|---|---|
| 2003/0054484 A1 | 3/2003 | Fong et al. |
| 2003/0068316 A1 | 4/2003 | Klein et al. |
| 2003/0068325 A1 | 4/2003 | Wang |
| 2003/0073655 A1 | 4/2003 | Chain |
| 2003/0092145 A1 | 5/2003 | Jira et al. |
| 2003/0135035 A1 | 7/2003 | Shannon |
| 2003/0147882 A1 | 8/2003 | Solomon et al. |
| 2003/0165496 A1 | 9/2003 | Basi et al. |
| 2003/0166557 A1 | 9/2003 | Minna et al. |
| 2003/0166558 A1 | 9/2003 | Frangione et al. |
| 2003/0202972 A1 | 10/2003 | Andya et al. |
| 2003/0207828 A1 | 11/2003 | Ishiwata et al. |
| 2004/0043418 A1 | 3/2004 | Holtzman et al. |
| 2004/0081657 A1 | 4/2004 | Schenk |
| 2004/0082762 A1 | 4/2004 | Basi et al. |
| 2004/0087777 A1 | 5/2004 | Basi et al. |
| 2004/0171815 A1 | 9/2004 | Schenk et al. |
| 2004/0171816 A1 | 9/2004 | Schenk et al. |
| 2004/0197324 A1 | 10/2004 | Liu et al. |
| 2004/0213800 A1 | 10/2004 | Seubert et al. |
| 2004/0219146 A1 | 11/2004 | Schenk |
| 2004/0241164 A1 | 12/2004 | Bales et al. |
| 2004/0247590 A1 | 12/2004 | Schenk et al. |
| 2004/0247591 A1 | 12/2004 | Schenk et al. |
| 2004/0247612 A1 | 12/2004 | Wang |
| 2004/0265301 A1 | 12/2004 | Schenk et al. |
| 2004/0265308 A1 | 12/2004 | Schenk |
| 2004/0265919 A1 | 12/2004 | Vanderstichlele et al. |
| 2005/0009150 A1 | 1/2005 | Basi et al. |
| 2005/0013815 A1 | 1/2005 | Schenk |
| 2005/0019328 A1 | 1/2005 | Schenk |
| 2005/0019330 A1 | 1/2005 | Schenk |
| 2005/0048049 A1 | 3/2005 | Schenk |
| 2005/0059591 A1 | 3/2005 | Schenk et al. |
| 2005/0059802 A1 | 3/2005 | Schenk et al. |
| 2005/0090648 A1 | 4/2005 | Tsurushita et al. |
| 2005/0118651 A1 | 6/2005 | Basi et al. |
| 2005/0123534 A1 | 6/2005 | Adair et al. |
| 2005/0123544 A1 | 6/2005 | Schenk et al. |
| 2005/0136054 A1 | 6/2005 | Adair et al. |
| 2005/0142132 A1 | 6/2005 | Schenk et al. |
| 2005/0147613 A1 | 7/2005 | Raso |
| 2005/0152878 A1 | 7/2005 | Solomon et al. |
| 2005/0158304 A1 | 7/2005 | Schenk et al. |
| 2005/0163788 A1 | 7/2005 | Schenk |
| 2005/0169925 A1 | 8/2005 | Bardroff et al. |
| 2005/0191292 A1 | 9/2005 | Schenk |
| 2005/0191314 A1 | 9/2005 | Schenk |
| 2005/0196399 A1 | 9/2005 | Schenk et al. |
| 2005/0214222 A1 | 9/2005 | McKinnon et al. |
| 2005/0249725 A1 | 11/2005 | Schenk et al. |
| 2005/0249727 A1 | 11/2005 | Schenk |
| 2005/0255122 A1 | 11/2005 | Schenk |
| 2006/0029611 A1 | 2/2006 | Schenk |
| 2006/0034858 A1 | 2/2006 | Schenk |
| 2006/0057701 A1 | 3/2006 | Rosenthal et al. |
| 2006/0099206 A1 | 5/2006 | Sinacore |
| 2006/0121038 A9 | 6/2006 | Schenk et al. |
| 2006/0153772 A1 | 7/2006 | Jacobsen |
| 2006/0160161 A1 | 7/2006 | Pavlikova et al. |
| 2006/0165682 A1 | 7/2006 | Basi et al. |
| 2006/0182321 A1 | 8/2006 | Hu et al. |
| 2006/0188512 A1 | 8/2006 | Yednock et al. |
| 2006/0193850 A1 | 8/2006 | Warne et al. |
| 2006/0198851 A1 | 9/2006 | Basi et al. |
| 2006/0210557 A1 | 9/2006 | Luisi et al. |
| 2006/0210964 A1 | 9/2006 | Hyslop et al. |
| 2006/0234912 A1 | 10/2006 | Wang et al. |
| 2006/0240486 A1 | 10/2006 | Johnson-Wood et al. |
| 2006/0257396 A1 | 11/2006 | Jacobsen |
| 2006/0280743 A1 | 12/2006 | Basi et al. |
| 2007/0021454 A1 | 1/2007 | Coburn et al. |
| 2007/0072307 A1 | 3/2007 | Godavarti et al. |
| 2007/0082367 A1 | 4/2007 | Godavarti et al. |
| 2007/0134762 A1 | 6/2007 | Arumugham et al. |
| 2007/0154480 A1 | 7/2007 | Schenk et al. |
| 2007/0161088 A1 | 7/2007 | Arumugham et al. |
| 2007/0196375 A1 | 8/2007 | Tobinick |
| 2007/0238154 A1 | 10/2007 | Basi et al. |
| 2008/0031954 A1 | 2/2008 | Paris et al. |
| 2008/0050367 A1 | 2/2008 | Basi et al. |
| 2008/0096818 A1 | 4/2008 | Schenk et al. |
| 2008/0145373 A1 | 6/2008 | Arumugham et al. |
| 2008/0219931 A1 | 9/2008 | Klunk et al. |
| 2009/0069544 A1 | 3/2009 | Basi et al. |
| 2009/0142270 A1 | 6/2009 | Schroeter et al. |
| 2009/0155256 A1 | 6/2009 | Black et al. |
| 2009/0297511 A1 | 12/2009 | Schenk |
| 2010/0221187 A1 | 9/2010 | Lieberburg et al. |
| 2011/0142824 A1 | 6/2011 | Burbidge et al. |
| 2011/0229413 A1 | 9/2011 | Lieberburg et al. |
| 2012/0070379 A1 | 3/2012 | Black et al. |

FOREIGN PATENT DOCUMENTS

| | | |
|---|---|---|
| EP | 0 391 714 A2 | 10/1990 |
| EP | 451 700 A1 | 10/1991 |
| EP | 506 785 B1 | 10/1992 |
| EP | 276 723 B1 | 12/1993 |
| EP | 613007 A2 | 2/1994 |
| EP | 616 814 A1 | 3/1994 |
| EP | 597 101 A1 | 5/1994 |
| EP | 0 613 007 A2 | 8/1994 |
| EP | 613 007 A2 | 8/1994 |
| EP | 620 276 A1 | 10/1994 |
| EP | 626 390 A1 | 11/1994 |
| EP | 666 080 A1 | 8/1995 |
| EP | 359 783 B1 | 11/1995 |
| EP | 683 234 A1 | 11/1995 |
| EP | 440 619 B1 | 1/1996 |
| EP | 758 248 B1 | 2/1997 |
| EP | 758 901 B1 | 2/1997 |
| EP | 526 511 B1 | 5/1997 |
| EP | 782 859 A1 | 7/1997 |
| EP | 783 104 A1 | 7/1997 |
| EP | 594 607 B1 | 8/1997 |
| EP | 752 888 B1 | 1/1998 |
| EP | 845 270 A1 | 6/1998 |
| EP | 1 690 547 A1 | 8/1998 |
| EP | 863 211 A1 | 9/1998 |
| EP | 868 918 A2 | 10/1998 |
| EP | 652 962 B1 | 12/1998 |
| EP | 911 036 A2 | 4/1999 |
| EP | 561 087 B1 | 8/1999 |
| EP | 639 081 B1 | 11/1999 |
| EP | 506 785 B1 | 3/2000 |
| EP | 1 172 378 A1 | 1/2002 |
| EP | 1 481 992 A2 | 12/2004 |
| EP | 1 481 992 A3 | 12/2004 |
| EP | 921 189 B1 | 1/2005 |
| EP | 1 033 998 B1 | 10/2005 |
| EP | 1 185 298 B1 | 6/2009 |
| EP | 1 690 547 B1 | 7/2009 |
| EP | 1 321 166 B1 | 1/2011 |
| EP | 1160256 B2 | 11/2011 |
| EP | 1842859 B1 | 1/2013 |
| GB | 2 220 211 A | 1/1990 |
| GB | 2 335 192 A | 9/1999 |
| JP | 62-267297 A | 11/1987 |
| JP | 07-132033 A | 5/1995 |
| JP | 09/208485 | 8/1997 |
| JP | 9215492 | 8/1997 |
| JP | 9208485 A | 12/1997 |
| JP | 9119929 A | 6/1999 |
| WO | WO 87/02671 A | 5/1987 |
| WO | WO 87/06838 A1 | 11/1987 |
| WO | WO 88/10120 A1 | 12/1988 |
| WO | WO 89/01343 A1 | 2/1989 |
| WO | WO 89/03687 A1 | 5/1989 |
| WO | WO 89/06242 A1 | 7/1989 |
| WO | WO 89/06689 A1 | 7/1989 |
| WO | WO 90/05142 A1 | 5/1990 |
| WO | WO 90/07861 | 7/1990 |
| WO | WO 90/12870 A1 | 11/1990 |
| WO | WO 90/12871 A1 | 11/1990 |
| WO | WO 90/14837 A1 | 12/1990 |
| WO | WO 90/14840 A1 | 12/1990 |
| WO | WO 91/08760 A1 | 6/1991 |
| WO | WO 91/09967 A1 | 7/1991 |

| | | | | | | |
|---|---|---|---|---|---|---|
| WO | WO 91/10741 A1 | 7/1991 | | WO | WO 97/36601 A1 | 10/1997 |
| WO | WO 91/12816 A1 | 9/1991 | | WO | WO 97/37031 A1 | 10/1997 |
| WO | WO 91/16819 A1 | 11/1991 | | WO | WO 97/40147 A1 | 10/1997 |
| WO | WO 91/16928 A1 | 11/1991 | | WO | WO 98/02462 A1 | 1/1998 |
| WO | WO 91/17271 A1 | 11/1991 | | WO | WO 98/04720 A1 | 2/1998 |
| WO | WO 91/19795 A1 | 12/1991 | | WO | WO 98/05350 A1 | 2/1998 |
| WO | WO 91/19810 A1 | 12/1991 | | WO | WO 98/07850 A2 | 2/1998 |
| WO | WO 92/01047 A1 | 1/1992 | | WO | WO 98/08098 A1 | 2/1998 |
| WO | WO 92/01059 A1 | 1/1992 | | WO | WO 98/08868 A1 | 3/1998 |
| WO | WO 92/05793 A1 | 4/1992 | | WO | WO 98/22120 A1 | 5/1998 |
| WO | WO 92/06187 A1 | 4/1992 | | WO | WO 98/33815 A1 | 8/1998 |
| WO | WO 92/06708 A1 | 4/1992 | | WO | WO 98/39303 A1 | 9/1998 |
| WO | WO 92/07944 A1 | 5/1992 | | WO | WO 98/44955 A1 | 10/1998 |
| WO | WO 92/13069 A1 | 8/1992 | | WO | WO 98/46642 A1 | 10/1998 |
| WO | WO 92/15330 A1 | 9/1992 | | WO | WO 96/37621 A2 | 11/1998 |
| WO | WO 92/19267 A1 | 11/1992 | | WO | WO 98/56418 A1 | 12/1998 |
| WO | WO 92/22653 A1 | 12/1992 | | WO | WO 99/00150 A2 | 1/1999 |
| WO | WO 93/02189 A1 | 2/1993 | | WO | WO 99/06066 A2 | 2/1999 |
| WO | WO 93/04194 A1 | 3/1993 | | WO | WO 99/08587 A2 | 2/1999 |
| WO | WO 93/12227 A1 | 6/1993 | | WO | WO 99/10008 A1 | 3/1999 |
| WO | WO 93/14200 A1 | 7/1993 | | WO | WO 99/27911 A1 | 6/1999 |
| WO | WO 93/15760 A1 | 8/1993 | | WO | WO 99/27944 A1 | 6/1999 |
| WO | WO 93/16724 A1 | 9/1993 | | WO | WO 99/27949 A1 | 6/1999 |
| WO | WO 93/21950 A1 | 11/1993 | | WO | WO 99/06545 A2 | 11/1999 |
| WO | WO 94/00153 A1 | 1/1994 | | WO | WO 99/58564 A1 | 11/1999 |
| WO | WO 94/01772 A1 | 1/1994 | | WO | WO 99/60021 A2 | 11/1999 |
| WO | WO 94/03208 A1 | 2/1994 | | WO | WO 99/60024 A1 | 11/1999 |
| WO | WO 94/03615 A1 | 2/1994 | | WO | WO 00/20027 A2 | 4/2000 |
| WO | WO 94/06311 A1 | 3/1994 | | WO | WO 00/23082 A1 | 4/2000 |
| WO | WO 94/09364 A1 | 4/1994 | | WO | WO 00/26238 A2 | 5/2000 |
| WO | WO 94/09823 A1 | 5/1994 | | WO | WO 00/43039 A1 | 7/2000 |
| WO | WO 94/10569 A1 | 5/1994 | | WO | WO 00/43049 A1 | 7/2000 |
| WO | WO 94/16731 A1 | 8/1994 | | WO | WO 00/88283 A2 | 11/2000 |
| WO | WO 94/17197 A1 | 8/1994 | | WO | WO 00/72870 A1 | 12/2000 |
| WO | WO 94/21288 A1 | 9/1994 | | WO | WO 00/72876 A2 | 12/2000 |
| WO | WO 94/28412 A1 | 12/1994 | | WO | WO 00/72876 A3 | 12/2000 |
| WO | WO 94/29459 A1 | 12/1994 | | WO | WO 00/72880 A2 | 12/2000 |
| WO | WO 95/04151 A2 | 2/1995 | | WO | WO 00/72880 A3 | 12/2000 |
| WO | WO 95/05393 A2 | 2/1995 | | WO | WO 00/77178 A1 | 12/2000 |
| WO | WO 95/05849 A1 | 3/1995 | | WO | WO 01/05355 A2 | 1/2001 |
| WO | WO 95/05853 A1 | 3/1995 | | WO | WO 01/10900 A2 | 2/2001 |
| WO | WO 95/06407 A1 | 3/1995 | | WO | WO 01/18169 A3 | 3/2001 |
| WO | WO 95/07301 A1 | 3/1995 | | WO | WO 01/39796 A2 | 6/2001 |
| WO | WO 95/07707 A1 | 3/1995 | | WO | WO 01/42306 A2 | 6/2001 |
| WO | WO 95/08999 A1 | 4/1995 | | WO | WO 01/62284 A2 | 8/2001 |
| WO | WO 95/11008 A2 | 4/1995 | | WO | WO 01/62801 A2 | 8/2001 |
| WO | WO 95/11311 A1 | 4/1995 | | WO | WO 01/77167 A2 | 10/2001 |
| WO | WO 95/11994 A1 | 5/1995 | | WO | WO 01/78777 A2 | 10/2001 |
| WO | WO 95/12815 A1 | 5/1995 | | WO | WO 01/90182 A2 | 11/2001 |
| WO | WO 95/17085 A1 | 6/1995 | | WO | WO 02/03911 A2 | 1/2002 |
| WO | WO 95/23186 a1 | 8/1995 | | WO | WO 02/21141 A2 | 3/2002 |
| WO | WO 95/23860 A2 | 9/1995 | | WO | WO 02/34777 A1 | 5/2002 |
| WO | WO 95/31996 A1 | 11/1995 | | WO | WO 02/34878 A2 | 5/2002 |
| WO | WO 96/01126 A1 | 1/1996 | | WO | WO 02/46237 A1 | 6/2002 |
| WO | WO 96/03144 A1 | 2/1996 | | WO | WO 02/46237 A3 | 6/2002 |
| WO | WO 96/08665 A2 | 3/1996 | | WO | WO 02/060481 A1 | 8/2002 |
| WO | WO 96/14061 A1 | 5/1996 | | WO | WO 02/88306 A2 | 11/2002 |
| WO | WO 96/15799 A1 | 5/1996 | | WO | WO 02/88307 A2 | 11/2002 |
| WO | WO 96/18900 A1 | 6/1996 | | WO | WO 02/096457 A2 | 12/2002 |
| WO | WO 96/22373 A1 | 7/1996 | | WO | WO 02/096937 A2 | 12/2002 |
| WO | WO 96/25435 A1 | 8/1996 | | WO | WO 03/009817 A2 | 2/2003 |
| WO | WO 96/28471 A1 | 9/1996 | | WO | WO 03/015691 A2 | 2/2003 |
| WO | WO 96/29421 A1 | 9/1996 | | WO | WO 03/016466 A2 | 2/2003 |
| WO | WO 96/33739 A1 | 10/1996 | | WO | WO 03/016467 A2 | 2/2003 |
| WO | WO 94/40895 A1 | 12/1996 | | WO | WO 03/016467 A3 | 2/2003 |
| WO | WO 96/39176 A1 | 12/1996 | | WO | WO 03/020212 A2 | 3/2003 |
| WO | WO 96/39834 A1 | 12/1996 | | WO | WO 03/039485 A2 | 5/2003 |
| WO | WO 96/40895 A1 | 12/1996 | | WO | WO 03/051374 A2 | 6/2003 |
| WO | WO 97/03192 A3 | 1/1997 | | WO | WO 03/072036 A2 | 9/2003 |
| WO | WO 97/05164 A1 | 2/1997 | | WO | WO 03/072036 A3 | 9/2003 |
| WO | WO 97/08320 A1 | 3/1997 | | WO | WO 03/074081 A1 | 9/2003 |
| WO | WO 97/10505 A1 | 3/1997 | | WO | WO 03/077858 A2 | 9/2003 |
| WO | WO 97/13855 A1 | 4/1997 | | WO | WO 03/077858 A3 | 9/2003 |
| WO | WO 97/17613 A1 | 5/1997 | | WO | WO 03/104437 A2 | 12/2003 |
| WO | WO 97/18855 A1 | 5/1997 | | WO | WO 03/105894 A1 | 12/2003 |
| WO | WO 97/21728 A1 | 6/1997 | | WO | WO 2004/013172 A2 | 2/2004 |
| WO | WO 97/26913 A1 | 7/1997 | | WO | WO 2004/013172 A3 | 2/2004 |
| WO | WO 97/28816 A1 | 8/1997 | | WO | WO 2004/016282 A1 | 2/2004 |
| WO | WO 97/32017 A1 | 9/1997 | | WO | WO 2004/031400 A2 | 4/2004 |

| | | |
|---|---|---|
| WO | WO 2004/044204 A2 | 5/2004 |
| WO | WO 2004/044204 A3 | 5/2004 |
| WO | WO 2004/055164 A2 | 7/2004 |
| WO | WO 2004/069182 A2 | 8/2004 |
| WO | WO 2004/071408 A2 | 8/2004 |
| WO | WO 2004/080419 A2 | 9/2004 |
| WO | WO 2004/080419 A3 | 9/2004 |
| WO | WO 2004/108895 A2 | 12/2004 |
| WO | WO 2004/108895 A3 | 12/2004 |
| WO | WO 2005/014041 A2 | 2/2005 |
| WO | WO 2005/026211 A2 | 3/2005 |
| WO | WO 2005/026211 A3 | 3/2005 |
| WO | WO 2005/035753 A | 4/2005 |
| WO | WO 2005/058940 A2 | 6/2005 |
| WO | WO 2005/058941 A2 | 6/2005 |
| WO | WO 2005/090315 A1 | 9/2005 |
| WO | WO 2006/031653 A2 | 3/2006 |
| WO | WO 2006/042158 A | 4/2006 |
| WO | WO 2006/066049 A2 | 6/2006 |
| WO | WO 2006/066171 A1 | 6/2006 |
| WO | WO 2006/081587 A2 | 8/2006 |
| WO | WO 2006/081587 A3 | 8/2006 |
| WO | WO 2006/083689 A2 | 8/2006 |
| WO | WO 2006/121656 A2 | 11/2006 |
| WO | WO 2008/011348 A2 | 1/2008 |
| WO | WO 2008/114801 A1 | 9/2008 |
| WO | WO 2008/131298 A2 | 10/2008 |
| WO | WO 2008/131298 A3 | 10/2008 |
| WO | WO 2008/131298 A3 | 12/2008 |
| WO | WO 2009/017467 A1 | 2/2009 |
| WO | WO 2009/052439 A2 | 4/2009 |
| WO | WO 2010/033861 A1 | 3/2010 |
| WO | WO 2010/044803 A1 | 4/2010 |
| WO | WO 2011/106732 A1 | 9/2011 |
| WO | WO 2011/133919 A1 | 10/2011 |

OTHER PUBLICATIONS

Friedland et al. Development of an anti-A beta monoclonal antibody for in vivo imaging of amyloid angiopathy in Alzheimer's disease. Mol Neurobiol. Aug.-Dec. 1994;9(1-3):107-13.*

Gross et al. Microvascular specializations promoting rapid interstitial solute dispersion in nucleus tractus solitarius. Am J Physiol Regul Integr Comp Physiol 259: R1131-R1138, 1990.*

Whitcomb et al. Characterization of saturable binding sites for circulating pancreatic polypeptide in rat brain. Am J Physiol Gastrointest Liver Physiol 259: G687-G691, 1990.*

PNAS Information for Authors (revised Jan. 1997), Retrieved Apr. 21, 2008 from http://web.archive.org/web/19970610092808/www.pnas.org/iforc.shtml.*

Wikipedia entry for Antibody, retrieved Mar. 15, 2009 from http://en.wikipedia.org/wiki/Antibody.*

U.S. Appl. No. 60/254,465, filed Dec. 8, 2000, Holtzman et al.
U.S. Appl. No. 60/254,498, filed Dec. 8, 2000, Holtzman et al.
U.S. Appl. No. 09/724,842, filed Nov. 28, 2000, Chalifour et al.
U.S. Appl. No. 60/186,295, filed Mar. 1, 2000, Rasmussen et al.
U.S. Appl. No. 60/184,601, filed Feb. 24, 2000, Holtzman et al.
U.S. Appl. No. 60/169,687, filed Dec. 8, 1999, Chain.
U.S. Appl. No. 60/168,594, filed Nov. 29, 1999, Chalifour et al.
U.S. Appl. No. 09/441,140, filed Nov. 16, 1999, Solomon et al.

Aguzzi et al., "Prion research: the next frontiers," *Nature*, 389:795-798 (1997).

Akiyama et al., "Occurrence of the Diffuse Amyloid β-Protein (Aβ) Deposits With Numerous Aβ-Containing Glial Cells in the Cerebral Cortex of Patients With Alzheimer's Disease," *Glia*, 25:324-331 (1999).

Akiyama et al., "Inflammation and Alzheimer's disease," *Neurobiology of Aging*, 21:383-421 (2000).

Andersen et al., "Do nonsteroidal anti-inflammatory drugs decrease the risk for Alzheimer's disease?", *Neurology*, 45:1441-1445 (1995).

Andrew et al., *Current Protocols in Immunology*, 2.7.1-2.9.8, John Wiley & Sons, Inc. (1997).

Arendiash et al., "Behavioral assessment of Alzheimer's transgenic mice following long-term Aβ vaccination: Task specificity and correlations between Aβ deposition and spatial memory," *DNA and Cell Biology*, 20(11):737-744 (2001).

Associated Press, "Immune cells may promote Alzheimer's, a study finds," *The Boston Globe* (Apr. 13, 1995).

Bacskai et al., "Imaging of amyloid-β deposits in brains of living mice permits direct observation of clearance of plaques with immunotherapy," *Nature Medicine*, 7(3):369-372 (2001).

Balbach et al., "Amyloid fibril formation by $A\beta_{16-22}$, a seven-residue fragment of the Alzheimer's β-amyloid peptide, and structural charcterization by solid state NMR," *Biochemistry*, 39:13748-13759 (2000).

Bard et al., "Peripherally administered antibodies against amyloid β-peptide enter the central nervous system and reduce pathology in a mouse model of Alzheimer disease," *Nature Medicine*, 6(8):916-919 (2000).

Barrow et al., "Solution Conformations and aggregational Properties of Synthetic Amyloid Beta-Peptides of Alzheimer's Disease. Analysis of Circular Dichroism Spectra," *J. Mol. Biol.*, 225(4):1075-1093 (1992).

Bauer et al., "Interleukin-6 and α-macroglobulin indicate an acute-phase state in Alzheimer's disease cortices," *FEBS Letters*, 285(1):111-114 (1991).

Beasley, "Alzheimer's traced to proteins caused by aging," Reuters, Apr. 20, 2001 7:56 PM ET.

Benjamini et al., from *IMMUNOLOGY A Short Course*, Second Edition, Chapter 4, Antibody Structure, pp. 49-65, 1991, published by Wiley-Liss, Inc., New York, New York.

Bercovici et al., "Chronic Intravenous Injections of Antigen Induce and Maintain Tolerance in T Cell Receptor-Transgenic Mice," *Eur. J. Immunol.*, 29:345-354 (1999).

Bickel et al., "Site Protected, Cationized Monoclonal Antibody Against Beta Amyloid as a Potential Diagnostic Imaging Technique for Alzheimer's Diseases," *Soc. for Neuroscience Abstracts* 18:764 (1992).

Blass, "Immunologic Treatment of Alzheimer's Disease," *New England J. Medicine*, 341(22):1694 (1999).

Bodmer et al., "Transforming Growth Factor-Beta Bound to Soluble Derivatives of the Beta Amyloid Precursor Protein of Alzheimer's Disease," *Biochem. Biophys. Res. Comm.*, 171(2):890-897 (1990).

Borchelt et al., "Accelerated Amyloid Deposition in the Brains of Transgenic Mice Coexpressing Mutant Presenilin 1 and Amyloid Precursor Proteins," *Neuron*. 19:939-945 (1997).

Boris-Lawrie et al., "Recent advances in retrovirus vector technology," *Cur. Opin. Genetic Develop.*, 3:102-109 (1993).

Bork et al., "Go hunting in sequence databases but watch out for the traps," *Trends in Genetics*, 12(10):425-427 (1996).

Bork, P., "Powers and Pitfalls in Sequence Analysis: The 70% Hurdle," *Genome Research* 10:398-400 (2000).

Brenner, S. E., "Errors in genome annotation " *Trends in Genetics*, 15(4):132-133 (1999).

Brice et al., "Absence of the amyloid precursor protein gene mutation (APP717 : Val→Ile) in 85 cases of early onset Alzheimer's disease," *J. Neurology, Neurosurg. Psychiatry*, 56:112-115 (1993).

Burdick et al., "Assernbty and aggregartion properties of synthelic Alzheimer's A4/β amyloid peptide antigens," *J. Biol. Chem.*, 267:546-555 (1992).

Cameron, "Recent Advances in Transgenic Technology," *Molecular Biotechnology* 7:253-265 (1997).

Caputo et al., "Therapeutic approaches targeted at the amyloid proteins in Alzheimer's disease," *Clin. Neuropharm.* 15:414A-414B (1992).

Castillo et al., "Amylin / Islet Amyloid Polypeptide: Biochemistry, Physiology, Patho-Physiology," *Diabete & Metabolisme* (Paris), 21:3-25 (1995).

Center for Biologics Evaluation and Research, U.S. Food and Drug Administration, Thimerosal in Vaccines (Mercury in Plasma-Derived Products), web site contents found at : http://www.fda.gov/cber/vaccine/thimerosal.htm, last updated May 16, 2002.

Chao et al., "Transforming Growth Factor-β Protects human Neurons Against β-Amyloid-Induced Injury," *Soc. Neurosci. Abstracts*, 19:513-7 (1993).

Chapman, "Model behavior," *Nature*, 408:915-916 (2000).

Check, "Battle of the Mind," *Nature* 422:370-372 (2003).

Chen et al., "Neurodegenerative Alzheimer-like pathology in PDAPP 717V→F transgenic mice," *Progress in Brain Research*, 117:327-337 (1998).

Chen et al., "A learning deficit related to age and beta-amyloid plaques in a mouse model of Alzheimer's disease," *Nature*, 408(6815):975-979 (2000).

Chen et al., "An Antibody to β Amyloid Precursor Protein Inhibits Cell-substratum Adhesion in Many Mammalian Cell Types," *Neuroscience Letters*, 125:223-226 (1991).

Chung et al., "Uptake, Degradation, and Release of Fibrillar and Soluble Forms of Alzheimer's Amyloid β-Peptide by Microglial Cells," *J. Biol. Chem.*, 274(45):32301-32308 (1999).

Co et al., "Chimeric and humanized antibodies with specificity for the CD33 antigen," *J. Immunol.*, 148:1169-1154 (1992).

Coloma et al., "Transport Across the Primate Blood-Brain Barrier of a Genetically Engineered Chimeric Monoclonal Antibody to the Human Insulin Receptor," *Pharm. Res.*, 17:266-274 (2000).

Conway et al., "Acceleration of oligomerization, not fibrilization, is a shared property of both α-synuclein mutations linked to early-onset Parkinson's disease: Implications for pathogenesis and therapy," *PNAS*, 97(2):571-576 (2000).

Cordell, B., "β-Amyloid formation as a potential therapeutic target for Alzheimer's disease," *Ann. Rev. Pharmacol. Toxicol.*, 34:69-89 (1994).

Costa et al., "Immunoassay for transthyretin variants associated with amyloid neuropathy," *Scand. J. Immunol.*, 38:177-182 (1993).

Daly, et al., "Detection of the membrane-retained carboxy-terminal tail containing polypeptides of the amyloid precursor protein in tissue from Alzheimer'Disease brain," *Life Sci.*, 63:2121-2131 (1998).

Das et al., "Amyloid-β Immunization Effectively Reduces Amyloid Deposition in FcRy Knock-Out-Mice," *J. Neuroscience*, 23(24):8532-8538 (2003).

Demattos et al., "Peripheral anti-Aβ antibody alters CNS and plasma clearance and decreases Aβ burden in a mouse model of Alzheimer's disease," *PNAS*, 98(15):8850-8855 (2001).

Demattos et al., "Peripheral Anti Aβ Antibody Alters CNS and Plasma Aβ Clearance and Decreases Brain Aβ Burden in a Mouse Model of Alzheimer's Disease," *PNAS early edition*, 10.1073/pnas.151261398 (2001).

Demattos et al., "Plaque-associated disruption of CSF and plasma amyloid-β (Aβ) equilibrium in a mouse model of Alzheimer's disease," *J. Neurochem.* 81:229-236 (2002).

Dickey et al., "Duration and specificity of humoral immune responses in mice vaccinated with the Alzheimer's disease-associated β-amyloid 1-42 peptide," *DNA and Cell Biology*, 20(11):723-729 (2001).

Dickson et al., "Neuroimmunology of Alzheimer's disease: a conference report," *Neurobiology of Aging*, 13(6):793-798 (1992), abstract only.

Diomede et al., "Activation effects of a prion protein fragment [PrP-(106-126)] on human leucocytes" *Biochem. J.*, 320:563-570 (1996).

Dodart, "Immunotherapy for Alzheimer's disease: will vaccination work?," *Trends in Molecular Medicine*, 9(3):85-87 (2003).

Doerks et al., "Protein annotation: detective work for function prediction," *Trends in Genetics*, 14(6):248-250 (1998).

Du et al., "Reduced levels of amyloid beta-peptide antibody in Alzheimer disease," *Neurology*, 57(5):801-5 (2001).

Duff et al., "Mouse model made," *Nature*, 373:476-477 (1995).

Dumery et al., "β-Amyloid protein aggregation: its implication in the physiopathology of Alzheimer's disease," *Pathol. Biol.* 49:72-85 (2001).

Eck et al., *Goodman and Gilman's The pharmacological basis of therapeutics*, Chapter 5, pp. 77-101 (1996).

El-Agnaf et al., "The influence of the central region containing residues 19-25 on the aggregation properties and secondary structure of Alzheimer's beta-amyloid peptide," *Eur. J. Biochem.*, 256(3):560-569 (1998).

Elan, "Elan and AHP Provide an Update on the Phase 2A Clinical Trial of AN-1792," Press Release. (Jan. 18, 2002).

Elan, "Elan and Wyeth Provide Update on Status of Alzheimer's Collaboration," Press Release (Mar. 1, 2002).

Elizan et al., "Antineurofilament antibodies in a postencephalitic and idiopathic Parkinson's disease," *J. Neurol. Sciences*, 59:341-347 (1983).

Esiri, "Is an effective immune intervention for Alzheimer's disease in prospect?", *Trends in Pharm. Sci.*, 22:2-3 (2001).

Esler et al., "Point substitution in the central hydrophobic cluster of a human β-amyloid congener disrupts peptide folding and abolishes plaque competence," *Biochemistry* 35:13914-13921 (1996).

Felsenstein et al., "Processing of the β-amyloid precursor protein carrying the familial, Dutch-type, and a novel recombinant C-terminal mutation," *Neuroscience Letters*, 152:185-189 (1993).

Felsenstein et al., "Transgenic Rat and In-Vitro Studies of B-Amyloid Precursor Protein Processing," *Alzheimer's and Parkinson's Diseases*, Hanin et al. Ed., pp. 401-409, Plenum Press, New York, (1995).

Finch et al., "Evolutionary Perspectives on Amyloid and Inflammatory Features of Alzheimer Disease," *Neurobiology of Aging*, 17(5):809-815 (1996).

Fisher et al., "Expression of the amyloid precursor protein gene in mouse oocytes and embryos," *PNAS*, 88:1779-1782 (1991).

Flanders et al., "Altered expression of transforming growth factor-β in Alzheimer's disease," *Neurology*, 45:1561-1569 (1995).

Flood et al., "An amyloid β-Protein fragment, A β [12-28J, equipotently impairs post-training memory processing when injected into different limbic system structures," *Brain Res*, 663(2):271-276 (1994).

Fonseca et al., "The Presence of Isoaspartic Acid in β-Amyloid Plaques Indicates Plaque Age," *Experimental Neurology* 157(2):277-288 (1999).

Frautschy et al., "Effects of injected Alzheimer β-amyloid cores in rat brain," *PNAS*, 88:8362-8366 (1991).

Frenkel et al., "Generation of auto-antibodies towards Alzheimer's disease vaccination," *Vaccine*, 19:2615-2619 (2001).

Frenkel et al., "High affinity binding of monoclonal antibodies to the sequential epitope EFRH of β-amyloid peptide is essential for modulation of fibrillar aggregation," *J. of Neuroimmunology*, 95:136-142 (1999).

Frenkel et al., "Immunization against Alzheimer's β-amyloid plaques via EFRH phage administration," *PNAS*, 97:11455-11459 (2000).

Frenkel et al., "N-terminal EFRH sequence of Alzheimer's β-amyloid peptide represents the epitope of its anti-aggregating antibodies," *J. of Neuroimmunology*, 88:85-90 (1998).

Frenkel, et al., "Modulation of Alzheimer's β-amyloid neurotoxicity by site-directed single chain antibody," *J. of Neuroimmunology*, 106:23-31 (2000).

Friedland et al., "Development of an anti-Aβ monoclonal antibody for in vivo imaging of amyloid angiopathy in Alzheimer's disease," *Mol. Neurology*, 9:107-113 (1994).

Friedland, et al., "Neuroimaging of Vessel Amyloid in Alzheimer's Disease," in *Cerebrovascular Pathology in Alzheimer's Disease*, eds. de la Torre and Hachinski, New York Academy of Sciences, New York, New York (1997).

Furlan et al., "Vaccination with amyloid-β peptide induces autoimmune encephalomyelitis in C57/BL6 mice," *Brain*, 126:285-291 (2003).

Games et al., "Alzheimer-type neuropathology in transgenic mice overexpressing V717F β-amyloid precursor protein" *Nature*, 373(6514):523-527 (1995).

Games et al., "Prevention and Reduction of AD-type Pathology in PDAPP Mice Immunized with $A\beta_{1-42}$," *Annals of the New York Academy of Science*, 920:274-284 (2000).

Gandy et al., "Amyloidogenesis in Alzheimer's disease: some possible therapeutic opportunities," *TiPS*, 13:108-113 (1992).

Gardella et al., "Intact Alzheimer amyloid precursor protein (APP) is present in platelet membranes and is encoded by platelet mRNA," *Biochem. Biophys. Res. Comm.*, 173:1292-1298 (1990).

Gaskin et al., "Human antibodies reactive with beta-amyloid protein in Alzheimer's disease " *J. Exp. Med.*, 177:1181-1186 (1993).

Geddes, "N-terminus truncated β-amyloid peptides and C-terminus truncated secreted forms of amyloid precursor protein: distinct roles in the pathogenesis of Alzheimer's disease," *Neurobiology of Aging*, 20:75-79 (1999).

Ghiso et al., "Epitope map of two polyclonal antibodies that recognize amyloid lesions in patients with Alzheimer's disease " *Biochem. J.*, 282 (Pt 2):517-522 (1992).
Giulian et al., "Specific domains of β-amyloid from Alzheimer plaque elicit neuron killing in human microglia," *J Neurosci.*, 16 (19):6021-6037 (1996).
Giulian, et al., "The HHQK Domain of b-Amyloid Provides a Structural Basis for the Immunopathology of Alzheimer's Disease," *J. Biol. Chem.*, 273:29719-29726 (1998).
Glenn et al., "Skin immunization made possible by cholera toxin," *Nature*, 391:851 (1998).
Glenner et al., "Alzheimer's Disease and Downs Syndrome: Sharing of a Unique Cerebrovascular Amyloid Fibril Protein," *Biochem. Biophys. Res. Comm.*, 122(3): 1131-1135 (1984).
Glenner et al., "Alzheimer's Disease: Initial Report of the Purification and Characterization of a Novel Cerebrovascular Amyloid Protein," *Biochem. Biophys. Res. Comm.*, 120(3): 885-890 (1994).
Goate et al., "Segregation of a missense mutation in the amyloid precursor protein gene with familial Alzheimer's disease" *Nature*, 349:704-706 (1991).
Goldfarb et al., "The Transmissible Spongiform Encephalopathies," *Ann. Rev. Med.*, 46:57-65 (1995).
Goldsby et al., "Vaccines," Chapter 18 from *Immunology, 4th Edition*, W.H. Freeman and Company, New York, pp. 449-465 (2000).
Goldsteins et al., "Goldsteins et al., Exposure of cryptic epitopes on transthyretin only in amypoid and in amyloidogenic mutants," *PNAS*, 96:3108-3113 (1999).
Gonzales-Fernandez et al., "Low antigen dose favors selection of somatic mutants with hallmarks of antibody affinity maturation," *Immunology*, 93:149-153 (1998).
Gorevic et al., "Ten to fourteen residue peptides of Alzheimer's disease protein are sufficient for amyloid fibril formation and its characteristic X ray diffraction pattern" *Biochem. and Biophy. Res. Commun.*, 147(2):854-862 (1987).
Gortner, *Outlines of Biochemistry*, pp. 322-323, John Wiley & Sons, Inc., New York (1949).
Gozes et al., "Neuroprotective strategy for Alzheimer disease: Intranasal administration of a fatty neuropeptide," *PNAS* 93:427-432 (1996).
Gravina et al., "Amyloid β Protein (Aβ) in Alzheimer's Disease," *J. Biol. Chem.*, 270(13):7013-7016 (1995).
Grubeck-Loebenstein, et al., "Immunization with β-amyloid: could T-cell activation have a harmful effect?", *TINS*, 23:114 (2000).
Gupta et al., "Differences in the immunogenicity of native and formalized cross reacting material (CRM197) of diptheria toxin in mice and guinea pigs and their implications on the development and control of diphtheria vaccine based on CRMs" *Vaccine*, 15(12/13): 1341-1343 (1997).
Haass et al. "Amyloid beta-peptide is produced by cultured cells during normal metabolism," *Nature*, 359(6393):322-325 (1992).
Haass et al., "Protofibrils, the unifying toxic molecule of neurodegenerative disorders?," *Nature Neuroscience*, 4(9):859-860 (2001).
Haga et al., "Synthetic Alzheimer amyloid β/A4 peptides enhance production of complement C3 component by cultured microglial cells," *Brain Research*, 601:88-94 (1993).
Hanan and Solomon, "Inhibitory effect of monoclonal antibodies on Alzheimer's β-amyloid peptide aggregation," *Int. J. Exp. Clin. Invest.*, 3:130-133 (1996).
Hanes et al., "New advances in microsphere-based single-dose vaccines," *Advanced Drug Delivery Reviews*, 28:97-119 (1997).
Hardy, "Amyloid, the presenilins and Alzheimer's disease," *TINS*, 20(4): 154-159 (1997).
Hardy, John, "New Insights into the Genetics of Alzheimer's Disease," *Annals of Med.*, 28:255-258 (1996).
Harigaya, et al., "Modified amyloid β protein ending at 42 or 40 with different solubility accumulates in the brain of Alzheimer's disease," *Biochem. Biophys. Res. Comm.*, 211:1015-1022 (1995).
Harrington et al., "Characterization of an epitope specific to the neuron-specific isoform of human enolase recognized by a monoclonal antibody raised against a synthetic peptide corresponding to the C-terminus of β / A4-protein," *Biochimica Biophysica Acta*, 1158:120-128 (1993).

Hazama, et al., "Intranasal Immunization Against Herpes Simplex Virus Infection by Using a Recombinant Glycoprotein D Fused With Immunomodulating Proteins, the B Subunit of *Escherichia coli* Heat-Labile Enterotoxin and Interleukin-2," *Immunology*, 78:643-649 (1993).
He et al., "Humanization and pharmacokinetics of a monoclonal antibody with specificity for both E- and P-selectin " *J. Immunol*, 160:1029-1035 (1998).
Helmuth, "Further Progress on a β-Amyloid Vaccine," *Science*, 289:375 (2000).
Hilbich et al., "Aggregation and secondary structure of synthetic amylold βA4 peptides of Alzheimer's disease," *J. Mol. Biol.*, 218:149-163 (1991).
Hilbich et al., "Substitutions of hydrophobic amino acid reduce the amyloidogenicity of Alzheimer's disease βA4 peptides" *J. Mol. Biol.*, 228:460-473 (1992).
Hilbich et al., "Human and rodent sequence analogs of Alzheimer's amyloid βA4 share similar properties and can be solubilized in buffers of pH 7.4," *Eur. J. Biochem.*, 201:61-69 (1991).
Holtzman et al., "Aβ immunization and anti-Aβ antibodies: potential therapies for the prevention and treatment of Alzheimer's disease," *Advanced Drug Delivery Reviews*, 54:1603-1613 (2002).
Hsiao et al., "Correlative Memory Deficits, Aβ Elevation, and Amyloid Plaques in Transgenic Mice," *Science*, 274: 99-102 (1996).
Huberman et al., "Correlation of cytokine secretion by mononuclear cells of Alzheimer's patients and their disease stage " *J. Neuroimmunology*, 52:147-152 (1994).
Hyman et al., "Molecular Epidemiology of Alzheimer's Disease," *N. E. J. Medicine*, 333(19)1283-1284 (1995).
Ikeda, et al., "Immunogold labeling of cerebrovascular and neuritic plaque amyloid fibrils in Alzheimer's disease with an anti-β protein monoclonal antibody," *Lab. Invest.*, 57:446-449 (1987).
Itagaki et al., "Relationship of microglia and astrocytes to amyloid deposits of Alzheimer's disease," *J. Neuroimmunology*, 24:173-182 (1989).
Iwatsubo et al., "Visualization of Aβ42(43) and Aβ40 in Senile Plaques with End-Specific Aβ Monoclonals: Evidence That an Initially Deposited Species Is Aβ 42(43)," *Neuron*, 13:45-53 (1994).
Jakes et al., "Characterisation of an Antibody Relevant to the Neuropathology of Alzheimer Disease," *Alzheimer Disease and Associated Disorders*, 9(1):47-51 (1995).
Jansen et al., "Immunotoxins: Hybrid Molecules Combining High Specificity and Potent Cytotoxicity," *Immun. Rev.*, 62: 185-216 (1982).
Janus et al., "A beta peptide immunization reduces behavioural impairment and plaques in a model of Alzheimer's disease," *Nature*, 408(6815):979-982 (2000).
Jen, et al., "Preparation and purification of antisera against different regions or isoforms of b-amyloid precursor protein," *Brain Research Protocols* 2:23-30 (1997).
Joachim et al., "Antibodies to Non-beta Regions of the Beta-amyloid Precursor Protein Detect a Subset of Senile Plaques," *Am. J. of Pathology*, 138:373-384 (1991).
Jobling et al., "Analysis of structure and function of the B subunit of cholera toxin by the use of site-directed mutagenesis," *Molecular Microbiology*, 5(7):1755-1767 (1991).
Johnson-Wood et al., "Amyloid precursor protein processing and Aβ$_{42}$ deposition in a transgenic mouse model of Alzheimer disease," *PNAS* 94:1550-1555 (1997).
Johnstone et al., Nuclear and Cytoplasmic Localization of the β-Amyloid Peptide (1-43) in Transfected 293 Cells, *Biochem. Biophys. Res. Comm.*, 220:710-718 (1996).
Jorbeck et al., "Artificial *Salmonella* Vaccines: *Salmonella typhimurium* O-antigen-Specific Oligosaccharide-Protein Conjugates Elicit Opsonizing Antibodies that Enhance Phagocytosis," *Infection and Immunity*, 32(2):497-502 (1981).
Kalaria, R. N., "Serum amyloid P and related molecules associated with the acute-phase response in Alzheimer's disease," *Res. Immunology*, 143:637-641 (1992).
Katzav-Gozansky et al., "Effect of monoclonal antibodies in preventing carboxypeptidase A aggregation," *Biotechnol. Appl. Biochem.*, 23:227-230 (1996).

Kawabata et al., "Amyloid plaques, neurofibrillary tangles and neuronal loss in brains of transgenic mice overexpressing a C-terminal fragment of human amyloid precursor protein," Nature, 354:476-478 (1991).

Kelly, J. W., "Alternative conformations of amyloidogenic proteins govern their behavior," Current Opinion in Structural Biology, 6:11-17 (1996).

Kida, et al., "Early amyloid-β deposits show different immunoreactivity to the amino- and carboxy-terminal regions of b-peptide in Alzheimer's disease and Down's syndrome brain," Neuroscience Letters, 193:105-108 (1995).

Klein et al., "Targeting small Aβ oligomers: the solution to an Alzheimer's disease conundrum?," Trends in Neurosciences, 24(4):219-224 (2001).

Konig et al., "Development and Characterization of a Monoclonal Antibody 369.2B Specific for the Carboxyl-Terminus of the βA4 Peptide," Annals of NY Acad. Sci., 777:344-355 (1996).

Kotilinek et al., "Reversible memory loss in a mouse transgenic model of Alzheimer's disease," J. Neurosci., 22(15):6331-6335 (2002).

Koudinov et al., "The soluble form of Alzheimer's amyloid beta protein is complexed to high density lipoprotein 3 and very high density lipoprotein in normal human plasma," Biochem. & Biophys. Res. Comm, 205:1164-1171 (1994).

Kovacs et al., "Mutations of the Prion Protein Gene Phenotypic Spectrum," J. Neurol., 249:1567-1582 (2002).

Kuo et al., "High levels of circulating Abeta42 are sequestered by plasma proteins in Alzheimer's disease," Biochem. Biophys. Res. Comm., 257(3):787-791 (1999).

Lambert et al., "Diffusible, nonfibrillar ligands derived from Aβ1-42 are potent central nervous system neurotoxins," PNAS, 95:6448-6453 (1998).

Lambert et al., "Vaccination with soluble Aβ oligomers generates toxicity-neutralizing antibodies," J. Neurochem., 79:595-605 (2001).

Lampert-Etchells et al., "Regional Localization of Cells Containing Complement C1q and C4 mRNAs in the Frontal Cortex During Alzheimer's Disease," Neurodegeneration, 2:111-121 (1993).

Langer, "New Methods of Drug Delivery," Science, 249:1527-1532 (1990).

Lannfelt et al., "Alzheimer's disease: molecular genetics and transgenic animal models," Behavioural Brain Res., 57:207-213 (1993).

Lansbury, Peter T., "Inhibition of amyloid formation: a strategy to delay the onset of Alzheimer's disease," Curr. Ops. in Chemical Biology, 1:260-267 (1997).

Lee et al., "Aβ immunization: Moving Aβ peptide from brain to blood," PNAS, 98(16):8931-8932 (2001).

Lemere et al., "Mucosal Administration of Aβ Peptide Decreases Cerebral Amyloid Burden in Pd-App Transgenic Mice," Society for Neuroscience Abstracts, 25(part )I, Abstract 519.6, 29th Annual Meeting, (Oct. 23-28, 1999).

Lemere, et al., "Nasal Aβ treatment induces anti-Aβ antibody production and decreases cerebral amyloid burden in PD-APP mice," Annals of the NY Acad. Sci., 920:328-331 (2000).

Levitt, M., "Molecular dynamics of native protein," J. Mol Biol. 168:595-620 (1983).

Levy et al., "Immunization for Alzheimer's disease: A shot in the arm or a whiff?," American Neurological Assoc, 48:553-554 (2000).

Li et al., "Thermal Stabilization of Carboxypeptidase A as a Function of PH and Ionic Milieu," Biochem. Mol. Biol. Int., 43(3):601-611 (1997).

Livingston et al., "The Hepatitis B Virus-Specific CTL Responses Induced in Humans by Lipopeptide Vaccination Are Comparable to Those Elicited by Acute Viral Infection," J. Immunol., 159:1383-1392 (1997).

Lopez et al., "Serum auto-antibodies in Alzheimer's disease," Acta. Neurol. Scand., 84:441-444 (1991).

Lue et al., "Soluble β-amyloid Peptide Concentration as a Predictor of Synaptic Change in Alzheimer's Disease," Am. J. Pathol., 155:853-562 (1999).

Maggio et al., "Brain Amyloid—A Physicochemical Perspective," Brain Pathology, 6:147-162 (1996).

Majocha et al., "Development of a Monoclonal Antibody Specific for β/A4 Amyloid in Alzheimer's Disease Brain for Application to In Vitro Imaging of Amyloid Angiopathy," The J. of Nuclear Med., 33:2184-2189 (1992).

Mak, et al., "Polyclonals to b-amyloid (1-42) identify most plaque and vascular deposits in Alzheimer cortex, but not striatum," Brain Research, 667:138-142 (1994).

Mann, et al., "Amyloid β protein (Aβ) deposition in chromosome 14-linked Alzheimer's disease: Predominance of $A\beta_{42(43)}$," Annals of Neurology, 40:149-156 (1996).

Mann, et al., "The extent of amyloid deposition in brain in patients with Down's syndrome does not depend upon the apolipoprotein E genotype," Neuroscience Letters, 196:105-108 (1995).

Marshall, E., "Gene Therapy's Growing Pains," Science, 269:1050-1055 (1995).

Masliah et al., "β-Amyloid peptides enhance α-synuclein accumulation and neuronal deficits in a transgenic mouse model linking Alzheimer's disease and Parkinson's disease," PNAS, 98(21):12245-12250 (2001).

Masters et al., "Amyloid Plaque core protein in Alzheimer Disease and Down Syndrome," PNAS, 82:4245-4249 (1985).

Mattson, "Cellular actions of beta-amyloid precursor protein and its soluble and fibrillogenic derivatives," Physiol Rev., 77(4):1081-132 (1997).

McGee et al., "The encapsulation of a model protein in poly (D, L lactide-co-glycolide) microparticles of various sizes: an evaluation of process reproducibility," J. Micro. Encap., 14(2):197-210 (1997).

McGeer, et al., "Immunohistochemical localization of beta-amyloid precursor protein sequences in Alzheimer and normal brain tissue by light and electron microscopy," J. of Neuroscience Res., 31:428-442 (1992).

McLean et al., "Soluble pool of Aβ amyloid as a determinant of severity of neurodegeneration in Alzheimer's disease," Amer. Neurological Assoc, 46:860-866 (1999).

McNeal et al., "Stimulation of local immunity and protection in mice by intramuscular immunization with triple- or double-layered rotavirus particles and QS-21," Virology, 243:158-166 (1998).

Meda et al., "Activation of microglial cells by β-amyloid protein and interferon-γ," Nature, 374:647-650 (1995).

Mena, et al., "Monitoring pathological assembly of tau and β-amyloid proteins in Alzheimer's disease," Acta Neuropathol., 89:50-56 (1995).

Merluzzi, et al., "Humanized antibodies as potential drugs for therapeutic use," Adv Clin Path., 4(2):77-85 (2000).

Miller et al., "Antigen-driven Bystander Suppression after Oral Administration of Antigens," J. Exp. Med., 174:791-798 (1991).

Monsonego et al., "Immune hyporesponsiveness to amyloid β-peptide in amyloid precursor protein transgenic mice: Implications for the pathogenesis and treatment of Alzheimer's disease," PNAS, 98(18):10273-10278 (2001).

Morgan, et al., "A beta peptide vaccination prevents memory loss in an animal model of Alzheimer's disease," Nature, 408(6815):982-985 (2000).

Mori et al., "Mass Spectrometry of Purified Amyloid β Protein in Alzheimer's Disease," J. Biol. Chem., 267(24):17082-17088 (1992).

Morris, et al., "The Consortium to Establish a registry for Alzheimer's Disease (CERAD)," Neurology, 39:1159-1165 (1989).

Munch et al., "Potentional neurotoxic inflammatory response to Aβ vaccination in humans," J. Neural Transm., 109:1081-1087 (2002).

Munson eds., Principals of Pharmacology: Basic Concepts & Clinical Applications, pp. 47-48, Chapman & Hall, New York, New York (1995).

Murphy et al., "Development of a Monoclonal Antibody Specific for the COOH-Terminal of β-Amyloid 1-42 and Its Immunohistochemical Reactivity in Alzheimer's Disease and Related Disorders," Am. J. Pathology, 144(5):1082-1088 (1994).

Mutschler et al., Drug Actions: Basic Principles and Therapeutic Aspects pp. 7, 11-12, Medpharm Scientific Publishers, Stuttgart, Germany (1995).

Nakamura et al., "Histopathological studies on senile plaques and cerebral amyloid angiopathy in aged cynomologus monkeys," Exp. Anim., 43:711-718 (1995).

Nakamura, et al., "Carboxyl end-specific monoclonal antibodies to amyloid β protein (Aβ) subtypes (Aβ40 and Aβ42(43) differentiate Ab in senile plaques and amyloid angiopathy in brains of aged cynomolgus monkeys," *Neuroscience Letters*, 201:151-154 (1995).

Nakayama et al., "Histopathological studies of senile plaques and cerebral amyloidosis in cynomolgus monkeys," *J. of Med. Primatology*, 27:244-252 (1998).

Nalbantoglu, J., "Beta-amyloid protein in Alzheimer's disease," *Can. J. Neurol. Sci.*, 18(3 suppl.):424-427 (1991), abstract only.

Naslund et al., "Correlation between elevated levels of amyloid β peptide in the brain and cognitive decline," *J. Am. Med. Assoc.*, 283:1571 (2000).

Nathanson et al., "Bovine Spongiform Encephalopathy (BSE): Causes and Consequences of a Common Source Epidemic," *Am. J. Epidemiol.*, 145(11):959-969 (1997).

New York Times National, "Anti-Inflammatory Drugs May Impede Alzheimer's," (Feb. 20, 1994).

Newcombe et al., "Solubility characteristics of isolated amyloid fibrils," *Biochim. Biophys. Acta*, 104:480-486 (1965).

Ngo et al., "Computational Complexity, Protein Structure Prediction, and the Levinthal Paradox," pp. 492-495 from Chapter 14 of *The Protein Folding Problem and Tertiary Structure Prediction*, Merz et al., eds., Birkhauser Boston (1994).

Nicoll et al., "Neuropathology of human Alzheimer's disease after immunization with amyloid-β peptide: a case report," *Nature Medicine*, 9(4):448-452 (2003).

Niemann, "Transgenic farm animals get off the ground;" *Transgenic Research*, 7:73-75 (1998).

Orkin et al., *Report and Recommendations of the Panel to Assess the NIH Investment in Research on Gene Therapy*, Dec. 7, 1995.

Palha et al., "Antibody recognition of amyloidogenic transthyretin variants in serum of patients with familial amyloidiotic polyneuropathy,"*J. Mol. Med.*, 7:703-707 (2001).

Pan et al., "Antibodies to β-Amyloid Decrease the Blood-to-Brain Transfer of β-Amyloid Peptide," *Exp. Biol. Med.*, 227(8):609-615 (2002).

Pardridge et al., "Chimeric peptides as a vehicle for peptide pharmaceutical delivery through the blood-brain barrier," *Biochem. Biophys. Res. Comm.*, 146:307-313 (1987).

Paresce et al., "Microglial cells influence aggregates of the Alzheimer's disease amyloid beta-protein via a scavenger receptor," *Neuron*, 17:553-565 (Sep. 1996).

Paul et al., "Transdermal immunization with large proteins by means of ultradeformable drug carriers," *Eur. J. Immunol.*, 25: 3521-3524 (1995).

Persson et al., "IgG subclass-associated affinity differences of specific antibodies in humans," *J. Immunology*, 140(11):3875-3879 (1988), abstract only.

Perutz et al., "Amyloid fibers are water-filed nanotubes," *PNAS*, 99(8):5591-5595 (2002).

Peterson, et al., "Recombinant Antibodies: Alternative Strategies for Developing and Manipulating Murine-Derived Monoclonal Antibodies," *Laboratory Animal Science*, 46(1):8-14 (1996).

Philippe, et al. "Generation of a monoclonal antibody to the carboxy-terminal domain of tau by immunization with the amino-terminal domain of the amyloid precursor protein," *J. of Neuroscience Res.*, 46:709-719 (1996).

Poduslo et al., "Permeability of proteins at the blood-brain barrier in the normal adult mouse and double transgenic mouse model of Alzheimer's disease," *Neurobiol. Dis.* 8(4):555-567 (2001).

Prieels et al., "Synergistic adjuvants for vaccines," *Chemical Abstracts*, 120(8):652, col. 1, abstract 86406t (1994).

Prusiner et al., "Ablation of the prion protein (PrP) gene in mice prevents scrapie and facilitates production of anti-PrP antibodies," *PNAS* 90:10608-10612 (1993).

Queen et al., "A humanized antibody that binds to the interleukin 2 receptor," *PNAS*, 86:10029-10033 (1989).

Quon et al., "Formation of β-Amyloid protein deposits in brains of transgenic mice," *Nature*, 352:239-241 (1991).

Ragusi et al., "Redistribution of Imipramine from Regions of the Brain Under the Influence of Circulating Specific Antibodies," *J. Neurochem.*, 70(5):2099-2105 (1998).

Raso, "Immunotherapy of Alzheimer's Disease," *Immunotherapy Weekly*, Abstract (Apr. 2, 1998).

Rogers et al., "Complement activation by β-amyloid in Alzheimer Disease," *PNAS*, 89:1-5 (1992).

Rossor et al., "Alzheimer's Disease Families with Amyloid Precursor Protein Mutations," *Annals of New York Academy of Sciences*, 695:198-202 (1993).

Rudinger, "Characteristics of the Amino Acids as Components of a Peptide Hormone Sequence," in *Peptide Hormones*, J.A. Parson, ed. University Park Press, Baltimore, pp. 1-7 (1976).

Saido et al., "Spatial Resolution of Fodrin Proteolysis in Postischemic Brain," *J. Biol. Chem.*, 268(33):25239-25243 (1993).

Saido et al., "Spatial Resolution of the Primary β-Amyloidogenic Process Induced in Postischemic Hippocampus," *J. Biol. Chem.*, 269(21):15253-15257 (1994).

Saito et al., "Vector-mediated delivery of $^{125}$I-labeled β-amyloid peptide $Ab^{1-40}$ through the blood-brain barrier and binding to Alzheimer disease amyloid of the $A\beta^{1-40}$ vector complex," *PNAS* 92:10227-10231 (1995).

Saitoh, N. et al., "Immunological analysis of Alzheimer's disease using anti- β-protein monoclonal antibodies," *Sapporo Med. J.*, 60:309-320 (1991).

Sasaki et al., "Human choroid plexus is an uniquely involved area of the brain in amyloidosis: a histochemical, immunohistochemical and ultrastructural study," *Brain Res.* 755:193-201 (1997).

Schenk et al., "Immunization with amyloid-β attenuates Alzheimer-disease-like pathology in the PDAPP mouse," *Nature*, 400:173-177 (1999).

Schenk et al., "Therapeutic Approaches Related to Amyloid-β Peptide and Alzheimer's Disease," *J. Med. Chem.*, 38(21):4141-4154 (1995).

Schenk et al., "β-peptide immunization," *Arch. Neurol.*, 57:934-936 (2000).

Schenk et al., "Immunotherapy with beta-amyloid for Alzheimer's disease: a new frontier," *DNA Cell Biol.*, 20(11):679-81 (2001).

Schenk, D., "Amyloid-β immunotherapy for Alzheimer's disease: the end of the beginning," *Nature Reviews*, 3:824-828 (2002).

Schwarzman et al., "Transthyretin sequesters amyloid β protein and prevents amytoid formation," *PNAS*, 91:8368-8372 (1994).

Selkoe, "Alzheimer's Disease: A Central Role for Amyloid," *J. Neuropathol. Exp. Neurol.*, 53(5): 438-447 (1994).

Selkoe, "Physiological production of the β-amyloid protein and the mechanism of Alzheimer's disease," *Trends in Neurosciences*, 16(10): 403-409 (1993).

Selkoe, "The cell biology of beta-amyloid precursor protein and presenilin in Alzheimer's disease," *Trends Cell Biol.*, 8(11):447-53 (1998).

Selkoe, D.J., "Imaging Alzheimer's Amyloid," *Nat. Biotech.*, 18:823-824 (2000).

Selkoe, Dennis J., "Alzheimer's Disease: Genotypes, Phenotype, and Treatments," *Science*, 275:630-631 (1997).

Selkoe, Dennis J., "Amyloid Protein and Alzheimer's Disease . . . ," *Scientific American*, pp. 68-78 (1991).

Selkoe, Dennis J., "In the Beginning . . . ," *Nature*, 354:432-433 (1991).

Selkoe, Dennis J., "The Molecular pathology of Alzheimer's Disease," *Neuron*, 6:487-498 (1991).

Seubert et al., "Isolation and quantification of soluble Alzheimer's β-peptide from biological fluids," *Nature* 359: 325-327 (1992).

Shiosaka, S., "Attempts to make models for Alzheimer's disease," *Neuroscience Res.*, 13:237-255 (1992).

Sigmund, "Viewpoint: Are Studies in Genetically Altered Mice Out of Control," *Arterioscler Thromb. Vasc Biol.*, 20:1425-1429 (2000).

Sigurdsson et al., "A safer vaccine for Alzheimer's disease?," *Neurobiology of Aging*, 23:1001-1008 (2002).

Sigurdsson et al., "Anti-priori antibodies for prophylaxis following prion exposure in mice," *Neurosciences Letters*, 336:185-187 (2003).

Sigurdsson et al., "Immunization Delays the Onset of Prion Disease in Mice," *American Journal of Pathology*, 161:13-17 (2002).

Sigurdsson, et al., "In vivo reversal of amyloid-beta lesions in rat brain," *J Neuropathol Exp Neurol.*, 59(1):11-17 (2000).

Simmons, L., "Secondary structure of amyloid β peptide correlates with neurotoxic activity in vitro," *Molecular Pharmacology*, 45:373-379 (1994).

Singh, K. S., "Neuroautoimmunity: Pathogenic implications for Alzheimer's Disease," *Gerontology*, 43:79-94 (1997).

Singh, V. K., "Studies of neuroimmune markers in Alzheimer's disease," *Mol. Neurobiology*, 9(1-3):73-81 (1994), abstract only.

Sinha, et al., "Recent advances in the understanding of the processing of APP to beta amyloid peptide," *Ann N Y Acad Sci.*, 920:206-8 (2000).

Sipe, "Amyloidosis," *Annu. Rev. Biochem.*, 61:947-975 (1992).

Skolnick and Fetrow, "From genes to protein structure and function: novel applications of computational approaches in the genomic era," *Trends in Biotech*, 18(1):34-39 (2000).

Small et al., "Alzheimer's disease and Abeta toxicity: from top to bottom," *Nat Rev Neurosci.*, 2(8):595-8 (2001).

Smith et al., "The challenges of genome sequence annotation or 'The devil is in the details,'" *Nature Biotechnology*, 15:1222-1223 (1997).

Smits et al., "Prion Protein and Scrapie Susceptibility," *Vet. Quart*, 19(3):101-105 (1997).

Solomon and et al., "Modulation of The Catalytic Pathway of Carboxypeptidase A by Conjugation with Polyvinyl Alcohols," *Adv. Mol. Cell Biology*, 15A:33-45 (1996).

Solomon et al., "Disaggregation of Alzheimer β-amyloid by site-directed mAb," *PNAS*, 94:4109-4112 (1997).

Solomon et al., "Monoclonal antibodies inhibit in vitro fibrillar aggregation of the Alzheimer β-amyloid peptide," *PNAS*, 93:452-455 (1996).

Solomon et al., "The Amino Terminus of the β-Amyloid Peptide Contains an Essential Epitope for Maintaining Its Solubility," from *Progress in Alzheimer's and Parkinson's Diseases*, edited by Fisher et al., Plenum Press, New York, pp. 205-211 (1995).

Soto et al., "Beta sheet breaker peptides inhibit fibrillogenesis in a rat brain model of amyloidosis: implications for Alzheimer's therapy," *Nature Medicine.*, 4(7):822-826 (1998).

Soto et al., "The α-helical to β-strand transition in the amino-terminal fragment of the amyloid β-peptide modulates amyloid formation," *J. Biol. Chem*, 270(7):3063-3067 (1995).

Southwick et al, "Assessment of Amyloid β protein in Cerebrospinal fluid as an Aid in the Diagnosis of Alzheimer's Disease," *J. Neurochemistry*, 66:259-265 (1996).

Spooner et al., "The generation and characterization of potentially therapeutic Aβ antibodies in mice: differences according to strain and immunization protocol," *Vaccine*, 21:290-297 (2002).

St. George-Hyslop et al., "Antibody clears senile plaques," *Nature*, 40:116-117 (1999).

Stein et al., "Lack of Neurodegeneration in Transgenic Mice Overexpressing Mutant Amyloid Precursor Protein is Associated with Increased Levels of Transthyretin and Activation of Cell Survival Pathways," *The Journal of Neuroscience*, 22(17):7380-7388 (2002).

Stern et al., "Antibodies to the β-amyloid peptide cross-react with conformational epitopes in human fibrinogen subunits from peripheral blood," *FEBS Letters*, 264(1):43-47 (1990).

Stoute et al., "A Preliminary Evaluation of a Recombinant Circumsporozoite Protein Vaccine Against *Plasmodium Falciparum* Malaria", *N. Engl. J. Med.*, 336(2):86-91 (1997).

Strbak et al., "Passive Immunization and Hypothalamic Peptide Secretion", *Neuroendocrinology*, 58:210-217 (1993).

Sturchler-Pierrat et al., "Two amyloid precursor protein transgenic mouse models with Alzheimer disease-like pathology," *PNAS*, 94: 13287-13292 (1997).

Su et al., "Intravascular infusions of soluble β-amyloid compromise the blood-brain barrier, activate CNS Glial cells and induce peripheral hemorrhage," *Brain Research*, 818:105-107 (1999).

Suo et al., "Soluble Alzheimers β-amyloid constricts the cerebral vasculature in vivo" *Neuroscience Letters*, 257:77-80 (1998).

Szendrei, et al., "The effects of aspartic acid-bond isomerization on in vitro properties of the amyloid β-peptide as modeled with N-terminal decapeptide fragments," *Int. J. Peptide Protein Res.*, 47:289-296 (1996).

Tabaton et al., "Soluble amyloid β-protein is a marker of Alzheimer amyloid in brain but not in cerebrospinal fluid," *Biochem. and Biophys. Res. Comm.*, 200(3):1598-1603 (1994).

Tal et al., "Complete Freund's Adjuvant Immunization Prolongs Survival in Experimental Prion Disease in Mice," *Journal of Neuroscience Research*, 71:286-290 (2003).

Tan et al., "Amyloidosis," *Histopathology*, 25:403-414 (1994).

Tanaka et al., "NC-1900, an active fragment analog of arginine vasopressin, improves learning and memory deficits induced by beta-amyloid protein in rats," *European J. Pharmacology*, 352:135-142 (1998).

Teller et al., "Presence of soluble amyloid β-peptide precedes amyloid plaque formation in Down's syndrome" *Nature Medicine*, 2(1):93-95 (1996).

Tennent et al., "Serum anyloid P component prevents proteolysis of the amyloid fibrils of Alzheimer's disease and systemic amyloidosis," *PNAS*, 92:4299-4303 (1995).

Thorsett, E.D. et al., "Therapeutic approaches to Alzheimer's disease," *Curr. Op. in Chem. Biology*, 4:377:382 (2000).

Tjernberg et al., "A molecular model for Alzheimer amyloid β-peptide fibril formation," *J. Biol. Chem.*, 274(18):12619-12625 (1999).

Tjernberg et al., "Arrest of β-amyloid fibril formation by a pentapeptide ligand," *J. Biol. Chem.*, 271:8545-8548 (1996).

Town et al., "Characterization of murine immunoglobulin G antibodies against human amyloid-$β_{1-42}$" *Neurosci. Lett.* 307:101-104 (2001).

Trieb et al., "Is Alzheimer beta amyloid precursor protein (APP) an autoantigen? Peptides corresponding to parts of the APP sequence stimulate T lymphocytes in normals, but not in patients with Alzheimer's disease," *Immunobiology*, 191(2-3):114-115 Abstract C.37, (1994).

Tsuzuki et al., "Amyloid β protein in rat soleus in choroquine-induced myopthy using end-specific antibodies for Aβ40 and Aβ42: immunohistochemical evidence for amyloid β protein," *Neuroscience Letters*, 2002:77-80 (1995).

Van Gool et al., "Concentrations of amyloid-β protein in cerebrospinal fluid increase with age in patients free from neurodegenerative disease," *Neuroscience Letters*, 172:122-124 (1994).

Vehmas et al., "Beta-Amyloid peptide vaccination results in marked changes in serum and brain Abeta levels in APPswe/PS1 DeltaE9 mice, as detected by SELDI-TOF-based ProteinChip® technology," *DNA Cell Biol.*, (11):713-721 (2001).

Velazquez et al., "Aspartate residue 7 in amyloid β-protein is critical for classical complement pathway activation: Implications for Alzheimer's disease pathogenesis," *Nature Medicine*, 3(1):77-79 (1997).

Verbeek et al., "Accumulation of Intercellular Adhesion Molecule-1 in Senile Plaques in Brain Tissue of patients with Alzheimer's Disease," *Amer. Journ. Pathology*, 144(1):104-116 (1994).

Verma et al., "Gene therapy—promises, problems and prospects," *Nature*, 389:239-242 (1997).

Walker et al., "Labeling of Cerebral Amyloid In Vivo with a Monoclonal Antibody," *J. Neuropath. Exp. Neurology*, 53(4):377-383 (1994).

Wang et al., "The levels of soluble versus insoluble brain Aβ distinguish Alzheimer's disease from normal and pathologic aging," *Experimental Neurology* 158:328-337 (1999).

Wang et al., "Soluble oligomers of β amyloid (1-42) inhibit long-term potentiation but not long-term depression in rate dentate gyrus," *Brain Research*, 924:133-140 (2002).

Weiner et al., "Nasal administration of amyloid-β peptide decreases cerebral amyloid burden in a mouse model of Alzheimer's disease," *Annals of Neurology*, 48:567-579 (2000).

Weiner et al., "Oral Tolerance: Immunologic Mechanisms and Treatment of Animal and Human Organ-Specific Autoimmune Diseases by Oral Administration of Autoantigens," *Annu. Rev. Immunol.*, 12:809-837 (1994).

Weissmann et al., "Bovine spongiform encephalopathy and early onset variant Creutzfeldt-Jakob disease," *Curr. Opin. Neurobiol.*, 7:695-700 (1997).

Weldon et al., "Neurotoxicity of Aβ Peptide: Confocal Imaging of Cellular Changes Induced by—Amyloid in Rat CNS In Vivo," *Society for Neuroscicence Abstracts*, 22(Part 1) (1996).
Wells, J. A., "Additivity of Mutational Effects in Proteins," *Biochemistry*, 29(37):8509-8517 (1990).
Wen, G.Y., "Alzheimer's Disease and Risk Factors," *J. Food Drug Analysis*, 6(2):465-476 (1998).
Wengenack et al., "Targeting Alzheimer amyloid plaques in vivo," *Nature Biotech.*, 18:868-872 (2000).
Winter et al., "Humanized antibodies" *Immunology Today*, 14(6):243-246 (1996).
Wisniewski et al., "Alzheimer's disease and soluble A beta," *Neurobiol. Aging*, 15(2):143-52 (1994).
Wisniewski et al., "Therapeutics in Alzheimer's and Prion Diseases," *Biochemical Society Transactions*, 30(4):574-587 (2002).
Wong et al., "Neuritic Plaques and Cerebrovascular Amyloid in Alzheimer Disease are Antigenically Related," *PNAS*, 82:8729-8732 (1985).
Wood et al., "Amyloid precursor protein processing and Aβ42 deposition in a transgenic mouse model of Alzheimer disease," *PNAS*, 94: 1550-1555 (1997).
Wood et al., "Prolines and amyloidogenicity in fragments of the Alzheimer's peptide β/A4" *Biochemistry*, 34:724-730 (1995).
Wu, et al., "Drug targeting of a peptide radiopharmaceutical through the primate blood-brain barrier in vivo with a monoclonal antibody to the human insulin receptor," *J. Clin. Invest.*, 100:1804-1812 (1997).
Xu et al., "Increased incidence of anti-β-amyloid autoantibodies secreted by Epstein-Barr virus transformed B cell lines from patients with Alzheimer's disease," *Mechanisms of Ageing and Development*, 94:213-222 (1997).
Yamaguchi et al., Diffuse plaques associated with astroglial amyloid β protein, possibly showing a disappearing stage of senile plaques, *Acta Neuropathol.*, 95:217-222 (1998).
Yang et al., "Effects of Racemization on the Aggregational Properties of the Amyloid β-Peptide in Alzheimer's Disease," abstract # 255 from American Chemical Society 214th National Meeting (1997).
Younkin, "Amyloid β vaccination: reduced plaques and improved cognition," *Nature Medicine*, 7:18-19 (2001).
Zlokovic et al., "Clearance of amyloid β-peptide from brain: transport or metabolism?," *Nature Medicine*, 6(7):718-719 (2000).
Bard et al., "Epitope and Isotype specificities of antibodies to β-amyloid peptide for protection against Alzheimer's disease-like neuropathology," *PNAS*, 100(4):2023-2028 (2003).
Bellotti et al., "Application of Monoclonal Anti-idiotypes in the Study of AL Amyloidosi: Therapeutic Implications," *Renal Failure*, 15(3):365-371 (1993).
Benjamin et al., from *Immunology A Short Course*, Second Edition, pp. 136-138, 143, 73-74, 372-373, and 400-401, 1991, published by Wiley-Liss, Inc., New York, New York.
Benkirane, et al, "Antigenicity and Immunogenicity of Modified Synthetic Peptides Containing D-Amino Acid Residues," *J. Biol. Chem.*, 258(23):26279-26285 (1993).
Chishti et al., "Early-onset Amyloid Deposition and Cognitive Deficits in Transgenic Mice Expressing a Double Mutant Form of Amyloid Precursor Protein 695," *J. Biol. Chem.*, 276(24):21562-70 (2001).
Chothia et al., "Domain Association in Immunoglobulin Molecules," *J. Mol. Biol.*, 188:651-663 (1985).
Cirrito et al., "Amyloid β and Alzheimer disease therapeutics: the devil may be in the details," *J. Clin. Invest.*, 112:321-323 (2000).
Cribbs et al, "All-D-Erantiomers of Beta-Amyloid Exhibit Similar Biological Properties to All-L-Beta-Amyloids," *J. Biol. Chem.*, 272:7431-7436 (1997).
Findeis et al, "Modified peptide inhibitors of amyloid β-peptide polymerization," *Biochemistry*, 38:6791-6800 (1999).
Flood, et al, "Topography of a binding site for small amnestic peptides deduced from structure-activity studies: Relation to amnestic effect of amyloid B protein," *PNAS*, 91:380-384 (1994).
Frazer et al., "Immunoglobulins: Structure and Function," chapter 3, pp. 37-74 from *Fundamental Immunology, fourth edition*, W.E. Paul, eds., Lippincott-Raven publishers, Philadelphia (1999).

Herlyn et al., "Monoclonal antibodies in cell-mediated cytotoxicity against human melanoma and colorectal carcinoma*," *Eur. J. Immunol.*, 9:557-549 (1979).
Hock et al., "Antibodies against β-Amyloid Slow Cognitive Decline in Alzheimer's Disease," *Neuron*, 38:542-554 (2003).
Irizarry et al., "Aβ Deposition is Associated with Neuropil Changes, but not with Overt Neuronal Loss in the Human Amyloid Precursor Protein V717F (PDAPP) Transgenic Mouse," *J. Neuroscience*, 17(18):7053-7059 (1997).
Jahrling et al., "Opsonization of Alphaviruses in Hamsters," *J. Medical Virology*, 12:1-16 (1983).
Kayed et al., "Conformational Transigtions of Islet Amyloid Polypeptide (IAPP) in Amyloid Formation In Vitro," *J. Mol. Biol.*, 2887:781-796 (1999).
Kettleborough et al., "Humanization of a mouse monoclonal antibody by CDR-grafting: the importance of framework residues on loop conformation," *Protein Engineering*, 4(7):773-783 (1991).
Lemere et al., "Intranasal Immunotherapy for the treatment of Alzheimer's disease: *Escherichia coli* LT and LT(R192G) as mucosal adjuvants," *Neurobiology of Aging*, 23(5):991-1000 (2002).
Leverone et al., "Aβ1-15 is less immunogenic than Aβ1-40/42 for intranasal immunization of wiki-type mice but may be effective for boosting," *Vaccine*, 21:2197-2206 (2003).
Masliah et al., "Comparison of Neurodegenerative Pathology in Transgenic Mice Overexpressing V717F β-Amyloid Precursor Protein and Alzheimer's Disease," *J. Neuroscience*, 16(18):5795-5811 (1986).
Novotny et al., "Structural Invariants of antigen binding: Comparison of Immunoglobulin $V_L$-$V_H$ and $V_L$-$V_L$ domain dimmers," *PNAS*, 82:4592-4598 (1985).
PCT Search Report of Dec. 14, 2004 for application PCT/US04/02858.
Sela et al, "Different roles of D-amino acids in immune phenomena," *FASEB J*, 11(6):449-456 (1999).
Sigurdsson et al., "Immunization with a Nontoxic/Nonfibrillar Amyloid-β Homologous Peptide Reduces Alzheimer's Disease-Associated Pathology in Transgenic Mice," *Am. J. Pathology*, 159(2):439-447 (2001).
Solomon, B., "Immunological approaches as therapy for Alzheimer's disease," *Expert Opin. Biol. Ther.*, 2(8):907-917 (2002).
Tjernberg, et al, "Controlling amyloid beta-peptide fibril formation with protease-stable ligands," *J. Biol Chem.*, 272(19):12601-12605 (1997).
Van Regenmortel et al, "D-peptides as immunogens and diagnostic reagents," *Curr. Opin. Biotechnol.*, 8(4):377-882 (1998).
*Vershigora A. E. Obshchaya Immynologiya*, pp. 35, 229-231 and 152-153.
Wu et al., "An Analysis of the Sequences of the Variable Regions of Benca Jones Proteins and Myeloma Light Chains and their implications for Antibody Complementarity*,"*J. Exp. Med.*, 132:211-280 (1970).
U.S. Appl. No. 11/245,524, filed Oct. 7, 2005, Schenk.
U.S. Appl. No. 11/245,916, filed Oct. 7, 2005, Schenk.
Alberts et al., eds. *Molecular Biology of the Cell, Third Edition*, chapter 23, pp. 1208-1209 (1994).
Amit et al., "Three-Dimensional Structure of an Antigen-Antibody Complex at 2.8 Å Resolution," *Science*, 233:747-753 (1986).
Anderson, J. P., "Exact cleavage site of Alzheimer amyloid precursor in neuronal PC-12 cells," *Neuroscience Letters*, 128(1):126-128 (1991).
Anderson, M. W., "Amending the amyloid hypothesis," *The Scientist*, 18(20):28-29 (2004).
Ankarcrona et al., "Biomarkers for apoptosis in Alzheimer's disease," *Int. J. Geriatric Psychiatry*, 20:101-105 (2005).
Auld et al., "Alzheimer's disease and the basal forebrain cholinergic system: relations to β-amyloid peptides, cognition, and treatment strategies," *Progress in Neurobiol.*, 68:209-245 (2002).
Bacskai et al., "Non-Fc-mediated mechanisms are involved in clearance of amyloid-β in vivo by immunotherapy," *J. Neurosci.*, 22(18):7873-7878 (2002).
Chimicon International, "Mouse Anti-Amyloid Beta Protein Monoclonal Antibody," Catalog # MAB1561.

Chromy et al., "Self-assembly of Aβ(1-42) into globular neurotoxins," *Biochemistry*, 42(44):12749-12760 (2003).
Citron et al., "Evidence that the 42- and 40-amino acid forms of amyloid-β protein are generated from the β-amyloid precursor protein by different protease activities," *PNAS*, 93(23):13170-13175 (1996).
Citron, M., "Alzheimer's disease: treatments in discovery and development," *Nat. Neurosci.*, 5:1055-1057 (2002).
Clayton et al., "Synucleins in Synaptic Plasticity and Neurodegenerative Disorders," *J. Neurosci. Res.*, 58:120-129 (1999).
Cox et al., "Adjuvants—a classification and review of their modes of action," *Vaccine*, 15(3):248-256 (1997).
De Lustig et al., "Peripheral Markers and Diagnostic Criteria in Alzheimer's Disease: Critical Evaluations," *Rev. In Neurosciences*, 5:213-225 (1994).
Demattos et al., "Brain to plasma amyloid-β efflux: a measure of brain amyoid burden in a mouse model of Alzheimer's disease," *Science*, 295(5563):2264-2267 (2002).
Dictionary.com definition of "prophylactic", pp. 1-3 downloaded from internet Oct. 12, 2005.
Dodart et al., "Immunization reverses memory deficits without reducing brain Aβ burden in Alzheimer's disease model," *Nat. Neurosci.*, 5(5):452-457 (2002).
Dodel et al., "Immunotherapy for Alzheimer's disease," *Lancet Neurol.*, 2(4):215-220 (2003).
Dovey et al., "Functional gamma-secretase inhibitors reduce beta-amyloid peptide levels in brain," *J. Neurochem.*, 76(1):173-181 (2001).
Duff et al., "Increased amyloid-β42(43) in brains of mice expressing mutant presenilin 1," *Nature*, 383(6602):710-713 (1996).
Eriksen et al., "NSAIDs and enantiomers of flurbiprofen target γ-secretase and lower Aβ42 in vivo," *J. Clin. Invest.*, 112(3):440-449 (2003).
Findeis, M. A., "Approaches to discovery and characterization of inhibitors of amyloid β-peptide polymerization," *Biochem. Biophys. Acta*, 1502(1):76-84 (2000).
Foote et al., "Antibody Framework Residues Affecting the Conformation of the Hypervariable Loops," *J. Mol. Biol.*, 224:487-499 (1992).
Frenkel et al., "Reduction of β-amyloid plaques in brain of transgenic mouse model of Alzheimer's disease by EFRH-phage immunization," *Vaccine*, 21(11-12):1060-1065 (2003).
Frenkel et al., "Towards Alzheimer's β-amyloid vaccination," *Biologicals*, 29(3-4):243-247 (2001).
Gelinas et al., "Immunotherapy for Alzheimer's disease," *PNAS*, 101(suppl. 2):14657-14662 (2004).
Genbank Accession No. AAB48800, "Anti-DNA immunoglobulin light chain IgG [Mus musculus]," Sep. 14, 2001.
Genbank Accession No. CAA46659, "IgE antibody light chain(VJ)," Jun. 15, 1993.
Genbank Accession No. X65775.1, "M.musculus DNA for IgE antibody light chain (VJ)," Jun. 15, 1993.
Genbank Accession No. AAD26773, "Immunoglobulin heavy chain VH3609-2H3 region [Mus Musculus]," Apr. 22, 1999.
Gong et al., "Alzheimer's disease-affected brain: presence of oligomeric Aβ ligands (ADDLs) suggests a molecular basis for reversible memory loss," *PNAS*, 100(18):10417-10422 (2003).
Greenberg et al., "Alzheimer disease's double-edged vaccine," *Nat. Med.*, 9(4):389-390 (2003).
Gupta et al., "Adjuvants for human vaccines—current status, problems, and future prospects," *Vaccine*, 13(14):1263-1275 (1995).
Haass, C., "New hope for Alzheimer disease vaccine," *Nat Med.*, 8(11):1195-1196 (2002).
Harlow et al., eds., *Antibodies: A Laboratory Manual*, pp. 71-82 (1998).
Hock et al., "Generation of antibodies specific for β-amyloid by vaccination of patients with Alzheimer disease," *Nat. Med.*, 8(11):1270-1275 (2002).
Ida et al., "Analysis of Heterogeneous βA4 Peptides in Juman Cerebrospinal Fluid and Blood by a Newly Developed Sensitive Western Blot Assay," *J. Biol. Chem.*, 271(37):22908-22914 (1996).
Irizarry et al., "Alzheimer disease therapeutics," *J. Neuropathol. Exp. Neurol.*, 60(10):923-928 (2001).
Janus et al., "Transgenic mouse models of Alzheimer's Disease," *Physiol. Behav.*, 73(5):873-886 (2001).
Jung et al., "Alzheimer's Beta-amyloid Precursor Protein is Expressed on the Surface of Immediately Ex Vivo Brain Cells: a Flow Cytomeric Study," *J. Neurosci. Res.*, 46:336-348 (1996).
Kofler et al., "Mechanism of Allergic Cross-Reactions—III. cDNA Cloning and Variable-Region Sequence Analysis of Two IgE Antibodies Specific for Trinitrophenyl," *Mol. Immunology*, 29(2):161-166 (1992).
Krishnan et al., "Correlation Between the Amino Acid Position of Arginine in VH-CDR3 for Specificity for Native DNA Among Autoimmune Antibodies[1,2]," *J. Immunol.*, 157(6):2430-2439 (1996).
Kuo et al., "Water-soluble Aβ (N—40, N—42) Oligomers in Normal and Alzheimer Disease Brains," *J. Biol. Chem.*, 271(8):4077-4081 (1996).
Landolfi et al., "The Integrity of the Ball- and Socket Joint Between V and C Domains is Essential for Complete Activity of a Humanized Antibody," *J. Immunology*, 166(3):1748-1754 (2001).
Lo et al., "High level expression and secretion of Fc-X fusion proteins in mammalian cells," *Protein Engineering*, 11(6):495-500 (1998).
Mandel et al., "Clinical trials in neurological disorders using AAV vectors: promises and challenges," *Curr. Opin. Mol. Ther.*, 6(5):482-490 (2004).
Mattson et al., "Good and bad amyloid antibodies," *Science*, 301(5641):1845-1849 (2003).
McLaurin et al., "Therapeutically effective antibodies against amyloid-β peptide target amyloid-β residues and 4-10 and inhibit cytotoxicity and fibrillogenesis," *Nat Med.*, 8(11):1263-1269 (2002).
Monsonego et al., "Increased T cell reactivity to amyloid β protein in older humans and patients with Alzheimer's disease," *J. Clin. Invest.*, 112(3):415-422 (2003).
Monsonego et al., "Immunotherapeutic approaches to Alzheimer's disease," *Science*, 302(5646):834-838 (2003).
Orlandi et al., "Cloning immunoglobulin variable domains for expression by the polymerase chain reaction," *PNAS*, 86:3833-3837 (1989).
Paganetti et al., "Amyloid precursor protein truncated at any of the γ-secretase sites is not cleaved to β-amyloid," *J. Neurosci. Res.*, 46(3):283-293 (1996).
Pallitto et al., "Recognition sequence design for peptidyl modulators of β-amyloid aggregation and toxicity," *Biochemistry*, 38(12):3570-3578 (1999).
Panka et al., "Variable region framework differences result in decreased or increased affinity of variant anti-digoxin antibodies," *PNAS*, 85:3080-3084 (1998).
Parnetti et al., "Cognitive Enhancement Therapy for Alzheimer's Disease, The Way Forward," *Drugs*, 53(5):752-768 (1997).
Paul, W. E., eds., *Fundamental Immunology*, Third Edition, pp. 292-295, Raven Press, New York (1993).
Pfeifer et al., "Cerebral hemorrhage after passive anti-Aβ immunotherapy," *Science*, 298(5597):1379 (2002).
Racke et al., "Exacerbation of Cerebral Amyloid Angiopathy-Assoiciated Microhemorrhage in Amyloid Precursor Protein Trasngenic Mice by Immunotherapy is Dependent on Antibody Recognition of Deposited Forms of amyloid β," *J. Neurosci.*, 25(3):629-636 (2005).
Research Corporation Technology News, "THP and SangStat Partner to Develop Humanized Polyclonal Antibody Drugs," Nov. 11, 2002.
"Researchers Develop Blood Test to Diagnose Alzheimer's-Type Changes in Mice," downloaded from www.businesswire.com on Dec. 15, 2004.
Rudikoff et al., "Single amino acid substitution altering antigen-binding specificity," *PNAS*, 79:1979-1983 (1982).
Schmid, R. E., "Study suggest Alzheimer vaccine fix," from www.msnbc.com/news, pp. 1-5 (2002).
Seidl et al., "Predominant $V_H$ genes expressed in innate antibodies are associated with distinctive antigen-binding sites," *PNAS*, 96:2262-2267 (1999).
Selkoe, D. J., "Alzheimer's disease is a synaptic failure," *Science*, 298(5594):789-791 (2002).
Sergeant et al., "Truncated beta-amyloid peptide species in pre-clinical Alzheimer's disease as new targets for the vaccination approach," *J. Neurochem.*, 85(6):1581-1591 (2003).

Small et al., "Cerebral metabolic and cognitive decline in persons at genetic risk for Alzheimer's disease," PNAS, 97(11):6037-6042 (2000).
Solomon, B., "Generation and brain delivery of anti-aggregating antibodies against β-amyloid plaques using phage display technology," J. Neural Transm. Suopl., 62:321-325 (2002).
Solomon, B., "Immunotherapeutic strategies for prevention and treatment of Alzheimer's disease," DNA and Cell Biology, 20(11):697-703 (2001).
Souder et al., "Overview of Alzheimer's disease," Nurs. Clin. N. Am., 39:545-559 (2004).
Valleix et al., "Hereditary renal amyloidosis caused by a new variant lysozyme W64R in a French family," Kidney International, 61:907-912 (2002).
Vickers, J. C., "A Vaccine Against Alzheimer's Disease," Drugs Aging, 19(7):487-494 (2002).
Walsh et al., "Naturally secreted oligomers of amyloid β protein potently inhibit hippocampal long-term potentiation in vivo," Nature, 416(6880):535-539 (2002).
Washington University in St. Louis School of Medicine, "Study gives Clues to Working of Anti-Alzheimer Antibody," downloaded from www.medicine.wustl.edu/~wumpa/news on Dec. 15, 2004.
Webster's New World Dictionary, p. 1387, therapeutic (1988).
Webster's New World Dictionary of American English, Third College Edition, p. 1078 (1988).
White et al., "Immunotherapy as a therapeutic treatment for neurodegenerative disorders," J. Neurochem., 87(4):801-808 (2003).
Zlokovic et al., "Glycoprotein 330/megalin: probable role in receptor-mediated transport of apolipoprotein J alone and in a complex with Alzheimer disease amyloid beta at the blood-brain and blood-cerebrospinal fluid barriers," PNAS, 93(9):4229-4334 (1996) abstract only.
Di Martino et al., "Production and Characterization of Antibodies to Mouse Scrapie-Amyloid Protein Elicited by Non-carrier Linked Synthetic Peptide Immunogens," J. Molecular Recognition, 4(2-3):85-91 (1991).
Hirschfield et al., "Amylodiosis: new strategies for treatment," Int. J. Biochem. & Cell Biol., 35:1608-1613 (2003).
Kascsak et al., "Mouse Polyclonal and Monoclonal Antibody to Scrapie-Associated Fibril Proteins," J. Virology, 61(12):3688-3693 (1987).
Kurashima et al., "Production of Monoclonal Antibody against Amyloid Fibril Protein and Its Immunohistochemical Application," Appl. Pathol., 3(1-2):39-54 (1985).
Licastro et al., "Is immunotherapy an effective treatment for Alzheimer's disease?," Immunity & Aging, 1:1-2 (2004).
Linke, "Monoclonal antibodies against amyloid fibril protein AA. Production, specificity, and use for immunohistochemical localization and classification of AA-type amyloidosis," J. Histochemistry and Cytochemistry, 32(3):322-328 (1982).
Manoj et al., "Approaches to Enhance the Efficacy of DNA Vaccines," Critical Rev. Clin. Lab. Sci., 41(1):1-39 (2004).
Marhaug et al., "Monoclonal hybridoma antibodies to human amyloid related protein SAA," Clin. Exp. Immunol., 50(2):390-396 (1982).
Maury et al., "Immunohistochemical Localization of Amyloid in Finnish Hereditary Amyloidosis with Antibodies to Gelsolin Peptides," Laboratory Investigation, 64(3):400-404 (1991).
Phelps et al., "Development and Characterization of Monoclonal Antibodies Specific for Amylin," Hybridoma, 15(5):379-386 (1996).
Weinreb et al., "NACP, A Protein Implicated in Alzheimer's Disease and Learning, is Natively Unfolded," Biochemistry, 35(43):13709-13715 (1996).
Yamada et al., "Generation and Characterization of Rat Monoclonal Antibodies Against Human Serum Amyloid A," Scand. J. Immunol., 46(2):175-179 (1997).
U.S. Appl. No. 60/067,740, filed Dec. 2, 1997, Schenk.
U.S. Appl. No. 60/067,219, filed Dec. 3, 1997, Weiner et al.
U.S. Appl. No. 60/079,697, filed Mar. 27, 1998, Weiner et al.
U.S. Appl. No. 60/080,970, filed Jan. 11, 1999, Schenk.
Alberts et al., Molecular Biology of the Cell, 2nd Edition, pp. 266-267, Garland Publishing Inc., New York (1989).
Bales et al., "Administration of an Anti-Aβ Fab Fragment to $APP^{V717F}$ Transgenic Mice Reduces Neuritic Plaque," Abstract P$-396, p. S587, presented at Poster Session P4: Therapeutics and Therapeutic Strategies—Therapeutic Strategies, Amyloid-Based.
Bickel et al., "Development and in Vitro Characterization of a Cationized Monoclonal Antibody against βA4 Protein: A Potential Probe for Alzheimer's Disease," Bioconjugate Chem., 5:119-125 (1994).
Blasberg et al., "Regional Localization of Glioma-assoicated Antigen Defined by Monoclonal Antibody 81C6 in Vivo: Kinetics and Implications for Diagnosis and Therapy," Cancer Research, 47:4432-4443 (1987).
Brazil et al., "Effects of Incorporation of Immunoglobulin G and Complement Component C1q on Uptake and Degradation of Alzheimer's Disease Amyloid Fibris by Microglia," J. Biol. Chem., 275(22):16941-16947 (2000).
Bussiere et al., "Morphological Characterization of Thioflavin-S-Positive Amyloid Plaques in Transgenic Alzheimer Mice and Effect of Passive Aβ Immunotherapy on Their Clearance," Am. J. Pathology, 165(3):987-995 (2004).
Coico et al., Immunology A Short Course, Fifth Edition, pp. 18-24 (2003).
Davis, S. S., "Nasal Vaccines," Advanced Drug Delivery Reviews, 51:21-42 (2001).
Dewitt et al., "Astrocytes regulate microglial phagocytosis of senile plaque cores of Alzheimer's disease," Experimental Neurology, 149:329-340 (1998).
Hara et al., "Development of a safe oral Aβ vaccine using recombinant adeno-associated virus vector for Alzheimer's disease," J. Alzheimer's Disease, 6:483-488 (2004).
Kajkowski et al., "β-Amyloid Peptide-induced Apoptosis Regulated by a Novel Protein Containing a G Protein Activation Module," J. Biol. Chem., 276(22):18748-18756 (2001).
Kofler et al., "Immunoglobulin $_k$ Light Chain Variable Region Gene Complex Organization and Immunoglobulin Genes Encoding Anti-DNA Autoantibodies in Lupus Mice," J. Clin. Invest., 82:852-860 (1988).
Lavie et al., "EFRH-Phage Immunization of Alzheimer's Disease Animal Model Improves Behavioral Performance in Morris Water Maze Trials," J. Molecular Neuroscience, 24:105-113 (2004).
Marotta et al., "Overexpression of amyloid preansor protein A4 (β-amyloid) immunoreactivity in genetically transformed cells: Implications for a cellular model of Alzheimer amyloidosis," PNAS, 86:337-341 (1989).
Okura et al, "Nonviral Aβ DNA vaccine therapy against Alzheimer's disease: Long-term effect and safety," PNAS, 103(25):9619-9624 (2006).
PCT Search Report of Aug. 11, 2006 for application PCT/US2006/002837.
Peeters et al., "Comparison of four bifunctional reagents for coupling peptides to proteins and the effect of the three moieties on the immunogenicity of the conjugates," J. Immunological Methods, 120:133-143 (1989).
Probert et al., "Spontaneous inflammatory demyelinating disease in transgenic mice showing central nervous system-specific expression of tunmor necrosisfactor α," PNAS, 92:11294-11298 (1995).
Qu et al., "$AB_{12}$ gene vaccination reduces brain amyloid plaque burden in transgenic mice," J. Neurological Sciences, 244:151-158 (2006).
Schenk et al., "Current progress in beta-amyloid immunotherapy," Curr. Opin. Immunology, 16(5):599-606 (2004).
Schmitt et al., "Interactions of the alzheimer β amyloid fragment$_{(25-35)}$ with peripheral blood dendritic cells," Mechanisms of Ageing and Development, 94:223-232 (1997).
Trieb et al., "APP Peptides Stimulate Lymphocyte Proliferation in Normals, But Not in Patients With Alzheimer's Disease," Neurobiology of Aging, 17(4):541-547 (1996).
Van Den Dobbelsteen et al., "Characteristics of Immune Responses to Native and Protein Conjugated Pneumococcal Polysaccharide Type 14," Scand. J. Immunol., 41:273-280 (1995).
Vidanovic et al., "Effects of nonionic surfactants on the physical stability of immunoglobulin G in aqueous solution during mechanical agitation," Die Pharmazie, 58(6):399-404 (2003).

Wang, W., "Instability, stabilization, and formulation of liquid protein pharmaceuticals," *Int. J. Pharmaceutics*, 185(2):129-188 (1999).
Weiner, H. L, "Oral tolerance: immune mechanisms and treatment of autoimmune diseases," *Immunology Today*, 18:335-343 (1997).
Wikipedia definition of "epitope" printed from internet on Apr. 26, 2006.
Wikipedia definition of "antigen" printed from internet on Apr. 26, 2006.
Wikipedia definition of "route of administration including parenteral" printed from internet on Apr. 26, 2006.
Zameer et al., "Single Chain Fv Antibodies against 25-35 Peptide Fragment of Amyloid-β: Potential Therapeutic for Alzheimer's Disease," Abstract P4-420, p. S593, presented at Poster Session P4:Therapartics and Therapeutic Strategies—Therapeutic Strateies, Amyloid-Based.
Zhang et al., "A novel recombinant adeno-associated virus vaccine reduces behavioral impairment and β-amyloid plaques in a mouse model of Alzheimer's disease," *Neurobiology of Disease*, 14:365-379 (2003).
Bales et al., "Cholinergic dysfunction in a mouse model of Alzheimer disease is reversed by an anti-Aβ antibody," *J. Clin. Invest.*, 116(3):825-832 (2006).
Borenstein, S., "New Alzheimer's vaccine to be tested on people soon, Early experiments on mice halted condition; considered safe for humans," *Free Press*, Jul. 23, 2001.
Brookmeyer et al., "Projections of Alzheimer's Disease in the United States and the Public Health Impact of Delaying Disease Onset," *Am. J. Public Health*, 88:1337-1342 (1998).
Cassell et al., "Demography and Epidemiology of Age-Associated Neuronal Impairment," chapter 4, pp. 31-50 from *Funcitional Neurobiology of Aging*, Hof et al., eds., Academic Press (2001).
Comery et al., "Passive Immunization Against β-Amyloid Leads to Acute Cognition Improvement," *Society for Neuroscience*, abstract, Washington DC, Nov. 12-16, 2005.
Das et al., "Reduced effectiveness of Aβ-42 immunization in APP transgenic mice with significant amyloid deposition," *Neurobiology of Aging*, 22:721-727 (2001).
De Felice et al., "β-Amyloid production, aggregation, and clearance as targets for therapy in Alzheimer's disease," *Cell Mol. Neurobiol.*, 22(5/6):545-563 (2002).
Disis et al., "Granulocyte-macrophage colony-stimulating factor: An effective adjuvant for protein and peptide-based vaccines," *Blood*, 88(1):202-210 (1996).
Du et al., "$α_2$-Macroglobulin as a β-Amyloid Peptide-Binding Plasma Protein," *J. Neurochemistry*, 69(1):299-305 (1997).
European Search Report of May 22, 2006 for European Application 06075704.4-2107.
European Search Report of May 22, 2006 for European Application 06075479.3-2107.
European Search Report of Jan. 16, 2007 for European Application 04776252.1-2405.
Fox et al., "Presymptomatic cognitive deficits in individuals at risk of familial Alzheimer's disease," *Brain*, 121:1631-1639 (1998).
Fukutani et al., "Cerebeller pathology in sporadic and familial Alzheimer's disease including APP 717 (Val→lle) mutation cases: A morphometric investigation," *J. Neurologic Sci.*, 149:177-184 (1997).
Geylis et al., "Immunotherapy of Alzheimer's disease 9AD): From murine models to anti-amyloid beta 9Ab) human monoclonal antibodies," *Autoimmunity Rev.*, 5:33-39 (2000).
Kalback et al., "APP Transgenic Mice Tg2576 Accumulate Aβ Peptides That Are Distinct from the Chemically Modified and Insoluble Peptides Deposited in Alzheimer's Disease Senile Plaques," *Biochemistry*, 41:922-928 (2002).
Kimchi et al., "Analysis of cerebral amyloid angiopathy in a transgenic mouse model of Alzheimer disease using in vivo multiphoton microscopy," *J. Neuropath Exp. Neurol.*, 60(30:274-279 (2001).
Klyubin et al., "Anti-Aβ Antibodies Prevent Block of Long-Term Potentiation in the CA1 Area of Rat Hippocampus InVivo by naturally Produced Aβ Oligomers," *Neurobiology of Aging* 25:S224-S225, abstract P2-004, pp. S224-S225 (2004).

Kuby, J., eds., Page 123 from *Immunology, Third Edition*, W.H. Freeman & co., (1997).
Kuo et al., "Comparative Analysis of Amyloid-β Chemical Structure and Amyloid Plaque Morphology of Transgenic Mouse and Alzheimer's Disease Brains," *J. Biol. Chem.*, 276(16):12991-12998 (2001).
LaDu et al., "Isoform-specific Binding of Apolipoprotein E to β-Amyloid," *J. Biol. Chem.*, 269(38):23403-23406 (1994).
Merriam-Webster online medical dictionary, entry for "cure", accessed Sep. 5, 2006.
Okie, S., "Promising Vaccine Targets Ravager of Minds," *Washington Post*, p. A01, May 8, 2001.
Pardridge et al., "The Blood-Brain Barrier: Bottleneck in Brain Drug Development," *J. Am. Soc. Exp. Neurotherapeutics*, 2:3-14 (2005).
PCT Search Report of Aug. 8, 2006 for appl;ication PCT/US2005/045515.
PCT Search Report of Apr. 6, 2006 and Written Opinion of Apr. 8, 2006 for application PCT/US04/44093.
Piera et al., "Cytokines as adjuvants: effects on the immunogenicity of NeuAc alpha 2-GalNAc alpha-O-Ser/Thr (sialyl-Tn)," *Int. J. Cancer*, 55(1):148-152 (1993).
Press Release, "Alzheimer's vaccine developer awarded Potamkin Prize," American Academy of Neurology, May 7, 2001.
Rosenberg, R. N., "The Potamkin Prize for Pick's, Alzheimer's Disease and Related Disorders," pp. 1-5.
Roses, A.D., "Apoplipoprotein E alleles as risk factors in Alzheimer's disease" *Annu. Rev. Med.*, 47:387-400 (1996).
Saldanha et al., "A single backmutation in the human kIV framework of a previously unsuccessfully humanized antibody restores the binding activity and increases the secretion in cos cells," *Molecular Immunology* 36:709-719 (1999).
Seubert et al., "Antibody Capture of Soluble Aβ does not Reduce Cortical Aβ Amyloidosis in the PDAPP Mouse," *Neurodegenerative Diseases*, (2007).
Shinkai et al., "Amyloid β-Proteins 1-40 and 1-42(43) in the Soluble Fraction of Extra- and Intracranial Blood Vessels," *Ann. Neurol.*, 38:421-428 (1995).
Signet Laboratories, Inc., Product data sheet for mouse monoclonal clone 6E10, revised Jul. 13, 2005.
Soto et al., "The conformation of Alzheimer's beta peptide determines the rate of amyloid formation and its resistance to proteolysis," *Biochem. J.*, 314:701-707 (1996).
Travis, J., "A Vaccine for Alzheimer's Disease?®," *Science News Online*, 156(2) pp. 1-3 downloaded from internet (1999).
Travis, J., "Saving the Mind Faces High Hurdles," *Science*, 309:731-734 (2005).
UniProtKB/Swiss-Prot entry P18525, pp. 1-3 downloaded from http://www.expasy.org/cgi-bin/niceprot.pl/printable?ac=P18525 on Feb. 8, 1997, "HV54_Mouse" (Nov. 1, 1990).
Urmoneit et al., "Cerebrovascular Smooth Muscle CElls Internalize Alzheimer Amyloid Beta Protein, via a Lipoprotein Pathway: Implications for Cerebral Amyloid Angiopathy," *Laboratory Investigation*, 77(2):157-166 (1997).
Van Leuven, F., "Single and multiple transgenic mice as models for Alzheimer's disease," *Progress in Neurobiology*, 61:305-312 (2000).
Zhang et al., "Specialized Applications, Purification of Recombinant Proteins and Study of Protein Interaction by Epitope Tagging," *Current Protocols in Mol. Biol.*, Supp 41, pp. 10.15.1 through 10.15.9 (1998).
U.S. Appl. No. 11/358,951, filed Feb. 22, 2006, Solomon et al.
Ard et al., "Scavenging of Alzheimer's Amyloid β-Protein by Microglia in Culture," *J. Neuroscience Research*, 43:190-202 (1996).
Askelof et al., "Protective immunogenicity of two synthetic peptides selected from the amino acid sequence of *Bordetella pertussis* toxin subunit S1," *PNAS*, 87:1347-1351 (1990).
Casadesus et al., "The Estrogen Myth: Potential Use of Gonadotropin-Releasing Hormone Agonists for the Treatment of Alzheimer's Disease," *Drugs R D*, 7(3):187-193 (2006).
Casey, S.O., "Posterior Reversible Encephalopathy Syndrome: Utility of Fluid-attenuated Inversion Recovery MR Imaging in the Detection of Cortical and Subcortical Lesions," *Amer J Neuroradiol*, 21:1199-1206 (2000).

De La Cruz et al, "Immumogenicity [sic] and Epitope Mapping of Foreign Sequences via Genetically Engineered Filamentous Phage," *J Biol Chem*, 263(9):4318-4322 (1988).

Gilman, S. et al., "Clinical Effects of Aβ Immunization (AN1792) in Patients with AD in an Interrupted Trial," *Neurology*, 64:1553-1562 (2005).

Idusogie et al., "Mapping of the C1q Binding Site on Rituxan, a Chimeric Antibody with a Human IgG1 FC," *J. Immunology*, 164:4178-4184 (2000).

Khatoon et al., "Levels of normal and abnormally phosphorylated tau in different cellular and regional compartments of Alzheimer's disease and control brains," *FEBS Letters*, 351:80-84 (1994).

Kuby, J., eds., pp. 108-109, 131-132 from *Immunology, Third Edition*, W.H. Freeman & co., (1997).

Liu et al., "Amyloid β peptide alters intracellular vesicle trafficking and cholesterol homeostasis," *Proc. Natl. Acad. Sci.*, 95:13266-13271 (1998).

Morgan et al., "The N-terminal end of the $C_H2$ domain of chimeric human IgG1 anti-HLA-DR is necessary for C1q, FcγRII and FcγRII binding," *Immunology*, 86:319-324 (1995).

PCT Search Report of Oct. 1, 2007 and Written Opinion of Oct. 1, 2007 for application PCT/US07/09499.

Perez et al., "The β-Amyloid Precursor Protein of Alzheimer's Disease Enhances Neuron Viability and Modulates Neuronal Polarity," *J. Neurosci.*, 17(24):9407-9414 (1997).

Pluckthun, A., "Mono- and Bivalent Antibody Fragments Produced in *Escherichia coli*: Engineering, Folding and Antigen Binding," *Immunological Reviews*, 130:151-188 (1992).

Seubert et al., "Antibody Capture of Soluble Aβ does not Reduce Cortical Aβ Amyloidosis in the PDAPP Mouse," *Neurodegenerative Diseases*, 5:65-71 (2008).

Wu et al., "Expression of immunogenic epitopes of hepatitis B surface antigen with hybrid flagellin proteins by a vaccine strain of *Salmonella*," *PNAS*, 86:4726-4730 (1989).

Wyeth, Annual Review 2005: Creating Value . . . Advancing Health (Feb. 27, 2006).

U.S. Appl. No. 09/201,430, Office Action mailed Dec. 21, 1999.
U.S. Appl. No. 09/201,430, Office Action mailed May 10, 2000.
U.S. Appl. No. 09/204,838, Office Action mailed Mar. 17, 2000.
U.S. Appl. No. 09/322,289, Office Action mailed Sep. 29, 2000.
U.S. Appl. No. 09/497,553, Office Action mailed Oct. 3, 2003.
U.S. Appl. No. 09/580,015, Office Action mailed Feb. 11, 2002.
U.S. Appl. No. 09/580,018, Office Action mailed Mar. 12, 2002.
U.S. Appl. No. 09/580,019, Office Action mailed Mar. 12, 2002.
U.S. Appl. No. 09/723,544, Office Action mailed Sep. 23, 2002.
U.S. Appl. No. 09/723,760, Office Action mailed Mar. 12, 2002.
U.S. Appl. No. 09/723,765, Office Action mailed Mar. 12, 2002.
U.S. Appl. No. 09/723,766, Office Action mailed Mar. 5, 2002.
U.S. Appl. No. 09/723,766, Office Action mailed Jun. 11, 2002.
U.S. Appl. No. 09/724,273, Office Action mailed Jul. 2, 2002.
U.S. Appl. No. 09/724,273, Office Action mailed Nov. 8, 2005.
U.S. Appl. No. 09/724,288, Office Action mailed Mar. 12, 2002.
U.S. Appl. No. 09/724,288, Office Action mailed May 3, 2004.
U.S. Appl. No. 09/724,319, Office Action mailed Jul. 21, 2003.
U.S. Appl. No. 09/724,495, Office Action mailed Sep. 24, 2002.
U.S. Appl. No. 09/724,495, Office Action mailed Mar. 13, 2003.
U.S. Appl. No. 09/724,551, Office Action mailed Jul. 2, 2002.
U.S. Appl. No. 09/724,552, Office Action mailed May 6, 2002.
U.S. Appl. No. 09/724,567, Office Action mailed Mar. 27, 2002.
U.S. Appl. No. 09/724,575, Office Action mailed Mar. 27, 2002.
U.S. Appl. No. 09/724,921, Office Action mailed Apr. 30, 2002.
U.S. Appl. No. 09/724,929, Office Action mailed Mar. 22, 2002.
U.S. Appl. No. 09/724,940, Office Action mailed Mar. 13, 2003.
U.S. Appl. No. 09/724,953, Office Action mailed Mar. 26, 2002.
U.S. Appl. No. 09/724,961, Office Action mailed Mar. 12, 2002.
U.S. Appl. No. 09/979,701, Office Action mailed Feb. 15, 2005.
U.S. Appl. No. 09/979,701, Office Action mailed Sep. 15, 2005.
U.S. Appl. No. 09/979,952, Office Action mailed Aug. 7, 2003.
U.S. Appl. No. 09/980,568, Office Action mailed May 29, 2003.
U.S. Appl. No. 10/010,942, Office Action mailed Sep. 24, 2003.
U.S. Appl. No. 10/232,030, Office Action mailed Dec. 2, 2004.
U.S. Appl. No. 10/388,214, Office Action mailed May 31, 2005.
U.S. Appl. No. 10/388,389, Office Action mailed Nov. 22, 2005.
U.S. Appl. No. 10/429,216, Office Action mailed Dec. 28, 2005.
U.S. Appl. No. 10/544,093, Office Action, mailed Jun. 16, 2008.
U.S. Appl. No. 10/625,854, Office Action mailed Nov. 10, 2005.
U.S. Appl. No. 10/703,713, Office Action mailed Nov. 5, 2004.
U.S. Appl. No. 10/704,070, Office Action mailed Nov. 5, 2004.
U.S. Appl. No. 10/771,174, Office Action mailed Sep. 14, 2006.
U.S. Appl. No. 10/777,792, Office Action mailed Mar. 2, 2006.
U.S. Appl. No. 10/788,666, Office Action mailed Jan. 12, 2005.
U.S. Appl. No. 10/789,273, Office Action mailed Sep. 22, 2006.
U.S. Appl. No. 10/822,968, Office Action mailed Mar. 22, 2006.
U.S. Appl. No. 10/823,463, Office Action mailed Feb. 4, 2005.
U.S. Appl. No. 10/828,548, Office Action mailed Feb. 4, 2005.
U.S. Appl. No. 10/828,548, Office Action mailed Sep. 29, 2005.
U.S. Appl. No. 10/858,855, Office Action mailed Jun. 22, 2006.
U.S. Appl. No. 10/923,267, Office Action mailed Jul. 21, 2006.
U.S. Appl. No. 10/923,469, Office Action mailed Mar. 29, 2007.
U.S. Appl. No. 10/923,474, Office Action mailed Feb. 15, 2005.
U.S. Appl. No. 10/928,926, Office Action mailed Jan. 12, 2007.
U.S. Appl. No. 10/934,819, Office Action mailed Oct. 14, 2005.
U.S. Appl. No. 11/058,757, Office Action mailed May 3, 2005.
U.S. Appl. No. 11/058,757, Office Action mailed Aug. 24, 2005.
U.S. Appl. No. 11/244,678, Office Action mailed Apr. 18, 2007.
U.S. Appl. No. 11/245,524, Office Action mailed May 15, 2007.
U.S. Appl. No. 11/245,916, Office Action mailed Jan. 13, 2006.
U.S. Appl. No. 11/260,047, Office Action mailed Oct. 26, 2006.
U.S. Appl. No. 11/303,478, Office Action mailed Apr. 1, 2008.
U.S. Appl. No. 11/303,478, Office Action mailed Oct. 16, 2008.
U.S. Appl. No. 11/304,072, Office Action mailed Dec. 20, 2006.
U.S. Appl. No. 11/304,986, Office Action mailed Jan. 2, 2008.
U.S. Appl. No. 11/305,889, Office Action mailed Jul. 25, 2008.
U.S. Appl. No. 11/305,889, Office Action mailed May 4, 2007.
U.S. Appl. No. 11/305,899, Office Action mailed Apr. 4, 2008.
U.S. Appl. No. 11/342,353, Office Action mailed Mar. 26, 2008.
U.S. Appl. No. 11/342,353, Office Action mailed Jul. 9, 2008.
U.S. Appl. No. 11/454,772, Office Action mailed Feb. 27, 2007.
U.S. Appl. No. 09/201,430, Office Action mailed Jan. 17, 2001.
U.S. Appl. No. 09/201,430, Examiner Interview Summary mailed May 30, 2001.
U.S. Appl. No. 09/204,838, Office Action mailed Dec. 21, 2000.
U.S. Appl. No. 09/322,289, Office Action mailed Jun. 19, 2001.
U.S. Appl. No. 09/322,289, Examiner Interview Summary mailed Jun. 27, 2006.
U.S. Appl. No. 09/497,553, Office Action mailed Nov. 29, 2005.
U.S. Appl. No. 09/580,018, Office Action mailed May 20, 2003.
U.S. Appl. No. 09/723,384, Office Action mailed Oct. 9, 2002.
U.S. Appl. No. 09/723,384, Examiner Interview Summary mailed Mar. 28, 2003.
U.S. Appl. No. 09/723,544, Office Action mailed Aug. 11, 2003.
U.S. Appl. No. 09/723,713, Office Action mailed Mar. 26, 2002.
U.S. Appl. No. 09/723,760, Office Action mailed Dec. 19, 2002.
U.S. Appl. No. 09/723,762, Office Action mailed Oct. 2, 2001.
U.S. Appl. No. 09/723,765, Office Action mailed Dec. 3, 2002.
U.S. Appl. No. 09/723,765, Examiner Interview Summary mailed Mar. 18, 2003.
U.S. Appl. No. 09/723,765, Examiner Interview Summary mailed Jan. 25, 2006.
U.S. Appl. No. 09/723,765, Examiner Interview Summary mailed Oct. 8, 2008.
U.S. Appl. No. 09/723,766, Office Action mailed Nov. 1, 2002.
U.S. Appl. No. 09/724,102, Office Action mailed Oct. 3, 2001.
U.S. Appl. No. 09/724,273, Office Action mailed Apr. 21, 2003.
U.S. Appl. No. 09/724,288, Office Action mailed Dec. 11, 2002.
U.S. Appl. No. 09/724,319, Office Action mailed Apr. 26, 2004.
U.S. Appl. No. 09/724,319, Examiner Interview Summary mailed Jul. 19, 2004.
U.S. Appl. No. 09/724,319, Examiner Interview Summary mailed Apr. 9, 2008.
U.S. Appl. No. 09/724,477, Office Action mailed Oct. 2, 2001.
U.S. Appl. No. 09/724,489, Office Action mailed Oct. 2, 2002.
U.S. Appl. No. 09/724,495, Office Action mailed Jan. 16, 2004.
U.S. Appl. No. 09/724,551, Office Action mailed Jun. 3, 2003.
U.S. Appl. No. 09/724,552, Office Action mailed Jun. 3, 2003.

U.S. Appl. No. 09/724,552, Examiner Interview Summary mailed Dec. 3, 2003.
U.S. Appl. No. 09/724,567, Office Action mailed Nov. 15, 2002.
U.S. Appl. No. 09/724,575, Office Action mailed Nov. 21, 2002.
U.S. Appl. No. 09/724,575, Examiner Interview Summary mailed May 6, 2005.
U.S. Appl. No. 09/724,921, Office Action mailed Jan. 28, 2003.
U.S. Appl. No. 09/724,929, Office Action mailed Jul. 22, 2003.
U.S. Appl. No. 09/724,940, Office Action mailed Dec. 24, 2003.
U.S. Appl. No. 09/724,953, Office Action mailed Nov. 27, 2002.
U.S. Appl. No. 09/724,961 Office Action mailed May 16, 2003.
U.S. Appl. No. 09/724,961, Examiner Interview Summary mailed Dec. 3, 2003.
U.S. Appl. No. 09/979,701, Office Action mailed Jan. 10, 2006.
U.S. Appl. No. 09/979,952, Office Action mailed Dec. 30, 2003.
U.S. Appl. No. 09/980,568, Office Action mailed Feb. 23, 2004.
U.S. Appl. No. 10/010,942, Office Action mailed May 26, 2004.
U.S. Appl. No. 10/010,942, Examiner Interview Summary mailed Nov. 18, 2004.
U.S. Appl. No. 10/010,942, Examiner Interview Summary mailed Jan. 19, 2005.
U.S. Appl. No. 10/010,942, Examiner Interview Summary mailed Feb. 22, 2006.
U.S. Appl. No. 10/010,942 ,Examiner Interview Summary mailed May 10, 2006.
U.S. Appl. No. 10/010,942 ,Examiner Interview Summary mailed May 11, 2006.
U.S. Appl. No. 10/010,942, Examiner Interview Summary mailed May 11, 2006.
U.S. Appl. No. 10/232,030, Office Action mailed Oct. 14, 2005.
U.S. Appl. No. 10/232,030, Examiner Interview Summary mailed Feb. 17, 2006.
U.S. Appl. No. 10/388,214, Office Action mailed Jan. 31, 2006.
U.S. Appl. No. 10/388,214, Examiner Interview Summary mailed Oct. 2, 2006.
U.S. Appl. No. 10/388,214, Examiner Interview Summary mailed Nov. 6, 2006.
U.S. Appl. No. 10/388,389, Examiner Interview Summary mailed May 22, 2006.
U.S. Appl. No. 10/388,389, Examiner Interview Summary mailed May 31, 2006.
U.S. Appl. No. 10/429,216, Office Action mailed Apr. 11, 2006.
U.S. Appl. No. 10/625,854, Office Action mailed Feb. 7, 2006.
U.S. Appl. No. 10/625,854, Examiner Interview Summary mailed Jun. 26, 2007.
U.S. Appl. No. 10/703,713, Office Action mailed Sep. 27, 2005.
U.S. Appl. No. 10/703,713, Examiner Interview Summary mailed Feb. 21, 2006.
U.S. Appl. No. 10/703,713, Examiner Interview Summary mailed Mar. 2, 2006.
U.S. Appl. No. 10/704,070, Office Action mailed Sep. 26, 2005.
U.S. Appl. No. 10/771,174, Office Action mailed Nov. 27, 2006.
U.S. Appl. No. 10/777,792, Office Action mailed Aug. 7, 2006.
U.S. Appl. No. 10/788,666, Office Action mailed Dec. 15, 2005.
U.S. Appl. No. 10/823,463, Office Action mailed Sep. 30, 2005.
U.S. Appl. No. 10/828,548, Office Action mailed Feb. 13, 2006.
U.S. Appl. No. 10/858,855, Office Action mailed Mar. 7, 2007.
U.S. Appl. No. 10/890,000, Office Action mailed Apr. 13, 2005.
U.S. Appl. No. 10/890,024, Office Action mailed Nov. 2, 2005.
U.S. Appl. No. 10/890,070, Office Action mailed Apr. 8, 2005.
U.S. Appl. No. 10/890,071, Office Action mailed Dec. 18, 2006.
U.S. Appl. No. 10/889,999, Office Action mailed Jan. 5, 2005.
U.S. Appl. No. 10/923,469, Examiner Interview Summary mailed Apr. 9, 2008.
U.S. Appl. No. 10/923,469, Office Action mailed Jul. 3, 2007.
U.S. Appl. No. 10/923,471, Office Action mailed Jan. 5, 2005.
U.S. Appl. No. 10/923,471, Examiner Interview Summary mailed Oct. 20, 2008.
U.S. Appl. No. 10/923,474 Office Action mailed Nov. 17, 2005.
U.S. Appl. No. 10/923,605, Office Action mailed Apr. 12, 2007.
U.S. Appl. No. 10/934,818, Office Action mailed Mar. 26, 2007.
U.S. Appl. No. 10/934,819, Office Action mailed Jan. 24, 2006.
U.S. Appl. No. 11/058,757, Office Action mailed Oct. 20, 2005.
U.S. Appl. No. 11/108,102, Office Action mailed Jan. 11, 2006.
U.S. Appl. No. 11/244,678, Office Action mailed Jul. 13, 2007.
U.S. Appl. No. 11/245,524, Office Action mailed Sep. 27, 2007.
U.S. Appl. No. 11/245,916, Office Action mailed May 19, 2006.
U.S. Appl. No. 11/260,047, Office Action mailed May 15, 2007.
U.S. Appl. No. 11/260,047, Examiner Interview Summary mailed May 15, 2007.
U.S. Appl. No. 11/274,493, Office Action mailed Apr. 23, 2007.
U.S. Appl. No. 11/305,889, Office Action mailed Aug. 14, 2007.
U.S. Appl. No. 11/342,353, Office Action mailed Nov. 14, 2008.
U.S. Appl. No. 11/457,772, Examiner Interview Summary mailed Apr. 13, 2007.
U.S. Appl. No. 11/454,772, Office Action mailed Jun. 27, 2007.
U.S. Appl. No. 11/842,023, Office Action mailed Nov. 13, 2008.
U.S. Appl. No. 09/201,430, Office Action mailed Oct. 1, 2002.
U.S. Appl. No. 09/204,838, Office Action mailed Apr. 18, 2003.
U.S. Appl. No. 09/322,289, Office Action mailed Feb. 24, 2005.
U.S. Appl. No. 09/322,289, Office Action mailed Nov. 17, 2006.
U.S. Appl. No. 09/322,289, Office Action mailed Feb. 7, 2008.
U.S. Appl. No. 09/322,289, Office Action mailed Nov. 4, 2008.
U.S. Appl. No. 09/723,713, Office Action mailed Oct. 24, 2003.
U.S. Appl. No. 09/723,713, Office Action mailed Apr. 19, 2005.
U.S. Appl. No. 09/723,725, Office Action mailed Dec. 9, 2002.
U.S. Appl. No. 09/723,760, Office Action mailed May 4, 2005.
U.S. Appl. No. 09/723,765, Office Action mailed May 22, 2008.
U.S. Appl. No. 09/723,765, Office Action mailed Aug. 10, 2004.
U.S. Appl. No. 09/724,273, Office Action mailed Jun. 22, 2004.
U.S. Appl. No. 09/724,273, Office Action mailed Jun. 8, 2006.
U.S. Appl. No. 09/724,273, Office Action mailed Dec. 22, 2006.
U.S. Appl. No. 09/724,288, Office Action mailed Dec. 14, 2004.
U.S. Appl. No. 09/724,288, Office Action mailed Jun. 21, 2006.
U.S. Appl. No. 09/724,288, Office Action mailed Apr. 23, 2007.
U.S. Appl. No. 09/724,288, Office Action mailed Oct. 3, 2007.
U.S. Appl. No. 09/724,288, Office Action mailed Mar. 18, 2008.
U.S. Appl. No. 09/724,319, Office Action mailed Aug. 15, 2005.
U.S. Appl. No. 09/724,319, Office Action mailed May 16, 2007.
U.S. Appl. No. 09/724,319, Office Action mailed Jan. 11, 2008.
U.S. Appl. No. 09/724,575, Office Action mailed May 6, 2005.
U.S. Appl. No. 09/724,575, Office Action mailed Oct. 17, 2005.
U.S. Appl. No. 09/724,575, Office Action mailed Mar. 31, 2006.
U.S. Appl. No. 09/980,568, Office Action mailed Nov. 2, 2004.
U.S. Appl. No. 10/010,942, Office Action mailed Jan. 19, 2005.
U.S. Appl. No. 10/010,942, Office Action mailed Oct. 3, 2005.
U.S. Appl. No. 10/232,030, Office Action mailed Jun. 15, 2007.
U.S. Appl. No. 10/429,216, Office Action mailed Jan. 28, 2008.
U.S. Appl. No. 10/625,854, Office Action mailed May 15, 2007.
U.S. Appl. No. 10/703,713, Office Action mailed Jun. 2, 2006.
U.S. Appl. No. 10/777,792, Office Action mailed Apr. 3, 2008.
U.S. Appl. No. 10/828,548, Office Action mailed Sep. 11, 2007.
U.S. Appl. No. 10/889,999, Office Action mailed Aug. 15, 2005.
U.S. Appl. No. 10/890,000, Office Action mailed Sep. 19, 2005.
U.S. Appl. No. 10/890,000, Office Action mailed Mar. 10, 2006.
U.S. Appl. No. 10/890,070, Office Action mailed Sep. 29, 2005.
U.S. Appl. No. 10/923,469, Office Action mailed Mar. 24, 2008.
U.S. Appl. No. 10/923,471, Office Action mailed Aug. 24, 2005.
U.S. Appl. No. 10/923,471, Office Action mailed May 15, 2006.
U.S. Appl. No. 10/923,471, Office Action mailed Jul. 31, 2007.
U.S. Appl. No. 10/923,474, Office Action mailed Jun. 26, 2007.
U.S. Appl. No. 11/244,678, Office Action mailed Sep. 23, 2008.
U.S. Appl. No. 11/245,524, Office Action mailed Jun. 4, 2008.
U.S. Appl. No. 11/245,916, Office Action mailed Jan. 28, 2008.
U.S. Appl. No. 11/245,916, Office Action mailed Oct. 31, 2008.
U.S. Appl. No. 11/342,353, Office Action mailed Jul. 22, 2008.
U.S. Appl. No. 09/201,430, Advisory Action mailed Jun. 18, 2002.
U.S. Appl. No. 09/201,430, Office Action mailed Nov. 26, 2001.
U.S. Appl. No. 09/204,838, Office Action mailed Sep. 27, 2001.
U.S. Appl. No. 09/322,289, Office Action mailed Jul. 17, 2007.
U.S. Appl. No. 09/322,289, Office Action mailed Oct. 16, 2005.
U.S. Appl. No. 09/322,289, Office Action mailed Nov. 29, 2005.
U.S. Appl. No. 09/723,713, Advisory Action mailed Dec. 20, 2004.
U.S. Appl. No. 09/723,713, Office Action mailed Jan. 11, 2006.
U.S. Appl. No. 09/723,713, Office Action mailed Feb. 12, 2002.
U.S. Appl. No. 09/723,713, Office Action mailed Jun. 3, 2004.

U.S. Appl. No. 09/723,760, Advisory Action mailed Dec. 16, 2004.
U.S. Appl. No. 09/723,760, Office Action mailed Feb. 23, 2004.
U.S. Appl. No. 09/723,760, Office Action mailed Dec. 29, 2005.
U.S. Appl. No. 09/723,765, Advisory Action mailed Feb. 9, 2004.
U.S. Appl. No. 09/723,765, Office Action mailed May 4, 2005.
U.S. Appl. No. 09/723,765, Office Action mailed Oct. 7, 2003.
U.S. Appl. No. 09/724,273, Advisory Action mailed Mar. 18, 2004.
U.S. Appl. No. 09/724,273, Advisory Action mailed Jun. 16, 2005.
U.S. Appl. No. 09/724,273, Office Action mailed Aug. 22, 2007.
U.S. Appl. No. 09/724,273, Office Action mailed Oct. 16, 2003.
U.S. Appl. No. 09/724,273, Office Action mailed Dec. 28, 2004.
U.S. Appl. No. 09/724,288, Advisory Action mailed Jan. 6, 2004.
U.S. Appl. No. 09/724,288, Advisory Action mailed Mar. 3, 2006.
U.S. Appl. No. 09/724,288, Office Action mailed Jul. 12, 2005.
U.S. Appl. No. 09/724,288, Office Action mailed Sep. 9, 2003.
U.S. Appl. No. 09/724,319 Office Action mailed May 2, 2006.
U.S. Appl. No. 09/724,495, Advisory Action mailed May 16, 2004.
U.S. Appl. No. 09/724,495, Office Action mailed Sep. 26, 2005.
U.S. Appl. No. 09/724,567, Office Action mailed Jul. 23, 2003.
U.S. Appl. No. 09/724,575, Advisory Action mailed Feb. 12, 2004.
U.S. Appl. No. 09/724,575, Office Action mailed Jul. 25, 2003.
U.S. Appl. No. 09/724,575, Office Action mailed Oct. 12, 2006.
U.S. Appl. No. 09/724,953, Office Action mailed Jul. 25, 2003.
U.S. Appl. No. 10/232,030, Advisory Action mailed Oct. 30, 2006.
U.S. Appl. No. 10/232,030, Office Action mailed Apr. 1, 2008.
U.S. Appl. No. 10/388,214, Office Action mailed Jul. 28, 2006.
U.S. Appl. No. 10/429,216, Office Action mailed Jan. 3, 2007.
U.S. Appl. No. 10/429,216, Office Action mailed Oct. 16, 2008.
U.S. Appl. No. 10/625,854, Advisory Action mailed Jan. 8, 2008.
U.S. Appl. No. 10/625,854, Office Action mailed Aug. 23, 2006.
U.S. Appl. No. 10/625,854, Office Action mailed Nov. 7, 2007.
U.S. Appl. No. 10/704,070, Office Action mailed Jun. 6, 2006.
U.S. Appl. No. 10/771,174, Office Action mailed Aug. 23, 2007.
U.S. Appl. No. 10/777,792, Office Action mailed May 8, 2007.
U.S. Appl. No. 10/777,792, Office Action mailed Nov. 18, 2008.
U.S. Appl. No. 10/828,548, Advisory Action mailed Jun. 8, 2007.
U.S. Appl. No. 10/828,548, Office Action mailed Jun. 4, 2008.
U.S. Appl. No. 10/828,548, Office Action mailed Oct. 24, 2006.
U.S. Appl. No. 10/858,855, Advisory Action mailed Apr. 7, 2008.
U.S. Appl. No. 10/858,855, Office Action mailed Nov. 23, 2007.
U.S. Appl. No. 10/889,999, Office Action mailed Mar. 14, 2006.
U.S. Appl. No. 10/890,000, Advisory Action mailed Jan. 14, 2008.
U.S. Appl. No. 10/890,000, Office Action mailed Nov. 24, 2006.
U.S. Appl. No. 10/890,024, Office Action mailed Jun. 1, 2006.
U.S. Appl. No. 10/890,070, Office Action mailed Jun. 1, 2006.
U.S. Appl. No. 10/923,471, Office Action mailed Apr. 24, 2008.
U.S. Appl. No. 10/923,471, Office Action mailed Dec. 29, 2006.
U.S. Appl. No. 10/923,474 Office Action mailed Aug. 4, 2006.
U.S. Appl. No. 10/923,474, Advisory Action mailed Feb. 22, 2007.
U.S. Appl. No. 11/058,757, Advisory Action mailed Mar. 5, 2007.
U.S. Appl. No. 11/058,757, Office Action mailed Aug. 11, 2006.
U.S. Appl. No. 11/108,102, Office Action mailed Sep. 6, 2006.
U.S. Appl. No. 11/244,678, Office Action mailed Mar. 24, 2008.
U.S. Appl. No. 11/245,916, Advisory Action mailed May 15, 2007.
U.S. Appl. No. 11/245,916, Advisory Action mailed Oct. 18, 2007.
U.S. Appl. No. 11/245,916, Office Action mailed Jan. 12, 2007.
U.S. Appl. No. 11/274,493, Office Action mailed Nov. 2, 2007.
U.S. Appl. No. 11/305,889, Office Action mailed May 23, 2008.
U.S. Appl. No. 11/454,772, Office Action mailed Dec. 21, 2007.
U.S. Appl. No. 09/201,430, Notice of Allowance mailed Mar. 26, 2003.
U.S. Appl. No. 09/201,430, Notice of Allowance mailed Sep. 23, 2003.
U.S. Appl. No. 09/724,477, Notice of Allowance mailed Apr. 30, 2003.
U.S. Appl. No. 09/724,477, Notice of Allowance mailed Sep. 23, 2003.
U.S. Appl. No. 09/723,927, Notice of Allowance mailed Sep. 23, 2003.
U.S. Appl. No. 09/723,762, Notice of Allowance mailed May 1, 2003.
U.S. Appl. No. 09/724,102, Notice of Allowance mailed Aug. 22, 2003.
U.S. Appl. No. 09/724,489, Notice of Allowance mailed Mar. 25, 2003.
U.S. Appl. No. 09/724,489, Notice of Allowance mailed Sep. 22, 2003.
U.S. Appl. No. 10/232,030, Notice of Allowance mailed Sep. 4, 2008.
U.S. Appl. No. 10/816,022, Notice of Allowance mailed Jul. 1, 2004.
U.S. Appl. No. 10/816,529, Notice of Allowance mailed Jul. 1, 2004.
U.S. Appl. No. 10/815,391, Notice of Allowance mailed Jul. 1, 2004.
U.S. Appl. No. 10/815,353, Notice of Allowance mailed Jul. 1, 2004.
U.S. Appl. No. 10/816,380, Notice of Allowance mailed Dec. 22, 2004.
U.S. Appl. No. 10/815,404, Notice of Allowance mailed Oct. 15, 2004.
U.S. Appl. No. 10/884,892, Notice of Allowance mailed Mar. 28, 2005.
U.S. Appl. No. 09/723,384, Notice of Allowance mailed Mar. 31, 2003.
U.S. Appl. No. 09/724,940, Notice of Allowance mailed Oct. 4, 2004.
U.S. Appl. No. 09/724,961, Notice of Allowance mailed Dec. 3, 2003.
U.S. Appl. No. 09/580,018, Notice of Allowance mailed Dec. 3, 2003.
U.S. Appl. No. 09/724,552, Notice of Allowance mailed Dec. 3, 2003.
U.S. Appl. No. 09/724,551, Notice of Allowance mailed Dec. 4, 2003.
U.S. Appl. No. 09/724,567, Notice of Allowance mailed Mar. 3, 2004.
U.S. Appl. No. 09/724,953, Notice of Allowance mailed Mar. 11, 2004.
U.S. Appl. No. 09/979,952, Notice of Allowance mailed Nov. 12, 2004.
U.S. Appl. No. 10/934,609, Notice of Allowance mailed Dec. 22, 2004.
U.S. Appl. No. 10/934,609, Notice of Allowance mailed Aug. 17, 2005.
U.S. Appl. No. 10/933,559, Notice of Allowance mailed Sep. 7, 2005.
U.S. Appl. No. 10/933,559, Notice of Allowance mailed Aug. 17, 2005.
U.S. Appl. No. 10/933,559, Notice of Allowance mailed Dec. 22, 2004.
U.S. Appl. No. 10/010,942, Notice of Allowance mailed May 11, 2006.
U.S. Appl. No. 10/388,389, Notice of Allowance mailed May 31, 2006.
U.S. Appl. No. 10/388,214, Notice of Allowance mailed Mar. 1, 2007.
U.S. Appl. No. 12/106,206, filed Apr. 18, 2008, Schroeter.
U.S. Appl. No. 12/037,045, filed Feb. 25, 2008, Seubert.
U.S. Appl. No. 60/999,423, filed Oct. 17, 2007, Black.
U.S. Appl. No. 11/894,789, filed Aug. 20, 2007, Basi.
U.S. Appl. No. 11/894,754, filed Aug. 20, 2007.
U.S. Appl. No. 11/894,714, filed Aug. 20, 2007, Basi.
U.S. Appl. No. 11/894,665, filed Aug. 20, 2007, Schenk.
U.S. Appl. No. 11/893,123, filed Aug. 20, 2007.
U.S. Appl. No. 11/893,110, filed Aug. 20, 2007.
U.S. Appl. No. 11/893,103, filed Aug. 20, 2007.
U.S. Appl. No. 11/893,094, filed Aug. 20, 2007.
U.S. Appl. No. 11/842,120, filed Aug. 20, 2007, Schenk.
U.S. Appl. No. 11/842,116, filed Aug. 20, 2007, Schenk.
U.S. Appl. No. 11/842,113, filed Aug. 20, 2007, Schenk.
U.S. Appl. No. 11/842,101, filed Aug. 20, 2007, Schenk.
U.S. Appl. No. 11/842,056, filed Aug. 20, 2007, Basi.
U.S. Appl. No. 11/842,042, filed Aug. 20, 2007, Basi.
U.S. Appl. No. 11/842,023, filed Aug. 20, 2007, Basi.
U.S. Appl. No. 11/841,993, filed Aug. 20, 2007, Arumugham.
U.S. Appl. No. 11/841,950, filed Aug. 20, 2007, Arumugham.
U.S. Appl. No. 11/841,919, filed Aug. 20, 2007, Arumugham.
U.S. Appl. No. 11/841,897, filed Aug. 20, 2007, Arumugham.
U.S. Appl. No. 11/841,882, filed Aug. 20, 2007, Arumugham.
U.S. Appl. No. 11/841,857, filed Aug. 20, 2007, Warne et al.
U.S. Appl. No. 11/841,849, filed Aug. 20, 2007, Arumugham.
U.S. Appl. No. 11/841,794, filed Aug. 20, 2007, Warne et al.

U.S. Appl. No. 11/841,832, filed Aug. 20, 2007, Warne et al.
U.S. Appl. No. 60/793,014, filed Apr. 18, 2006.
U.S. Appl. No. 11/396,417, filed Mar. 30, 2006, Schenk.
U.S. Appl. No. 11/396,391, filed Mar. 30, 2006, Schenk.
U.S. Appl. No. 60/736,119, filed Nov. 10, 2005, Jacobson.
U.S. Appl. No. 60/736,045, filed Nov. 10, 2005, Johnson-Wood.
U.S. Appl. No. 60/735,687, filed Nov. 10, 2005, Jacobson.
U.S. Appl. No. 60/691,821, filed Jun. 17, 2005, Godavarti.
U.S. Appl. No. 09/980,568, filed Mar. 12, 2005, Hirtzer.
U.S. Appl. No. 60/648,639, filed Jan. 28, 2005, Luisi et al.
U.S. Appl. No. 60/648,631, filed Jan. 28, 2005, Luisi et al.
U.S. Appl. No. 60/637,253, filed Dec. 16, 2004, Jacobson.
U.S. Appl. No. 60/637,138, filed Dec. 16, 2004, Jacobson.
U.S. Appl. No. 60/636,842, filed Dec. 15, 2004, Jacobson.
U.S. Appl. No. 60/636,810, filed Dec. 15, 2004, Jacobson.
U.S. Appl. No. 60/636,776, filed Dec. 15, 2004, Basi.
U.S. Appl. No. 60/636,687, filed Dec. 15, 2004, Johnson-Wood.
U.S. Appl. No. 60/636,684, filed Dec. 15, 2004, Basi.
U.S. Appl. No. 60/622,525, filed Oct. 26, 2004, Pavliakova.
U.S. Appl. No. 60/616,474, filed Oct. 5, 2004, Sinacore.
U.S. Appl. No. 60/530,481, filed Dec. 17, 2003, Arumugham.
U.S. Appl. No. 60/474,654, filed May 30, 2003, Basi.
U.S. Appl. No. 60/444,150, filed Feb. 1, 2003, Yednock.
U.S. Appl. No. 09/979,701, filed Mar. 13, 2002, Schenk.
U.S. Appl. No. 60/363,751, filed Mar. 12, 2002, Basi.
U.S. Appl. No. 60/251,892, filed Dec. 6, 2000, Basi et al.
U.S. Appl. No. 09/724,929, filed Nov. 28, 2000, Weiner.
U.S. Appl. No. 09/724,921, filed Nov. 28, 2000, Weiner.
U.S. Appl. No. 09/724,575, filed Nov. 28, 2000, Schenk.
U.S. Appl. No. 09/724,291, filed Nov. 28, 2000, Schenk.
U.S. Appl. No. 09/724,288, filed Nov. 28, 2000, Schenk.
U.S. Appl. No. 09/724,273, filed Nov. 28, 2000, Schenk.
U.S. Appl. No. 09/723,765, filed Nov. 28, 2000, Schenk.
U.S. Appl. No. 09/723,544, filed Nov. 28, 2000, Schenk.
U.S. Appl. No. 09/724,495, filed Nov. 27, 2000, Schenk.
U.S. Appl. No. 09/724,319, filed Nov. 27, 2000, Schenk.
U.S. Appl. No. 09/723,766, filed Nov. 27, 2000, Hirtzer.
U.S. Appl. No. 09/723,760, filed Nov. 27, 2000, Schenk.
U.S. Appl. No. 09/723,725, filed Nov. 27, 2000, Hirtzer.
U.S. Appl. No. 09/723,713, filed Nov. 27, 2000, Schenk.
U.S. Appl. No. 09/580,019, filed May 26, 2000, Schenk.
U.S. Appl. No. 09/580,015, filed May 26, 2000, Schenk.
U.S. Appl. No. 09/579,690, filed May 26, 2000, Brayden.
U.S. Appl. No. 09/497,553, filed Feb. 3, 2000, Schenk.
U.S. Appl. No. 60/139,408, filed Jun. 16, 1999, Raso.
U.S. Appl. No. 60/137,047, filed Jun. 1, 1999, Hirtzer.
U.S. Appl. No. 60/137,010, filed Jun. 1, 1999, Schenk.
U.S. Appl. No. 60/136,655, filed May 28, 1999, Brayden.
U.S. Appl. No. 09/322,289, filed May 28, 1999, Schenk.
U.S. Appl. No. 09/204,838, filed Dec. 3, 1998, Weiner.
Aisen, P., "Inflammation and Alzheimer's Disease: Mechanisms and Therapeutic Strategies," *Gerontology*, 43:143-149 (1997).
Akiyama et al., "The amino-terminally truncated forms of amyloid β-protein in brain macrophages in the ischemic lesions of Alzheimer's disease patients," *Neuroscience Letters*, 219:115-118 (1996).
Alberts et al., eds. *Molecular Biology of the Cell, Third Edition*, chapter 23, pp. 1216-1218 (1994).
American Type Culture Collection (ATCC) Search Results for "1KTR, 1ETZ, 1JRH", http://www.atcc.org/, pp. 1-3, Feb. 22, 2007.
Avis, "Perenteral Preparations," *Remington's Pharmaceutical Sciences*, 17:1518-1519 (1985).
Bending, "Humanization of Rodent Monoclonal Antibodies by CDR Grafting," *A Companion to Methods in Enzymology*, 8:83-93 (1995).
Ben-Yedidia et al., "Design of peptide and polypeptide vaccines," *Current Opinion in Biotechnology*, 8:442-448 (1997).
Britt et al., "Formulation of an immunogenic human cytomegalovirus vaccine: responses in mice," *J. Infect. Dis.*, 171:18-25 Abstract (1995).
Casset et al., "A Peptide Mimetic of an Anti-CD4 Monoclonal Antibody by Rational Design," *Biochemical and Biophysical Research Commiunications*, 307:198-205 (2003).

Chakrabarti et al., "Vaccinia Virus Expression Vector: Coexpression of B-Galactosidas Provides Visual Screening of Recombinant Virus Plaques," *Molecular and Cellular Biology*, 5(12):3403-3409 (1985).
Chang et al., "Adjuvant activity of incomplete Freund's adjuvant," *Advanced Drug Delivery Reviews*, 32:173-186 (1998).
Chen et al., "Selection and Analysis of an Optimized Anti-VEGF Antibody: Crystal Structure of an Affinity-matured Fab in Complex with Antigen," *J. Mol. Biol.*, 293:865-881 (1999).
Clark et al., *Chemical Immunology Antibody Engineering IgG Effector Mechanisms*, 65:88-110 (1997).
Colman, "Effects of Amino Acid Sequence Changes on Antibody-Antigen Interactions," *Research in Immunology*, 145:33-36 (1994).
Colombian Patent Application No. 98071271, Technical Opinion of Jean Paul Vernot submitted on Jun. 22, 2005 as evidence with the brief amending the nullity action (with English translation) (drafted Nov. 2004).
Corey-Bloom et al., "Clinical features distinguishing large cohorts with possible AD, probable AD, and mixed dementia," *J. Am. Geriatr. Soc.*, 41(1):31-37 Abstract (1993).
Dialog/Derwent, Abstract of WPI Acc No. 1995-261292/199534: Novel monoclonal antibody against human high-affinity IgE receptor—and DNA fragment encoding the MAb, for the specific identification of human Fc-epsilon RI, Derwent WPI database (1995).
Drew et al., "Vaccination by cholera toxin conjugated to a herpes simplex virus type 2 glycoprotein D peptide," *Journal of General Virology*, 73:2357-2366 (1992).
Ecuador Patent Application No. SP 98/2764, English translation of Expert Report submitted Apr. 19, 2007 in support of the Appeal filed on Jul. 29, 2005.
European Examination Report of Mar. 9, 2007 for European Application 01995364.5-1222.
European Examination Report of Sep. 26, 2007 for European Application 04720353.4-1222.
European Examination Report of Oct. 8, 2007 for European Application 01995364.5-1222.
Fragione et al., Familial cerebral amyloid angiopathy related to stroke and dementia. *Amyloid*, 8(Suppl 1):36-42 (2001), abstract only.
Gibson et al., "Abnormalities in Alzheimer's Disease Fibroblasts Bearing the APP670/671 Mutation," *Neurobiology of Aging*, 18(6):573-580 (1997).
Harlow et al., eds., *Antibodies: A Laboratory Manual*, pp. 71-82 (1988).
Harlow et al., eds., *Antibodies: A Laboratory Manual*, p. 98 (1988).
Holmes et al., "Long-term Effects of $A\beta_{42}$ Immunisation in Alzheimer's Disease: Follow-up of a Randomised, Placebo-controlled Phase I Trial," *Lancet*, 372: 216-223 (2008).
Hopp et al., "Prediction of protein antigenic determiniants from amino acid sequences," *Proc. Natl. Acad. Sci. USA* 78:3824-3828 (1981).
Hussain et al., "Selective Increases in Antibody Isotopes and Immunoglobulin G Subclass Responses to Secreted Antigens in Tuberculosis Patients and Healthy Household Contacts of the Patients," *Clinical and Diagnostic Laboratory Immunology*, 2(6): 726-732 (1995).
Hyslop et al., "Will Anti-amyloid Therapies Work for Alzheimer's Disease?," *Lancet*, 372:180-182 (2008).
Jansen et al., "Use of Highly Encapsulated *Streptococcus pneumoniae* Strains in a Flow-Cytometric Assay for Assessment of the Phagocytic Capacity of Serotype-Specifid Antibodies," *Clinical & Diagnostic Lab. Immunol.*, 5(5):703-710 (1998).
MacCallum et al., Antibody-antigen Interactions: *Contact Analysis and Binding Site Topography*, 262:732-745 (1996).
Mamikonyan et al., "Anti-$A\beta_{1-11}$ Antibody Binds to Different β-Amyloid Species, Inhibits Fibril Formation, and Disaggregates Preformed Fibrils but Not the Most Toxic Oligomers," *J Biol Chem*, 282(31) 22376-22386 (2007).
Manning et al., "Genetic Immunization with Adeno-Associated Virus Vectors Expressing Herpes Simplex Virus Type 2 Glycoproteins B and D," *Journal of Virology*, 71(10):7960-7962 (1997).
Masliah et al., "Amyloid Protien Precursor Stimulates Excitatory Amino Acid Transport," *The Journal of Biological Chemisrty*, 273(20):12548-12554 (1998).

Nashar et al., "Current progress in the development of the B subunits of cholera toxin and *Escherichia coli* heat-labile enterotoxin as carries for the oral delivery of herterologous antigens and epitopes," *Vaccine*, 11(2):235-40 (1993), abstract only.
Pascalis et al., "Grafting of "Abbreviated" Complementarity-Determining Containing Specifictiy-Determining Residues Essential for Ligand Contact to Engineer a Less Immunogenic Humanized Monoclonal Antibody," *The Journanal Immunology*, 169:3076-3084 (2002).
PCT International Preliminary Examination Report of Feb. 9, 2004 for application PCT/US01/46587.
PCT Written Opinion of Dec. 14, 2004 for application PCT/US04/02856.
PCT International Preliminary Report on Patentability (Chapter I) of Sep. 16, 2005 with Written Opinion of May 9, 2005 for application PCT/US04/007503.
PCT International Preliminary Report on Patentability (Chapter II) of Dec. 21, 2006 for application PCT/US2006/002837.
PCT International Preliminary Report on Patentability (Chapter I) of Jul. 31, 2007 with Written Opinion for application PCT/US2006/004741.
PCT Written Opinion of Aug. 11, 2006 for application PCT/US2006/002837.
PCT International Preliminary Report on Patentability (Chapter II) of Apr. 27, 2006 for application PCT/US04/007503.
Putative CDR determination for SEQ Id Nos. 2 and 4 (pp. 1-2), Jun. 10, 2004.
Rammensee, H.G., "Chemistry of peptides associated with MHC class I and class II molecules," *Current Opinion in Immunology*, 7:85-96 (1995).
Rodriguez et al., "Enfermedad de Azlheimer. Situacion Actual y Estrategias Terapeuticas" (Alzheimer Disease: present situation and therapeutic strategies), *Rev Cubana Med* [online], 38(2):134-142 (1999).
Rolph et al., "Recombinant viruses as vaccines and immunological tools," *Immunity to Infection*, 9:517-521 (1997).
Small, "The Role of the Amyloid Protien Precursors (APP) in Alzheimer's Disease: Does the Normal Function of APP Explain the Topography of Neurodegeneration?," *Neurochemical Research*, 23(5):795-806 (1997).
Smith et al., "Phage Display," *Chemical Reviews, American Chemical Society*, 97(2):391-410 (1997).
Spellerberg et al., "DNA Vaccines Against Lymphoma," *Journal of Immunology*, 159:1885-1892 (1997).
Staunton et al., "Primary structures of ICAM-1 demonstrates interaction between members of the immunoglobulin and intergrin supergene families," *Cell* 52(6):925-33 (1988), abstract only.
Supplementary Partial European Search Report of Apr. 10, 2007 for European Application 04720353.4-1222.
Tang et al., "Genetic immunization is a siple method for eliciting an immune response," *Nature*, 356:152-154 (1992).
Ulvestad et al., "Fc Receptors for IgG on Cultured Human Microglia Mediate Cytotoxicity and Phagocytosis of Antibody-coated Targets," *Journal of Neuropathology and Experimental Neurology*, 53(1):27-36 (1994).
U.S. Appl. No. 09/316,387, Office Action mailed Sep. 10, 2007.
U.S. Appl. No. 09/316,387, Response to Jun. 20, 2005 Office Action filed Dec. 20, 2005.
U.S. Appl. No. 09/316,387, Declaration of Solomon, Hrncic, and Wall under 37 C.F.R. § 1.131 filed Mar. 6, 2006.
U.S. Appl. No. 09/316,387, Office Action mailed Jun. 20, 2005.
Vajdos et al., "Comprehensive Functional Maps of the Antigen-binging site of an Anti__ErbB2 Antibody Obtained with Shotgun Scanning Mutagenesis," *J. Mol. Biol.*, 320:415-428 (2002).
Vanderstichele et al., "Standardization of Measurement of B-amyloid(1-42) in Cerebrospinal Fluid and Plasma:," *Int. J. Exp. Clin. Invest.*, 7(4):245-258 (2000).
Wilson et al., "Phage display: applications, innovations, and issues in phage and host biology," *Can. J. Microbiol*, 44:313-329 (1998).
Winblad et al., "Hints of a therapeutic Vaccine for Alzheimer's?" *Neuron*, 38:517-519 (2003).

Wu et al., "Humanization of a Murine Monoclonal Antibody by Simultaneous Optimization of Framework and CDR Residues," *J. Mol. Biol.*, 294:151-162 (1999).
Xiang et al., "Manipulation of the immune response to a plasmid-encoded viral antigen by coinoculation with plasmids expressing cytokines," *Immunity*, 2(2):129-135 Abstract (1995).
Yankner et al., "Neurotrophic and Neurotoxic effects of Amyloid β Protein: Reversal by Tachykinin Neuropeptides," *Science*, 250:279-282 (1990).
U.S. Appl. No. 11/842,085, filed Aug. 20, 2007, Schenk.
Allen et al, "Reversible posterior leukoencephalopathy syndrome after bevacizumab/FOLFIRI Regimen for Metastatic Colon Caner," *Arch. Neurol.*, 63(10): 1475-1478 (2006), abstract only.
Armour et al., "Recombinant human IgG molecules lacking Fcγ receptor I binding and monocyte triggering activities," *J. Immunol*, 29:2613-2624 (1999).
Brinkman, "Splice Variants as Cancer Biomarkers," *Clinical Biochemistry*, 37(7):584-594 (2004).
Choi et al., "A Generic Intron Increases Gene Expression in Transgenic Mice," Molecular and Cellular Biology, 11(6):3070-3074 (1991).
Corcoran et al., "Overexpression of hAPPswe Impairs Rewarded Alternation and Contextual Fear Conditioning in a Transgenic Mouse Model of Alzheimer's Disease," Learn Mem. 9(5):243-252:2000.
Database Geneseq, "Nucleotide Sequence of a Variable Heavy Chain of IgG4," EBI Accession No. GSN:ADZ51216 (2005).
Extended European Search Report of Dec. 18, 2008 for European Application 05812436.6-1212.
European Examination Report of Sep. 23, 2008 for European Application 04776252.1-2405.
European Examination Report as part of Dec. 8, 2008 communication for European Application 04720353.4.
European Examination Report of Nov. 20, 2008 for European Application 08011409.3.
Family and legal status of EP0613007, Inpadoc Search (2009).
Genbank Accession No. AAA69734, Schroeder et al., "Immunoglobulin heavy chain [*Homo sapiens*]", Anti-DNA immunoglobulin light chain IgG [Mus musculus], Jul. 11, 1995.
Genbank Accession No. BAC01733, Akahori et al., "Immunoglobulin kappa light chain VLJ region [*Homo sapiens*]", Jul. 2, 2002.
Hezareh et al., "Effector Function Activities of a Panel of Mutants of a Broadly Neutralizing Antibody against Human Immunodeficiency Virus Type 1," *Journal of Virology*, 24(75):12161-12168 (2001).
Janeway et al., *Immunobiology*, 3$^{rd}$ edition, pp. 8:18-8:19 (1997).
Mann et al., "Atypical Amyloid (ABeta) Deposition in the cerebellum in Alzheimer's Disease: An Immunohistochemical Study Using End-Specific ABeta Monoclonal Antibodies," *ACTA Neuropathologica*, 91:647-653 (1996).
Mann et al., "Predominant Deposition of amyloid-beta 42(43) in Plaques in Cases of Alzheimer's disease and Hereditary Cerebral Hemorrhage Associated with Mutation in the amyloid Precursor Protein Gene," The *American Journal of Pathology APR*, 4(148): 1257-1266 (1996).
Mavragani et al., "A Case of Reversible Posterior Leucoencephalopathy Syndrome After Rityximab Infusion," Rheumatology, 43(11) 1450-1451 (2006).
Myers et. al., "Targeting Immune Effector Molecules to Human Tumor Cells Through Genetic Delivery of 5T4-Specific SCFV Fusion Proteins," Cancer Gene Therapy, 9(11):884-896 (2002).
Padlan et al., Structure of an Antibody-Antigen Complex: Crystal Structure of the HyHEL-10 Fab-lysozyme Complex, Immunology, 86:5938-5942 (1989).
PCT Written Opinion of Dec. 22, 2008 for application PCT/US2008/80370.
PCT Search Report of Jan. 22, 2009 for application PCT/US2008/80370.
Pangalos et al., "Disease Modifying Strategies for the Treatment of Alzheimer's Disease Targeted at Modulating Levels of β-amyloid Peptide," Biochemical Society Transactions, 33(4):553-558 (2005).
Prada et al., "Antibody-Mediated Clearance of Amyloid-β Peptide From Cerebral Amyloid Angiopathy Revealed by quantitative in Vivo Imaging," Journal of Neuroscience, 27(8):1973-1980 (2007).

Qu et al., "Aβ$_{42}$ gene Vaccine Prevents Aβ$_{42}$ deposition in brain of Double Trangenic Mice," *J. Neurological Sciences*, 260:204-213 (2007).
Robbins et al., "The Intronic Region of an Incompletely Spliced gp100 Gene Transcript Encodes an Epitope Recognized by Melanoma-Reactive Tumor-Infiltrating Lymphocytes," Journal of Immunology, 159(1):303-308 (1997).
Schmidt et al., "Monoclonal Antibodies to a 100-kd protein reveal abundant A beta-negative plaques throughout gray matter of Alzheimer's disease brains," *The American Journal of Pathology*, 1(151):69-80 (1997).
Schroeder et al., "Preferential Utilization of Conserved Immunoglobulin Heavy Chain Variable Gene Segments During Human Fetal Life," *Immunology*, 87:6146-6150 (1990).
Seabrook et al., "Species-specific Immune response to Immunization with Human Versus rodent Abeta Peptide," Neurobiology of Aging, 25(9) 1141-1151 (2004).
Shepherd et al., "The design of the humanized antibody," Monoclonal Antibodies: A Practical Approach 58-66 (2000).
Studnicka et al., "Human-engineered monoclonal antibodies retain full specific binding activity by preserving non-CDR complementary-modulating residues," Protein Eng., 7(6):805-814 (1994), Abstract only.
Tamaokaet al., "Antibodies to amyloid beta protein (A beta) crossreact with glyceraldehyde-3-phosphate dehydrogenase (GAPDH)," *Neurobiology of Aging*, 3(17):405-414 (1996).
Trang et al., "Pharmacokinetics of a Mouse/Human Chimeric Monoclonal Antibody (C-17-1A) in Metastatic Adencarcinoma Patients," Pharmaceutical Research 7(6):587-592 (1990).
Ward et al., "Spontaneous Deletions in IG Heavy Chain Genes Flaking Sequences Influence Splice Site Selection Nucleic Acids Research," 19(23): 6475-6480 (1991).
Wikipedia entry for Antibody, retrieved Apr. 27, 2009 from http://en.wikipedia.org/wiki/Antibody.
Yanagisawa K et al., "Amyloid BETA-protein (Alpha-Beta) associated with lipid molecules: immunoreactivity distinct from that of soluble Alpha-Beta," FEBS Letters, 1(420): 43-46 (1997).
Yang et al., "Monoclonal Antibody to the C-terminus of Beta-Amyloid," Neuroreport, 16(5):2117-2120 (1994).
U.S. Appl. No. 11/516,724, Office Action mailed Jan. 27, 2009.
U.S. Appl. No. 11/520,438, Office Action mailed Apr. 2, 2009.
U.S. Appl. No. 11/707,639 Office Action mailed Apr. 3, 2009.
U.S. Appl. No. 11/842,085, Office Action mailed Apr. 14, 2009.
U.S. Appl. No. 11/842,120, Office Action mailed Apr. 14, 2009.
U.S. Appl. No. 09/322,289, Examiner Interview Summary mailed Jan. 15, 2009.
U.S. Appl. No. 09/723,765, Examiner Interview Summary mailed Jan. 16, 2009.
U.S. Appl. No. 10/429,216, Examiner Interview Summary mailed Mar. 6, 2006.
U.S. Appl. No. 10/544,093, Office Action mailed Feb. 9, 2009.
U.S. Appl. No. 11/303,478, Office Action mailed Mar. 18, 2009.
U.S. Appl. No. 11/304,986, Office Action mailed Dec. 31, 2008.
U.S. Appl. No. 11/305,899Office Action mailed Dec. 10, 2008.
U.S. Appl. No. 11/842,056, Office Action mailed May 6, 2009.
U.S. Appl. No. 12/181,238, Office Action mailed May 28, 2009.
U.S. Appl. No. 10/858,855 Office Action mailed Dec. 12, 2008.
U.S. Appl. No. 10/923,471, Office Action mailed Mar. 20, 2009.
U.S. Appl. No. 11/245,524, Office Action mailed Apr. 17, 2009.
U.S. Appl. No. 09/322,289, Office Action mailed Jun. 4, 2009.
U.S. Appl. No. 09/723,765, Office Action mailed Dec. 5, 2008.
U.S. Appl. No. 09/724,288, Office Action mailed Dec. 22, 2008.
U.S. Appl. No. 09/724,319 Office Action mailed Apr. 8, 2009.
U.S. Appl. No. 10/429,216, Office Action mailed Mar. 6, 2009.
U.S. Appl. No. 10/923,469. Advisory Action mailed Apr. 16, 2009.
U.S. Appl. No. 10/923,469. Office Action mailed Dec. 29, 2008.
U.S. Appl. No. 09/724,288, Notice of Allowance mailed Mar. 23, 2009.
Biewenga et al., "Cleavage of Protein A-binding IgA1 with IgA1 Protease From *Streptococcus sangus*," *Immunol Commun.*, 12(5):491-500 (1983), abstract only.

Hogarth, Fc Receptors Are Major Mediators of Antibody Based Inflammation in Autoimmunity, *Current Opinion in Immunology*, 14:798-802 (2002).
Mavragani et al., "A Case of Reversible Posterior Leucoencephalopathy Syndrome After Rityximab Infusion," *Rheumatology* 43(11) 1450-1451 (2006).
Padlan et al., "Structure of an Antibody-Antigen Complex: Crystal Structure of the HyHEL-10 Fab-lysozyme Complex," *Immunology*, 86:5938-5942 (1989).
Qu et al., "Aβ$_{42}$ gene Vaccine Prevents Aβ$_{42}$ deposition in brain of Double Transgenic Mice," *J. Neurological Sciences*, 260:204-213 (2007).
Trang et al., "Pharmacokinetics of a Mouse/Human Chimeric Monoclonal Antibody (C-17-1A) in Metastatic Adencarcinoma Patients," *Pharmaceutical Research*, 7(6):587-592 (1990).
U.S. Appl. No. 11/520,438, Office Action mailed Aug. 6, 2009.
U.S. Appl. No. 11/842,042, Office Action mailed Jun. 24, 2009.
U.S. Appl. No. 11/842,023, Office Action mailed Aug. 14, 2009.
U.S. Appl. No. 11/245,916, Office Action mailed Jun. 10, 2009.
U.S. Appl. No. 11/842,113, Office Action mailed Dec. 17, 2009.
U.S. Appl. No. 11/842,116, Office Action mailed Mar. 31, 2010.
U.S. Appl. No. 12/106,206, Office Action mailed Feb. 5, 2010.
U.S. Appl. No. 12/253,929, Office Action mailed Jan. 25, 2010.
U.S. Appl. No. 12/297,636, Office Action mailed Jul. 20, 2011.
U.S. Appl. No. 12/297,636, Office Action mailed Oct. 28, 2011.
U.S. Appl. No. 12/328,740, Office Action mailed Oct. 9, 2009.
U.S. Appl. No. 12/608,869, Office Action mailed Jul. 5, 2011.
U.S. Appl. No. 13/123,898, Office Action mailed Nov. 15, 2011.
"AAB-001 in Patients with Mild to Moderate Alzheimer's Disease" ClinicalTrials.gov last updated Sep. 22, 2009 3 pages.
Abcam, "Anti-beta Amyloid antibody 6F/3D", Nucleic Acids Res. 38:D142-D148 (2010).
Aihara, et al., "Immunocytochemical Localization of Immunoglobulins in the Rat Brain: Relationship to the Blood-Brain Barrier", *J of Comparative Neurology* 342:481-496 (1994).
Alzheimer Research Forum, "Drugs in Clinical Trials" Oct. 18, 2010.
Andrews, et al., "Amino acid sequence of the variable regions of heavy chains from two idiotypically cross-reactive human IgM anti-gamma-globulins of the Wa group", *Biochemistry*, Sep. 29, 1981;20(20):5822-5830.
Andrews, et al., "Complete amino acid sequence of variable domains from two monoclonal human anti-gamma globulins of the Wa cross-idiotypic group: Suggestion that the J segments are involved in the structural correlate of the idiotype", *Proc. Natl. Acad. Sci. USA*, vol. 78, No. 6, pp. 3799-3803, Jun. 1981.
Applicants' submission in EP 07012421.9 dated Jun. 16, 2009.
Aquila Press Release, PR Newswire. May 6, 1997.
Assignment executed Dec. 8, 2000 in respect of U.S. Appl. No. 60/067,740.
Assignment executed Dec. 8, 2000 in respect of U.S. Appl. No. 60/080,970.
Bach et al., "Vaccination with AB-Displaying Virus-Like Particles Reduces Soluble and Insoluble Cerebral AB and Lowers Plaque Burden in APP Transgenic Mice," J. Immunol., 2009, 182 7613-7624.
Bales et al., "Administration of an Anti-Aβ Fab Fragment to APP$^{V717F}$ Transgenic Mice Reduces Neuritic Plaque," Abstract P4-396, presented at Poster Session P4: Therapeutics and Therapeutic Strategies—Therapeutic Strategies, Amyloid-Based, *Neurogiology of Acting*, 25:S587 (2004).
Birmingham et al., "Set back to Alzheimer vaccine studies" Nature Medicine 8(3):199-200 (2002).
Boraschi et al., "Interleukin-1 and Interleukin-1 Fragments a Vaccine Adjuvants", Methods, 1999, 19, pp. 108-113.
Bruggermann, et al. "The Immunogenicity of Chimeric Antibodies" *J. Exp Med*., 170(2):153-2157 (1989).
Burbach et al. "Vessel ultrastructure in APP23 transgenic mice after passive anti-Aβ immunotherapy and subsequent intracerebral hemorrhage" Neurobiology of Aging 28:202-212 (2007).
Capra, et al., "Structure of Antibodies with Shared Idiotypy: The Complete Sequence of the Heavy Chain Variable Regions of Two Immunoglobulin M Anti-Gamma Globulins", *Proc. Nat. Acad. Sci. USA*, vol. 71, No. 10, pp. 4032-4036, Oct. 1974.

Chalmers et al., "APOE epsilon 4 influences the pathological phenotype of Alzhemier's disease by favouring cerebrovascular over parechyma accumulation of A beta protein", Neuropathology and Applied Neurobiology, vol. 29, No. 3 pp. 231-238 (2003).

Chauhan et al. "Intracerebroventricular Passive Immunization With Anti-Aβ Antibody in Tg2576" J of Neuroscience 74:142-147 (2003).

Chemical Abstract database, Abstract of "Injection of Newborn Mice with Seven Chemical Adjuvants to Help Determine Their Safety in Use in Biologicals," Chemical Abstract database, 75:242 (1971).

Claudio, "Ultrastructural features of the blood-brain barrier in biopsy tissue for Alzheimer's disease patients." *Acta Neuropathol*. 91:6-14 (1996).

Communication in EP 07012421.9 pursuant to Art. 94(3) EPC dated Nov. 5, 2010.

Constantino, Expert opinion Sep. 17, 2010.

Cribbs et al., "Adjuvant-dependant modulation of th1 and th2 responses to immunization with B-amyloid", International Immunology, 2003, vol. 15, No. 4, pp. 505-514.

Decision of Opposition Division in EP 1 160 256 dated Feb. 17, 2011.

Declaration by Dr. Dale Schenk dated Nov. 21, 2011.

Declaration of Dr. Mattias Staufenbiel Ph D. Jul. 15, 2011.

Declaration of Shyra J. Gardai dated Mar. 2, 2009.

Do et al., "Reprogramming Somatic Gene Activity by Fusion With Pluripotent Cells" *Stem Cell Reviews*., 2:257-264 (2006).

Druckexemplar in EP 1 160 256 dated Jan. 25, 2010.

Elan Reports First Quarter 2006 Financial Results. Business Wire (May 4, 2006) XP002620724.

Elan Reports First Quarter 2006 Financial Results. Business Wire (May 4, 2006) XP002620725.

European Extended Search Report of Dec. 6, 2011 for European Application 10183051.1.

European Extended Search Report of Mar. 1, 2012 for European Application 08839961.

European Extended Search Report of Mar. 15, 2012 for European Application 09075267.6.

European Search Report of Feb. 7, 2011 for European Application EP 08 74 6362.6.

Extract from EPO patent register of EP 1 160 256 retrieved on Sep. 7, 2011.

Extract from EPO patent register of EP 1 842 859 retrieved on Sep. 7, 2011.

Gambetti, et al., "Human brain amyloidosis," *Nephrology Dialysis Transplantation*, 13(Suppl. 7):33-40, (1998).

GenBank, Accession No. AAA38630.1, "Immunoglobulin gamma-1 chain [Mus musculus]" May 5, 1994.

Ghersi-Egea et al., "Fate of Cerebrospinal Fluid-Borne Amyloid β-Peptide: Rapid Clearance into Blood and Appreciable Accunulation by Cerebral Arteries," *Journal of Neurochemistry*. vol. 67 No. 2:880-883 (1996).

Ghochikyan, "Rationale for Peptide and DNA Based Epitope Vaccine for Alzheimer's Disease Immunotherapy", CNS Neurol Disord Drug Targets, 2009: 8(2): 128 1-18.

Greaves, et al., "Posterior reversible encephalopathy syndrome following anti-lymphocyte globulin treatment for severe aplastic anaemia" *British Journal of Heamatology*, Aug. 2006: 13493):251.

Greenberg et al. "Amyloid Angiopathy-Related Vascular Congnitive Impairment" Stoke., 35:2616-2619 (2004).

Greisman et al., "A General Strategy for Selecting High-Affinity Zinc finger Proteins for Diverse DNA Target Sites" Science vol. 275:657-661 (1997).

Gustavsson et al., "Mechanisms of Transthyretin Amyloidogenesis Antigenic Mapping of Transthyretin Pruified from Plasma and Amyloid Fibrils and within in Situ Tissure Localizations" American Journal of Pathology 44(6):1301-1311 (1994).

Hampel et al., "Measurement of Phosphorylated Tau epitopes in the Differential Diagnosis of Alzheimer Disease", Arch Gen Psychiatry (2004) 61(1):95-102.

Hartwig, "Immune ageing and Alzheimer's disease," *NeuroReport*, 6:1274-1276 (1995).

Hyman, et al. "Kunitz Protease Inhibitor-Containing Amyloid β Protein Precursor Immunoreactivity in Alzheimer's Disease", *J. of Neuropathology*, 51(1):76-83 (1992).

Invitrogen Data Sheet, "Mouse anti-β-Amyloid Peptide", Catalog No. 13-0100Z (Rev Oct. 2008) DCC-08-1089.

Jagust et al., "Brain Imaging Evidence of preclinical Alzheimer's disease in normal aging" Ann Neurol, (2006) 59:67-681: abstract p. 676, table 1.

Janeway, et al., *Immunobiology: The Immune System in Health and Disease* 3rd Edition; cover pages and pp. 3.22-3.27 (1997).

Jefferis, "Antibody therapeutic: isotype and glycoform selection", *Expert Opin. Biol. Ther*. 7(9):1401-1413 (2007).

Kim et al., "In Vivo Engineering of a Cellular Immune Response by Coadministration of 1L-12 Expression Vector with a DNA Immunogen," *J. Immunol*., 158:816-826 (1997).

Klafki et al., "Therapeutic approaches to Alzheimer's disease" *Brain* 129:2840-2825 (2006).

Kuby, *Immunology*, 2nd Ed., Freeman pp. 126 and 168-171 (1994).

Lemere, "Developing novel immunogens for a safe and effective Alzheimer's disease vaccine" Prog Brain Res. 2009; 175: 83 1-13.

Marx et al., "Immune recognition of the Alzheimer amyloid β protein" Poster presentation; Autoreactive T. cells P.5.18.03 Jun. 25, 1997.

Moretto, et al., "Conformation-sensitive Antibodies against Alzheimer Amyloid-β by Immunization with a Thioredoxin-constrained B-cell Epitope Peptide", *J of Biological Chemistry*, 282(14):11436-11445 (2007).

Mount et al. "Alzheimer disease: progress or profit?" Market Analysis Nature Medicine 12(7) 780-784 (Jul. 2006).

Movsesyan et al., "Reducing AD-Lide Pathology in 3xTg-AD Mouse Model by DNA epitope Vaccine—A Novel Immunotherapeutic Strategy", PloS ONE, 2008, vol. 3, issue 5, e2124 1-13.

Patentee's Grounds of Appeal in EP Patent No. 1 033 996 dated Jul. 18, 2011.

PCT International Preliminary Report on Patentability (Chapter I) and Written Opinion Completed Dec. 22, 2008 for PCT/US2008/080370.

PCT/US2011/026365 International Preliminary Report on Patenability mailed Mar. 5, 2012.

PCT/US2011/026365 International Written Opinion and Search Report mailed Jul. 13, 2011.

PCT/US2011/033649 International Written Opinion and Search Report mailed Aug. 26, 2011.

Plant et al., "The Production of Amyloid β Peptide Is a Critical Requirement for the Viability of Central Neurons," *The Journal of Neuroscience*, 23(13):5531-5535, (2003).

Poduslo et al., "Macromolecular permeability across the blood-nerve and blood-brain barriers." *Proc. Natl. Acad. Sci USA*. vol. 91 pp. 5705-5709 (1994).

Raber, et al., "ApoE genotype accounts for the vast majority of AD risk and AD pathology" *Neurobiology of Aging*, 25:641-650 (2004).

Ramshaw et al., "DNA vaccines for the treatment of autoimmune disease," *Immunology and Cell Biology*, 75:409-413 (1997).

Ray. "Wyeth Study Finds Alzheimer's Drug Works in ApoE4 Non-Carriers". Poster 2008, [retrieved from the internet 16.06;.2011: <URL: http://elan2006.blogspot.com/2008/07/elan-wyeth-studfindalzheimerdrug.html>].

Robert et al., Engineered antibody intervention strategies for Alzheimer's disease and related dementias by targeting amyloid and toxic oligomers:, Protein Eng Des Sel. (2009) 22:(2):199-208.

Solomon et al., "Activity of monoclonal antibodies in prevention of in vitro aggregation of their antigens," abstract, *Immunotechnology*, 2(4):305 (1996).

Stern, et al. "Monoclonal Antibodies to a Synthetic Peptide Homologous with the First 28 Amino Acids of Alzheimer's Disease β-Protein Recognize Amyloid and Diverse Glial and Neuronal Cell Types in the Central Nervous System" *Am J of Pathology*, 134(5):973-978 (1989).

Takahashi, et al. "Monoclonal antibody to β peptide, recognizing amyloid deposits, neuronal cells and lipofuscin pigments in systemic organs", *Acta Neuropathol*, 85:159-166 (1993).

Tam, "Synthetic peptide vaccine design: synthesis and properties of a high-density multiple antigenic peptide system", Proc. Natl. Acad. Sci., 1988, vol. 85, pp. 5409-5413.

Van Dam et al., "Symptomatic effect of donepezil, rivastigmine, galantamine and memantine on cognitive deficits in the APP23 model" *Psychopharmacology* 180:177-190 (2005).

Van Noort, Multiple sclerosis: an altered immune response or an altered stress response?, *J Mol Med* 74:285-296 (1996).

Vanengelen, et al "Immunoglobulin treatment in human and experimental epilepsy" *J of Neuro* (1994); 57 (supplement):72-75.

Vastag, "Monoclonals expand into neural disorders" Nature 24:6 p. 595-596 (Jun. 2006).

Viswanathan et al., "Cerebral Microhemorrhage", *Stroke.*, 37:550-555 (2006).

Wang et al, "Site-specific UBITh amyloid-β vaccine for immunotherapy of Alzheimer's disease" *Vaccine* 25 (2007) 3041-3052.

Wehner, Declaration May 21, 2007.

Wiessner, et al "The Second-Generation Active Aβ Immunotherapy CAD106 Reduces Amyloid Accumulation in APP Transgenic Mice While Minimizing Potential Side Effects", *J. Neurosci.* 31(25):9323-9331 (2011).

Wikipedia entry for "Monoclonal antibody therapy" accessed on Sep. 22, 2011.

Wilcock, et al. "Deglycosylated anti-Amyloid-β Antibodies Eliminate Cognitive Deficits and Reduce Parenchymal Amyloid with Minimal Vascular Consequences in Aged Amyloid Precursor Protein Transgenic Mice" Neurobiology of Disease 26(20:5340-5346 (May 17, 2006).

Wisconsin Alumni Research Foundation, "Injection of Newborn Mice with Seven Chemical Adjuvants to Help Determine Their Safety in Use in Biologicals", U.S. Govt. Res. Develop. Rep., 70(24), 56 (1969).

Wu et al., "Saponin Adjuvant Enhancement of Antigen-Specific Immune Responses to an Experimental HIV-1 Vaccine" J of Immunology 149:1519-1525 (1992).

Zhao et al., "Macrophage-Mediated Degradation of β-Amyloid via an Apolipoprotein E Isoform-Dependent Mechanism", Neurobiology of disease (Mar. 18, 2009) 29(11):3603-3612.

Zlokovic et al., "Blood-Brain Barrier Transport of Circulating Alzheimer's Amyloid β." *Biochemical and Biophysical Research Communications*. vol. 197, No. 3, pp. 1034-1040 (1993).

Zotova et al., "Inflammation in Azheimer's disease: relevance to pathogenesis and therapy" Alzheimer's Research & Therapy 2:1 p. 2-9 (2010).

U.S. Appl. No. 11/842,085, Office Action mailed Sep. 30, 2009.
U.S. Appl. No. 11/842,116, Office Action mailed Nov. 26, 2010.
U.S. Appl. No. 12/037,045, Office Action mailed Apr. 28, 2010.
U.S. Appl. No. 12/181,238, Examiner Interview Summary mailed Mar. 5, 2010.
U.S. Appl. No. 12/253,929, Office Action mailed Apr. 28, 2010.
U.S. Appl. No. 12/336,340, Office Action mailed Mar. 4, 2010.
U.S. Appl. No. 12/608,869, Office Action mailed Oct. 25, 2011.
U.S. Appl. No. 12/738,396, Office Action mailed Feb. 13, 2012.
U.S. Appl. No. 12/977,013, Office Action mailed Jan. 6, 2012.
U.S. Appl. No. 10/429,216, Office Action mailed Mar. 12, 2010.
U.S. Appl. No. 10/429,216, Office Action mailed Sep. 15, 2010.
U.S. Appl. No. 10/544,093, Office Action mailed Jan. 22, 2010.
U.S. Appl. No. 10/858,855, Office Action mailed Dec. 15, 2009.
U.S. Appl. No. 11/245,524, Office Action mailed Dec. 10, 2010.
U.S. Appl. No. 11/245,916, Office Action mailed Feb. 14, 2011.
U.S. Appl. No. 11/245,916, Office Action mailed May 18, 2010.
U.S. Appl. No. 11/809,552, Office Action mailed Feb. 17, 2011.
U.S. Appl. No. 11/841,919, Office Action mailed Mar. 28, 2011.
U.S. Appl. No. 11/842,113, Office Action mailed Aug. 24, 2010.
U.S. Appl. No. 11/893,123, Office Action mailed May 11, 2011.
U.S. Appl. No. 12/106,206, Office Action mailed Jul. 9, 2010.
U.S. Appl. No. 60/530,480, filed Dec. 17, 2003, Arumugham.

Ecuadorian Search Report of Jul. 2, 2009 for Ecuador Patent Application No. SP 03-4685.

Mitchell et al, "Prevention of Intracerebral Hemorrhage," *Current Drug Targets*, 8(7):832-838 (2007).

Riechmann et al., "Reshaping Human Antibodies for Therapy," Nature, 332:323-327 (1988).

Hillen-Maske et al., "Konichalcit", *Rompp Chemie Lexilkon*, 9$^{th}$ edition, p. 2322 (1990).

Mutschler et al., "*Arzneimittel-Wirkungen, Lehrbuch der Pharmakologie und Taxiklogie,*" Wissenschftliche Verlagsgesellschaft mbH Stuttgart, 6$^{th}$ edition, pp. 651-656 (1991), (German Article).

Saido et al., "Autolytic Transition of μ-Calpain Upon Activation as Resolved by Antibodies Distinguishing Between the Pre- and Post-Autolysis Forms," J. Biochem., 111:81-86 (1992).

Sood et al., "Synthetic Peptides: A Modern Approach to Vaccination," *Indian Journal of Experimental Biology*, 34:849-861 (1998).

Buttini et al., "β-Amyloid Immunotherapy Prevents Synaptic Degeneration in a Mouse Model of Alzheimer's Disease," *The Journal of Neuroscience*, 25(40):9096-9101 (2005).

Golding et al., "Vaccine Strategies: Targeting Helper T Cell Responses," *Annals New York Academy of Sciences*, 31:126-137 (1995).

Borras-Cuesta et al., "Engineering of Immunogenic Peptides by Co-Linear Synthesis of Determinants Recognized by B and T Cells," Eur. J. Immunol., 17:1213-1215 (1987).

Ghetie et al., "CD4 Peptide-Protein Conjugates, But Not Recombinant Human CD4, Bind to Recombinant gp120 From the Human Immunodeficiency Virus in the Presence of Serum From AIDS Patients.," Proc. Natl. Acad. Sci., 88:5690-5693 (1991).

PCT Search Report of Oct. 9, 2008 for application PCT/US2008/060926.

PCT International Preliminary Report on Patentability (Chapter I) of Oct. 20, 2009 with Written Opinion of Oct. 3, 2008 for application PCT/US2008/060926.

PCT International Preliminary Report on Patentability (Chapter I) of Feb. 2, 2010 for application PCT/US07/09499.

Auclair et al., "Effect of Active Immunization Against Oestriadiol in Developing Ram Lambs on Plasma Gonadotrophin and Testosterone Concentrations, Time of Onset of Puberty and Testicular Blood Flow," *Journal of Reproduction and Fertility*, 104:7-16 (1995).

Black et al., "A Single Ascending Dose Study of Bainezumab, A Humanized Monoclonal Antibody to Aβ, In AD," 9$^{th}$ *International Geneva/Springfield Symposium on Advances in Alzheimer Therapy*, 1 page (Apr. 20, 2006). Abstract only.

Janeway et al., *Immunobiology*, 3$^{rd}$ edition, pp. 2:7, 2:9, 2:12, 8:16-8:17, 12:43 (1997).

Barelli et al., "Characterization of New Polyclonal Antibodies Specific for 40 and 42 Amino Acid-Long Amyloid β Peptides: Their Use to Examine the Cell Biology of Presenilins and the Immunohistochemistry of Sporadic Alzheimer's Disease and Cerebral Amyloid Angiopathy Cases," Molecular Medicine, 3(10):695-707 (1997).

Hellman et al., "Allergy Vaccines—A Review of Developments," *Clin. Immunother.*, 6(2):130-142 (Aug. 1996).

Kardana et al., "Serum HCG β-Core Fragment is Masked by Associated Macromolecules," *Journal of Clinical Endocrinology and Metabolism*, 71(5):1393-1395, 1990.

Koller et al., "Active Immunization of Mice with a Aβ-Hsp70 Vaccine," Neurodegenerative Disases, 1:20-28 (2004).

Check, "Nerve Inflamtion Halts Trail for Alzheimer's Drugs," Nature, 415:462 (2002).

Gauthier et al., "Alzheimer's Disease: Current Knowledge, Management and Research," Can. Med. Assoc. J., 157:1047-1052 (Oct. 15, 1997).

Huang et al., "Amyloid β-Peptide Possesses a Transforming Growth Factor-β-Activity," *The Journal of Biological Chemistry*, 273(42):27640-27644 (Oct. 16, 1998).

Tahtinen et al., "Minimal Size of HIV-1 NEF Antigenic Epitopes Reconzied by Human Sera," Int. Conf. AIDS Jun. 16-21, 1991, Published Jun. 1991, abstract No. W.A. 1334.

Jarrett et al., "The Carboxy Terminus of the β Amyloid Protein is Critical for the Seeding of Amyloid Formation: Implications for the Pathogenesis of Alzheimer's Disease," *Biochemistry*, 32:4693-4697 (Nov. 5, 1993).

Welling et al., "Choice of Peptide and Peptide Length for the Generation of Antibodies Reactive With the Intact Protein," *FEBS Letters*, 182(1):81-84 (Mar. 1985).

Agadjanyan et al., "Prototype Alzheimer's Disease Vaccine Using the Immunodominant B Cell Epitope From {beta}-Amyloid and Promiscuous T Cell Epitope Pan HLA DR-Binding Peptide," *J. Immunol.*, 174:1580-1586 (2005).

Novartis, "Novartis MF59™—Adjuvanted Influenza Vaccine (Fluad®) Significantly Reduces Hospitalization in Elderly," Novartis Press Release, Oct. 19, 2007.

Donnelly, "New Developments in Adjuvants," *Mechanism of Ageing and Development*, 93:171-177 (1997).

Jennings, "Review of Selected Adjuvants Used in Antibody Production," *ILAR Journal*, 37(3)(1995).

Bandlow et al., "Untersuchungen Zum Mechanismus Der Immunologischen Adjvanswirung des Vacciniavirus[1],"*Archiv für due gesamte Virusfoschung*, 38:192-204 (1972). German article.

Khan et al., "Immunopotentiation and Delivery Systems for Antigens for Single-Step Immunization: Recent Trends and Progress," *Pharmaceutical Research*, 11(1):2-11 (1994).

Hamilton, "Molecular Engineering: Applications to the Clinical Laboratory," *Clin. Chem.* 39(9):1988-1997 (1993).

Sheehan et al., "The Utilization of Individual $V_H$ Exons in the Primary Repertoire of Adult BALB/c Mice[1]," *The Journal of Immunology*, 151(10):5364-5375 (Nov. 15, 1993).

Hermanson et al., "Amino Acids as Spacers," *Immobilized Affinity Ligand Techniques*, section 3.1.1.5:150-152 (1992).

Harlow et al., eds., *Antibodies: A Laboratory Manual*, pp. 139-195 (1988).

Hudson et al., "Antibody as a Probe," *Practical Immunology*, Chapter 2, pp. 34-85 (1989).

Begley, "Delivery of Therapeutic Agents to the Central Nervouse System: The Problems and the Possibilities," *Pharmacol. Therapy*, 104(1): 29-45 (Oct. 2004).

Misra et al., "Drug Delivery to the Central Nervous System: A review," *J. Pharm Pharm Sci.*, 6(2):252-273 (May 2003). Abstract.

Kallberg et al., "Prediction of Amyloid Fibril-Forming Proteins," *The Journal of Biological Chemistry*, 276(16):12945-12950 (Apr. 20, 2001).

Genbank Accession No. AAB35009.1, Wang et al., "Antiidiotypic Ig 1F7 Light Chain Variable Region [Human, 1F7 Hybridoma Cells, Peptide Partial, 120aa]," Oct. 28, 1995.

Genbank Accession No. AAD00856.1, "Igm Heavy Chain Variable Region [*Homo sapiens*]," Jul. 31, 2001.

Saido et al., "Amino-and-Carboxyl-Terminal Heterogeneity of β-Amyloid Peptides Deposited in Human Brain," Neuroscience Letters, 215:173-176 (Aug. 8, 1996).

*Stedman's Medical Dictionary*, 27th Edition, "Vaccine," p. 1922, lines 1-3 (2000).

Kinnecom et al., "Course of Cerebral Amyloid Angiopathy? Related Inflation," *Neurology*, 68(17)1411-1416 (2007).

Kofke et al., "Remifentanil-Induced Cerebral Blood Flow Effects in Normal Humans: Dose and ApoE genotype," *Neurosurg Anesthes Neurosci.*, 105(1):167-175 (2007).

PCT Written Opinion of Mar. 8, 2009 for application PCT/US2008/80382.

PCT Search Report of Mar. 25, 2009 for application PCT/US2008/80382.

Aylward et al., "Cerebellar Volume in Adults With Down Syndrome," *Arch Neurol.*, 4(2):209-212 (1997). Abstract only.

Holm et al., "Functional Mapping and Single Chain Construction of the Anti-Cytokeratin 8 Monoclonal Antibody TS1," *Mol. Immunol.*, 44(6):1075-1084 (Feb. 2007).

U.S. Appl. No. 12/608,869, Advisory Action mailed Mar. 13, 2013.
U.S. Appl. No. 12/608,869, Office Action mailed Aug. 23, 2012.
U.S. Appl. No. 12/738,396, Office Action mailed Apr. 16, 2013.
U.S. Appl. No. 12/977,013, Office Action mailed Sep. 14, 2012.

Abbott, et al., "Transporting therapeutics across the blood-brain barrier" *Molecular Medicine Today*, pp. 106-113, Mar. 1996.

Arriagada, et al., "Neurofibrillary tangles but not senile plaques parallel duration and severity of Alzheimer's disease", *Neurology*, 42:631-639 (1992).

Castillo, "Poor results halt production, studies on promising Alzheimer's drug bapineuzumab" *CBS Interactive Inc.*, Nov. 7, 2012 pp. 1/1.

Centers for Disease Control and Prevention, "Vaccine Safety" Retrieved from www.cdc.gov/vaccinesafety/concerns/adjuants.html (Oct. 18, 2012) pp. 1-2.

Check, "Nerve inflammation halts trial for Alzheimer's drug", *Nature*, vol. 415:462 Jan. 2002.

Curriculum Vitae Professor Nancy Joan Abbott, Mar. 2013.

Deane, et al. "IgG-Assisted Age-Dependent Clearance of Alzheimer's Amyloid β Peptide by the Blood-Brain Barrier Neonatal Fc Receptor" *The Journal of Neuroscience*, Dec. 14, 2005 25(50):11495-11503.

Declaration of Georg Friedrich Melchers with CV and list of publications Apr. 6, 2013.

Declaration of Professor Nancy Joan Abbott, Apr. 8, 2013.

Dohi et al., "Reactivity of a Mouse/Human Chimeric Anti-GM2 Antibody KM966 with Brain Tumors" *Anticancer Research*, 14:2577-2582 (1994).

Eli Lilly, "Eli Lilly and Company Announces Top-Line Results on Solanezumab Phase 3 Clinical Trials in Patients with Alzheimer's Disease" Press Release, Aug. 24, 2012.

EP 1160256 B2 Response to Notice of Opposition Jan. 19, 2009.

Extract from EPO patent register of EP1842859 Communication under Rule 71(3) Mar. 28, 2013.

Extract from EPO patent register of EP1842859 Decision to Grant Mar. 28, 2012.

Farlow, et al., "Safety and biomarker effects of solanezumab in patients with Alzheimer's disease" *Alzheimer's & Dementia*, 8:261-271 (2012).

Geeraedts et al., "Superior Immunogenicity of Inactivated Whole Virus H5N1 Influenza Vaccine is Primarily Controlled by Toll-like Receptors Signalling", *PLoS Pathogens*, 2008, 4:1-8.

Gerald, et al., "Alzheimer's disease market: hope deferred", *Nature*, vol. 12:Jan. 19-20, 2013.

Gluck et al., "Immunopotentiating Reconstituted Influenza Virus Virosome Vaccine Delivery System for Immunization against Hepatitis A", *J. Clin. Invest.*,(1992) vol. 90:2491-2495.

Gluck, "Immunopotentiating reconstituted influenza virosomes (IRIVs) and other adjuvants for improved presentation of small antigens", *Vaccine*, vol. 10, Issue 13 (1992) 915-919.

Hagen, Declaration Oct. 31, 2011.

Janeway et al., Immunobiology, 3rd edition, pp. 8:32-8:36 (1997).

Johnson & Johnson, "Johnson & Johnson Announces Discontinuation of Phase 3 Development of Bapineuzumab Intravenous (IV) in Mild-to-Moderate Alzheimer's Disease", Press Release, Aug. 6, 2012.

Karran, "Current status of vaccination therapies in Alzheimer's disease" *Journal of Neurochemistry*, 123:647-651 (2012).

Kerchner, et al., "Bapineuzumab", NIH Public Access, Expert Opin Biol Ther., 10(7) 1121-1130 Jul. 2010.

Laino, "Cerebral Edema Common, but Found to Be Manageable, With Bapineuzumab", *Neurology Today*, Aug. 19, 2011.

Lee et al., "Aspects of Immunobiology and Immunotherapy and Uses of Monoclonal Antibodies and Biologic Immune Modifiers in Human Gliomas" *Neurologic Clinics*, vol. 3, No. 4, Nov. 1985, 901-917.

Lemere et al., "Amyloid-Beta Immunotherapy for the Prevention and Treatment of Alzheimer Disease: Lessons from Mice, Monkeys, and Humans", Rejuvenation Research 9(1):77-84 (2006).

Lu, "In Vitro Binding Analysis of LY2062430: Surface Plasmon Resonance and FACS Analysis" Report: bTDR185 Eli Lilly and Company Apr. 2012.

Marx et al., "The Possible Role of the Immune System in Alzheimer's Disease" *Exp Gerontology*, vol. 33, Nos. 7/8 pp. 871-881, 1998.

Miller et al., "Comparative efficacy of two immunocontraceptive vaccines" *Vaccine*, (1997) 15(17-18):1858-1862 (abstract only).

Oh, et al., "Reversible leukoencephalopathy associated with cerebral amyloid angiopathy", *Neurology*, 62 (Feb. 2004) 494-497.

Orgogozo, et al., "Subacute meningoencephalitis in a subset of patients with AD after Aβ42 immunization" *Neurology*, 61:46-54 (2003).

Pfizer Announces Co-Primary Clinical Endpoints Not Met in Second Phase 3 Bapineuzumab Study in Mild-to-Moderate Alzheimer's Disease Patients Who Do Not Carry the Apoe4 Genotype, Press Release, Aug. 6, 2012.

Pfizer Halts Development of AB Antibody, Alzheimer Research Forum, Nov. 2, 2011.

Pfizer, "Pfizer Announces Topline Results of First of Four Studies in Bapineuzumab Phase 3 Program", Press Release, Jul. 23, 2012.
Remes et al., "Hereditary dementia with intracerevbral hemorrhages and cerebral amyloid angiopathy". *Neurology* 63(2):234-240 (2004).
Rieber, et al., "The Effect of Freund's Adjuvants on Blood-Cerebrospinal Fluid Barrier Permeability" *Journal of the Neurological Sciences*, 63:55-61 (1984).
Rivero et al., "Suppression of experimental autoimmune encephalomyelitis (EAE) by intraperitoneal administration of soluble myelin antigens in Wistar rats" *J. Neuroimmunology*, (1997) 72, 3-10.
Roitt, Extracts from Roitt's Essential Immunology, Ninth Edition, (1997).
Solomon, "Alzheimer's Disease and Immunotherapy", *Current Alzheimer Research*, 2004, 1, 149-163.
Solomon, "Beta-Amyloid-Based Immunotherapy as a Treatment of Alzheimer's Disease", *Drugs of Today*, 2007, 43(5):333-342.
Spack, "Antigen-specific therapies for the treatment of multiple sclerosis: a clinical trial update", *Exp. Opin. Invest. Drugs*, (1997) 6(11):1715-1727.
Sperling, et al., "Amyloid-related imaging abnormalities in amyloid-modifying therapeutic trials: Recommendations from the Alzheimer's Association Research Roundtable Workgroup" *Alzheimer's & Dementia*, 7 (2011) 397-385.
Thompson, et al., "Laboratory investigation of cerebrospinal fluid proteins" *Ann Clin. Biochem*, 27:425-435 (1990).
Triguero, et al., "Blood-brain barrier transport of cationized immunoglobulin G: Enhanced delivery compared to native protein" *Proc. Natl. Acad. Sci. USA*, vol. 86:4761-4765 Jun. 1989.
Triozzi et al., "Effects of a beta-human chorionic gonadotropin subunit immunogen administered in aqueous solution with a novel nonionic block copolymer adjuvant in patients with advanced cancer", *Clin. Cancer Res.*, (1997) 3(12 pt 1):2355-2362 (abstract only).
Trojano, et al., "Serum IgG to brain microvascular endothelial cells in multiple sclerosis" *Journal of the Neurological Sciences*, 143:107-113 (1996).
Tuomanen, et al., "Reversible opening of the blood-brain barrier by anti-bacterial antibodies" *Proc. Natl. Acad. Sci. USA*, vol. 90:7824-7828 (Aug. 1993).
Walls, et al., "Autoantibody responses in the cerebrospinal fluid of guinea pigs with chronic relapsing experimental allergic encephalomyelitis", *Acta Neruol. Scan.*, 78:422-428 (1988).
Wick et al., "The Aging Immune System: Primary and Secondary Alterations of Immune Reactivity in the Elderly" *Exp. Geronology*, vol. 32, Nos. 4/5, pp. 401-413, 1997.
Wilcock, et al. "Passive Amyloid Immunotherapy Clears Amyloid and Transiently Activates Microglia in a Transgenic Mouse Model of Amyloid Deposition" *The Journal of Neuroscience*, Jul. 7, 2004 24(27):6144-6151.
Wilcock, et al., "Number of AB Inoculations in APP+PSI Transgenic Mice Influences Antibody Titers, Microglial Activation, and Congophilic Plaque Levels" *DNA and Celll Biology*, vol. 20 No. 11:731-736 (2001).
U.S. Appl. No. 12/297,636, Office Action mailed Oct. 15, 2012.
U.S. Appl. No. 13/076,379, Office Action mailed Nov. 28, 2012.
U.S. Appl. No. 13/123,898, Office Action mailed Jul. 20, 2012.
U.S. Appl. No. 13/271,081, Office Action mailed Mar. 1, 2013.
U.S. Appl. No. 10/923,471, Office Action mailed Apr. 23, 2013.
U.S. Appl. No. 12/738,396, Office Action mailed Sep. 21, 2012.
U.S. Appl. No. 13/123,898, Office Action mailed Apr. 17, 2013.
U.S. Appl. No. 11/304,986, Notice of Allowance mailed Jul. 10, 2009.
U.S. Appl. No. 11/707,639, Notice of Allowance mailed Aug. 20, 2009.
U.S. Appl. No. 09/724,319, Advisory Action mailed Oct. 28, 2009.
U.S. Appl. No. 09/724,319, Office Action mailed Dec. 21, 2010.
U.S. Appl. No. 09/724,495, Advisory Action mailed May 16, 2006.
U.S. Appl. No. 10/429,216, Office Action mailed May 24, 2011.
U.S. Appl. No. 10/544,093, Office Action mailed Oct. 13, 2010.
U.S. Appl. No. 10/777,792, Advisory Action mailed Mar. 6, 2009.
U.S. Appl. No. 10/923,471, Office Action mailed Dec. 24, 2009.
U.S. Appl. No. 11/245,524, Office Action mailed Nov. 20, 2009.
U.S. Appl. No. 11/664,865, Office Action mailed Feb. 11, 2011.
U.S. Appl. No. 11/842,042, Office Action mailed Mar. 30, 2010.
U.S. Appl. No. 12/037,045, Office Action mailed Nov. 4, 2011.
U.S. Appl. No. 09/322,289, Notice of Allowance mailed Nov. 15, 2010.
U.S. Appl. No. 10/858,855, Notice of Allowance mailed Jul. 12, 2010.
U.S. Appl. No. 10/923,469, Notice of Allowance mailed Jun. 1, 2011.
U.S. Appl. No. 11/842,023, Notice of Allowance mailed Oct. 6, 2010.
U.S. Appl. No. 11/893,123, Notice of Allowance mailed Nov. 2, 2011.
U.S. Appl. No. 12/181,238, Notice of Allowance mailed Mar. 5, 2010.
U.S. Appl. No. 12/181,238, Notice of Allowance mailed Mar. 11, 2011.
U.S. Appl. No. 09/723,765, BPAI Decision on Request for Re-Hearing mailed Oct. 16, 2007.
U.S. Appl. No. 09/723,765, BPAI Order Returning Appeal to Examiner mailed Jun. 27, 2006.
U.S. Appl. No. 09/723,765, Examiner's Answer mailed Jan. 25, 2006.
U.S. Appl. No. 09/723,765, Reply Brief Noted mailed Jun. 16, 2006.
U.S. Appl. No. 10/777,792, BPAI Decision mailed Aug. 30, 2010.
U.S. Appl. No. 10/777,792, BPAI Decision on Request for Reconsideration mailed Nov. 30, 2010.
U.S. Appl. No. 10/777,792, Examiner's Answer mailed Oct. 27, 2009.
U.S. Appl. No. 10/777,792, Reply Brief Noted mailed Jan. 11, 2010.
U.S. Appl. No. 10/923,469, BPAI Decision mailed Feb. 22, 2011.
U.S. Appl. No. 10/923,469, Reply Brief Noted mailed Mar. 9, 2010.
Annual Report of Johnson and Johnson pp. 1-6 (2012).
Barbour, et al., Presentation of "Efficacy and Neuropathology of Passively Administered N-Terminal and Midregion Anti-Abeta Antibodies Alone and In Combination in the PDAPP Mouse" *Elan Report* pp. 1-99, May 2007.
Claim No. HC11 003400 in the High Court of Justice, Chancery Division,. Patents Court, Between: Eli Lilly and Company (Claimant) and Janssen Alzheimer Immunotherapy (Defendant), Approved Judgment, Jun. 25, 2013.
Declaration of Dr. Michael John Owen with CV and list of publications, May 10, 2013.
EP 1 994 937 Decision of Oral Proceedings from EPO Opposition Division, Jul. 24, 2013.
Hyslop et al., "Antibody Clears Senile Plaques" *Nature*, vol. 400, Jul. 8, 1999, pp. 116-117.
Jacobsen, et al., "Reversal of CM Deficits: A) 2nd Generation of mAbs to central AB epitopes B) PSAPP (18 mo) by 12A11 hv. 1. 0 & m266", *Wyeth Presentation*, Apr. 27, 2004.
Janeway, at al., *Basic Concepts in In-arnonology*: pp. 1:21-1:13 and 8:1-8:2 (1997).
Sperling, at al., Presentation and Transcript of "Bapineuzumab Phase 3 trials in mild to moderate Alzheimer's disease dementia in apolipoprotein E є4 carriers (Study 302) and non-carriers (Study 301)", *American Neurological Association*, Oct. 8, 2012.

\* cited by examiner

CORTEX

| PBS CONTROL | | UNTREATED CONTROL | |
|---|---|---|---|
| 624-165 | 272 | 764-181 | 3470 |
| 625-166 | 1802 | 785-182 | 171 |
| 626-167 | 62 | 766-183 | 91 |
| 633-168 | 4696 | 767-184 | 6692 |
| 634-169 | 3090 | 768-185 | 1353 |
| 671-170 | 2417 | 771-186 | 1153 |
| 672-171 | 2840 | 772-187 | 3800 |
| 829-172 | 3320 | 780-188 | 3740 |
| 830-173 | 1833 | 843-189 | 163 |
| 831-174 | 416 | 844-190 | 122 |
| 792-175 | 126 | 845-191 | 427 |
| 793-176 | 2559 | 846-192 | 2674 |
| 794-177 | 289 | 887-193 | 453 |
| 732-178 | 179 | 888-194 | 2996 |
| 733-179 | 1329 | 889-195 | 1075 |
| 734-180 | 5665 | | |
| MEDIAN p VALUE (M-W) | 1817 | MEDIAN p VALUE (M-W) | 1153 |
| MEAN | 1931 | MEAN | 1825 |
| ST. DEV. | 1718 | ST. DEV. | 1769 |
| % CV | 89 | % CV | 97 |
| p VALUE (t TEST) | n=16 | p VALUE (t TEST) | n=15 |

FIG. 15A

CORTEX

| 2 mg ALUM 100 μg AN1528 | | 50 μg ALUM 100 μg AN1528 | |
|---|---|---|---|
| 660-083 | 295 | 643-105 | 385 |
| 661-084 | 3180 | 644-106 | 2640 |
| 662-085 | 2480 | 645-107 | 2403 |
| 633-086 | 3014 | 654-108 | 1741 |
| 664-087 | 5870 | 655-109 | 3053 |
| 665-088 | 5978 | 656-110 | 5990 |
| 693-089 | 1620 | 678-111 | 3360 |
| 694-090 | 35 | 679-112 | 1230 |
| 695-091 | 3400 | 704-114 | 2680 |
| 697-092 | 2630 | 705-115 | 78 |
| 698-093 | 983 | 706-116 | 1290 |
| 699-094 | 5327 | 729-117 | 3180 |
| 701-095 | 1862 | 730-118 | 1833 |
| 702-096 | 1849 | 731-119 | 4590 |
| 703-097 | 2239 | 736-120 | 1112 |
| 739-098 | 806 | 737-121 | 1653 |
| 740-099 | 5303 | 757-122 | 992 |
| 741-100 | 459 | 758-123 | 4692 |
| 800-103 | 154 | 808-124 | 785 |
| 801-104 | 852 | 809-125 | 244 |
|  |  | 810-126 | 32 |
| MEDIAN p VALUE (M-W) | 2051 | MEDIAN p VALUE (M-W) | 1741 |
| MEAN ST. DEV. % CV p VALUE (t TEST) | 2407 1913 79 n=20 | MEAN ST. DEV. % CV p VALUE (t TEST) | 2140 1659 78 n=21 |

FIG. 15B

CORTEX

| 25 μg QS21 100 μg AN1528 | | CFA/IFA 100 μg AN1792 | |
|---|---|---|---|
| 615-128 | 1257 | 539-068 | 693 |
| 616-129 | 361 | 640-069 | 508 |
| 617-130 | 1008 | 641-070 | 440 |
| 536-131 | 3290 | 642-071 | 467 |
| 637-132 | 2520 | 690-072 | 42 |
| 638-133 | 3880 | 691-073 | 2491 |
| 744-134 | 627 | 692-074 | 121 |
| 745-135 | 58 | 795-075 | 137 |
| 746-136 | 2610 | 796-076 | 822 |
| 747-137 | 1509 | 797-077 | 475 |
| 769-138 | 1788 | 748-087 | 600 |
| 770-139 | 988 | 749-079 | 78 |
| 773-140 | 1199 | 750-080 | 1267 |
| 774-141 | 339 | 751-081 | 1351 |
| 775-142 | 402 | 761-082 | 69 |
| 776-143 | 537 | | |
| 840-144 | 1119 | | |
| 841-145 | 194 | | |
| 821-146 | 1259 | | |
| 822-147 | 5413 | | |
| 823-148 | 2233 | | |
| MEDIAN p VALUE (M-W) | 1199 | MEDIAN p VALUE (M-W) | 475 0.0481 |
| MEAN ST. DEV. % CV p VALUE (t TEST) | 1552 1364 88 n=21 | MEAN ST. DEV. % CV p VALUE (t TEST) | 637 655 103 0.0106 n=15 |

FIG. 15C

CORTEX

| 5 μg THIMEROSAL/PBS 10 μg AN1792 | | 2 mg ALUM 100 μg AN1792 | |
|---|---|---|---|
| 635-149 | 1337 | 610-001 | 432 |
| 669-150 | 4644 | 611-002 | 1012 |
| 670-151 | 6335 | 612-003 | 3607 |
| 673-152 | 3700 | 613-004 | 508 |
| 674-153 | 2750 | 620-005 | 465 |
| 676-154 | 1687 | 621-006 | 16 |
| 681-156 | 185 | 622-007 | 28 |
| 682-157 | 8031 | 623-008 | 217 |
| 683-158 | 3450 | 708-009 | 2738 |
| 754-159 | 157 | 709-010 | 927 |
| 755-160 | 6857 | 710-011 | 1609 |
| 756-161 | 482 | 716-012 | 1608 |
| 805-162 | 524 | 784-014 | 3890 |
| 806-163 | 397 | 785-015 | 1614 |
| 807-164 | 234 | 786-018 | 285 |
| | | 787-017 | 3102 |
| | | 788-018 | 1617 |
| | | 789-019 | 1474 |
| | | 815-020 | 424 |
| | | 816-021 | 1375 |
| | | 817-022 | 2323 |
| MEDIAN p VALUE (M-W) | 1687 | MEDIAN p VALUE (M-W) | 1375 0.5000 |
| MEAN ST. DEV. % CV p VALUE (t TEST) | 2718 2685 99 n=15 | MEAN ST. DEV. % CV p VALUE (t TEST) | 1394 1166 84 0.2650 n=21 |

FIG. 15D

CORTEX

| 50 µg MPL<br>100 µg AN1792 | | 25 µg QS21<br>100 µg AN1792 | |
|---|---|---|---|
| 646-023 | 2002 | 627-045 | 91 |
| 647-024 | 147 | 628-046 | 3397 |
| 648-025 | 1304 | 631-049 | 3702 |
| 649-026 | 34 | 632-050 | 1776 |
| 650-027 | 980 | 667-052 | 1832 |
| 724-028 | 1282 | 668-053 | 3023 |
| 726-030 | 1966 | 686-054 | 189 |
| 727-031 | 733 | 687-055 | 891 |
| 720-032 | 2563 | 688-056 | 240 |
| 721-033 | 5563 | 689-057 | 110 |
| 802-034 | 113 | 712-059 | 3311 |
| 803-035 | 671 | 825-061 | 1009 |
| 804-036 | 51 | 826-082 | 18165 |
| 811-037 | 613 | 827-063 | 73 |
| 812-038 | 332 | 828-064 | 78 |
| 813-039 | 1454 | 837-065 | 1051 |
| 814-040 | 2441 | 838-066 | 270 |
| 833-014 | 742 | 839-067 | 371 |
| 834-042 | 40 | | |
| 836-044 | 807 | | |
| MEDIAN | 774 | MEDIAN | 950 |
| p VALUE (M-W) | 0.1710 | p VALUE (M-W) | 0.4076 |
| MEAN | 1192 | MEAN | 2199 |
| ST. DEV. | 1299 | ST. DEV. | 4187 |
| % CV | 109 | % CV | 190 |
| p VALUE (t TEST) | 0.1506 | p VALUE (t TEST) | 0.8131 |
| | n=21 | | n=18 |

FIG. 15E

SEQUENCE LISTING

<160> NUMBER OF SEQ ID NOS: 5

<210> SEQ ID NO 1
<211> LENGTH: 42
<212> TYPE: PRT
<213> ORGANISM: Homo sapiens

```
<220> FEATURE:
<223> OTHER INFORMATION: human Abeta42 beta-amyloid peptide

<400> SEQUENCE: 1

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
             20                  25                  30

Gly Leu Met Val Gly Gly Val Val Ile Ala
         35                  40

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence:Abeta1-12
      peptide with carboxyl terminal Cys residue
      inserted

<400> SEQUENCE: 2

Asp Ala Glu Phe Arg His Asp Ser Gly Tyr Glu Val Cys
 1               5                  10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:Abeta1-5
      peptide with carboxyl terminal Cys residue
      inserted

<400> SEQUENCE: 3

Asp Ala Glu Phe Arg Cys
 1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence:Abeta33-42
      peptide with carboxyl terminal Cys residue
      inserted
<220> FEATURE:
<221> NAME/KEY: MOD_RES
<222> LOCATION: (2)
<223> OTHER INFORMATION: Xaa = amino hepatanoic acid

<400> SEQUENCE: 4

Cys Xaa Gly Leu Met Val Gly Gly Val Val Ile Ala
 1               5                  10

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence:Abeta13-28
      peptide with carboxyl terminal Cys residue
      inserted and two added Gly residues
```

```
<220> FEATURE:
<221> NAME/KEY: MOD_RES
<222> LOCATION: (1)
<223> OTHER INFORMATION: Xaa = acetyl histidine

<400> SEQUENCE: 5

Xaa His Gln Lys Leu Val Phe Phe Ala Glu Asp Val Gly Ser Asn Lys
 1               5                  10                  15

Gly Gly Cys
```

PREVENTION AND TREATMENT OF AMYLOIDOGENIC DISEASE

CROSS-REFERENCES TO RELATED APPLICATIONS

This application is a divisional of U.S. application Ser. No. 09/724,319, filed Nov. 27, 2000, which is a continuation of U.S. application Ser. No. 09/322,289, filed May 28, 1999, which is a continuation-in-part of U.S. application Ser. No. 09/201,430, filed Nov. 30, 1998, which claims the benefit under 35 U.S.C. 119(e) of U.S. Application No. 60/080,970, filed Apr. 7, 1998, and U.S. Application 60/067,740, filed Dec. 2, 1997, all of which are incorporated by reference in their entirety for all purposes.

TECHNICAL FIELD

The invention resides in the technical fields of immunology and medicine.

BACKGROUND OF THE INVENTION

Alzheimer's disease (AD) is a progressive disease resulting in senile dementia. See generally Selkoe, *TINS* 16, 403-409 (1993); Hardy et al., WO 92/13069; Selkoe, *J. Neuropathol. Exp. Neurol.* 53, 438-447 (1994); Duff et al., *Nature* 373, 476-477 (1995); Games et al., *Nature* 373, 523 (1995). Broadly speaking the disease falls into two categories: late onset, which occurs in old age (65+ years) and early onset, which develops well before the senile period, i.e, between 35 and 60 years. In both types of disease, the pathology is the same but the abnormalities tend to be more severe and widespread in cases beginning at an earlier age. The disease is characterized by at least two types of lesions in the brain, senile plaques and neurofibrillary tangles. Senile plaques are areas of disorganized neuropil up to 150 μm across with extracellular amyloid deposits at the center visible by microscopic analysis of sections of brain tissue. Neurofibrillary tangles are intracellular deposits of microtubule associated tau protein consisting of two filaments twisted about each other in pairs.

The principal constituent of the plaques is a peptide termed Aβ or β-amyloid peptide. Aβ peptide is an internal fragment of 39-43 amino acids of a precursor protein termed amyloid precursor protein (APP). Several mutations within the APP protein have been correlated with the presence of Alzheimer's disease. See, e.g., Goate et al., *Nature* 349, 704) (1991) (valine$^{717}$ to isoleucine); Chartier Harlan et al. *Nature* 353, 844 (1991)) (valine$^{717}$ to glycine); Murrell et al., *Science* 254, 97 (1991) (valine$^{717}$ to phenylalanine); Mullan et al., *Nature Genet.* 1, 345 (1992) (a double mutation changing lysine$^{595}$-methionine$^{596}$ to asparagine$^{595}$-leucine$^{596}$). Such mutations are thought to cause Alzheimer's disease by increased or altered processing of APP to Aβ, particularly processing of APP to increased amounts of the long form of Aβ (i.e., Aβ1-42 and Aβ1-43). Mutations in other genes, such as the presenilin genes, PS1 and PS2, are thought indirectly to affect processing of APP to generate increased amounts of long form Aβ (see Hardy, *TINS* 20, 154 (1997)). These observations indicate that Aβ, and particularly its long form, is a causative element in Alzheimer's disease.

McMichael, EP 526,511, proposes administration of homeopathic dosages (less than or equal to $10^{-2}$ mg/day) of Aβ to patients with preestablished AD. In a typical human with about 5 liters of plasma, even the upper limit of this dosage would be expected to generate a concentration of no more than 2 pg/ml. The normal concentration of Aβ in human plasma is typically in the range of 50-200 pg/ml (Seubert et al., *Nature* 359, 325-327 (1992)). Because EP 526,511's proposed dosage would barely alter the level of endogenous circulating Aβ and because EP 526,511 does not recommend use of an adjuvant, as an immunostimulant, it seems implausible that any therapeutic benefit would result.

By contrast, the present invention is directed inter alia to treatment of Alzheimer's and other amyloidogenic diseases by administration of Aβ, other active immunogen or antibody to Aβ to a patient under conditions that generate a beneficial immune response in the patient. The invention thus fulfills a longstanding need for therapeutic regimes for preventing or ameliorating the neuropathology and, in some patients, the cognitive impairment associated with Alzheimer's disease.

SUMMARY OF THE CLAIMED INVENTION

In one aspect, the invention provides methods of preventing or treating a disease characterized by amyloid deposit in a patient. Such methods entail administering an effective dosage of an antibody that specifically binds to the amyloid deposit or a component thereof to the patient. Such methods are particularly useful for preventing or treating Alzheimer's disease in which case the amyloid deposit is Aβ. The methods can be used on both asymptomatic patients and those currently showing symptoms of disease.

The antibody used in such methods can be a human, humanized, chimeric or nonhuman antibody and can be monoclonal or polyclonal. In some methods, the antibody is prepared from a human immunized with Aβ peptide, which human can be the patient to be treated with antibody.

In some methods, the antibody used binds to an epitope within residues 1-28 of Aβ. In some methods the antibody binds to an epitope within residues 1-10, and in some methods within residues 1-5. In some methods, the antibody specifically binds to Aβ peptide without binding to full-length amyloid precursor protein (APP).

In some methods antibody is administered at a dosage of at least 1 mg/kg body weight antibody. In some methods, the antibody is administered in multiple dosages over a period of at least six months. In some methods, the antibody is administered as a sustained release composition. The antibody can be administered, for example, intraperitoneally, orally, subcutaneously, intracranially, intramuscularly, topically or intravenously.

In some methods, the antibody is administered by administering a polynucleotide encoding at least one antibody chain to the patient. The polynucleotide is expressed to produce the antibody chain in the patient. Optionally, the polynucleotide encodes heavy and light chains of the antibody. The polynucleotide is expressed to produce the heavy and light chains in the patient.

In some methods, the patient is monitored for level of administered antibody in the blood of the patient.

In another aspect, the invention provides methods of preventing or treating Alzheimer's disease. These methods entail administering an effective dosage of a polypeptide comprising an active fragment of Aβ that induces an immune response to Aβ in the patient. In some methods, the fragment comprises an epitope within amino acids 1-12 of Aβ. In some method, the fragment comprises an epitope within amino acids 1-16 of Aβ. In some methods, the fragment comprises an epitope within amino acids 13-28 of Aβ. In some methods, the fragment is free of at least the 5 C-terminal amino acids in Aβ43. In some methods, the fragment comprises up to 20 contiguous amino acids from Aβ. Fragments are typically administered at greater than 10 micrograms per dose per patient.

In some methods, the fragment is administered with an adjuvant that enhances the immune response to the Aβ peptide. The adjuvant and fragment can be administered in either order of together as a composition. The adjuvant can be, for example, alum, MPL, QS-21 or incomplete Freund's adjuvant.

The invention further provides pharmaceutical compositions comprising active fragments of Aβ, such as described above, and an adjuvant.

The invention further provides methods of screening an antibody to Aβ or an active fragment of Aβ for use in treatment of Alzheimer's disease. Such methods entail administering an antibody that specifically binds to Aβ or a fragment of Aβ to a transgenic animal disposed to develop characteristics of Alzheimer's disease. One then detects a reduction in the extent or rate of development of the characteristics relative to a control transgenic animal as a measure of the efficacy of the antibody or fragment. Optionally, antibodies can also be screened for capacity to bind an epitope within amino acids 1-28 or other epitope of Aβ.

BRIEF DESCRIPTION OF THE DRAWINGS

FIGS. 15A-E: Aβ levels in the cortex of 12-month old PDAPP mice treated with AN1792 or AN1528 in combination with different adjuvants. The Aβ level for individual mice in each treatment group, and the median, mean, and p values for each treatment group are shown.

FIG. 15A: The values for mice for the PBS-treated control group and the untreated control group.

FIG. 15B: The values for mice in the AN1528/alum and AN1528/MPL-treatment groups.

FIG. 15C: The values for mice in the AN1528/QS21 and AN1792/Freund's adjuvant treatment groups.

FIG. 15D: The values for mice in the AN1792/Thimerosol and AN1792/alum treatment groups.

FIG. 15E: The values for mice in the AN1792/MPL and AN1792/QS21 treatment groups.

DEFINITIONS

Figure 1:
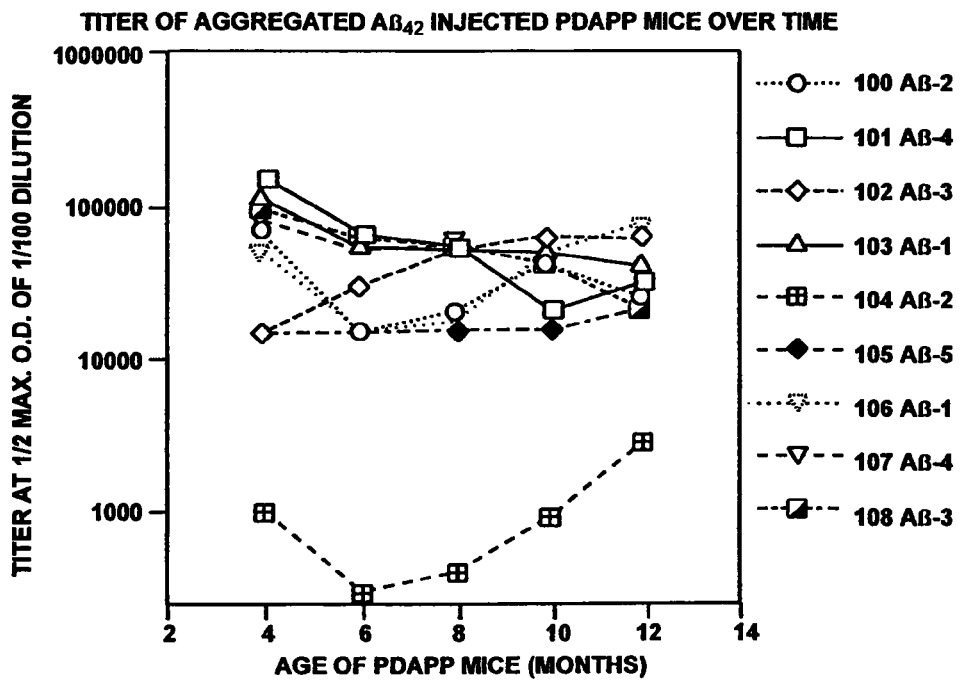
FIG. 1: Antibody titer after injection of transgenic mice with Aβ1-42.

The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). One example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. Typically, default program parameters can be used to perform the sequence comparison, although customized parameters can also be used. For amino acid sequences, the BLASTP program uses as defaults a wordlength (W) of 3, an expectation (B) of 10, and the BLOSUM62 scoring matrix (see Henikoff & Henikoff, *Proc. Natl. Acad. Sci. USA* 89, 10915 (1989)).

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained.

Specific binding between two entities means an affinity of at least $10^6$, $10^7$, $10^8$, $10^9$ $M^{-1}$, or $10^{10}$ $M^{-1}$. Affinities greater than $10^8$ $M^{-1}$ are preferred.

The term "antibody" or "immunoglobulin" is used to include intact antibodies and binding fragments thereof Typically, fragments compete with the intact antibody from which they were derived for specific binding to an antigen fragments including separate heavy chains, light chains Fab, Fab' F(ab') 2, Fabc, and Fv. Fragments are produced by recombinant DNA techniques, or by enzymatic or chemical separation of intact immunoglobulins. The term "antibody" also includes one or more immunoglobulin chain that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

$APP^{695}$, $APP^{751}$, and $APP^{770}$ refer, respectively, to the 695, 751, and 770 amino acid residue long polypeptides encoded by the human APP gene. See Kang et al., *Nature* 325, 773 (1987); Ponte et al., *Nature* 331, 525 (1988); and Kitaguchi et al., *Nature* 331, 530 (1988). Amino acids within the human amyloid precursor protein (APP) are assigned numbers according to the sequence of the APP770 isoform. Terms such as Aβ39, Aβ40, Aβ41, Aβ42 and Aβ43 refer to an Aβ peptide containing amino acid residues 1-39, 1-40, 1-41, 1-42 and 1-43.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., *J. Inf. Dis.* 170, 1110-19 (1994)), by antigen-dependent killing (cytotoxic T lymphocyte assay, Tigges et al., *J. Immunol.* 156, 3901-3910) or by cytokine secretion.

The term "immunological" or "immune" response is the development of a beneficial humoral (antibody mediated) and/or a cellular (mediated by antigen-specific T cells or their secretion products) response directed against an amyloid peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays ($CD4^+$ T cells) or CTL (cytotoxic T lymphocyte) assays (see Burke, supra; Tigges, supra). The relative contributions of humoral and cellular responses to the protective or therapeutic effect of an immunogen can be distinguished by seperately isolating antibodies and T-cells from an immunized syngeneic animal and measuring protective or therapeutic effect in a second subject.

An "immunogenic agent" or "immunogen" is capable of inducing an immunological response against itself on administration to a patient, optionally in conjunction with an adjuvant.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

The term "patient" includes human and other mammalian subjects that receive either prophylactic or therapeutic treatment.

Disaggregated or monomeric Aβ means soluble, monomeric peptide units of Aβ. One method to prepare monomeric Aβ is to dissolve lyophilized peptide in neat DMSO with sonication. The resulting solution is centrifuged to remove any insoluble particulates. Aggregated Aβ is a mixture of oligomers in which the monomeric units are held together by noncovalent bonds.

Competition between antibodies is determined by an assay in which the immunoglobulin under test inhibits specific binding of a reference antibody to a common antigen such as Aβ. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using I-125 label (see Morel et al., Molec. Immunol. 25(1):7-15 (1988)); solid phase direct biotin-avidin EIA (Cheung et al., Virology 176:546-552 (1990)); and direct labeled RIA (Moldenhauer et al., Scand. J. Immunol. 32:77-82 (1990)). Typically, such an assay involves the use of purified antigen bound to a solid surface or cells bearing either of these, an unlabelled test immunoglobulin and a labelled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

Compositions or methods "comprising" one or more recited elements may include other elements not specifically recited. For example, a composition that comprises Aβ peptide encompasses both an isolated Aβ peptide and Aβ peptide as a component of a larger polypeptide sequence.

DETAILED DESCRIPTION

I. General

The invention provides pharmaceutical compositions and methods for prophylactic and therapeutic treatment of diseases characterized by accumulation of amyloid deposits. Amyloid deposits comprise a peptide aggregated to an insoluble mass. The nature of the peptide varies in different diseases but in most cases, the aggregate has β-pleated sheet structure and stains with Congo Red dye. Diseases characterized by amyloid deposits include Alzheimer's disease (AD), both late and early onset. In both diseases, the amyloid deposit comprises a peptide termed Aβ, which accumulates in the brain of affected individuals. Examples of some other diseases characterized by amyloid deposits are SAA amyloidosis, hereditary Icelandic syndrome, multiple myeloma, and spongiform encephalopathies, including mad cow disease, Creutzfeldt Jakob disease, sheep scrapie, and mink spongiform encephalopathy (see Weissmann et al., Curr. Opin. Neurobiol. 7, 695-700 (1997); Smits et al., Veterinary Quarterly 19, 101-105 (1997); Nathanson et al., Am. J. Epidemiol. 145, 959-969 (1997)). The peptides forming the aggregates in these diseases are serum amyloid A, cystanin C, IgG kappa light chain respectively for the first three, and prion protein for the others.

II. Therapeutic Agents
A. Alzheimer's Disease
1. Agents Inducing Active Immune Response Therapeutic agents for use in the present invention induce an immune response against Aβ peptide. These agents include Aβ peptide itself and variants thereof, analogs and mimetics of Aβ peptide that induce and/or crossreact with antibodies to Aβ peptide, and antibodies or T-cells reactive with Aβ peptide. Induction of an immune response can be active as when an immunogen is administered to induce antibodies or T-cells reactive with Aβ in a patient, or passive, as when an antibody is administered that itself binds to Aβ in patient.

Aβ, also known as β-amyloid peptide, or A4 peptide (see U.S. Pat. No. 4,666,829; Glenner & Wong, Biochem. Biophys. Res. Commun. 120, 1131 (1984)), is a peptide of 39-43 amino acids, which is the principal component of characteristic plaques of Alzheimer's disease. Aβ is generated by processing of a larger protein APP by two enzymes, termed β and γ secretases (see Hardy, TINS 20, 154 (1997)). Known mutations in APP associated with Alzheimer's disease occur proximate to the site of β or γ secretase, or within Aβ. For example, position 717 is proximate to the site of γ-secretase cleavage of APP in its processing to Aβ, and positions 670/671 are proximate to the site of β-secretase cleavage. It is believed that the mutations cause AD by interacting with the cleavage reactions by which Aβ is formed so as to increase the amount of the 42/43 amino acid form of Aβ generated.

Aβ has the unusual property that it can fix and activate both classical and alternate complement cascades. In particular, it binds to C1q and ultimately to C3bi. This association facilitates binding to macrophages leading to activation of B cells. In addition, C3bi breaks down further and then binds to CR2 on B cells in a T cell dependent manner leading to a 10,000 increase in activation of these cells. This mechanism causes Aβ to generate an immune response in excess of that of other antigens.

The therapeutic agent used in the claimed methods can be any of the naturally occurring forms of Aβ peptide, and particularly the human forms (i.e., Aβ39, Aβ40, Aβ41, Aβ42 or Aβ43). The sequences of these peptides and their relationship to the APP precursor are illustrated by FIG. 1 of Hardy et al., TINS 20, 155-158 (1997). For example, Aβ42 has the sequence:

(SEQ ID NO: 1)
H$_2$N-Asp-Ala-Glu-Phe-Arg-His-Asp-Ser-Gly-Tyr-Glu-

Val-His-His-Gln-Lys-Leu-Val-Phe-Phe-Ala-Glu-Asp-

Val-Gly-Ser-Asn-Lys-Gly-Ala-Ile-Ile-Gly-Leu-Met-

Val-Gly-Gly-Val-Val-Ile-Ala-OH.

Aβ41, Aβ40 and Aβ39 differ from Aβ42 by the omission of Ala, Ala-Ile, and Ala-Ile-Val respectively from the C-terminal end. Aβ43 differs from Aβ42 by the presence of a threonine residue at the C-terminus. The therapeutic agent can also be an active fragment or analog of a natural Aβ peptide that contains an epitope that induces a similar protective or therapeutic immune response on administration to a human. Immunogenic fragments typically have a sequence of at least 3, 5, 6, 10 or 20 contiguous amino acids from a natural peptide. Immunogenic fragments include Aβ1-5, 1-6, 1-12, 13-28, 17-28, 1-28, 25-35, 35-40 and 35-42. Fragments lacking at least one, and sometimes at least 5 or 10 C-terminal amino acid present in a naturally occurring forms of Aβ are used in some methods. For example, a fragment lacking 5 amino acids from the C-terminal end of AB43 includes the first 38 amino acids from the N-terminal end of AB. Fragments from the N-terminal half of Aβ are preferred in some methods. Analogs include allelic, species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are α, α-disubstituted amino acids, N-alkyl amino acids, lactic acid, 4-hydroxyproline, γ-carboxyglutamate, γ-N,N,N-trimethyllysine, γ-N-acetyllysine, O-phosphoserine, N-acetylserine, N-formylmethionine, 3-methylhistidine, 5-hydroxylysine, ω-N-methylarginine. Fragments and analogs can be screened for prophylactic or therapeutic efficacy in transgenic animal models in comparison with untreated or placebo controls as described below.

Aβ, its fragments, analogs and other amyloidogenic peptides can be synthesized by solid phase peptide synthesis or recombinant expression, or can be obtained from natural sources. Automatic peptide synthesizers are commercially available from numerous suppliers, such as Applied Biosystems, Foster City, Calif. Recombinant expression can be in bacteria, such as *E. coli*, yeast, insect cells or mammalian cells. Procedures for recombinant expression are described by Sambrook et al., *Molecular Cloning: A Laboratory Manual* (C.S.H.P. Press, NY 2d ed., 1989). Some forms of Aβ peptide are also available commercially (e.g., American Peptides Company, Inc., Sunnyvale, Calif. and California Peptide Research, Inc. Napa, Calif.).

Therapeutic agents also include longer polypeptides that include, for example, an Aβ peptide, active fragment or analog together with other amino acids. For example, Aβ peptide can be present as intact APP protein or a segment thereof, such as the C-100 fragment that begins at the N-terminus of Aβ and continues to the end of APP. Such polypeptides can be screened for prophylactic or therapeutic efficacy in animal models in comparison with untreated or placebo controls as described below. The Aβ peptide, analog, active fragment or other polypeptide can be administered in associated form (i.e., as an β-amyloid peptide) or in dissociated form. Therapeutic agents also include multimers of monomeric immunogenic agents.

In a further variation, an immunogenic peptide, such as Aβ, can be presented as a viral or bacterial vaccine. A nucleic acid encoding the immunogenic peptide is incorporated into a genome or episome of the virus or bacteria. Optionally, the nucleic acid is incorporated in such a manner that the immunogenic peptide is expressed as a secreted protein or as a fusion protein with an outersurface protein of a virus or a transmembrane protein of a bacteria so that the peptide is displayed. Viruses or bacteria used in such methods should be nonpathogenic or attenuated. Suitable viruses include adenovirus, HSV, vaccinia and fowl pox. Fusion of an immunogenic peptide to HBsAg of HBV is particularly suitable. Therapeutic agents also include peptides and other compounds that do not necessarily have a significant amino acid sequence similarity with Aβ but nevertheless serve as mimetics of Aβ and induce a similar immune response. For example, any peptides and proteins forming β-pleated sheets can be screened for suitability. Anti-idiotypic antibodies against monoclonal antibodies to Aβ or other amyloidogenic peptides can also be used. Such anti-Id antibodies mimic the antigen and generate an immune response to it (see *Essential Immunology* (Roit ed., Blackwell Scientific Publications, Palo Alto, 6th ed.), p. 181).

Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980.

Combinatorial libraries and other compounds are initially screened for suitability by determining their capacity to bind to antibodies or lymphocytes (B or T) known to be specific for Aβ or other amyloidogenic peptides. For example, initial screens can be performed with any polyclonal sera or monoclonal antibody to Aβ or other amyloidogenic peptide. Compounds identified by such screens are then further analyzed for capacity to induce antibodies or reactive lymphocytes to Aβ or other amyloidogenic peptide. For example, multiple dilutions of sera can be tested on microtiter plates that have been precoated with Aβ peptide and a standard ELISA can be performed to test for reactive antibodies to Aβ. Compounds can then be tested for prophylactic and therapeutic efficacy in transgenic animals predisposed to an amyloidogenic disease, as described in the Examples. Such animals include, for example, mice bearing a 717 mutation of APP described by Games et al., supra, and mice bearing a Swedish mutation of APP such as described by McConlogue et al., U.S. Pat. No. 5,612,486 and Hsiao et al., *Science* 274, 99 (1996); Staufenbiel et al., *Proc. Natl. Acad. Sci.* USA 94, 13287-13292 (1997); Sturchler-Pierrat et al., *Proc. Natl. Acad. Sci. USA* 94, 13287-13292 (1997); Borchelt et al., *Neuron* 19, 939-945 (1997)). The same screening approach can be used on other potential agents such as fragments of Aβ, analogs of Aβ and longer peptides including Aβ, described above.

2. Agents Inducing Passive Immune Response

Therapeutic agents of the invention also include antibodies that specifically bind to Aβ or other component of amyloid plaques. Such antibodies can be monoclonal or polyclonal. Some such antibodies bind specifically to the aggregated form of Aβ without binding to the dissociated form. Some bind specifically to the dissociated form without binding to the aggregated form. Some bind to both aggregated and dissociated forms. Some such antibodies bind to a naturally occurring short form of Aβ (i.e., Aβ39, 40 or 41) without binding to a naturally occurring long form of Aβ (i.e., Aβ42 and Aβ43). Some antibodies bind to a long form without binding to a short form. Some antibodies bind to Aβ without binding to full-length amyloid precursor protein. Some antibodies bind to Aβ with a binding affinity greater than or equal to about $10^6$, $10^7$, $10^8$, $10^9$ or $10^{10}$ $M^{-1}$.

Polyclonal sera typically contain mixed populations of antibodies binding to several epitopes along the length of Aβ. Monoclonal antibodies bind to a specific epitope within Aβ that can be a conformational or nonconformational epitope. Some monoclonal antibodies bind to an epitope within residues 1-28 of Aβ (with the first N terminal residue of natural Aβ designated 1). Some monoclonal antibodies bind to an epitope within residues 1-10 of Aβ Some monoclonal antibodies bind to an epitope within residues 1-16 of Aβ. Some monoclonal antibodies bind to an epitope within residues 1-25 of Aβ. Some monoclonal antibodies bind to an epitope within amino acids 1-5, 5-10, 10-15, 15-20, 25-30, 10-20, 20-30, or 10-25 of Aβ. Prophylactic and therapeutic efficacy of antibodies can be tested using the transgenic animal model procedures described in the Examples.

i. General Characteristics of Immunoglobulins

The basic antibody structural unit is known to comprise a tetramer of subunits. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y., 1989), Ch. 7 (incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989).

ii. Production of Nonhuman Antibodies

The production of non-human monoclonal antibodies, e.g., murine, guinea pig, rabbit or rat, can be accomplished by, for example, immunizing the animal with Aβ. A longer polypeptide comprising Aβ or an immunogenic fragment of Aβ or anti-idiotypic antibodies to an antibody to Aβ. See Harlow & Lane, *Antibodies, A Laboratory Manual* (CSHP NY, 1988) (incorporated by reference for all purposes). Such an immunogen can be obtained from a natural source, by peptide synthesis or by recombinant expression. Optionally, the immunogen can be administered fused or otherwise complexed with a carrier protein, as described below. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to Aβ. Optionally, antibodies are further screened for binding to a specific region of Aβ. The latter screening can be accomplished by determining binding of an antibody to a collection of deletion mutants of an Aβ peptide and determining which deletion mutants bind to the antibody. Binding can be assessed, for example by Western blot or ELISA. The smallest fragment to show specific binding to the antibody defines the epitope of the antibody. Alternatively, epitope specificity can be determined by a competition assay is which a test and reference antibody compete for binding to Aβ. If the test and reference antibodies compete, then they bind to the same epitope or epitopes sufficiently proximal that binding of one antibody interferes with binding of the other.

iii. Chimeric and Humanized Antibodies

Chimeric and humanized antibodies have the same or similar binding specificity and affinity as a mouse or other non-human antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions substantially from a mouse-antibody, (referred to as the donor immunoglobulin). See, Queen et al., *Proc. Natl. Acad. Sci. USA* 86:10029-10033 (1989) and WO 90/07861, U.S. Pat. No. 5,693,762, U.S. Pat. No. 5,693,761, U.S. Pat. No. 5,585, 089, U.S. Pat. No. 5,530,101 and Winter, U.S. Pat. No. 5,225, 539 (incorporated by reference in their entirety for all purposes). The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 A of a CDR region), or
(4) participates in the VL-VH interface.

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

iv. Human Antibodies

Human antibodies against Aβ are provided by a variety of techniques described below. Some human antibodies are selected by competitive binding experiments, or otherwise, to have the same epitope specificity as a particular mouse antibody, such as one of the mouse monoclonals described in Example XI. Human antibodies can also be screened for a particular epitope specificity by using only a fragment of Aβ as the immunogen, and/or by screening antibodies against a collection of deletion mutants of Aβ.

(1) Trioma Methodology

The basic approach and an exemplary cell fusion partner, SPAZ-4, for use in this approach have been described by Oestberg et al., *Hybridoma* 2:361-367 (1983); Oestberg, U.S. Pat. No. 4,634,664; and Engleman et al., U.S. Pat. No. 4,634,666 (each of which is incorporated by reference in its entirety for all purposes). The antibody-producing cell lines obtained by this method are called triomas, because they are descended from three cells—two human and one mouse. Initially, a mouse myeloma line is fused with a human B-lymphocyte to obtain a non-antibody-producing xenogeneic hybrid cell, such as the SPAZ-4 cell line described by Oestberg, supra. The xenogeneic cell is then fused with an immunized human B-lymphocyte to obtain an antibody-producing trioma cell line. Triomas have been found to produce antibody more stably than ordinary hybridomas made from human cells.

The immunized B-lymphocytes are obtained from the blood, spleen, lymph nodes or bone marrow of a human donor. If antibodies against a specific antigen or epitope are desired, it is preferable to use that antigen or epitope thereof for immunization. Immunization can be either in vivo or in vitro. For in vivo immunization, B cells are typically isolated from a human immunized with Aβ, a fragment thereof, larger polypeptide containing Aβ or fragment, or an anti-idiotypic antibody to an antibody to Aβ. In some methods, B cells are isolated from the same patient who is ultimately to be administered antibody therapy. For in vitro immunization, B-lymphocytes are typically exposed to antigen for a period of 7-14 days in a media such as RPMI-1640 (see Engleman, supra) supplemented with 10% human plasma.

The immunized B-lymphocytes are fused to a xenogeneic hybrid cell such as SPAZ-4 by well known methods. For example, the cells are treated with 40-50% polyethylene glycol of MW 1000-4000, at about 37 degrees, for about 5-10 min. Cells are separated from the fusion mixture and propagated in media selective for the desired hybrids (e.g., HAT or AH). Clones secreting antibodies having the required binding specificity are identified by assaying the trioma culture medium for the ability to bind to Aβ or a fragment thereof. Triomas producing human antibodies having the desired specificity are subcloned by the limiting dilution technique and grown in vitro in culture medium. The trioma cell lines obtained are then tested for the ability to bind Aβ or a fragment thereof.

Although triomas are genetically stable they do not produce antibodies at very high levels. Expression levels can be increased by cloning antibody genes from the trioma into one or more expression vectors, and transforming the vector into standard mammalian, bacterial or yeast cell lines.

(2) Transgenic Non-Human Mammals

Human antibodies against Aβ can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, *Nature* 148, 1547-1553 (1994), *Nature Biotechnology* 14, 826 (1996), Kucherlapati, WO 91/10741 (1991) (each of which is incorporated by reference in its entirety for all purposes). Transgenic mice are particularly suitable. Anti-Aβ antibodies are obtained by immunizing a transgenic nonhuman mammal, such as described by Lonberg or Kucherlapati, supra, with Aβ or a fragment thereof. Monoclonal antibodies are prepared by, e.g., fusing B-cells from such mammals to suitable myeloma cell lines using conventional Kohler-Milstein technology. Human polyclonal antibodies can also be provided in the form of serum from humans immunized with an immunogenic agent. Optionally, such polyclonal antibodies can be concentrated by affinity purification using Aβ or other amyloid peptide as an affinity reagent.

(3) Phage Display Methods

A further approach for obtaining human anti-Aβ antibodies is to screen a DNA library from human B cells according to the general protocol outlined by Huse et al., *Science* 246: 1275-1281 (1989). As described for trioma methodology, such B cells can be obtained from a human immunized with Aβ, fragments, longer polypeptides containing Aβ or fragments or anti-idiotypic antibodies. Optionally, such B cells are obtained from a patient who is ultimately to receive antibody treatment. Antibodies binding to Aβ or a fragment thereof are selected. Sequences encoding such antibodies (or a binding fragments) are then cloned and amplified. The protocol described by Huse is rendered more efficient in combination with phage-display technology. See, e.g., Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332 (each of which is incorporated by reference in its entirety for all purposes). In these methods, libraries of phage are produced in which members display different antibodies on their outer surfaces. Antibodies are usually displayed as Fv or Fab fragments. Phage displaying antibodies with a desired specificity are selected by affinity enrichment to an Aβ peptide or fragment thereof.

In a variation of the phage-display method, human antibodies having the binding specificity of a selected murine antibody can be produced. See Winter, WO 92/20791. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. A phage showing strong specific binding for Aβ (e.g., at least $10^8$ and preferably at least $10^9$ $M^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for Aβ are selected. These phage display the variable regions of completely human anti-Aβ antibodies. These antibodies usually have the same or similar epitope specificity as the murine starting material.

v. Selection of Constant Region

The heavy and light chain variable regions of chimeric, humanized, or human antibodies can be linked to at least a portion of a human constant region. The choice of constant region depends, in part, whether antibody-dependent complement and/or cellular mediated toxicity is desired. For example, isotopes IgG1 and IgG3 have complement activity and isotypes IgG2 and IgG4 do not. Choice of isotype can also affect passage of antibody into the brain. Light chain constant regions can be lambda or kappa. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

vi. Expression of Recombinant Antibodies

Chimeric, humanized and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. Saccharomyces is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines, various COS cell lines, HeLa cells, L cells and myeloma cell lines. Preferably, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. No. 5,741,957, U.S. Pat. No. 5,304,489, U.S. Pat. No. 5,849,992). Suitable trangenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calacium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures of the art, including HPLC purification, column chromatography, gel electrophoresis and the like (see generally, Scopes, *Protein Purification* (Springer-Verlag, NY, 1982)).

4. Other Therapeutic Agents

Therapeutic agents for use in the present methods also include T-cells that bind to Aβ peptide. For example, T-cells can be activated against Aβ peptide by expressing a human MHC class I gene and a human β-2-microglobulin gene from an insect cell line, whereby an empty complex is formed on the surface of the cells and can bind to Aβ peptide. T-cells contacted with the cell line become specifically activated against the peptide. See Peterson et al., U.S. Pat. No. 5,314, 813. Insect cell lines expressing an MHC class II antigen can similarly be used to activate CD4 T cells.

B. Other Diseases

The same or analogous principles determine production of therapeutic or preventative agents for amyloidogenic diseases. In general, the agents noted above for use in treatment of Alzheimer's disease can also be used for treatment early onset Alzheimer's disease associated with Down's syndrome. In mad cow disease, prion peptide, active fragments, and analogs, and antibodies to prion peptide are used in place of Aβ peptide, active fragments, analogs and antibodies to Aβ peptide in treatment of Alzheimer's disease. In treatment of multiple myeloma, IgG light chain and analogs and antibodies thereto are used, and so forth in other diseases.

1. Carrier Proteins

Some agents for inducing an immune response contain the appropriate epitope for inducing an immune response against amyloid deposits but are too small to be immunogenic. In this situation, a peptide immunogen can be linked to a suitable carrier to help elicit an immune response. Suitable carriers include serum albumins, keyhole limpet hemocyanin, immunoglobulin molecules, thyroglobulin, ovalbumin, tetanus toxoid, or a toxoid from other pathogenic bacteria, such as diphtheria, *E. coli*, cholera, or *H. pylori*, or an attenuated toxin derivative. Other carriers for stimulating or enhancing an immune response include cytokines such as IL-1, IL-1α and β peptides, IL-2, γINF, IL-10, GM-CSF, and chemokines, such as MIP1α a and β and RANTES. Immunogenic agents can also be linked to peptides that enhance transport across tissues, as described in O'Mahony, WO 97/17613 and WO 97/17614.

Immunogenic agents can be linked to carriers by chemical crosslinking. Techniques for linking an immunogen to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the å-amino on a lysine, or other free amino group in other amino acids. A variety of such disulfide/amide-forming agents are described by *Immun. Rev.* 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

Immunogenic peptides can also be expressed as fusion proteins with carriers. The immunogenic peptide can be linked at the amino terminus, the carboxyl terminus, or internally to the carrier. Optionally, multiple repeats of the immunogenic peptide can be present in the fusion protein.

The same or similar carrier proteins and methods of linkage can be used for generating immunogens to be used in generation of antibodies against Aβ for use in passive immunization. For example, Aβ or a fragment linked to a carrier can be administered to a laboratory animal in the production of monoclonal antibodies to Aβ.

4. Nucleic Acid Encoding Therapeutic Agents

Immune responses against amyloid deposits can also be induced by administration of nucleic acids encoding Aβ peptide, other peptide immunogens, or antibodies and their component chains used for passive immunization. Such nucleic acids can be DNA or RNA. A nucleic acid segment encoding an immunogen is typically linked to regulatory elements, such as a promoter and enhancer, that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors.

A number of viral vector systems are available including retroviral systems (see, e.g., Lawrie and Tumin, *Cur. Opin. Genet. Develop.* 3, 102-109 (1993)); adenoviral vectors (see, e.g., Bett et al., *J. Virol.* 67, 5911 (1993)); adeno-associated virus vectors (see, e.g., Zhou et al., *J. Exp. Med.* 179, 1867 (1994)), viral vectors from the pox family including vaccinia virus and the avian pox viruses, viral vectors from the alpha virus genus such as those derived from Sindbis and Semliki Forest Viruses (see, e.g., Dubensky et al., *J. Virol.* 70, 508-519 (1996)), and papillomaviruses (Ohe et al., *Human Gene Therapy* 6, 325-333 (1995); Woo et al., WO 94/12629 and Xiao & Brandsma, *Nucleic Acids. Res.* 24, 2630-2622 (1996)).

DNA encoding an immunogen, or a vector containing the same, can be packaged into liposomes. Suitable lipids and related analogs are described by U.S. Pat. Nos. 5,208,036, 5,264,618, 5,279,833 and 5,283,185. Vectors and DNA encoding an immunogen can also be adsorbed to or associated with particulate carriers, examples of which include polymethyl methacrylate polymers and polylactides and poly (lactide-co-glycolides), see, e.g., McGee et al., *J. Micro Encap.* (1996).

Gene therapy vectors or naked DNA can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346). DNA can also be administered using a gene gun. See Xiao & Brandsma, supra. The DNA encoding an immunogen is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. Middleton Wis. is suitable. Alternatively, naked DNA can pass through skin into the blood stream simply by spotting the DNA onto skin with chemical or mechanical irritation (see WO 95/05853).

In a further variation, vectors encoding immunogens can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

III. Patients Amenable to Treatment

Patients amenable to treatment include individuals at risk of disease but not showing symptoms, as well as patients presently showing symptoms. In the case of Alzheimer's disease, virtually anyone is at risk of suffering from Alzheimer's disease if he or she lives long enough. Therefore, the present methods can be administered prophylactically to the general population without any assessment of the risk of the subject patient. The present methods are especially useful for individuals who do have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by ADRDA criteria as discussed in the Examples section.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody, or activated T-cell or B-cell responses to the therapeutic agent (e.g., Aβ peptide) over time. If the response falls, a booster dosage is indicated. In the case of potential Down's syndrome patients, treatment can begin antenatally by administering therapeutic agent to the mother or shortly after birth.

IV. Treatment Regimes

In prophylactic applications, pharmaceutical compositions or medicants are administered to a patient susceptible to, or otherwise at risk of, a particular disease in an amount sufficient to eliminate or reduce the risk or delay the outset of the disease. In therapeutic applications, compositions or medicants are administered to a patient suspected of, or already suffering from such a disease in an amount sufficient to cure, or at least partially arrest, the symptoms of the disease and its complications. An amount adequate to accomplish this is defined as a therapeutically- or pharmaceutically-effective dose. In both prophylactic and therapeutic regimes, agents are usually administered in several dosages until a sufficient immune response has been achieved. Typically, the immune response is monitored and repeated dosages are given if the immune response starts to fade.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human, but in some diseases, such as mad cow disease, the patient can be a nonhuman mammal, such as a bovine. Treatment dosages need to be titrated to optimize safety and efficacy. The amount of immunogen depends on whether adjuvant is also administered, with higher dosages being required in the absence of adjuvant. The amount of an immunogen for administration sometimes varies from 1-500 µg per patient and more usually from 5-500 µg per injection for human administration. Occasionally, a higher dose of 1-2 mg per injection is used. Typically about 10, 20, 50 or 100 µg is used for each human injection. The timing of injections can vary significantly from once a day, to once a year, to once a decade. On any given day that a dosage of immunogen is given, the dosage is greater than 1 µg/patient and usually greater than 10 µg/patient if adjuvant is also administered, and greater than 10 µg/patient and usually greater than 100 µg/patient in the absence of adjuvant. A typical regimen consists of an immunization followed by booster injections at 6 week intervals. Another regimen consists of an immunization followed by booster injections 1, 2 and 12 months later. Another regimen entails an injection every two months for life. Alternatively, booster injections can be on an irregular basis as indicated by monitoring of immune response.

For passive immunization with an antibody, the dosage ranges from about 0.0001 to 100 mg/kg, and more usually 0.01 to 5 mg/kg, of the host body weight. For example dosages can be 1 mg/kg body weight or 10 mg/kg body weight. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to Aβ in the patient. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 µg to 10 mg, or 30-300 µg DNA per patient. Doses for infectious viral vectors vary from 10-109, or more, virions per dose.

Agents for inducing an immune response can be administered by parenteral, topical, intravenous, oral, subcutaneous, intraperitoneal, intranasal or intramuscular means for prophylactic and/or therapeutic treatment. The most typical route of administration of an immunogenic agent is subcutaneous although others can be equally effective. The next most common is intramuscular injection. This type of injection is most typically performed in the arm or leg muscles. Intravenous injections as well as intraperitoneal injections, intraarterial, intracranial, or intradermal injections are also effective in generating an immune response. In some methods, agents are injected directly into a particular tissue where deposits have accumulated, for example intracranial injection. Intramuscular injection on intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in treatment of amyloidogenic disease. In the case of Alzheimer's and Down's syndrome, in which amyloid deposits occur in the brain, agents of the invention can also be administered in conjunction with other agents that increase passage of the agents of the invention across the blood-brain barrier.

Immunogenic agents of the invention, such as peptides, are sometimes administered in combination with an adjuvant. A variety of adjuvants can be used in combination with a peptide, such as Aβ, to elicit an immune response. Preferred adjuvants augment the intrinsic response to an immunogen without causing conformational changes in the immunogen that affect the qualitative form of the response. Preferred adjuvants include alum, 3 De-O-acylated monophosphoryl lipid A (MPL) (see GB 2220211). QS-21 is a triterpene glycoside or saponin isolated from the bark of the Quillaja Saponaria Molina tree found in South America (see Kensil et al., in *Vaccine Design: The Subunit and Ajuvant Approach* (eds. Powell & Newman, Plenum Press, NY, 1995); U.S. Pat. No. 5,057,540). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)). Another adjuvant is CpG (*Bioworld Today*, Nov. 15, 1998). Alternatively, Aβ can be coupled to an adjuvant. However, such coupling should not substantially change the conformation of Aβ so as to affect the nature of the immune response thereto. Adjuvants can be administered as a component of a therapeutic composition with an active agent or can be administered separately, before, concurrently with, or after administration of the therapeutic agent.

A preferred class of adjuvants is aluminum salts (alum), such as aluminum hydroxide, aluminum phosphate, aluminum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine(thr-MDP), N-acetyl-normuramyl-L-alanyl-D-isoglutamine(nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramideTM), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalane, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi Immunochem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™). Another class of preferred adjuvants is saponin adjuvants, such as Stimulon™ (QS-21, Aquila, Worcester, Mass.) or particles generated therefrom such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), tumor necrosis factor (TNF).

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 are preferred. Optionally, two or more different adjuvants can be used simultaneously. Preferred combinations include alum with MPL, alum with QS-21, MPL with QS-21, and alum, QS-21 and MPL together. Also, Incomplete Freund's adjuvant can be used (Chang et al., *Advanced Drug Delivery Reviews* 32, 173-186 (1998)), optionally in combination with any of alum, QS-21, and MPL and all combinations thereof.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. However, some reagents suitable for administration to animals, such as Complete Freund's adjuvant are not typically included in compositions for human use.

Pharmaceutical compositions can also include large, slowly metabolized macromolecules such as proteins, polysaccharides such as chitosan, polylactic acids, polyglycolic acids and copolymers (such as latex functionalized sepharose, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249, 1527 (1990) and Hanes, *Advanced Drug Delivery Reviews* 28, 97-119 (1997). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., *Eur. J. Immunol.* 25, 3521-24 (1995); Cevc et al., *Biochem. Biophys. Acta* 1368, 201-15 (1998)).

V. Methods of Diagnosis

The invention provides methods of detecting an immune response against Aβ peptide in a patient suffering from or susceptible to Alzheimer's disease. The methods are particularly useful for monitoring a course of treatment being administered to a patient. The methods can be used to monitor both therapeutic treatment on symptomatic patients and prophylactic treatment on asymptomatic patients. The methods are useful for monitoring both active immunization (e.g., antibody produced in response to administration of immunogen) and passive immunization (e.g., measuring level of administered antibody).

1. Active Immunization

Some methods entail determining a baseline value of an immune response in a patient before administering a dosage of agent, and comparing this with a value for the immune response after treatment. A significant increase (i.e., greater than the typical margin of experimental error in repeat measurements of the same sample, expressed as one standard deviation from the mean of such measurements) in value of the immune response signals a positive treatment outcome (i.e., that administration of the agent has achieved or augmented an immune response). If the value for immune response does not change significantly, or decreases, a negative treatment outcome is indicated. In general, patients undergoing an initial course of treatment with an immunogenic agent are expected to show an increase in immune response with successive dosages, which eventually reaches a plateau. Administration of agent is generally continued while the immune response is increasing. Attainment of the plateau is an indicator that the administered of treatment can be discontinued or reduced in dosage or frequency.

In other methods, a control value (i.e., a mean and standard deviation) of immune response is determined for a control population. Typically the individuals in the control population have not received prior treatment. Measured values of immune response in a patient after administering a therapeutic agent are then compared with the control value. A significant increase relative to the control value (e.g., greater than one standard deviation from the mean) signals a positive treatment outcome. A lack of significant increase or a decrease signals a negative treatment outcome. Administration of agent is generally continued while the immune response is increasing relative to the control value. As before, attainment of a plateau relative to control values in an indicator that the administration of treatment can be discontinued or reduced in dosage or frequency.

In other methods, a control value of immune response (e.g., a mean and standard deviation) is determined from a control population of individuals who have undergone treatment with a therapeutic agent and whose immune responses have plateaued in response to treatment. Measured values of immune response in a patient are compared with the control value. If the measured level in a patient is not significantly different (e.g., more than one standard deviation) from the control value, treatment can be discontinued. If the level in a patient is significantly below the control value, continued administration of agent is warranted. If the level in the patient persists below the control value, then a change in treatment regime, for example, use of a different adjuvant may be indicated.

In other methods, a patient who is not presently receiving treatment but has undergone a previous course of treatment is monitored for immune response to determine whether a resumption of treatment is required. The measured value of immune response in the patient can be compared with a value of immune response previously achieved in the patient after a previous course of treatment. A significant decrease relative to the previous measurement (i.e., greater than a typical margin of error in repeat measurements of the same sample) is an indication that treatment can be resumed. Alternatively, the value measured in patient can be compared with a control value (mean plus standard deviation) determined in population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

The tissue sample for analysis is typically blood, plasma, serum, mucous or cerebrospinal fluid from the patient. The sample is analyzed for indication of an immune response to any form of Aβ peptide, typically Aβ42. The immune response can be determined from the presence of, e.g., antibodies or T-cells that specifically bind to Aβ peptide. ELISA methods of detecting antibodies specific to Aβ are described in the Examples section. Methods of detecting reactive T-cells have been described above (see Definitions).

2. Passive Immunization

In general, the procedures for monitoring passive immunization are similar to those for monitoring active immunization described above. However, the antibody profile following passive immunization typically shows an immediate peak in antibody concentration followed by an exponential decay. Without a further dosage, the decay approaches pretreatment levels within a period of days to months depending on the half-life of the antibody administered. For example the half-life of some human antibodies is of the order of 20 days.

In some methods, a baseline measurement of antibody to Aβ in the patient is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dosage of antibody is administered. In some methods, peak or subsequent measured levels less background are compared with reference levels previously determined to constitute a beneficial prophylactic or therapeutic treatment regime in other patients. If the measured antibody level is significantly less than a reference level (e.g., less than the mean minus one standard deviation of the reference value in population of patients benefiting from treatment) administration of an additional dosage of antibody is indicated.

3. Diagnostic Kits

The invention further provides diagnostic kits for performing the diagnostic methods described above. Typically, such kits contain an agent that specifically binds to antibodies to Aβ or reacts with T-cells specific for Aβ. The kit can also include a label. For detection of antibodies to Aβ, the label is typically in the form of labelled anti-idiotypic antibodies. For detection of antibodies, the agent can be supplied prebound to a solid phase, such as to the wells of a microtiter dish. For detection of reactive T-cells, the label can be supplied as 3H-thymidine to measure a proliferative response. Kits also typically contain labelling providing directions for use of the kit. The labelling may also include a chart or other correspondence regime correlating levels of measured label with levels of antibodies to Aβ or T-cells reactive with Aβ. The term labelling refers to any written or recorded material that is attached to, or otherwise accompanies a kit at any time during its manufacture, transport, sale or use. For example, the term labelling encompasses advertising leaflets and brochures, packaging materials, instructions, audio or video cassettes, computer discs, as well as writing imprinted directly on kits.

EXAMPLES

I. Prophylactic Efficacy of Aβ Against AD

These examples describe administration of Aβ42 peptide to transgenic mice overexpressing APP with a mutation at position 717 ($APP_{717V \rightarrow F}$) that predisposes them to develop Alzheimer's-like neuropathology. Production and characteristics of these mice (PDAPP mice) is described in Games et al., Nature, supra. These animals, in their heterozygote form, begin to deposit Aβ at six months of age forward. By fifteen months of age they exhibit levels of Aβ deposition equivalent to that seen in Alzheimer's disease. PDAPP mice were injected with aggregated $A\beta_{42}$ (aggregated $A\beta_{42}$) or phosphate buffered saline. Aggregated $A\beta_{42}$ was chosen because of its ability to induce antibodies to multiple epitopes of Aβ.

A. Methods

1. Source of Mice

Thirty PDAPP heterogenic female mice were randomly divided into the following groups: 10 mice to be injected with aggregated Aβ42 (one died in transit), 5 mice to be injected with PBS/adjuvant or PBS, and 10 uninjected controls. Five mice were injected with peptides dervied from the sequence of serum amyloid protein (SAP).

2. Preparation of Immunogens

Preparation of aggregated Aβ42: two milligrams of Aβ42 (US Peptides Inc, lot K-42-12) was dissolved in 0.9 ml water and made up to 1 ml by adding 0.1 ml 10×PBS. This was vortexed and allowed to incubate overnight 37° C., under which conditions the peptide aggregated. Any unused Aβ was stored as a dry lyophilized powder at −20° C. until the next injection.

3. Preparation of Injections

For each injection, 100 µg of aggregated Aβ42 in PBS per mouse was emulsified 1:1 with Complete Freund's adjuvant (CFA) in a final volume of 400 µl emulsion for the first immunization, followed by a boost of the same amount of immunogen in Incomplete Freund's adjuvant (IFA) at 2 weeks. Two additional doses in IFA were given at monthly intervals. The subsequent immunizations were done at monthly intervals in 500 µl of PBS. Injections were delivered intraperitoneally (i.p.).

PBS injections followed the same schedule and mice were injected with a 1:1 mix of PBS/Adjuvant at 400 µl per mouse, or 500 µl of PBS per mouse. SAP injections likewise followed the same schedule using a dose of 100 µg per injection.

4. Titration of Mouse Bleeds, Tissue Preparation and Immunohistochemistry

The above methods are described infra in General Materials and Methods.

B. Results

PDAPP mice were injected with either aggregated Aβ42 (aggregated Aβ42), SAP peptides, or phosphate buffered saline. A group of PDAPP mice were also left as uninjected, positive controls. The titers of the mice to aggregated Aβ42 were monitored every other month from the fourth boost until the mice were one year of age. Mice were sacrificed at 13 months. At all time points examined, eight of the nine aggregated Aβ42 mice developed a high antibody titer, which remained high throughout the series of injections (titers greater than $1/10000$). The ninth mouse bad a low, but measurable titer of approximately $1/1000$ (FIG. 1, Table 1). SAPP-injected mice had titers of 1:1,000 to 1:30,000 for this immunogen with only a single mouse exceeding 1:10,0000.

The PBS-treated mice were titered against aggregated Aβ42 at six, ten and twelve months. At a $1/100$ dilution the PBS mice when titered against aggregated Aβ42 only exceeded 4 times background at one data point, otherwise, they were less than 4 times background at all time points (Table 1). The SAP-specific response was negligible at these time points with all titers less than 300.

Seven out of the nine mice in the aggregated Aβ1-42 treated group had no detectable amyloid in their brains. In contrast, brain tissue from mice in the SAP and PBS groups contained numerous amyloid deposits in the hippocampus, as well as in the frontal and cingulate cortices. The pattern of deposition was similar to that of untreated controls, with characteristic involvement of vulnerable subregions, such as the outer molecular layer of the hippocampal dentate gyrus. One mouse from the Aβ 1-42-injected group had a greatly reduced amyloid burden, confined to the hippocampus. An isolated plaque was identified in another Aβ 1-42-treated mouse.

Figure 2:
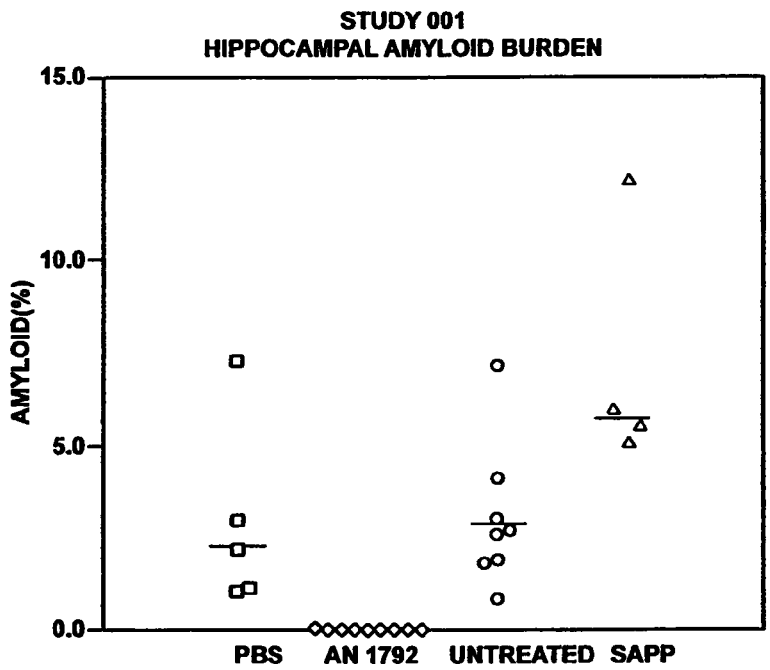
FIG. 2: Amyloid burden in the hippocampus. The percentage of the area of the hippocampal region occupied by amyloid plaques, defined by reactivity with the Aβ-specific monoclonal antibody 3D6, was determined by computer-assisted quantitative image analysis of immunoreacted brain sections. The values for individual mice are shown sorted by treatment group. The horizontal line for each grouping indicates the median value of the distribution.

Quantitative image analyses of the amyloid burden in the hippocampus verified the dramatic reduction achieved in the Aβ42(AN1792)-treated animals (FIG. 2). The median values of the amyloid burden for the PBS group (2.22%), and for the untreated control group (2.65%) were significantly greater than for those immunized with AN1792 (0.00%, p=0.0005). In contrast, the median value for the group immunized with SAP peptides (SAPP) was 5.74%. Brain tissue from the untreated, control mice contained numerous Aβ amyloid deposits visualized with the Aβ-specific monoclonal antibody (mAb) 3D6 in the hippocampus, as well as in the retrosplenial cortex. A similar pattern of amyloid deposition was also seen in mice immunized with SAPP or PBS (FIG. 2). In addition, in these latter three groups there was a characteristic involvement of vulnerable subregions of the brain classically seen in AD, such as the outer molecular layer of the hippocampal dentate gyrus, in all three of these groups.

Figure 3:
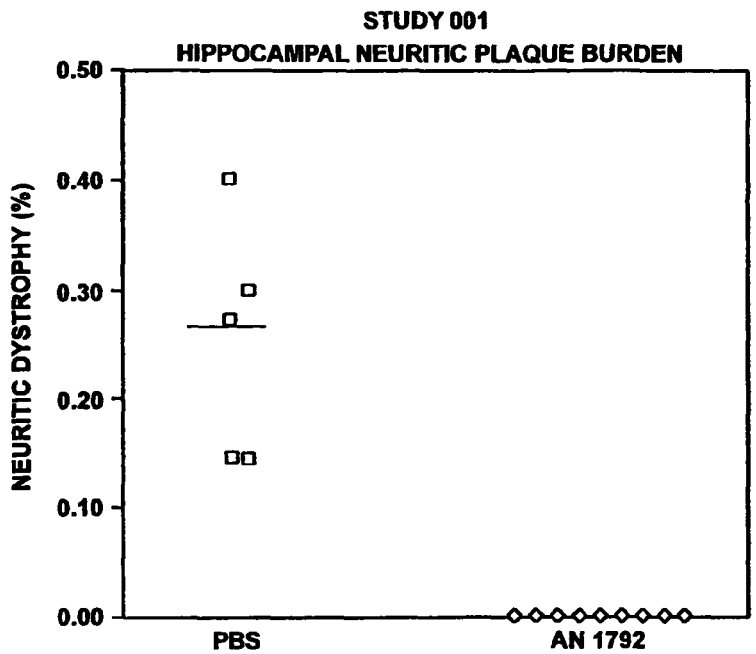
FIG. 3: Neuritic dystrophy in the hippocampus. The percentage of the area of the hippocampal region occupied by dystrophic neurites, defined by their reactivity with the human APP-specific monoclonal 8E5, was determined by quantitative computer-assisted image analysis of immunoreacted brain sections. The values for individual mice are shown for the AN1792-treated group and the PBS-treated control group. The horizontal line for each grouping indicates the median value of the distribution.

The brains that contained no Aβ deposits were also devoid of neuritic plaques that are typically visualized in PDAPP mice with the human APP antibody 8E5. All of brains from the remaining groups (SAP-injected, PBS and uninjected mice) had numerous neuritic plaques typical of untreated PDAPP mice. A small number of neuritic plaques were present in one mouse treated with AN1792, and a single cluster of dystrophic neurites was found in a second mouse treated with AN1792. Image analyses of the hippocampus, and shown in FIG. 3, demonstrated the virtual elimination of dystrophic neurites in AN1792-treated mice (median 0.00%) compared to the PBS recipients (median 0.28%, p=0.0005).

Astrocytosis characteristic of plaque-associated inflammation was also absent in the brains of the Aβ1-42 injected group. The brains from the mice in the other groups contained abundant and clustered GFAP-positive astrocytes typical of Aβ plaque-associated gliosis. A subset of the GFAP-reacted slides were counter-stained with Thioflavin S to localize the Aβ deposits. The GFAP-positive astrocytes were associated with Aβ plaques in the SAP, PBS and untreated controls. No such association was found in the plaque-negative Aβ1-42 treated mice, while minimal plaque-associated gliosis was identified in one mouse treated with AN1792.

Figure 4:
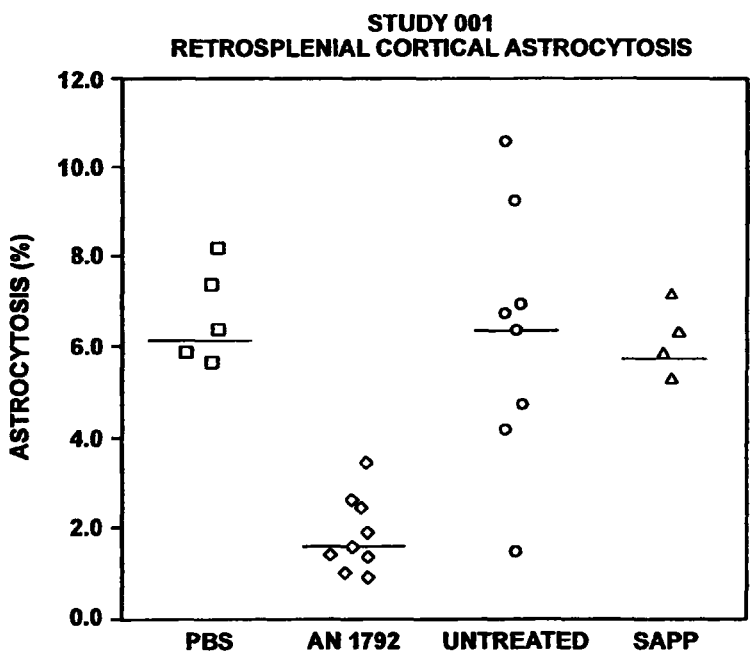
FIG. 4: Astrocytosis in the retrosplenial cortex. The percentage of the area of the cortical region occupied by glial fibrillary acidic protein (GFAP)-positive astrocytes was determined by quantitative computer-assisted image analysis of immunoreacted brain sections. The values for individual mice are shown sorted by treatment group and median group values are indicated by horizontal lines.

Image analyses, shown in FIG. 4 for the retrosplenial cortex, verified that the reduction in astrocytosis was significant with a median value of 1.56% for those treated with AN1792 versus median values greater than 6% for groups immunized with SAP peptides, PBS or untreated (p=0.0017)

Evidence from a subset of the Aβ1-42- and PBS-injected mice indicated plaque-associated MHC II immunoreactivity was absent in the Aβ1-42 injected mice, consistent with lack of an Aβ-related inflammatory response.

Sections of the mouse brains were also reacted with a mAb specific with a monoclonal antibody specific for MAC-1, a cell surface protein. MAC-1 (CD11b) is an integrin family member and exists as a heterodimer with CD18. The CD11b/CD18 complex is present on monocytes, macrophages, neutrophils and natural killer cells (Mak and Simard). The resident MAC-1-reactive cell type in the brain is likely to be microglia based on similar phenotypic morphology in MAC-1 immunoreacted sections. Plaque-associated MAC-1 labeling was lower in the brains of mice treated with AN1792 compared to the PBS control group, a finding consistent with the lack of an Aβ-induced inflammatory response.

C. Conclusion

The lack of Aβ plaques and reactive neuronal and gliotic changes in the brains of the Aβ1-42-injected mice indicate that no or extremely little amyloid was deposited in their brains, and pathological consequences, such as gliosis and neuritic pathology, were absent. PDAPP mice treated with Aβ1-42 show essentially the same lack of pathology as control nontransgenic mice. Therefore, Aβ1-42 injections are highly effective in the prevention of deposition or clearance of human Aβ from brain tissue, and elimination of subsequent neuronal and inflammatory degenerative changes. Thus, administration of Aβ peptide can have both preventative and therapeutic benefit in prevention of AD.

II. Dose Response Study

Groups of five-week old, female Swiss Webster mice (N=6 per group) were immunized with 300, 100, 33, 11, 3.7, 1.2, 0.4, or 0.13 ug of Aβ formulated in CFA/IFA administered intraperitoneally. Three doses were given at biweekly intervals followed by a fourth dose one month later. The first dose was emulsified with CFA and the remaining doses were emulsified with IFA. Animals were bled 4-7 days following each immunization starting after the second dose for measurement of antibody titers. Animals in a subset of three groups, those immunized with 11, 33, or 300 µg of antigen, were additionally bled at approximately monthly intervals for four months following the fourth immunization to monitor the decay of the antibody response across a range of vaccine doses. These animals received a final fifth immunization at seven months after study initiation. They were sacrificed one week later to measure antibody responses to AN1792 and to perform toxicological analyses.

Figure 5:
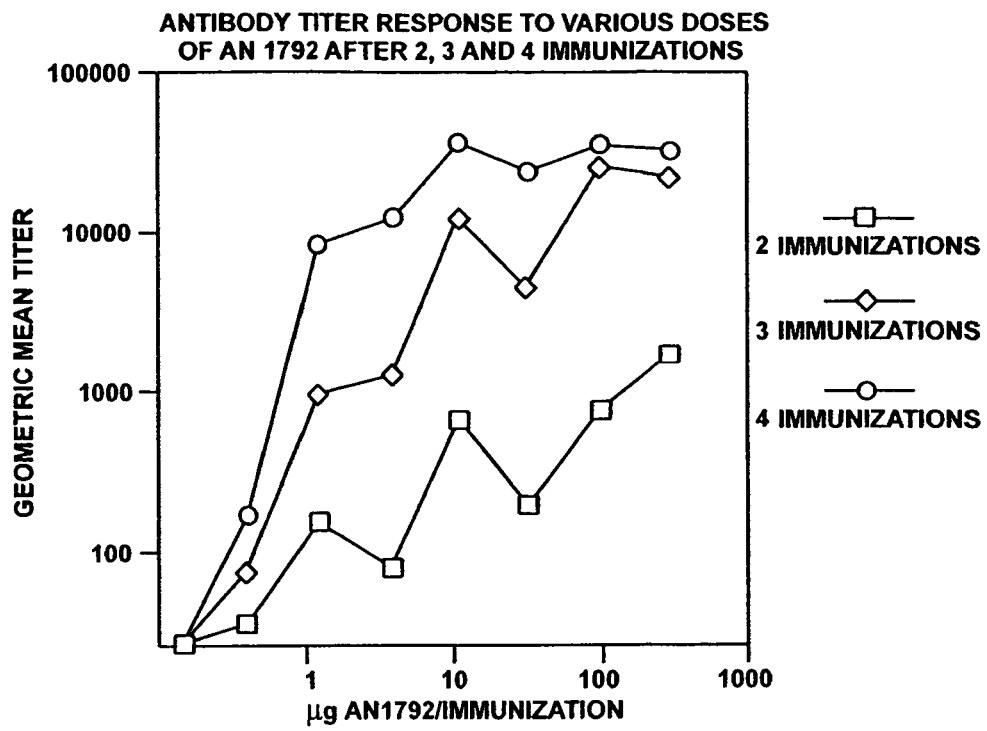
FIG. 5: Geometric mean antibody titers to Aβ1-42 following immunization with a range of eight doses of AN1792 containing 0.14, 0.4, 1.2, 3.7, 11, 33, 100, or 300 µg.

A declining dose response was observed from 300 to 3.7 µg with no response at the two lowest doses. Mean antibody titers are about 1:1000 after 3 doses and about 1:10,000 after 4 doses of 11-300 µg of antigen (see FIG. 5).

Antibody titers rose dramatically for all but the lowest dose group following the third immunization with increases in GMTs ranging from 5- to 25-fold. Low antibody responses were then detectable for even the 0.4 µg recipients. The 1.2 and 3.7 µg groups had comparable titers with GMTs of about 1000 and the highest four doses clustered together with GMTs of about 25,000, with the exception of the 33 µg dose group with a lower GMT of 3000. Following the fourth immunization, the titer increase was more modest for most groups. There was a clear dose response across the lower antigen dose groups from 0.14 µg to 11 µg ranging from no detectable antibody for recipients of 0.14 µg to a GMT of 36,000 for recipients of 11 µg. Again, titers for the four highest dose groups of 11 to 300 µg clustered together. Thus following two immunizations, the antibody titer was dependent on the antigen dose across the broad range from 0.4 to 300 µg. By the third immunization, titers of the highest four doses were all comparable and they remained at a plateau after an additional immunization.

Figure 6:
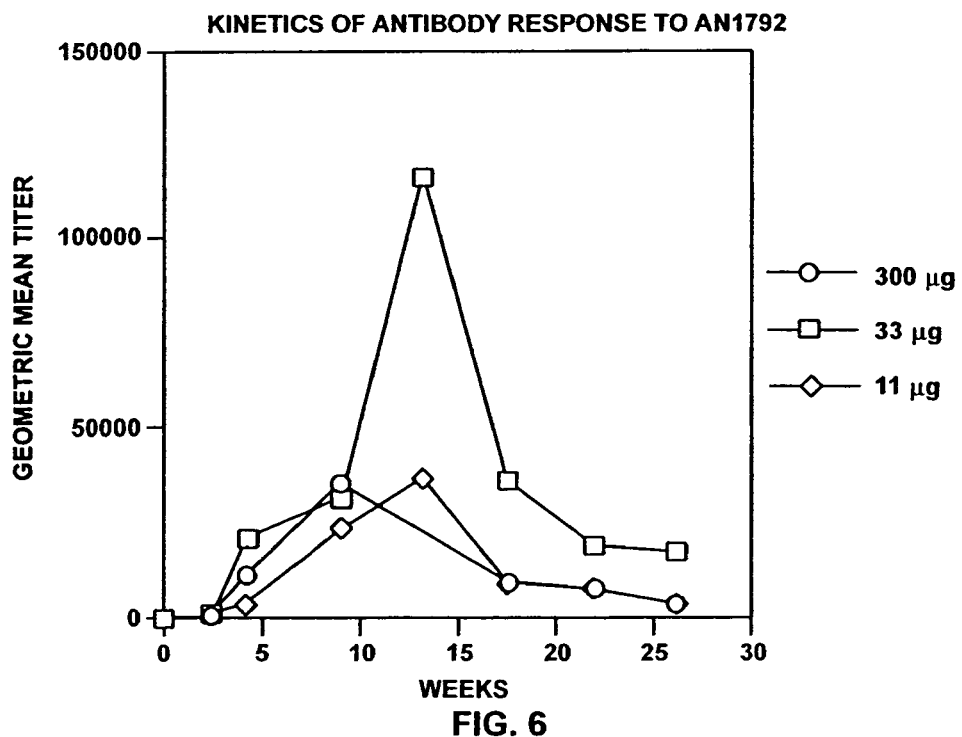
FIG. 6: Kinetics of antibody response to AN1792 immunization. Titers are expressed as geometric means of values for the 6 animals in each group.

One month following the fourth immunization, titers were 2- to 3-fold higher in the 300 µg group than those measured from blood drawn five days following the immunization (FIG. 6). This observation suggests that the peak anamnestic antibody response occurred later than 5 days post-immunization. A more modest (50%) increase was seen at this time in the 33 µggroup. In the 300 µg dose group at two months following the last dose, GMTs declined steeply by about 70%. After another month, the decline was less steep at 45% (100 µg) about 14% for the 33 and 11 µg doses. Thus, the rate of decline in circulating antibody titers following cessation of immunization appears to be biphasic with a steep decline the first month following peak response followed by a more modest rate of decrease thereafter.

The antibody titers and the kinetics of the response of these Swiss Webster mice are similar to those of young heterozygous PDAPP transgenic mice immunized in a parallel manner. Dosages effective to induce an immune response in humans are typically similar to dosages effective in mice.

III. Screen for Therapeutic Efficacy Against Established AD

This assay is designed to test immunogenic agents for activity in arresting or reversing neuropathologic characteristics of AD in aged animals. Immunizations with 42 amino acid long Aβ (AN1792) were begun at a time point when amyloid plaques are already present in the brains of the PDAPP mice.

Over the time course used in this study, untreated PDAPP mice develop a number of neurodegenerative changes that resemble those found in AD (Games et al., supra and Johnson-Wood et al., Proc. Natl. Acad. Sci. USA 94, 1550-1555 (1997)). The deposition of Aβ into amyloid plaques is associated with a degenerative neuronal response consisting of aberrant axonal and dendritic elements, called dystrophic neurites. Amyloid deposits that are surrounded by and contain dystrophic neurites called neuritic plaques. In both AD and the PDAPP mouse, dystrophic neurites have a distinctive globular structure, are immunoreactive with a panel of antibodies recognizing APP and cytoskeletal components, and display complex subcellular degenerative changes at the ultrastructural level. These characteristics allow for disease-relevant, selective and reproducible measurements of neuritic plaque formation in the PDAPP brains. The dystrophic neuronal component of PDAPP neuritic plaques is easily visualized with an antibody specific for human APP (monoclonal antibody 8E5), and is readily measurable by computer-assisted image analysis. Therefore, in addition to measuring the effects of AN1792 on amyloid plaque formation, we monitored the effects of this treatment on the development of neuritic dystrophy.

Astrocytes and microglia are non-neuronal cells that respond to and reflect the degree of neuronal injury. GFAP-positive astrocytes and MHC II-positive microglia are commonly observed in AD, and their activation increases with the severity of the disease. Therefore, we also monitored the development of reactive astrocytosis and microgliosis in the AN1792-treated mice.

A. Materials and Methods

Forty-eight, heterozygous female PDAPP mice, 11 to 11.5 months of age, obtained from Charles River, were randomly divided into two groups: 24 mice to be immunized with 100 μg of AN1792 and 24 mice to be immunized with PBS, each combined with Freund's adjuvant. The AN1792 and PBS groups were again divided when they reached 15 months of age. At 15 months of age approximately half of each group of the AN1792- and PBS-treated animals were euthanized (n=10 and 9, respectively), the remainder continued to receive immunizations until termination at ~18 months (n=9 and 12, respectively). A total of 8 animals (5 AN1792, 3 PBS) died during the study. In addition to the immunized animals, one-year old (n=10), 15-month old (n=10) and 18-month old (n=10) untreated PDAPP mice were included for comparison in the ELISAs to measure aβ and APP levels in the brain; the one-year old animals were also included in the immunohistochemical analyses.

Methodology was as in Example 1 unless otherwise indicated. US Peptides lot 12 and California Peptides lot ME0339 of AN1792 were used to prepare the antigen for the six immunizations administered prior to the 15-month time point. California Peptides lots ME0339 and ME0439 were used for the three additional immunizations administered between 15 and 18 months.

For immunizations, 100 μg of AN1792 in 200 μl PBS or PBS alone was emulsified 1:1 (vol:vol) with Complete Freund's adjuvant (CFA) or Incomplete Freund's adjuvant (IFA) or PBS in a final volume of 400 μl. The first immunization was delivered with CFA as adjuvant, the next four doses were given with IFA and the final four doses with PBS alone without added adjuvant. A total of nine immunizations were given over the seven-month period on a two-week schedule for the first three doses followed by a four-week interval for the remaining injections. The four-month treatment group, euthanized at 15 months of age, received only the first 6 immunizations.

B. Results

1. Effects of AN1792 Treatment on Amyloid Burden

Figure 7:
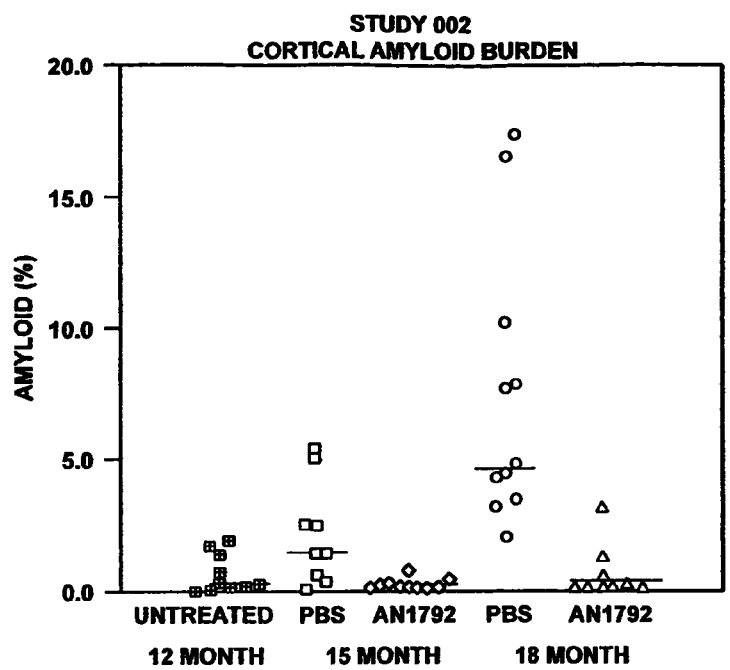
FIG. 7: Quantitative image analysis of the cortical amyloid burden in PBS- and AN1792-treated mice.

The results of AN1792 treatment on cortical amyloid burden determined by quantitative image analysis are shown in FIG. 7. The median value of cortical amyloid burden was 0.28% in a group of untreated 12-month old PDAPP mice, a value representative of the plaque load in mice at the study's initiation. At 18 months, the amyloid burden increased over 17-fold to 4.87% in PBS-treated mice, while AN1792-treated mice had a greatly reduced amyloid burden of only 0.01%, notably less than the 12-month untreated and both the 15- and 18-month PBS-treated groups. The amyloid burden was significantly reduced in the AN1792 recipients at both 15 (96% reduction; $p=0.003$) and 18 (>99% reduction; $p=0.0002$) months.

Typically, cortical amyloid deposition in PDAPP mice initiates in the frontal and retrosplenial cortices (RSC) and progresses in a ventral-lateral direction to involve the temporal and entorhinal cortices (EC). Little or no amyloid was found in the EC of 12 month-old mice, the approximate age at which AN1792 was first administered. After 4 months of AN1792 treatment, amyloid deposition was greatly diminished in the RSC, and the progressive involvement of the EC was entirely eliminated by AN1792 treatment. The latter observation showed that AN1792 completely halted the progression of amyloid that would normally invade the temporal and ventral cortices, as well as arrested or possibly reversed deposition in the RSC.

The profound effects of AN1792 treatment on developing cortical amyloid burden in the PDAPP mice are further demonstrated by the 18-month group, which had been treated for seven months. A near complete absence of cortical amyloid was found in the AN1792-treated mouse, with a total lack of diffuse plaques, as well as a reduction in compacted deposits.

2. AN1792 Treatment-associated Cellular and Morphological

Changes

A population of Aβ-positive cells was found in brain regions that typically contain amyloid deposits. Remarkably, in several brains from AN1792 recipients, very few or no extracellular cortical amyloid plaques were found. Most of the Aβ immunoreactivity appeared to be contained within cells with large lobular or clumped soma. Phenotypically, these cells resembled activated microglia or monocytes. They were immunoreactive with antibodies recognizing ligands expressed by activated monocytes and microglia (MHC II and CD11b) and were occasionally associated with the wall or lumen of blood vessels. Comparison of near-adjacent sections labeled with Aβ and MHC II-specific antibodies revealed that similar patterns of these cells were recognized by both classes of antibodies. Detailed examination of the AN1792-treated brains revealed that the MHC II-positive cells were restricted to the vicinity of the limited amyloid remaining in these animals. Under the fixation conditions employed, the cells were not immunoreactive with antibodies that recognize T cell (CD3, CD3e) or B cell (CD45RA, CD45RB) ligands or leukocyte common antigen (CD45), but were reactive with an antibody recognizing leukosialin (CD43) which cross-reacts with monocytes. No such cells were found in any of the PBS-treated mice.

PDAPP mice invariably develop heavy amyloid deposition in the outer molecular layer of the hippocampal dentate gyrus. The deposition forms a distinct streak within the perforant pathway, a subregion that classically contains amyloid plaques in AD. The characteristic appearance of these deposits in PBS-treated mice resembled that previously characterized in untreated PDAPP mice. The amyloid deposition consisted of both diffuse and compacted plaques in a continuous band. In contrast, in a number of brains from AN1792-treated mice this pattern was drastically altered. The hippocampal amyloid deposition no longer contained diffuse amyloid, and the banded pattern was completely disrupted. Instead, a number of unusual punctate structures were present that are reactive with anti-Aβ antibodies, several of which appeared to be amyloid-containing cells.

MHC II-positive cells were frequently observed in the vicinity of extracellular amyloid in AN1792-treated animals. The pattern of association of Aβ-positive cells with amyloid was very similar in several brains from AN1792-treated mice. The distribution of these monocytic cells was restricted to the proximity of the deposited amyloid and was entirely absent from other brain regions devoid of Aβ plaques.

Quantitative image analysis of MHC II and MAC I-labeled sections revealed a trend towards increased immunoreactivity in the RSC and hippocampus of AN1792-treated mice compared to the PBS group which reached significance with the measure of MAC 1 reactivity in hippocampus.

These results are indicative of active, cell-mediated removal of amyloid in plaque-bearing brain regions.

3. AN1792 Effects on Aβ Levels: ELISA Determinations (a) Cortical Levels

In untreated PDAPP mice, the median level of total Aβ in the cortex at 12 months was 1,600 ng/g, which increased to 8,700 ng/g by 15 months (Table 2). At 18 months the value was 22,000 ng/g, an increase of over 10-fold during the time course of the experiment. PBS-treated animals had 8,600 ng/g total Aβ at 15 months which increased to 19,000 ng/g at 18 months. In contrast, AN1792-treated animals had 81% less total Aβ at 15 months (1,600 ng/g) than the PBS-immunized group. Significantly less (p=0.0001) total Aβ (5,200 ng/g) was found at 18 months when the AN1792 and PBS groups were compared (Table 2), representing a 72% reduction in the Aβ that would otherwise be present. Similar results were obtained when cortical levels of Aβ42 were compared, namely that the AN1792-treated group contained much less Aβ42, but in this case the differences between the AN1792 and PBS groups were significant at both 15 months (p=0.04) and 18 months (p=0.0001, Table 2).

TABLE 2

Median Aβ Levels (ng/g) in Cortex

| | UNTREATED | | | PBS | | | AN1792 | | |
|---|---|---|---|---|---|---|---|---|---|
| Age | Total | Aβ42 | (n) | Total | Aβ42 | (n) | Total | Aβ42 | (n) |
| 12 | 1,600 | 1,300 | (10) | | | | | | |
| 15 | 8,700 | 8,300 | (10) | 8,600 | 7,200 | (9) | 1,600 | 1,300* | (10) |
| 18 | 22,200 | 18,500 | (10) | 19,000 | 15,900 | (12) | 5,200** | 4,000** | (9) |

*p = 0.0412
**p = 0.0001

(b) Hippocampal Levels

In untreated PDAPP mice, median hippocampal levels of total Aβ at twelve months of age were 15,000 ng/g which increased to 51,000 ng/g at 15 months and further to 81,000 ng/g at 18 months (Table 3). Similarly, PBS immunized mice showed values of 40,000 ng/g and 65,000 ng/g at 15 months and 18 months, respectively. AN1792 immunized animals exhibited less total Aβ, specifically 25,000 ng/g and 51,000 ng/g at the respective 15-month and 18-month time points. The 18-month AN1792-treated group value was significantly lower than that of the PBS treated group (p=0.0105; Table 3). Measurement of Aβ42 gave the same pattern of results, namely that levels in the AN1792-treated group were significantly lower than in the PBS group (39,000 ng/g vs. 57,000 ng/g, respectively; p=0.002) at the 18-month evaluation (Table 3).

TABLE 3

Median Aβ Levels (ng/g) in Hippocampus

| | UNTREATED | | | PBS | | | AN1792 | | |
|---|---|---|---|---|---|---|---|---|---|
| Age | Total | Aβ42 | (n) | Total | Aβ42 | (n) | Total | Aβ42 | (n) |
| 12 | 15,500 | 11,100 | (10) | | | | | | |
| 15 | 51,500 | 44,400 | (10) | 40,100 | 35.70 | (9) | 24.50 | 22,100 | (10) |
| 18 | 80,800 | 64,200 | (10) | 65,400 | 57.10 | (12) | 50.90 | 38,900** | (9) |

*p = 0.0105
**p = 0.0022

(c) Cerebellar Levels

In 12-month untreated PDAPP mice, the median cerebellar level of total Aβ was 15 ng/g (Table 4). At 15 months, this median increased to 28 ng/g and by 18 months had risen to 35 ng/g. PBS-treated animals displayed median total Aβ values of 21 ng/g at 15 months and 43 ng/g at 18 months. AN1792-treated animals were found to have 22 ng/g total Aβ at 15 months and significantly less (p=0.002) total Aβ at 18 months (25 ng/g) than the corresponding PBS group (Table 4).

TABLE 4

Median Aβ Levels (ng/g) in Cerebellum

| | UNTREATED | | PBS | | AN1792 | |
|---|---|---|---|---|---|---|
| Age | Total Aβ | (n) | Total Aβ | (n) | Total Aβ | (n) |
| 12 | 15.6 | (10) | | | | |
| 15 | 27.7 | (10) | 20.8 | (9) | 21.7 | (10) |
| 18 | 35.0 | (10) | 43.1 | (12) | 24.8* | (9) |

*p = 0.0018

4. Effects of AN1792 Treatment on APP Levels

APP-α and the full-length APP molecule both contain all or part of the Aβ sequence and thus could be potentially impacted by the generation of an AN1792-directed immune response. In studies to date, a slight increase in APP levels has been noted as neuropathology increases in the PDAPP mouse. In the cortex, levels of either APP-á/FL (full length) or APP-α were essentially unchanged by treatment with the exception that APP-á was reduced by 19% at the 18-month timepoint in the AN1792-treated vs. the PBS-treated group. The 18-month AN1792-treated APP values were not significantly different from values of the 12-month and 15-month untreated and 15-month PBS groups. In all cases the APP values remained within the ranges that are normally found in PDAPP mice.

5. Effects of AN1792 Treatment on Neurodegenerative and Gliotic Pathology

Figure 8:
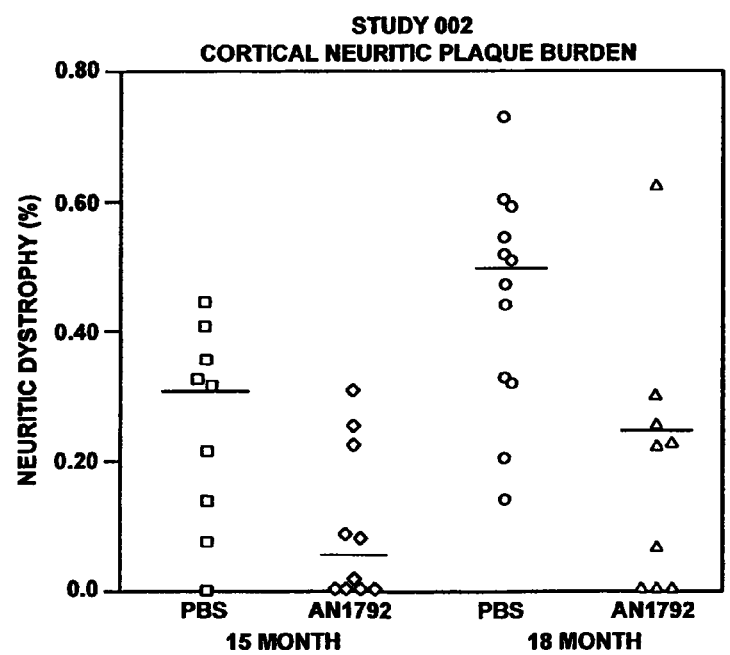
FIG. 8: Quantitative image analysis of the neuritic plaque burden in PBS- and AN1792-treated mice.

Neuritic plaque burden was significantly reduced in the frontal cortex of AN1792-treated mice compared to the PBS group at both 15 (84%; p=0.03) and 18 (55%; p=0.01) months of age (FIG. 8). The median value of the neuritic plaque burden increased from 0.32% to 0.49% in the PBS group between 15 and 18 months of age. This contrasted with the greatly reduced development of neuritic plaques in the AN1792 group, with median neuritic plaque burden values of 0.05% and 0.22%, in the 15 and 18 month groups, respectively.

Figure 9:
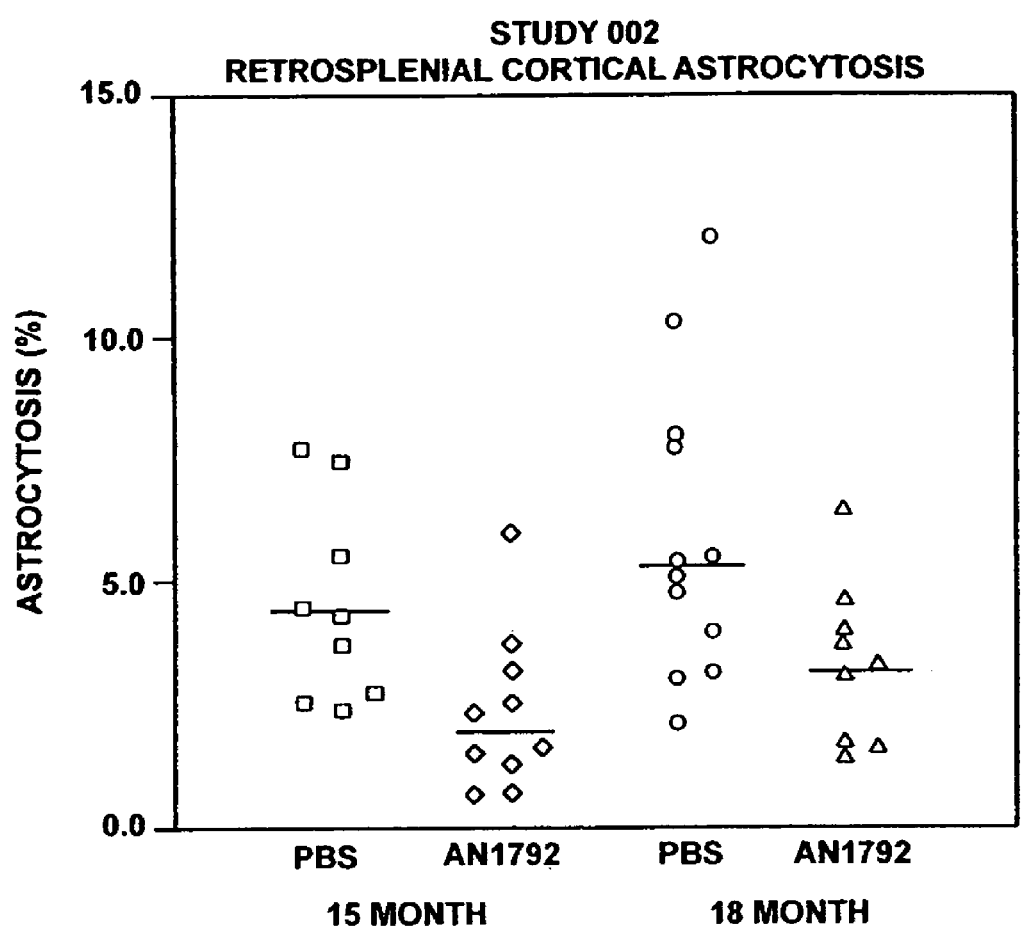
FIG. 9: Quantitative image analysis of the percent of the retrosplenial cortex occupied by astrocytosis in PBS- and AN1792-treated mice.

Immunizations with AN1792 seemed well tolerated and reactive astrocytosis was also significantly reduced in the RSC of AN1792-treated mice when compared to the PBS group at both 15 (56%; p=0.011) and 18 (39%; p=0.028) months of age (FIG. 9). Median values of the percent of astrocytosis in the PBS group increased between 15 and 18 months from 4.26% to 5.21%. AN1792-treatment suppressed the development of astrocytosis at both time points to 1.89% and 3.2%, respectively. This suggests the neuropil was not being damaged by the clearance process.

6. Antibody Responses

As described above, eleven-month old, heterozygous PDAPP mice (N=24) received a series of 5 immunizations of 100 μg of AN1792 emulsified with Freund's adjuvant and administered intraperitoneally at weeks 0, 2, 4, 8, and 12, and a sixth immunization with PBS alone (no Freund's adjuvant) at week 16. As a negative control, a parallel set of 24 age-matched transgenic mice received immunizations of PBS emulsified with the same adjuvants and delivered on the same schedule. Animals were bled within three to seven days following each immunization starting after the second dose. Antibody responses to AN1792 were measured by ELISA. Geometric mean titers (GMT) for the animals that were immunized with AN1792 were approximately 1,900, 7,600, and 45,000 following the second, third and last (sixth) doses respectively. No Aβ-specific antibody was measured in control animals following the sixth immunization.

Approximately one-half of the animals were treated for an additional three months, receiving immunizations at about 20, 24 and 27 weeks. Each of these doses was delivered in PBS vehicle alone without Freund's adjuvant. Mean antibody titers remained unchanged over this time period. In fact, antibody titers appeared to remain stable from the fourth to the eighth bleed corresponding to a period covering the fifth to the ninth injections.

To determine if the Aβ-specific antibodies elicited by immunization that were detected in the sera of AN1792-treated mice were also associated with deposited brain amyloid, a subset of sections from the AN1792- and PBS-treated mice were reacted with an antibody specific for mouse IgG. In contrast to the PBS group, Aβ plaques in AN1792-treated brains were coated with endogenous IgG. This difference between the two groups was seen in both 15- and 18-month groups. Particularly striking was the lack of labeling in the PBS group, despite the presence of a heavy amyloid burden in these mice. These results show that immunization with a synthetic Aβ protein generates antibodies that recognize and bind in vivo to the Aβ in amyloid plaques.

7. Cellular-Mediated Immune Responses

Figure 10A:
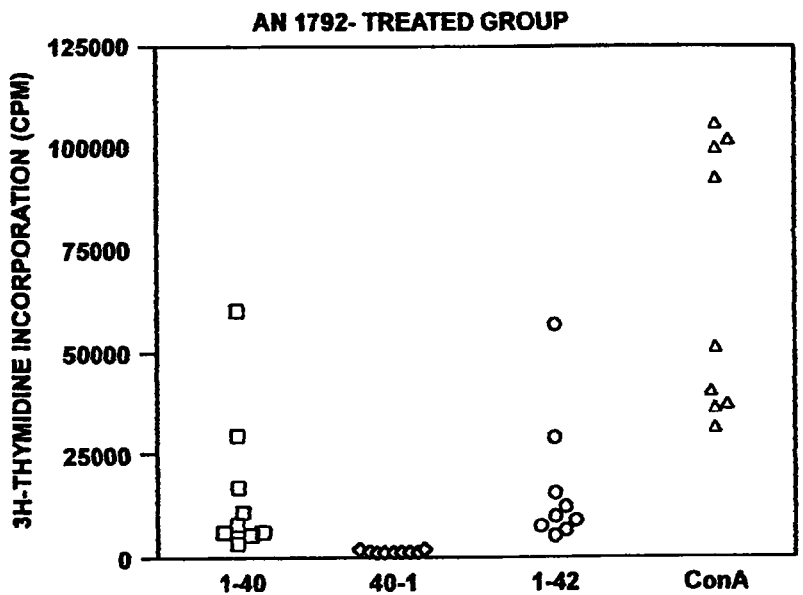
FIG. 10: Lymphocyte Proliferation Assay on spleen cells from AN1792-treated (FIG. 10A) or PBS-treated (FIG. 10B).
Figure 10B:
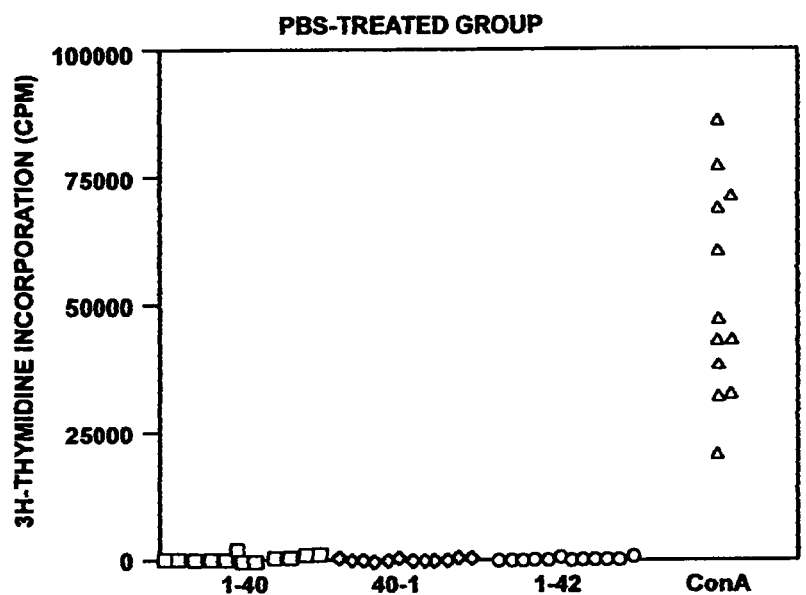

Spleens were removed from nine AN1792-immunized and 12 PBS-immunized 18-month old PDAPP mice 7 days after the ninth immunization. Splenocytes were isolated and cultured for 72 h in the presence of Aβ40, Aβ42, or Aβ40-1 (reverse order protein). The mitogen Con A served as a positive control. Optimum responses were obtained with >1.7 μM protein. Cells from all nine AN1792-treated animals proliferated in response to either Aβ1-40 or Aβ1-42 protein, with equal levels of incorporation for both proteins (FIG. 10A). There was no response to the Aβ40-1 reverse protein. Cells from control animals did not respond to any of the Aβ proteins (FIG. 10B).

C. Conclusion

The results of this study show that AN1792 immunization of PDAPP mice possessing existing amyloid deposits slows and prevents progressive amyloid deposition and retard consequential neuropathologic changes in the aged PDAPP mouse brain. Immunizations with AN1792 essentially halted amyloid developing in structures that would normally succumb to amyloidosis. Thus, administration of Aβ peptide has therapeutic benefit in the treatment of AD.

IV. Screen of Aβ Fragments

100 PDAPP mice age 9-11 months were immunized with 9 different regions of APP and Aβ to determine which epitopes convey the efficacious response. The 9 different immunogens and one control are injected i.p. as described above. The immunogens include four human Aβ peptide conjugates 1-12, 13-28, 32-42, 1-5, all coupled to sheep anti-mouse IgG via a cystine link; an APP polypeptide amino acids 592-695, aggregated human Aβ 1-40, and aggregated human Aβ 25-35, and aggregated rodent Aβ42. Aggregated Aβ42 and PBS were used as positive and negative controls, respectively. Ten mice were used per treatment group. Titers were monitored as above and mice are euthanized at the end of 4 months of injections. Histochemistry, Aβ levels, and toxicology analysis was determined post mortem.

A. Materials and Methods

1. Preparation of Immunogens

Preparation of coupled Aβ peptides: four human Aβ peptide conjugates (amino acid residues 1-5, 1-12, 13-28, and 33-42, each conjugated to sheep anti-mouse IgG) were prepared by coupling through an artificial cysteine added to the Aβ peptide using the crosslinking reagent sulfo-EMCS. The Aβ peptide derivatives were synthesized with the following final amino acid sequences. In each case, the location of the inserted cysteine residue is indicated by underlining. The Aβ13-28 peptide derivative also had two glycine residues added prior to the carboxyl terminal cysteine as indicated.

```
                                                    (SEQ ID NO: 2)
Aβ1-12 peptide      NH₂-DAEFRHDSGYEVC-COOH (SEQ ID NO: 3)
Aβ1-5 peptide       NH₂-DAEFRC-COOH (SEQ ID NO: 4)
Aβ33-42 peptide     NH₂-C-amino-heptanoic
                    acid-GLMVGGVVIA-COOH (SEQ ID NO: 5)
Aβ13-28 peptide     Ac-NH-HHQKLVFFAEDVGSNKGGC-COOH
```

To prepare for the coupling reaction, ten mg of sheep anti-mouse IgG (Jackson ImmunoResearch Laboratories) was dialyzed overnight against 10 mM sodium borate buffer, pH 8.5. The dialyzed antibody was then concentrated to a volume of 2 mL using an Amicon Centriprep tube. Ten mg sulfo-EMCS [N(γ-maleimidocuproyloxy) succinimide] (Molecular Sciences Co.) was dissolved in one mL deionized water. A 40-fold molar excess of sulfo-EMCS was added dropwise with stirring to the sheep anti-mouse IgG and then the solution was stirred for an additional ten min. The activated sheep anti-mouse IgG was purified and buffer exchanged by passage over a 10 mL gel filtration column (Pierce Presto Column, obtained from Pierce Chemicals) equilibrated with 0.1 M NaPO4, 5 mM EDTA, pH 6.5. Antibody containing fractions, identified by absorbance at 280 nm, were pooled and diluted to a concentration of approximately 1 mg/mL, using 1.4 mg per OD as the extinction coefficient. A 40-fold molar excess of Aβ peptide was dissolved in 20 mL of 10 mM NaPO4, pH 8.0, with the exception of the Aβ33-42 peptide for which 10 mg was first dissolved in 0.5 mL of DMSO and then diluted to 20 mL with the 10 mM NaPO4 buffer. The peptide solutions were each added to 10 mL of activated sheep anti-mouse IgG and rocked at room temperature for 4 hr. The resulting conjugates were concentrated to a final volume of less than 10 mL using an Amicon Centriprep tube and then dialyzed against PBS to buffer exchange the buffer and remove free peptide. The conjugates were passed through 0.22 μm-pore size filters for sterilization and then aliquoted into fractions of 1 mg and stored frozen at −20° C. The concentrations of the conjugates were determined using the BCA protein assay (Pierce Chemicals) with horse IgG for the standard curve. Conjugation was documented by the molecular weight increase of the conjugated peptides relative to that of the activated sheep anti-mouse IgG. The Aβ1-5 sheep anti-mouse conjugate was a pool of two conjugations, the rest were from a single preparation.

2. Preparation of Aggregated Aβ Peptides

Human 1-40 (AN1528; California Peptides Inc., Lot ME0541), human 1-42 (AN1792; California Peptides Inc., Lots ME0339 and ME0439), human 25-35, and rodent 1-42 (California Peptides Inc., Lot ME0218) peptides were freshly solubilized for the preparation of each set of injections from lyophilized powders that had been stored desiccated at −20° C. For this purpose, two mg of peptide were added to 0.9 ml of deionized water and the mixture was vortexed to generate a relatively uniform solution or suspension. Of the four, AN1528 was the only peptide soluble at this step. A 100 μl aliquot of 10×PBS (1×PBS: 0.15 M NaCl, 0.01 M sodium phosphate, pH 7.5) was then added at which point AN1528 began to precipitate. The suspension was vortexed again and incubated overnight at 37° C. for use the next day.

Preparation of the pBx6 protein: An expression plasmid encoding pBx6, a fusion protein consisting of the 100-amino acid bacteriophage MS-2 polymerase N-terminal leader sequence followed by amino acids 592-695 of APP (βAPP) was constructed as described by Oltersdorf et al., J. Biol. Chem. 265, 4492-4497 (1990). The plasmid was transfected into E. coli and the protein was expressed after induction of the promoter. The bacteria were lysed in 8 M urea and pBx6 was partially purified by preparative SDS PAGE. Fractions containing pBx6 were identified by Western blot using a rabbit anti-pBx6 polyclonal antibody, pooled, concentrated using an Amicon Centriprep tube and dialysed against PBS. The purity of the preparation, estimated by Coomassie Blue stained SDS PAGE, was approximately 5 to 10%.

B. Results and Discussion

1. Study Design

One hundred male and female, nine- to eleven-month old heterozygous PDAPP transgenic mice were obtained from Charles River Laboratory and Taconic Laboratory. The mice were sorted into ten groups to be immunized with different regions of Aβ or APP combined with Freund's adjuvant. Animals were distributed to match the gender, age, parentage and source of the animals within the groups as closely as possible. The immunogens included four Aβ peptides derived from the human sequence, 1-5, 1-12, 13-28, and 33-42, each conjugated to sheep anti-mouse IgG; four aggregated Aβ peptides, human 1-40 (AN1528), human 1-42 (AN1792), human 25-35, and rodent 1-42; and a fusion polypeptide, designated as pBx6, containing APP amino acid residues 592-695. A tenth group was immunized with PBS combined with adjuvant as a control.

For each immunization, 100 μg of each Aβ peptide in 200 μl PBS or 200 μg of the APP derivative pBx6 in the same volume of PBS or PBS alone was emulsified 1:1 (vol:vol) with Complete Freund's adjuvant (CFA) in a final volume of 400 μl for the first immunization, followed by a boost of the same amount of immunogen in Incomplete Freund's adjuvant (IFA) for the subsequent four doses and with PBS for the final dose. Immunizations were delivered intraperitoneally on a biweekly schedule for the first three doses, then on a monthly schedule thereafter. Animals were bled four to seven days following each immunization starting after the second dose for the measurement of antibody titers. Animals were euthanized approximately one week after the final dose.

2. Aβ and APP Levels in the Brain

Following about four months of immunization with the various Aβ peptides or the APP derivative, brains were removed from saline-perfused animals. One hemisphere was prepared for immunohistochemical analysis and the second was used for the quantitation of Aβ and APP levels. To measure the concentrations of various forms of beta amyloid peptide and amyloid precursor protein, the hemisphere was dissected and homogenates of the hippocampal, cortical, and cerebellar regions were prepared in 5 M guanidine. These were diluted and the level of amyloid or APP was quantitated by comparison to a series of dilutions of standards of Aβ peptide or APP of known concentrations in an ELISA format.

The median concentration of total Aβ for the control group immunized with PBS was 5.8-fold higher in the hippocampus than in the cortex (median of 24,318 ng/g hippocampal tissue compared to 4,221 ng/g for the cortex). The median level in the cerebellum of the control group (23.4 ng/g tissue) was about 1,000-fold lower than in the hippocampus. These levels are similar to those that we have previously reported for heterozygous PDAPP transgenic mice of this age (Johnson-Woods et al., 1997, supra).

Figure 11:
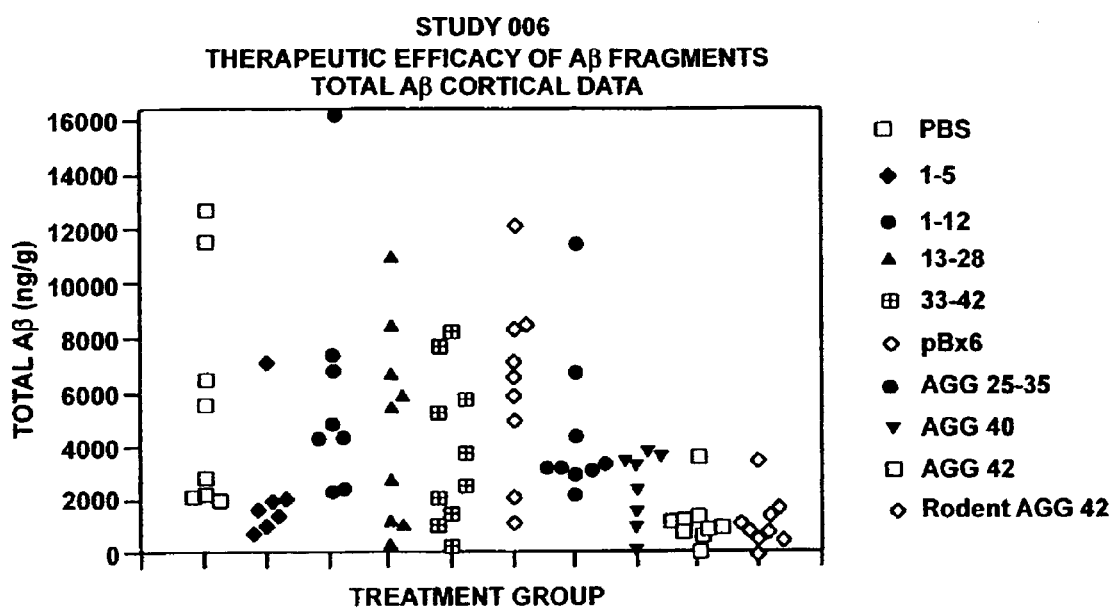
FIG. 11: Total Aβ levels in the cortex. A scatterplot of individual Aβ profiles in mice immunized with Aβ or APP derivatives combined with Freund' adjuvant.

For the cortex, a subset of treatment groups had median total Aβ and Aβ1-42 levels which differed significantly from those of the control group (p<0.05), those animals receiving AN1792, rodent Aβ1-42 or the Aβ1-5 peptide conjugate as shown in FIG. 11. The median levels of total Aβ were reduced by 75%, 79% and 61%, respectively, compared to the control for these treatment groups. There were no discernable correlations between Aβ-specific antibody titers and Aβ levels in the cortical region of the brain for any of the groups.

In the hippocampus, the median reduction of total Aβ associated with AN1792 treatment (46%, p=0.0543) was not as great as that observed in the cortex (75%, p=0.0021). However, the magnitude of the reduction was far greater in the hippocampus than in the cortex, a net reduction of 11,186 ng/g tissue in the hippocampus versus 3,171 ng/g tissue the cortex. For groups of animals receiving rodent Aβ1-42 or Aβ1-5, the median total Aβ levels were reduced by 36% and 26%, respectively. However, given the small group sizes and the high variability of the amyloid peptide levels from animal to animal within both groups, these reductions were not significant. When the levels of Aβ1-42 were measured in the hippocampus, none of the treatment-induced reductions reached significance. Thus, due to the smaller Aβ burden in the cortex, changes in this region are a more sensitive indicator of treatment effects. The changes in Aβ levels measured by ELISA in the cortex are similar, but not identical, to the results from the immunohistochemical analysis (see below).

Total Aβ was also measured in the cerebellum, a region typically minimally affected with AD pathology. None of the median Aβ concentrations of any of the groups immunized with the various Aβ peptides or the APP derivative differed from that of the control group in this region of the brain. This result suggests that non-pathological levels of Aβ are unaffected by treatment.

APP concentration was also determined by ELISA in the cortex and cerebellum from treated and control mice. Two different APP assays were utilized. The first, designated APP-á/FL, recognizes both APP-alpha (á, the secreted form of APP which has been cleaved within the Aβ sequence), and full-length forms (FL) of APP, while the second recognizes only APP-α. In contrast to the treatment-associated diminution of Aβ in a subset of treatment groups, the levels of APP were unchanged in all of the treated compared to the control animals. These results indicate that the immunizations with Aβ peptides are not depleting APP; rather the treatment effect is specific to Aβ.

In summary, total Aβ and Aβ1-42 levels were significantly reduced in the cortex by treatment with AN1792, rodent Aβ1-42 or Aβ1-5 conjugate. In the hippocampus, total Aβ was significantly reduced only by AN1792 treatment. No other treatment-associated changes in Aβ or APP levels in the hippocampal, cortical or cerebellar regions were significant.

2. Histochemical Analyses

Figure 12:
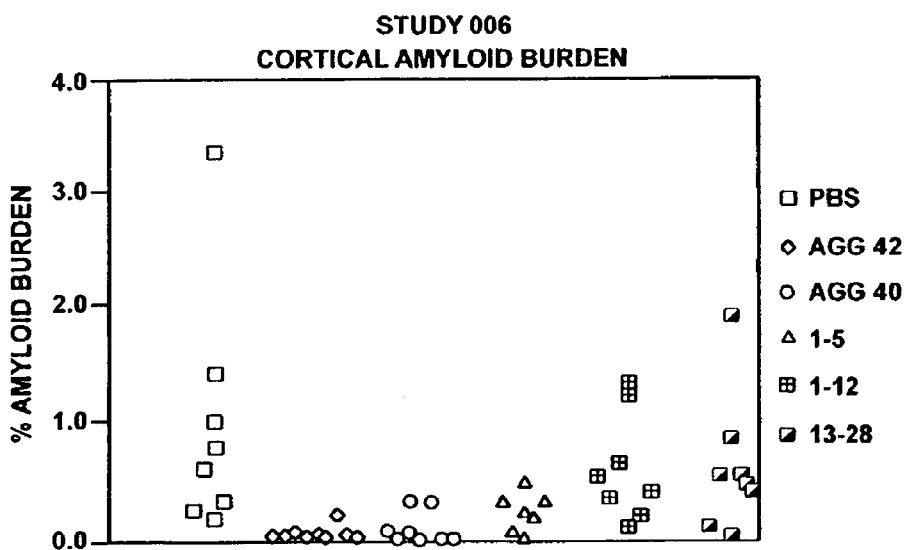
FIG. 12: Amyloid burden in the cortex was determined by quantitative image analysis of immunoreacted brain sections for mice immunized with the Aβ peptide conjugates Aβ1-5, Aβ1-12, and Aβ13-28; the full length Aβ aggregates AN1792 (Aβ1-42) and AN1528 (Aβ1-40) and the PBS-treated control group.

Brains from a subset of six groups were prepared for immunohistochemical analysis, three groups immunized with the Aβ peptide conjugates Aβ1-5, Aβ1-12, and Aβ13-28; two groups immunized with the full length Aβ aggregates AN1792 and AN1528 and the PBS-treated control group. The results of image analyses of the amyloid burden in brain sections from these groups are shown in FIG. 12. There were significant reductions of amyloid burden in the cortical regions of three of the treatment groups versus control animals. The greatest reduction of amyloid burden was observed in the group receiving AN1792 where the mean value was reduced by 97% (p=0.001). Significant reductions were also observed for those animals treated with AN1528 (95%, p=0.005) and the Aβ1-5 peptide conjugate (67%, p=0.02).

The results obtained by quantitation of total Aβ or Aβ1-42 by ELISA and amyloid burden by image analysis differ to some extent. Treatment with AN1528 had a significant impact on the level of cortical amyloid burden when measured by quantitative image analysis but not on the concentration of total Aβ in the same region when measured by ELISA. The difference between these two results is likely to be due to the specificities of the assays. Image analysis measures only insoluble Aβ aggregated into plaques. In contrast, the ELISA measures all forms of Aβ, both soluble and insoluble, monomeric and aggregated. Since the disease pathology is thought to be associated with the insoluble plaque-associated form of Aβ, the image analysis technique may have more sensitivity to reveal treatment effects. However since the ELISA is a more rapid and easier assay, it is very useful for screening purposes. Moreover it may reveal that the treatment-associated reduction of Aβ is greater for plaque-associated than total Aβ.

To determine if the Aβ-specific antibodies elicited by immunization in the treated animals reacted with deposited brain amyloid, a subset of the sections from the treated animals and the control mice were reacted with an antibody specific for mouse IgG. In contrast to the PBS group, Aβ-containing plaques were coated with endogenous IgG for animals immunized with the Aβ peptide conjugates Aβ1-5, Aβ1-12, and Aβ13-28; and the full length Aβ aggregates AN1792 and AN1528. Brains from animals immunized with the other Aβ peptides or the APP peptide pBx6 were not analyzed by this assay.

3. Measurement of Antibody Titers

Figure 13:
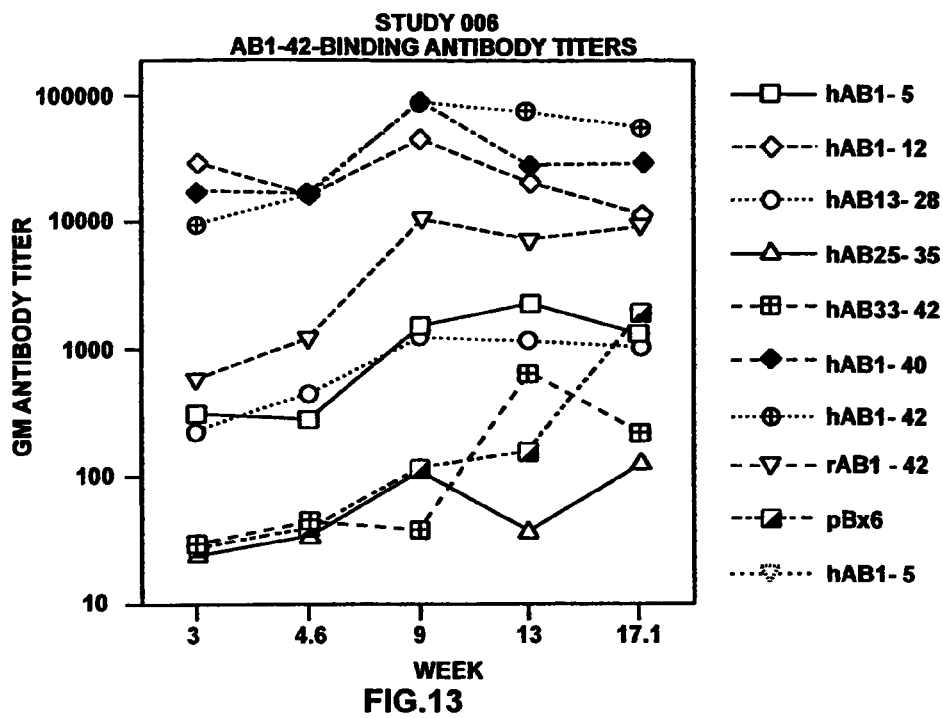
FIG. 13: Geometric mean titers of Aβ-specific antibody for groups of mice immunized with Aβ or APP derivatives combined with Freund's adjuvant.

Mice were bled four to seven days following each immunization starting after the second immunization, for a total of five bleeds. Antibody titers were measured as Aβ1-42-binding antibody using a sandwich ELISA with plastic multi-well plates coated with Aβ1-42. As shown in FIG. 13, peak antibody titers were elicited following the fourth dose for those four vaccines which elicited the highest titers of AN1792-specific antibodies: AN1792 (peak GMT: 94,647), AN1528 (peak GMT: 88,231), Aβ1-12 conjugate (peak GMT: 47,216) and rodent Aβ1-42 (peak GMT: 10,766). Titers for these groups declined somewhat following the fifth and sixth doses. For the remaining five immunogens, peak titers were reached following the fifth or the sixth dose and these were of much lower magnitude than those of the four highest titer groups: Aβ1-5 conjugate (peak GMT: 2,356), pBx6 (peak GMT: 1,986), Aβ13-28 conjugate (peak GMT: 1,183), Aβ33-42 conjugate (peak GMT: 658), Aβ25-35 (peak GMT: 125). Antibody titers were also measured against the homologous peptides using the same ELISA sandwich format for a subset of the immunogens, those groups immunized with Aβ1-5, Aβ13-28, Aβ25-35, Aβ33-42 or rodent Aβ1-42. These titers were about the same as those measured against Aβ1-42 except for the rodent Aβ1-42 immunogen in which case antibody titers against the homologous immunogen were about two-fold higher. The magnitude of the AN1792-specific antibody titer of individual animals or the mean values of treatment groups did not correlate with efficacy measured as the reduction of Aβ in the cortex.

4. Lymphoproliferative Responses

Aβ-dependent lymphoproliferation was measured using spleen cells harvested approximately one week following the final, sixth, immunization. Freshly harvested cells, 105 per well, were cultured for 5 days in the presence of Aβ1-40 at a concentration of 5 μM for stimulation. Cells from a subset of seven of the ten groups were also cultured in the presence of the reverse peptide, Aβ40-1. As a positive control, additional cells were cultured with the T cell mitogen, PHA, and, as a negative control, cells were cultured without added peptide.

Lymphocytes from a majority of the animals proliferated in response to PHA. There were no significant responses to the Aβ40-1 reverse peptide. Cells from animals immunized with the larger aggregated Aβ peptides, AN1792, rodent Aβ1-42 and AN1528 proliferated robustly when stimulated with Aβ1-40 with the highest cpm in the recipients of AN1792. One animal in each of the groups immunized with Aβ1-12 conjugate, Aβ13-28 conjugate and Aβ25-35 proliferated in response to Aβ1-40. The remaining groups receiving Aβ1-5 conjugate, Aβ33-42 conjugate pBx6 or PBS had no animals with an Aβ-stimulated response. These results are summarized in Table 5 below.

TABLE 5

| Immunogen | Conjugate | Aβ Amino Acids | Responders |
|---|---|---|---|
| Aβ1-5 | Yes | 5-mer | 0/7 |
| Aβ1-12 | Yes | 12-mer | 1/8 |
| Aβ13-28 | Yes | 16-mer | 1/9 |
| Aβ25-35 | | 11-mer | 1/9 |
| Aβ33-42 | Yes | 10-mer | 0/10 |
| Aβ1-40 | | 40-mer | 5/8 |
| Aβ1-42 | | 42-mer | 9/9 |
| r Aβ1-42 | | 42-mer | 8/8 |
| pBx6 | | | 0/8 |
| PBS | | 0-mer | 0/8 |

These results show that AN1792 and AN1528 stimulate strong T cell responses, most likely of the CD4+ phenotype. The absence of an Aβ-specific T cell response in animals immunized with Aβ1-5 is not surprising since peptide epitopes recognized by CD4+ T cells are usually about 15 amino acids in length, although shorter peptides can sometimes function with less efficiency. Thus the majority of helper T cell epitopes for the four conjugate peptides are likely to reside in the IgG conjugate partner, not in the Aβ region. This hypothesis is supported by the very low incidence of proliferative responses for animals in each of these treatment groups. Since the Aβ1-5 conjugate was effective at significantly reducing the level of Aβ in the brain, in the apparent absence of Aβ-specific T cells, the key effector immune response induced by immunization with this peptide appears to be antibody.

Lack of T-cell and low antibody response from fusion peptide pBx6, encompassing APP amino acids 592-695 including all of the Aβ residues may be due to the poor immunogenicity of this particular preparation. The poor immunogenicity of the Aβ25-35 aggregate is likely due to the peptide being too small to be likely to contain a good T cell epitope help the induction of an antibody response. If this peptide were conjugated to a carrier protein, it would probably be more immunogenic.

V. Preparation of Polyclonal Antibodies for Passive Protection 125 non-transgenic mice were immunized with Aβ, plus adjuvant, and euthanized at 4-5 months. Blood was collected from immunized mice. IgG was separated from other blood components. Antibody specific for the immunogen may be partially purified by affinity chromatography. An average of about 0.5-1 mg of immunogen-specific antibody is obtained per mouse, giving a total of 60-120 mg.

VI. Passive Immunization with Antibodies to Aβ

Groups of 7-9 month old PDAPP mice each are injected with 0.5 mg in PBS of polyclonal anti-Aβ or specific anti-Aβ monoclonals as shown below. The cell line designated RB44-10D5.19.21 producing the antibody 10D5 has the American Type Culture Collection (ATCC) accession number PTA-5129, having been deposited on Apr. 8, 2003. The cell line producing the antibody 266 has the ATCC accession number PTA-6123 having been deposited on Jul. 20, 2004.

All antibody preparations are purified to have low endotoxin levels. Monoclonals can be prepared against a fragment by injecting the fragment or longer form of Aβ into a mouse, preparing hybridomas and screening the hybridomas for an antibody that specifically binds to a desired fragment of Aβ without binding to other nonoverlapping fragments of Aβ.

TABLE 6

| Antibody | Epitope |
| --- | --- |
| 2H3 | Aβ 1-12 |
| 10D5 | Aβ 1-12 |
| 266 | Aβ 13-28 |
| 21F12 | Aβ 33-42 |
| Mouse polyclonal anti-human Aβ42 | Anti-Aggregated Aβ42 |

Mice were injected ip as needed over a 4 month period to maintain a circulating antibody concentration measured by ELISA titer of greater than 1/1000 defined by ELISA to Aβ42 or other immunogen. Titers were monitored as above and mice were euthanized at the end of 6 months of injections. Histochemistry, Aβ levels and toxicology were performed post mortem. Ten mice were used per group.

VII. Comparison of Different Adjuvants

This example compares CFA, alum, an oil-in water emulsion and MPL for capacity to stimulate an immune response.

A. Materials and Methods

1. Study Design

One hundred female Hartley strain six-week old guinea pigs, obtained from Elm Hill, were sorted into ten groups to be immunized with AN1792 or a palmitoylated derivative thereof combined with various adjuvants. Seven groups received injections of AN1792 (33 µg unless otherwise specified) combined with a) PBS, b) Freund's adjuvant, c) MPL, d) squalene, e) MPL/squalene f) low dose alum, or g) high dose alum (300 µg AN1792). Two groups received injections of a palmitoylated derivative of AN1792 (33 µg) combined with a) PBS or b) squalene. A final, tenth group received PBS alone without antigen or additional adjuvant. For the group receiving Freund's adjuvant, the first dose was emulsified with CFA and the remaining four doses with IFA. Antigen was administered at a dose of 33 µg for all groups except the high dose alum group, which received 300 µg of AN1792. Injections were administered intraperitoneally for CFA/IFA and intramuscularly in the hind limb quadriceps alternately on the right and left side for all other groups. The first three doses were given on a biweekly schedule followed by two doses at a monthly interval). Blood was drawn six to seven days following each immunization, starting after the second dose, for measurement of antibody titers.

2. Preparation of Immunogens

Two mg Aβ42 (California Peptide, Lot ME0339) was added to 0.9 ml of deionized water and the mixture was vortexed to generate a relatively uniform suspension. A 100 µl aliquot of 10×PBS (1×PBS, 0.15 M NaCl, 0.01 M sodium phosphate, pH 7.5) was added. The suspension was vortexed again and incubated overnight at 37° C. for use the next day. Unused Aβ1-42 was stored with desiccant as a lyophilized powder at −20° C.

A palmitoylated derivative of AN1792 was prepared by coupling palmitic anhydride, dissolved in dimethyl formamide, to the amino terminal residue of AN1792 prior to removal of the nascent peptide from the resin by treatment with hydrofluoric acid.

To prepare vaccine doses with Complete Freund's adjuvant (CFA) (group 2), 33 µg of AN1792 in 200 µl PBS was emulsified 1:1 (vol:vol) with CFA in a final volume of 400 µl for the first immunization. For subsequent immunizations, the antigen was similarly emulsified with Incomplete Freund's adjuvant (IFA).

To prepare vaccine doses with MPL for groups 5 and 8, lyophilized powder (Ribi ImmunoChem Research, Inc., Hamilton, Mont.) was added to 0.2% aqueous triethylamine to a final concentration of 1 mg/ml and vortexed. The mixture was heated to 65 to 70° C. for 30 sec to create a slightly opaque uniform suspension of micelles. The solution was freshly prepared for each set of injections. For each injection in group 5, 33 µg of AN1792 in 16.5 µl PBS, 50 µg of MPL (50 µl) and 162 µl of PBS were mixed in a borosilicate tube immediately before use.

To prepare vaccine doses with the low oil-in-water emulsion, AN1792 in PBS was added to 5% squalene, 0.5% Tween 80, 0.5% Span 85 in PBS to reach a final single dose concentration of 33 µg AN1792 in 250 µl (group 6). The mixture was emulsified by passing through a two-chambered hand-held device 15 to 20 times until the emulsion droplets appeared to be about equal in diameter to a 1.0 µm diameter standard latex bead when viewed under a microscope. The resulting suspension was opalescent, milky white. The emulsions were freshly prepared for each series of injections. For group 8, MPL in 0.2% triethylamine was added at a concentration of 50 µg per dose to the squalene and detergent mixture for emulsification as noted above. For the palmitoyl derivative (group 7), 33 µg per dose of palmitoyl-NH-Aβ1-42 was added to squalene and vortexed. Tween 80 and Span 85 were then added with vortexing. This mixture was added to PBS to reach final concentrations of 5% squalene, 0.5% Tween 80, 0.5% Span 85 and the mixture was emulsified as noted above.

To prepare vaccine doses with alum (groups 9 and 10), AN1792 in PBS was added to Alhydrogel (aluminum hydroxide gel, Accurate, Westbury, N.Y.) to reach concentrations of 33 µg (low dose, group 9) or 300 µg (high dose, group 10) AN1792 per 5 mg of alum in a final dose volume of 250 µl. The suspension was gently mixed for 4 hr at RT.

3. Measurement of Antibody Titers

Guinea pigs were bled six to seven days following immunization starting after the second immunization for a total of four bleeds. Antibody titers against Aβ42 were measured by ELISA as described in General Materials and Methods.

4. Tissue Preparation

After about 14 weeks, all guinea pigs were administered $CO_2$. Cerebrospinal fluid was collected and the brains were removed and three brain regions (hippocampus, cortex and cerebellum) were dissected and used to measure the concentration of total Aβ protein using ELISA.

B. Results

1. Antibody Responses

Figure 14:
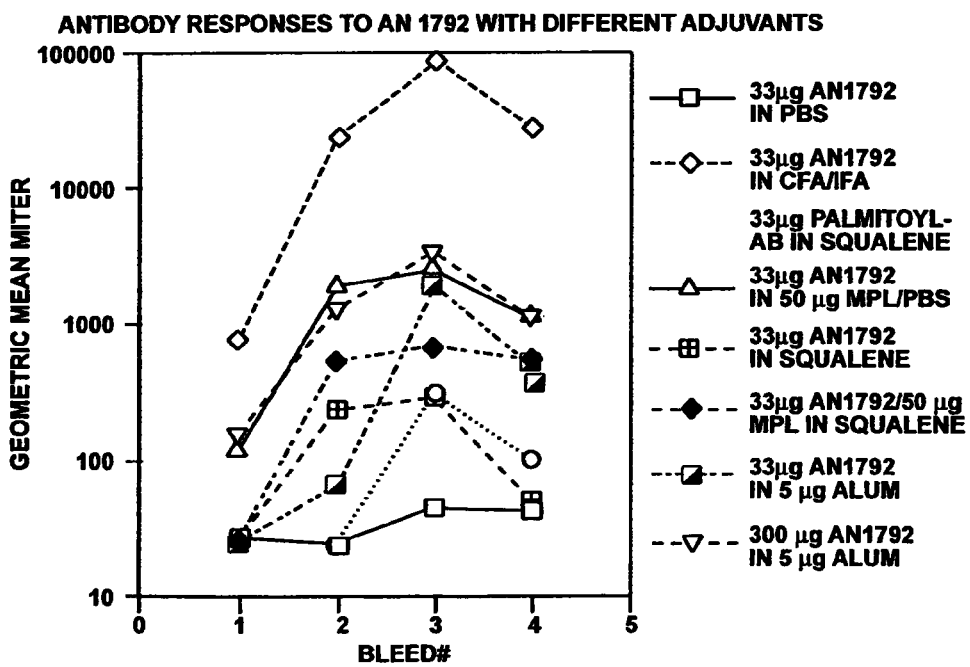
FIG. 14: Geometric mean titers of Aβ-specific antibody for groups of guinea pigs immunized with AN1792, or a palmitoylated derivative thereof, combined with various adjuvants.

There was a wide range in the potency of the various adjuvants when measured as the antibody response to AN1792 following immunization. As shown in FIG. 14, when AN1792 was administered in PBS, no antibody was detected following two or three immunizations and negligible responses were detected following the fourth and fifth doses with geometric mean titers (GMTs) of only about 45. The o/w emulsion induced modest titers following the third dose (GMT 255) that were maintained following the fourth dose (GMT 301) and fell with the final dose (GMT 54). There was a clear antigen dose response for AN1792 bound to alum with 300 µg being more immunogenic at all time points than 33 µg. At the peak of the antibody response, following the fourth immunization, the difference between the two doses was 43% with GMTs of about 1940 (33 µg) and 3400 (300 µg). The antibody response to 33 µg AN1792 plus MPL was very similar to that generated with almost a ten-fold higher dose of antigen (300 µg) bound to alum. The addition of MPL to an o/w emulsion decreased the potency of the vaccine relative to that with MPL as the sole adjuvant by as much as 75%. A palmitoylated derivative of AN1792 was completely non-immunogenic when administered in PBS and gave modest titers when presented in an o/w emulsion with GMTs of 340 and 105 for the third and fourth bleeds. The highest antibody titers were generated with Freund's adjuvant with a peak GMT of about 87,000, a value almost 30-fold greater than the GMTs of the next two most potent vaccines, MPL and high dose AN1792/alum.

The most promising adjuvants identified in this study are MPL and alum. Of these two, MPL appears preferable because a 10-fold lower antigen dose was required to generate the same antibody response as obtained with alum. The response can be increased by increasing the dose of antigen and/or adjuvant and by optimizing the immunization schedule. The o/w emulsion was a very weak adjuvant for AN1792 and adding an o/w emulsion to MPL adjuvant diminished the intrinsic adjuvant activity of MPL alone.

2. Aβ Levels In The Brain

At about 14 weeks the guinea pigs were deeply anesthetized, the cerebrospinal fluid (CSF) was drawn and brains were excised from animals in a subset of the groups, those immunized with Freund's adjuvant (group 2), MPL (group 5), alum with a high dose, 300 µg, of AN1792 (group 10) and the PBS immunized control group (group 3). To measure the level of Aβ peptide, one hemisphere was dissected and homogenates of the hippocampal, cortical, and cerebellar regions were prepared in 5 M guanidine. These were diluted and quantitated by comparison to a series of dilutions of Aβ standard protein of known concentrations in an ELISA format. The levels of Aβ protein in the hippocampus, the cortex and the cerebellum were very similar for all four groups despite the wide range of antibody responses to Aβ elicited by these vaccines. Mean Aβ levels of about 25 ng/g tissue were measured in the hippocampus, 21 ng/g in the cortex, and 12 ng/g in the cerebellum. Thus, the presence of a high circulating antibody titer to Aβ for almost three months in some of these animals did not alter the total Aβ levels in their brains. The levels of Aβ in the CSF were also quite similar between the groups. The lack of large effect of AN1792 immunization on endogenous Aβ indicates that the immune response is focused on pathological formations of Aβ.

VIII. Immune Response to Different Adjuvants in Mice

Six-week old female Swiss Webster mice were used for this study with 10-13 animals per group. Immunizations were given on days 0, 14, 28, 60, 90 and 20 administered subcutaneously in a dose volume of 200 µl. PBS was used as the buffer for all formulations. Animals were bleed seven days following each immunization starting after the second dose for analysis of antibody titers by ELISA. The treatment regime of each group is summarized in Table 7.

TABLE 7

Experimental Design of Study 010

| Group | $N^a$ | Adjuvant[b] | Dose | Antigen | Dose (µg) |
|---|---|---|---|---|---|
| 1 | 10 | MPL | 12.5 µg | AN1792 | 33 |
| 2 | 10 | MPL | 25 µg | AN1792 | 33 |
| 3 | 10 | MPL | 50 µg | AN1792 | 33 |
| 4 | 13 | MPL | 125 µg | AN1792 | 33 |
| 5 | 13 | MPL | 50 µg | AN1792 | 150 |
| 6 | 13 | MPL | 50 µg | AN1528 | 33 |
| 7 | 10 | PBS | | AN1792 | 33 |
| 8 | 10 | PBS | | None | |
| 9 | 10 | Squalene emulsified | 5% | AN1792 | 33 |
| 10 | 10 | Squalene admixed | 5% | AN1792 | 33 |
| 11 | 10 | Alum | 2 mg | AN1792 | 33 |
| 12 | 13 | MPL + Alum | 50 µg/2 mg | AN1792 | 33 |
| 13 | 10 | QS-21 | 5 µg | AN1792 | 33 |
| 14 | 10 | QS-21 | 10 µg | AN1792 | 33 |
| 15 | 10 | QS-21 | 25 AN1792 | AN1792 | 33 |
| 16 | 13 | QS-21 | 25 AN1792 | AN1792 | 150 |
| 17 | 13 | QS-21 | 25 AN1792 | AN1528 | 33 |
| 18 | 13 | QS-21 + MPL | 25 µg/50 µg | AN1792 | 33 |
| 19 | 13 | QS-21 + Alum | 25 µg/2 mg | AN1792 | 33 |

Footnotes:
[a]Number of mice in each group at the initiation of the experiment.
[b]The adjuvants are noted. The buffer for all these formulations was PBS. For group 8, there was no adjuvant and no antigen.

The ELISA titers of antibodies against Aβ42 in each group are shown in Table 8 below.

TABLE 8

Geometric Mean Antibody Titers
Week of Bleed

| Treatment Group | 2.9 | 5.0 | 8.7 | 12.9 | 16.7 |
|---|---|---|---|---|---|
| 1 | 248 | 1797 | 2577 | 6180 | 4177 |
| 2 | 598 | 3114 | 3984 | 5287 | 6878 |
| 3 | 1372 | 5000 | 7159 | 12333 | 12781 |
| 4 | 1278 | 20791 | 14368 | 20097 | 25631 |
| 5 | 3288 | 26242 | 13229 | 9315 | 23742 |

TABLE 8-continued

Geometric Mean Antibody Titers
Week of Bleed

| Treatment Group | 2.9 | 5.0 | 8.7 | 12.9 | 16.7 |
|---|---|---|---|---|---|
| 6 | 61 | 2536 | 2301 | 1442 | 4504 |
| 7 | 37 | 395 | 484 | 972 | 2149 |
| 8 | 25 | 25 | 25 | 25 | 25 |
| 9 | 25 | 183 | 744 | 952 | 1823 |
| 10 | 25 | 89 | 311 | 513 | 817 |
| 11 | 29 | 708 | 2618 | 2165 | 3666 |
| 12 | 198 | 1458 | 1079 | 612 | 797 |
| 13 | 38 | 433 | 566 | 1080 | 626 |
| 14 | 104 | 541 | 3247 | 1609 | 838 |
| 15 | 212 | 2630 | 2472 | 1224 | 1496 |
| 16 | 183 | 2616 | 6680 | 2085 | 1631 |
| 17 | 28 | 201 | 375 | 222 | 1540 |
| 18 | 31699 | 15544 | 23095 | 6412 | 9059 |
| 19 | 63 | 243 | 554 | 299 | 441 |

The table shows that the highest titers were obtained for groups 4, 5 and 18, in which the adjuvants were 125 μg MPL, 50 μg MPL and QS-21 plus MPL.

The table shows that the highest titers were obtained for groups 4, 5 and 18, in which the adjuvants were 125 μg MPL, 50 μg MPL and QS-21 plus MPL.

IX. Therapeutic Efficacy of Different Adjuvants

A therapeutic efficacy study was conducted in PDAPP transgenic mice with a set of adjuvants suitable for use in humans to determine their ability to potentiate immune responses to Aβ and to induce the immune-mediated clearance of amyloid deposits in the brain.

One hundred eighty male and female, 7.5- to 8.5-month old heterozygous PDAPP transgenic mice were obtained from Charles River Laboratories. The mice were sorted into nine groups containing 15 to 23 animals per group to be immunized with AN1792 or AN1528 combined with various adjuvants. Animals were distributed to match the gender, age, and parentage of the animals within the groups as closely as possible. The adjuvants included alum, MPL, and QS-21, each combined with both antigens, and Freund's adjuvant (FA) combined with only AN1792. An additional group was immunized with AN1792 formulated in PBS buffer plus the preservative thimerosal without adjuvant. A ninth group was immunized with PBS alone as a negative control.

Preparation of aggregated Aβ peptides: human Aβ1-40 (AN1528; California Peptides Inc., Napa, Calif.; Lot ME0541) and human Aβ1-42 (AN1792; California Peptides Inc., Lot ME0439) peptides were freshly solubilized for the preparation of each set of injections from lyophilized powders that had been stored desiccated at −20° C. For this purpose, two mg of peptide were added to 0.9 ml of deionized water and the mixture was vortexed to generate a relatively uniform solution or suspension. AN1528 was soluble at this step, in contrast to AN1792. A 100 μl aliquot of 10×PBS (1×PBS: 0.15 M NaCl, 0.01 M sodium phosphate, pH 7.5) was then added at which point AN1528 began to precipitate. The suspensions were vortexed again and incubated overnight at 37° C. for use the next day.

To prepare vaccine doses with alum, Aβ peptide in PBS was added to Alhydrogel (two percent aqueous aluminum hydroxide gel, Sargeant, Inc., Clifton, N.J.) to reach concentrations of 100 μg Aβ peptide per 2 mg of alum. 10×PBS was added to a final dose volume of 200 μl in 1×PBS. The suspension was then gently mixed for approximately 4 hr at RT prior to injection.

To prepare vaccine doses for with MPL (Groups 2 and 6), lyophilized powder (Ribi ImmunoChem Research, Inc., Hamilton, Mont.; Lot 67039-E0896B) was added to 0.2% aqueous triethylamine to a final concentration of 1 mg/ml and vortexed. The mixture was heated to 65 to 70° C. for 30 sec to create a slightly opaque uniform suspension of micelles. The solution was stored at 4° C. For each set of injections, 100 μg of peptide per dose in 50 μl PBS, 50 μg of MPL per dose (50 μl) and 100 μl of PBS per dose were mixed in a borosilicate tube immediately before use.

To prepare vaccine doses with QS-21 (Groups 3 and 7), lyophilized powder (Aquila, Framingham, Mass.; Lot A7018R) was added to PBS, pH 6.6-6.7 to a final concentration of 1 mg/ml and vortexed. The solution was stored at −20° C. For each set of injections, 100 μg of peptide per dose in 50 μl PBS, 25 μg of QS-21 per dose in 25 μl PBS and 125 μl of PBS per dose were mixed in a borosilicate tube immediately before use.

To prepare vaccine doses with Freund's Adjuvant (Group 4), 100 μg of AN1792 in 200 μl PBS was emulsified 1:1 (vol:vol) with Complete Freund's Adjuvant (CFA) in a final volume of 400 μl for the first immunization. For subsequent immunizations, the antigen was similarly emulsified with Incomplete Freund's Adjuvant (IFA). For the vaccines containing the adjuvants alum, MPL or QS-21, 100 μg per dose of AN1792 or AN1528 was combined with alum (2 mg per dose) or MPL (50 μg per dose) or QS-21 (25 μg per dose) in a final volume of 200 μl PBS and delivered by subcutaneous inoculation on the back between the shoulder blades. For the group receiving FA, 100 μg of AN1792 was emulsified 1:1 (vol:vol) with Complete Freund's adjuvant (CFA) in a final volume of 400 μl and delivered intraperitoneally for the first immunization, followed by a boost of the same amount of immunogen in Incomplete Freund's adjuvant (IFA) for the subsequent five doses. For the group receiving AN1792 without adjuvant, 10 μg AN1792 was combined with 5 μg thimerosal in a final volume of 50 μl PBS and delivered subcutaneously. The ninth, control group received only 200 μl PBS delivered subcutaneously. Immunizations were given on a biweekly schedule for the first three doses, then on a monthly schedule thereafter on days 0, 16, 28, 56, 85 and 112. Animals were bled six to seven days following each immunization starting after the second dose for the measurement of antibody titers. Animals were euthanized approximately one week after the final dose. Outcomes were measured by ELISA assay of Aβ and APP levels in brain and by immunohistochemical evaluation of the presence of amyloid plaques in brain sections. In addition, Aβ-specific antibody titers, and Aβ-dependent proliferative and cytokine responses were determined.

Table 9 shows that the highest antibody titers to Aβ1-42 were elicited with FA and AN1792, titers which peaked following the fourth immunization (peak GMT: 75,386) and then declined by 59% after the final, sixth immunization. The peak mean titer elicited by MPL with AN1792 was 62% lower than that generated with FA (peak GMT: 28,867) and was also reached early in the immunization scheme, after 3 doses, followed by a decline to 28% of the peak value after the sixth immunization. The peak mean titer generated with QS-21 combined with AN1792 (GMT: 1,511) was about 5-fold lower than obtained with MPL. In addition, the kinetics of the response were slower, since an additional immunization was required to reach the peak response. Titers generated by alum-bound AN1792 were marginally greater than those obtained with QS-21 and the response kinetics were more rapid. For AN1792 delivered in PBS with thimerosal the frequency and size of titers were barely greater than that for PBS alone. The peak titers generated with MPL and AN1528 (peak GMT 3099) were about 9-fold lower than those with AN1792. Alum-bound AN1528 was very poorly immunogenic with low titers generated in only some of the animals. No antibody responses were observed in the control animals immunized with PBS alone.

TABLE 9

Geometric Mean Antibody Titers[a]
Week of Bleed

| Treatment | 3.3 | 5.0 | 9.0 | 13.0 | 17.0 |
|---|---|---|---|---|---|
| Alum/ | 102 | 1,081 | 2,366 | 1,083 | 572 |
| AN1792 | (12/21)[b] | (17/20) | (21/21) | (19/21) | (18/21) |
| MPL/ | 6241 | 28,867 | 1,1242 | 5,665 | 8,204 |
| AN1792 | (21/21) | (21/21) | (21/21) | (20/21) | (20/20) |
| QS-21/ | 30 | 227 | 327 | 1,511 | 1,188 |
| AN1792 | (1/20) | (10/19) | (10/19) | (17/18) | (14/18) |
| CFA/ | 10,076 | 61,279 | 75,386 | 41,628 | 30,574 |
| AN1792 | (15/15) | (15/15) | (15/15) | (15/15) | (15/15) |
| Alum/ | 25 | 33 | 39 | 37 | 31 |
| AN1528 | (0/21) | (1/21) | (3/20) | (1/20) | (2/20) |
| MPL/ | 184 | 2,591 | 1,653 | 1,156 | 3,099 |
| AN1528 | (15/21) | (20/21) | (21/21) | (20/20) | (20/20) |
| QS-21/ | 29 | 221 | 51 | 820 | 2,994 |
| AN1528 | (1/22) | (13/22) | (4/22) | (20/22) | (21/22) |
| PBS plus | 25 | 33 | 39 | 37 | 47 |
| Thimerosal | (0/16) | (2/16) | (4/16) | (3/16) | (4/16) |
| PBS | 25 | 25 | 25 | 25 | 25 |
|  | (0/16) | (0/16) | (0/15) | (0/12) | (0/16) |

Footnotes:
[a]Geometric mean antibody titers measured against Aβ1-42
[b]Number of responders per group The results of AN1792 or AN1592 treatment with various adjuvants, or thimerosal on cortical amyloid burden in 12-month old mice determined by ELISA are shown in FIGS. 15A-15E. In PBS control PDAPP mice (FIG. 15A), the median level of total A in the cortex at 12 months was 1,817 ng/g. Notably reduced levels of A were observed in mice treated with AN1792 plus CFA/IFA (FIG. 15C), AN1792 plus alum (FIG. 15D), AN1792 plus MPL (FIG. 15E) and QS21 plus AN1792 (FIG. 15E). The reduction reached statistical significance ($p<0.05$) only for AN1792 plus CFA/IFA (FIG. 15C). However, as shown in Examples I and III, the effects of immunization in reducing A levels become substantially greater in 15 month and 18 month old mice. Thus, it is expected that at least the AN1792 plus alum, AN1792 plus MPL and AN1792 plus QS21 compositions will achieve statistical significance in treatment of older mice. By contrast, the AN1792 plus the preservative thimerosal (FIG. 15D) showed a median level of A about the same as that in the PBS treated mice. Similar results were obtained when cortical levels of A42 were compared. The median level of A42 in PBS controls was 1624 ng/g. Notably reduced median levels of 403, 1149, 620 and 714 were observed in the mice treated with AN1792 plus CFA/IFA, AN 1792 plus alum, AN1792 plus MPL and AN1792 plus QS21 respectively, with the reduction achieving statistical significance ($p=0.05$) for the AN1792 CFA/IFA treatment group. The median level in the AN1792 thimerosal treated mice was 1619 ng/g A42.

X. Toxicity Analysis

Tissues were collected for histopathologic examination at the termination of studies described in Examples 2, 3 and 7. In addition, hematology and clinical chemistry were performed on terminal blood samples from Examples 3 and 7. Most of the major organs were evaluated, including brain, pulmonary, lymphoid, gastrointestinal, liver, kidney, adrenal and gonads. Although sporadic lesions were observed in the study animals, there were no obvious differences, either in tissues affected or lesion severity, between AN1792 treated and untreated animals. There were no unique histopathological lesions noted in AN-1528-immunized animals compared to PBS-treated or untreated animals. There were also no differences in the clinical chemistry profile between adjuvant groups and the PBS treated animals in Example 7. Although there were significant increases in several of the hematology parameters between animals treated with AN1792 and Freund's adjuvant in Example 7 relative to PBS treated animals, these type of effects are expected from Freund's adjuvant treatment and the accompanying peritonitis and do not indicate any adverse effects from AN1792 treatment. Although not part of the toxicological evaluation, PDAPP mouse brain pathology was extensively examined as part of the efficacy endpoints. No sign of treatment related adverse effect on brain morphology was noted in any of the studies. These results indicate that AN1792 treatment is well tolerated and at least substantially free of side effects.

XI. Therapeutic Treatment with Anti-Aβ Antibodies

This examples tests the capacity of various monoclonal and polyclonal antibodies to Aβ to inhibit accumulation of Aβ in the brain of heterozygotic transgenic mice.

1. Study Design

Sixty male and female, heterozygous PDAPP transgenic mice, 8.5 to 10.5 months of age were obtained from Charles River Laboratory. The mice were sorted into six groups to be treated with various antibodies directed to Aβ. Animals were distributed to match the gender, age, parentage and source of the animals within the groups as closely as possible. As shown in Table 10, the antibodies included four murine Aβ-specific monoclonal antibodies, 2H3 (directed to Aβ residues 1-12), 10D5 (directed to Aβ residues 1-16), 266 (directed to Aβ residues 13-28 and binds to monomeric but not to aggregated AN1792), 21F12 (directed to Aβ residues 33-42). The cell line designated hybridoma resulting from fusion of SP/20 with A/J mouse spleen: 266.2 producing the antibody 266 has the ATCC accession number PTA-6123, having been deposited on Jul. 20, 2004 at the American Type Culture Collection 10801 University Boulevard, Manassas, Va. 20110-2209. A fifth group was treated with an Aβ-specific polyclonal antibody fraction (raised by immunization with aggregated AN1792). The negative control group received the diluent, PBS, alone without antibody.

The monoclonal antibodies were injected at a dose of about 10 mg/kg (assuming that the mice weighed 50 g). Injections were administered intraperitoneally every seven days on average to maintain anti-Aβ titers above 1000. Although lower titers were measured for mAb 266 since it does not bind well to the aggregated AN1792 used as the capture antigen in the assay, the same dosing schedule was maintained for this group. The group receiving monoclonal antibody 2H3 was discontinued within the first three weeks since the antibody was cleared too rapidly in vivo. Animals were bled prior to each dosing for the measurement of antibody titers. Treatment was continued over a six-month period for a total of 196 days. Animals were euthanized one week after the final dose.

TABLE 10

EXPERIMENTAL DESIGN OF STUDY 006

| Treatment Group | N[a] | Treatment Antibody | Antibody Specificity | Antibody Isotype |
|---|---|---|---|---|
| 1 | 9 | none (PBS alone) | NA[b] | NA |
| 2 | 10 | Polyclonal | Aβ1-42 | mixed |
| 3 | 0 | mAb[c] 2H3 | Aβ1-12 | IgG1 |
| 4 | 8 | mAb 10D5 | Aβ1-16 | IgG1 |
| 5 | 6 | mAb 266 | Aβ13-28 | IgG1 |
| 6 | 8 | mAb 21F12 | Aβ33-42 | IgG2a |

Footnotes
[a]Number of mice in group at termination of the experiment. All groups started with 10 animals per group.
[b]NA: not applicable
[c]mAb: monoclonal antibody 2. Materials and Methods
a. Preparation of the Antibodies The anti-Aβ polyclonal antibody was prepared from blood collected from two groups of animals. The first group consisted of 100 female Swiss Webster mice, 6 to 8 weeks of age. They were immunized on days 0, 15, and 29 with 100 μg of AN1792 combined with CFA/IFA. A fourth injection was given on day 36 with one-half the dose of AN1792. Animals were exsanguinated upon sacrifice at day 42, serum was prepared and the sera were pooled to create a total of 64 ml. The second group consisted of 24 female mice isogenic with the PDAPP mice but nontransgenic for the human APP gene, 6 to 9 weeks of age. They were immunized on days 0, 14, 28 and 56 with 100 μg of AN1792 combined with CFA/IFA. These animals were also exsanguinated upon sacrifice at day 63, serum was prepared and pooled for a total of 14 ml. The two lots of sera were pooled. The antibody faction was purified using two sequential rounds of precipitation with 50% saturated ammonium sulfate. The final precipitate was dialyzed against PBS and tested for endotoxin. The level of endotoxin was less than 1 EU/mg.

The anti-Aβ monoclonal antibodies were prepared from ascities fluid. The fluid was first delipidated by the addition of concentrated sodium dextran sulfate to ice-cold ascites fluid by stirring on ice to a reach a final concentration of 0.238%. Concentrated $CaCl_2$ was then added with stirring to reach a final concentration of 64mM. This solution was centrifuged at 10,000×g and the pellet was discarded. The supernatant was stirred on ice with an equal volume of saturated ammonium sulfate added dropwise. The solution was centrifuged again at 10,000×g and the supernatant was discarded. The pellet was resuspended and dialyzed against 20 mM Tris-HCl, 0.4 M NaCl, pH 7.5. This fraction was applied to a Pharmacia FPLC Sepharose Q Column and eluted with a reverse gradient from 0.4 M to 0.275 M NaCl in 20 mM Tris-HCl, pH 7.5.

The antibody peak was identified by absorbance at 280 nm and appropriate fractions were pooled. The purified antibody preparation was characterized by measuring the protein concentration using the BCA method and the purity using SDS-PAGE. The pool was also tested for endotoxin. The level of endotoxin was less than 1 EU/mg. titers, titers less than 100 were arbitrarily assigned a titer value of 25.

3. Aβ and APP Levels in the Brain:

Following about six months of treatment with the various anti-Aβ antibody preparations, brains were removed from the animals following saline perfusion. One hemisphere was prepared for immunohistochemical analysis and the second was used for the quantitation of Aβ and APP levels. To measure the concentrations of various forms of beta amyloid peptide and amyloid precursor protein (APP), the hemisphere was dissected and homogenates of the hippocampal, cortical, and cerebellar regions were prepared in 5M guanidine. These were serially diluted and the level of amyloid peptide or APP was quantitated by comparison to a series of dilutions of standards of Aβ peptide or APP of known concentrations in an ELISA format.

The levels of total Aβ and of Aβ1-42 measured by ELISA in homogenates of the cortex, and the hippocampus and the level of total Aβ in the cerebellum are shown in Tables 11, 12, and 13, respectively. The median concentration of total Aβ for the control group, inoculated with PBS, was 3.6-fold higher in the hippocampus than in the cortex (median of 63,389 ng/g hippocampal tissue compared to 17,818 ng/g for the cortex). The median level in the cerebellum of the control group (30.6 ng/g tissue) was more than 2,000-fold lower than in the hippocampus. These levels are similar to those that we have previously reported for heterozygous PDAPP transgenic mice of this age (Johnson-Woods et al., 1997).

For the cortex, one treatment group had a median Aβ level, measured as Aβ1-42, which differed significantly from that of the control group (p<0.05), those animals receiving the polyclonal anti-Aβ antibody as shown in Table 11. The median level of Aβ1-42 was reduced by 65%, compared to the control for this treatment group. The median levels of Aβ1-42 were also significantly reduced by 55% compared to the control in one additional treatment group, those animals dosed with the mAb 10D5 (p=0.0433).

TABLE 11

| | | CORTEX | | | | | | |
|---|---|---|---|---|---|---|---|---|
| | | Medians | | | | | | Means |
| Treatment | | Total Aβ | | | Aβ42 | | | Total Aβ | Aβ42 |
| Group | N[a] | ELISA value[b] | P value[c] | % Change | ELISA value | P value | % Change | ELISA value | ELISA value |
| PBS | 9 | 17818 | NA[d] | NA | 13802 | NA | NA | 16150 +/− 7456[e] | 12621 +/− 5738 |
| Polyclonal anti-Aβ42 | 10 | 6160 | 0.0055 | −65 | 4892 | 0.0071 | −65 | 5912 +/− 4492 | 4454 +/− 3347 |
| mAb 10D5 | 8 | 7915 | 0.1019 | −56 | 6214 | 0.0433 | −55 | 9695 +/− 6929 | 6943 +/− 3351 |
| mAb 266 | 6 | 9144 | 0.1255 | −49 | 8481 | 0.1255 | −39 | 9204 +/− 9293 | 7489 +/− 6921 |
| mAb 21F12 | 8 | 15158 | 0.2898 | −15 | 13578 | 0.7003 | −2 | 12481 +/− 7082 | 11005 +/− 6324 |

Footnotes:
f. Number of animals per group at the end of the experiment
g. ng/g tissue
h. Mann Whitney analysis
i. NA: not applicable
j. Standard Deviation In the hippocampus, the median percent reduction of total Aβ associated with treatment with polyclonal anti-Aβ antibody (50%, p=0.0055) was not as great as that observed in the cortex (65%) (Table 12). However, the absolute magnitude of the reduction was almost 3-fold greater in the hippocampus than in the cortex, a net reduction of 31,683 ng/g tissue in the hippocampus versus 11,658 ng/g tissue in the cortex. When measured as the level of the more amyloidogenic form of Aβ, Aβ1-42, rather than as total Aβ, the reduction achieved with the polyclonal antibody was significant (p=0.0025). The median levels in groups treated with the mAbs 10D5 and 266 were reduced by 33% and 21%, respectively.

TABLE 12

HIPPOCAMPUS

| | | Medians | | | | | Means | |
| | | Total Aβ | | | Aβ42 | | | |
| Treatment Group | N[a] | ELISA value[b] | P value[c] | % Change | ELISA value | P value | % Change | Total Aβ ELISA value | Aβ42 ELISA value |
|---|---|---|---|---|---|---|---|---|---|
| PBS | 9 | 63389 | NA[d] | NA | 54429 | NA | NA | 58351 +/− 13308[e] | 52801 +/− 14701 |
| Polyclonal anti-Aβ42 | 10 | 31706 | 0.0055 | −50 | 27127 | 0.0025 | −50 | 30058 +/− 22454 | 24853 +/− 18262 |
| mAb 10D5 | 8 | 46779 | 0.0675 | −26 | 36290 | 0.0543 | −33 | 44581 +/− 18632 | 36465 +/− 17146 |
| mAb 266 | 6 | 48689 | 0.0990 | −23 | 43034 | 0.0990 | −21 | 36419 +/− 27304 | 32919 +/− 25372 |
| mAb 21F12 | 8 | 51563 | 0.7728 | −19 | 47961 | 0.8099 | −12 | 57327 +/− 28927 | 50305 +/− 23927 |

Footnotes:
[a]Number of animals per group at the end of the experiment
[b]ng/g tissue
[c]Mann Whitney analysis
[d]NA: not applicable
[e]Standard Deviation Total Aβ was also measured in the cerebellum (Table 13). Those groups dosed with the polyclonal anti-Aβ and the 266 antibody showed significant reductions of the levels of total Aβ (43% and 46%, p=0.0033 and p=0.0184, respectively) and that group treated with 10D5 had a near significant reduction (29%, p=0.0675).

TABLE 13

CEREBELLUM

| | | Medians Total Aβ | | | Means |
| Treatment Group | N[a] | ELISA value[b] | P value[c] | % Change | Total Aβ ELISA value |
|---|---|---|---|---|---|
| PBS | 9 | 30.64 | NA[d] | NA | 40.00 +/− 31.89[e] |
| Polyclonal anti-Aβ42 | 10 | 17.61 | 0.0033 | −43 | 18.15 +/− 4.36 |
| mAb 10D5 | 8 | 21.68 | 0.0675 | −29 | 27.29 +/− 19.43 |
| mAb 266 | 6 | 16.59 | 0.0184 | −46 | 19.59 +/− 6.59 |
| mAb 21F12 | 8 | 29.80 | >0.9999 | −3 | 32.88 +/− 9.90 |

Footnotes:
aNumber of animals per group at the end of the experiment
[b]ng/g tissue
[c]Mann Whitney analysis
[d]NA: not applicable
[e]Standard Deviation APP concentration was also determined by ELISA in the cortex and cerebellum from antibody-treated and control, PBS-treated mice. Two different APP assays were utilized. The first, designated APP-α/FL, recognizes both APP-alpha (α, the secreted form of APP which has been cleaved within the Aβ sequence), and full-length forms (FL) of APP, while the second recognizes only APP-α. In contrast to the treatment-associated diminution of Aβ in a subset of treatment groups, the levels of APP were virtually unchanged in all of the treated compared to the control animals. These results indicate that the immunizations with Aβ antibodies deplete Aβ without depleting APP.

In summary, Aβ levels were significantly reduced in the cortex, hippocampus and cerebellum in animals treated with the polyclonal antibody raised against AN1792. To a lesser extent monoclonal antibodies to the amino terminal region of Aβ1-42, specifically amino acids 1-16 and 13-28 also showed significant treatment effects.

4. Histochemical Analyses:

The morphology of Aβ-immunoreactive plaques in subsets of brains from mice in the PBS, polyclonal Aβ42, 21F12, 266 and 10D5 treatment groups was qualitatively compared to that of previous studies in which standard immunization procedures with Aβ42 were followed.

The largest alteration in both the extent and appearance of amyloid plaques occurred in the animals immunized with the polyclonal Aβ42 antibody. The reduction of amyloid load, eroded plaque morphology and cell-associated Aβ immunoreactivity closely resembled effects produced by the standard immunization procedure. These observations support the ELISA results in which significant reductions in both total Aβ and Aβ42 were achieved by administration of the polyclonal Aβ42 antibody.

In similar qualitative evaluations, amyloid plaques in the 10D5 group were also reduced in number and appearance, with some evidence of cell-associated Aβ immunoreactivity. Major differences were not seen when the 21F12 and 266 groups were compared with the PBS controls.

Figure 16:
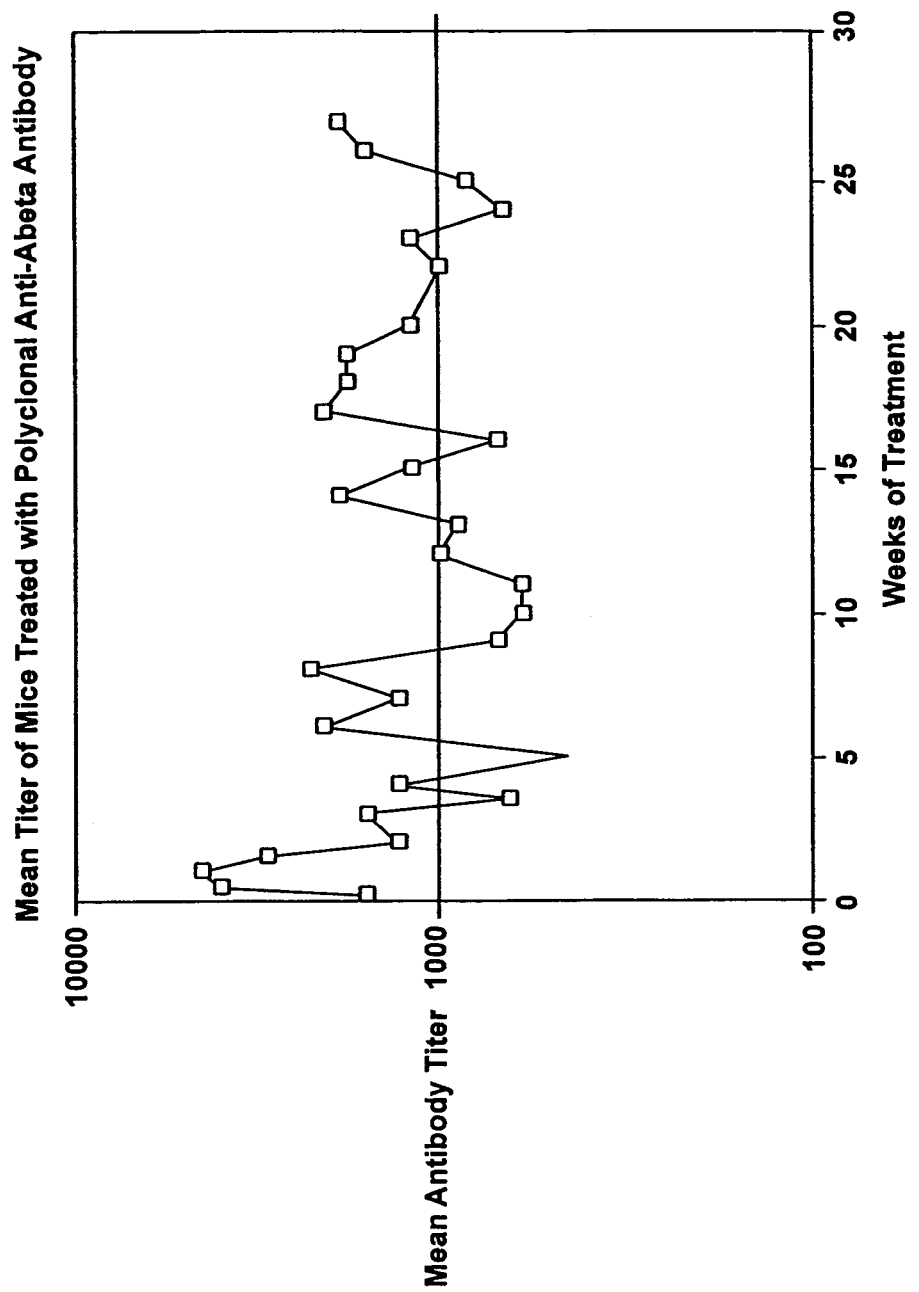
FIG. 16: Mean titer of mice treated with polyclonal antibody to Aβ.
Figure 17:
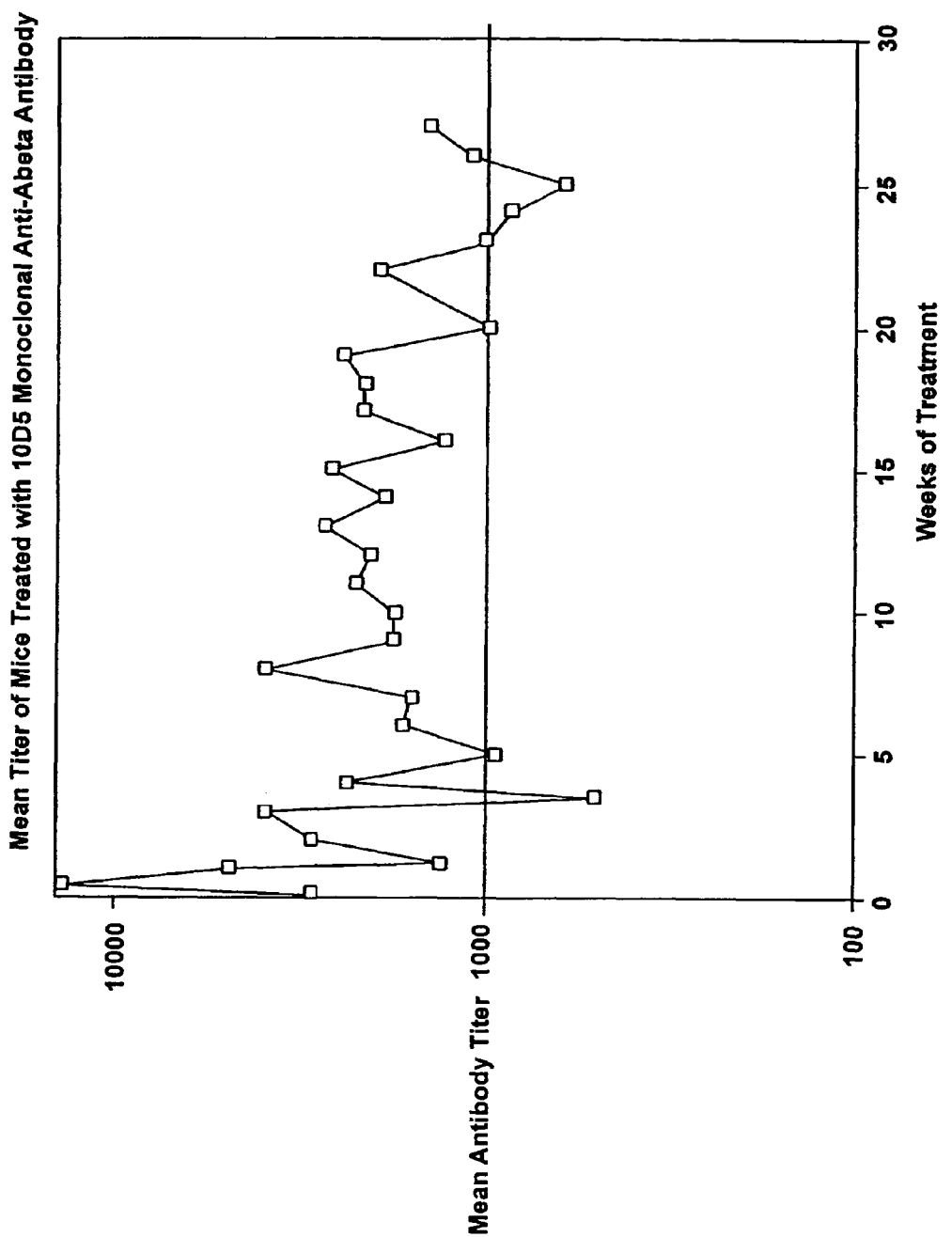
FIG. 17: Mean titer of mice treated with monoclonal antibody 10D5 to Aβ.
Figure 18:
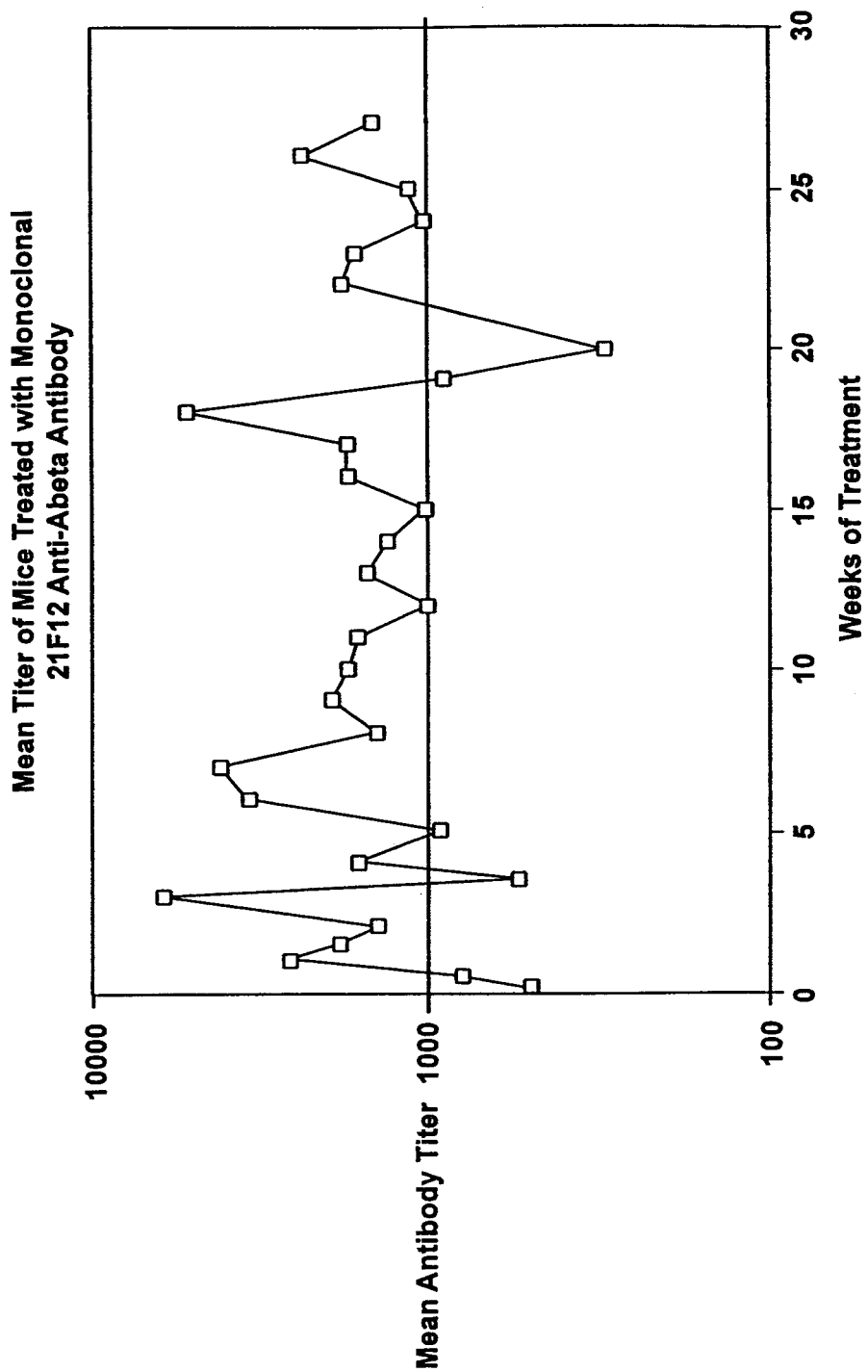
FIG. 18: Mean titer of mice treated with monoclonal antibody 2F12 to Aβ.

5. Measurement of Antibody Titers:

A subset of three randomly chosen mice from each group were bled just prior to each intraperitoneal inoculation, for a total of 30 bleeds. Antibody titers were measured as Aβ1-42-binding antibody using a sandwich ELISA with plastic multiwell plates coated with Aβ1-42 as described in detail in the General Materials and Methods. Mean titers for each bleed are shown in FIGS. 16-18 for the polyclonal antibody and the monoclonals 10D5 and 21F12, respectively. Titers averaged about 1000 over this time period for the polyclonal antibody preparation and were slightly above this level for the 10D5- and 21F12-treated animals.

6. Lymphoproliferative Responses:

Aβ-dependent lymphoproliferation was measured using spleen cells harvested eight days following the final antibody infusion. Freshly harvested cells, $10^5$ per well, were cultured for 5 days in the presence of Aβ1-40 at a concentration of 5 μM for stimulation. As a positive control, additional cells were cultured with the T cell mitogen, PHA, and, as a negative control, cells were cultured without added peptide.

Splenocytes from aged PDAPP mice passively immunized with various anti-Aβ antibodies were stimulated in vitro with AN1792 and proliferative and cytokine responses were measured. The purpose of these assays was to determine if passive immunization facilitated antigen presentation, and thus priming of T cell responses specific for AN1792. No AN1792- specific proliferative or cytokine responses were observed in mice passively immunized with the anti-Aβ antibodies.

XII. Prevention and Treatment of Subjects

A single-dose phase I trial is performed to determine safety. A therapeutic agent is administered in increasing dosages to different patients starting from about 0.01 the level of presumed efficacy, and increasing by a factor of three until a level of about 10 times the effective mouse dosage is reached.

A phase II trial is performed to determine therapeutic efficacy. Patients with early to mid Alzheimer's Disease defined using Alzheimer's disease and Related Disorders Association (ADRDA) criteria for probable AD are selected. Suitable patients score in the 12-26 range on the Mini-Mental State Exam (MMSE). Other selection criteria are that patients are likely to survive the duration of the study and lack complicating issues such as use of concomitant medications that may interfere. Baseline evaluations of patient function are made using classic psychometric measures, such as the MMSE, and the ADAS, which is a comprehensive scale for evaluating patients with Alzheimer's Disease status and function. These psychometric scales provide a measure of progression of the Alzheimer's condition. Suitable qualitative life scales can also be used to monitor treatment. Disease progression can also be monitored by MRI. Blood profiles of patients can also be monitored including assays of immunogen-specific antibodies and T-cells responses.

Following baseline measures, patients begin receiving treatment. They are randomized and treated with either therapeutic agent or placebo in a blinded fashion. Patients are monitored at least every six months. Efficacy is determined by a significant reduction in progression of a treatment group relative to a placebo group.

A second phase II trial is performed to evaluate conversion of patients from non-Alzheimer's Disease early memory loss, sometimes referred to as age-associated memory impairment (AAMI), or mild cognitive impairment (MCI), to probable Alzheimer's disease as defined as by ADRDA criteria. Patients with high risk for conversion to Alzheimer's Disease are selected from a non-clinical population by screening reference populations for early signs of memory loss or other difficulties associated with pre-Alzheimer's symptomatology, a family history of Alzheimer's Disease, genetic risk factors, age, sex, and other features found to predict high-risk for Alzheimer's Disease. Baseline scores on suitable metrics including the MMSE and the ADAS together with other metrics designed to evaluate a more normal population are collected. These patient populations are divided into suitable groups with placebo comparison against dosing alternatives with the agent. These patient populations are followed at intervals of about six months, and the endpoint for each patient is whether or not he or she converts to probable Alzheimer's Disease as defined by ADRDA criteria at the end of the observation.

XIII. General Materials and Methods

1. Measurement of Antibody Titers

Mice were bled by making a small nick in the tail vein and collecting about 200 µl of blood into a microfuge tube. Guinea pigs were bled by first shaving the back hock area and then using an 18 gauge needle to nick the metatarsal vein and collecting the blood into microfuge tubes. Blood was allowed to clot for one hr at room temperature (RT), vortexed, then centrifuged at 14,000×g for 10 min to separate the clot from the serum. Serum was then transferred to a clean microfuge tube and stored at 4° C. until titered.

Antibody titers were measured by ELISA. 96-well microtiter plates (Costar EIA plates) were coated with 100 µl of a solution containing either 10 µg/ml either Aβ42 or SAPP or other antigens as noted in each of the individual reports in Well Coating Buffer (0.1 M sodium phosphate, pH 8.5, 0.1% sodium azide) and held overnight at RT. The wells were aspirated and sera were added to the wells starting at a 1/100 dilution in Specimen Diluent (0.014 M sodium phosphate, pH 7.4, 0.15 M NaCl, 0.6% bovine serum albumin, 0.05% thimerosal). Seven serial dilutions of the samples were made directly in the plates in three-fold steps to reach a final dilution of 1/218,700. The dilutions were incubated in the coated-plate wells for one hr at RT. The plates were then washed four times with PBS containing 0.05% Tween 20. The second antibody, a goat anti-mouse Ig conjugated to horseradish peroxidase (obtained from Boehringer Mannheim), was added to the wells as 100 µl of a 1/3000 dilution in Specimen Diluent and incubated for one hr at RT. Plates were again washed four times in PBS, Tween 20. To develop the chromogen, 100 µl of Slow TMB (3,3',5,5'-tetramethyl benzidine obtained from Pierce Chemicals) was added to each well and incubated for 15 min at RT. The reaction was stopped by the addition of 25 µl of 2 M $H_2SO_4$. The color intensity was then read on a Molecular Devices Vmax at (450 nm-650 nm).

Titers were defined as the reciprocal of the dilution of serum giving one half the maximum OD. Maximal OD was generally taken from an initial 1/100 dilution, except in cases with very high titers, in which case a higher initial dilution was necessary to establish the maximal OD. If the 50% point fell between two dilutions, a linear extrapolation was made to calculate the final titer. To calculate geometric mean antibody titers, titers less than 100 were arbitrarily assigned a titer value of 25.

2. Lymphocyte Proliferation Assay

Mice were anesthetized with isoflurane. Spleens were removed and rinsed twice with 5 ml PBS containing 10% heat-inactivated fetal bovine serum (PBS-FBS) and then homogenized in a 50° Centricon unit (Dako A/S, Denmark) in 1.5 ml PBS-FBS for 10 sec at 100 rpm in a Medimachine (Dako) followed by filtration through a 100 micron pore size nylon mesh. Splenocytes were washed once with 15 ml PBS-FBS, then pelleted by centrifugation at 200×g for 5 min. Red blood cells were lysed by resuspending the pellet in 5 mL buffer containing 0.15 M NH4Cl, 1 M KHCO3, 0.1 M NaEDTA, pH 7.4 for five min at RT. Leukocytes were then washed as above. Freshly isolated spleen cells ($10^5$ cells per well) were cultured in triplicate sets in 96-well U-bottomed tissue culture-treated microtiter plates (Corning, Cambridge, Mass.) in RPMI 1640 medium (JRH Biosciences, Lenexa, Kans.) supplemented with 2.05 mM L glutamine, 1% Penicillin/Streptomycin, and 10% heat-inactivated inactivated FBS, for 96 hr at 37° C. Various Aβ peptides, Aβ1-16, Aβ1-40, Aβ1-42 or Aβ40-1 reverse sequence protein were also added at doses ranging from 5 to 0.18 micromolar in four steps. Cells in control wells were cultured with Concanavalin A (Con A) (Sigma, cat. # C-5275, at 1 microgram/ml) without added protein. Cells were pulsed for the final 24 hr with 3H-thymidine (1 µCi/well obtained from Amersham Corp., Arlington Heights Ill.). Cells were then harvested onto Uni-Filter plates and counted in a Top Count Microplate Scintillation Counter (Packard Instruments, Downers Grove, Ill.). Results are expressed as counts per minute (cpm) of radioactivity incorporated into insoluble macromolecules.

4. Brain Tissue Preparation

After euthanasia, the brains were removed and one hemisphere was prepared for immunohistochemical analysis, while three brain regions (hippocampus, cortex and cerebellum) were dissected from the other hemisphere and used to measure the concentration of various Aβ proteins and APP forms using specific ELISAs (Johnson-Wood et al., supra).

Tissues destined for ELISAs were homogenized in 10 volumes of ice-cold guanidine buffer (5.0 M guanidine-HCl, 50 mM Tris-HCl, pH 8.0). The homogenates were mixed by gentle agitation using an Adams Nutator (Fisher) for three to four hr at RT, then stored at −20° C. prior to quantitation of Aβ and APP. Previous experiments had shown that the analytes were stable under this storage condition, and that synthetic Aβ protein (Bachem) could be quantitatively recovered when spiked into homogenates of control brain tissue from mouse littermates (Johnson-Wood et al., supra).

5. Measurement of Aβ Levels

The brain homogenates were diluted 1:10 with ice cold Casein Diluent (0.25% casein, PBS, 0.05% sodium azide, 20 μg/ml aprotinin, 5 mM EDTA pH 8.0, 10 μg/ml leupeptin) and then centrifuged at 16,000×g for 20 min at 4° C. The synthetic Aβ protein standards (1-42 amino acids) and the APP standards were prepared to include 0.5 M guanidine and 0.1% bovine serum albumin (BSA) in the final composition. The "total" Aβ sandwich ELISA utilizes monoclonal antibody monoclonal antibody 266, specific for amino acids 13-28 of Aβ (Seubert, et al.), as the capture antibody, and biotinylated monoclonal antibody 3D6, specific for amino acids 1-5 of Aβ (Johnson-Wood, et al), as the reporter antibody. The 3D6 monoclonal antibody does not recognize secreted APP or full-length APP, but detects only Aβ species with an amino-terminal aspartic acid. This assay has a lower limit of sensitivity of ~50 ñg/ml (11 ñM) and shows no cross-reactivity to the endogenous murine Aβ protein at concentrations up to 1 ng/ml (Johnson-Wood et al., supra).

The brain homogenates were diluted 1:10 with ice cold Casein Diluent (0.25% casein, PBS, 0.05% sodium azide, 20 μg/ml aprotinin, 5 mM EDTA pH 8.0, 10 μg/ml leupeptin) and then centrifuged at 16,000×g for 20 min at 4 C. The synthetic Aβ protein standards (1-42 amino acids) and the APP standards were prepared to include 0.5 M guanidine and 0.1% bovine serum albumin (BSA) in the final composition. The "total" Aβ sandwich ELISA utilizes monoclonal antibody (mAb) 266, specific for amino acids 13-28 of Aβ (Seubert, et al.), as the capture antibody, and biotinylated mAb 3D6, specific for amino acids 1-5 of Aβ (Johnson-Wood, et al), as the reporter antibody. The 3D6 mAb does not recognize secreted APP or full-length APP, but detects only Aβ species with an amino-terminal aspartic acid. The cell line producing the antibody 3D6 has the ATCC accession number PTA-5130, having been deposited on Apr. 8, 2003. This assay has a lower limit of sensitivity of ~50 pg/ml (11 pM) and shows no cross-reactivity to the endogenous murine Aβ protein at concentrations up to 1 ng/ml (Johnson-Wood et al., supra).

The Aβ1-42 specific sandwich ELISA employs mAβ 21F12, specific for amino acids 33-42 of Aβ (Johnson-Wood, et al.), as the capture antibody. Biotinylated mAβ 3D6 is also the reporter antibody in this assay which has a lower limit of sensitivity of about 125 μg/ml (28 μM, Johnson-Wood et al.). For the Aβ ELISAs, 100 μl of either mAβ 266 (at 10 μg/ml) or mAβ 21F12 at (5 μg/ml) was coated into the wells of 96-well immunoassay plates (Costar) by overnight incubation at RT. The solution was removed by aspiration and the wells were blocked by the addition of 200 μl of 0.25% human serum albumin in PBS buffer for at least 1 hr at RT. Blocking solution was removed and the plates were stored desiccated at 4° C. until used. The plates were rehydrated with Wash Buffer [Tris-buffered saline (0.15 M NaCl, 0.01 M Tris-HCl, pH 7.5), plus 0.05% Tween 20] prior to use. The samples and standards were added in triplicate aliquots of 100 μl per well and then incubated overnight at 4° C. The plates were washed at least three times with Wash Buffer between each step of the assay. The biotinylated mAβ 3D6, diluted to 0.5 μg/ml in Casein Assay Buffer (0.25% casein, PBS, 0.05% Tween 20, pH 7.4), was added and incubated in the wells for 1 hr at RT. An avidin-horseradish peroxidase conjugate, (Avidin-HRP obtained from Vector, Burlingame, Calif.), diluted 1:4000 in Casein Assay Buffer, was added to the wells for 1 hr at RT. The colorimetric substrate, Slow TMB-ELISA (Pierce), was added and allowed to react for 15 minutes at RT, after which the enzymatic reaction was stopped by the addition of 25 μl 2 N H2SO4. The reaction product was quantified using a Molecular Devices Vmax measuring the difference in absorbance at 450 nm and 650 nm.

6. Measurement of APP Levels

Two different APP assays were utilized. The first, designated APP-α/FL, recognizes both APP-alpha (α) and full-length (FL) forms of APP. The second assay is specific for APP-α. The APP-α/FL assay recognizes secreted APP including the first 12 amino acids of Aβ. Since the reporter antibody (2H3) is not specific to the α-clip-site, occurring between amino acids 612-613 of APP695 (Esch et al., Science 248, 1122-1124 (1990)); this assay also recognizes full length APP (APP-FL). Preliminary experiments using immobilized APP antibodies to the cytoplasmic tail of APP-FL to deplete brain homogenates of APP-FL suggest that approximately 30-40% of the APP-α/FL APP is FL (data not shown). The capture antibody for both the APP-α/FL and APP-α assays is mAb 8E5, raised against amino acids 444 to 592 of the APP695 form (Games et al., supra). The reporter mAb for the APP-α/FL assay is mAb 2H3, specific for amino acids 597-608 of APP695 (Johnson-Wood et al., supra) and the reporter antibody for the APP-α assay is a biotinylated derivative of mAb 16H9, raised to amino acids 605 to 611 of APP. The lower limit of sensitivity of the APP-αFL assay is about 11 ng/ml (150 pM) (Johnson-Wood et al.) and that of the APP-α specific assay is 22 ng/ml (0.3 nM). For both APP assays, mAb 8E5 was coated onto the wells of 96-well EIA plates as described above for mAb 266. Purified, recombinant secreted APP-α was used as the reference standard for the APP-α assay and the APP-α/FL assay (Esch et al., supra). The brain homogenate samples in 5 M guanidine were diluted 1:10 in ELISA Specimen Diluent (0.014 M phosphate buffer, pH 7.4, 0.6% bovine serum albumin, 0.05% thimerosal, 0.5 M NaCl, 0.1% NP40). They were then diluted 1:4 in Specimen Diluent containing 0.5 M guanidine. Diluted homogenates were then centrifuged at 16,000×g for 15 seconds at RT. The APP standards and samples were added to the plate in duplicate aliquots and incubated for 1.5 hr at RT. The biotinylated reporter antibody 2H3 or 16H9 was incubated with samples for 1 hr at RT. Streptavidin-alkaline phosphatase (Boehringer Mannheim), diluted 1:1000 in specimen diluent, was incubated in the wells for 1 hr at RT. The fluorescent substrate 4-methyl-umbellipheryl-phosphate was added for a 30-min RT incubation and the plates were read on a Cytofluor tm 2350 fluorimeter (Millipore) at 365 nm excitation and 450 nm emission.

7. Immunohistochemistry

Brains were fixed for three days at 4° C. in 4% paraformaldehyde in PBS and then stored from one to seven days at 4° C. in 1% paraformaldehyde, PBS until sectioned. Forty-micron-thick coronal sections were cut on a vibratome at RT and stored in cryoprotectant (30% glycerol, 30% ethylene glycol in phosphate buffer) at −20° C. prior to immunohistochemical processing. For each brain, six sections at the level of the dorsal hippocampus, each separated by consecutive 240 μm intervals, were incubated overnight with one of the following antibodies: (1) a biotinylated anti-Aβ (mAb, 3D6, specific for human Aβ) diluted to a concentration of 2 μg/ml in PBS and 1% horse serum; or (2) a biotinylated mAb specific for human APP, 8E5, diluted to a concentration of 3 µg/ml in PBS and 1.0% horse serum; or (3) a mAb specific for glial fibrillary acidic protein (GFAP; Sigma Chemical Co.) diluted 1:500 with 0.25% Triton X-100 and 1% horse serum, in Tris-buffered saline, pH 7.4 (TBS); or (4) a mAb specific for CD11b, MAC-1 antigen, (Chemicon International) diluted 1:100 with 0.25% Triton X-100 and 1% rabbit serum in TBS; or (5) a mAb specific for MHC II antigen, (Pharmingen) diluted 1:100 with 0.25% Triton X-100 and 1% rabbit serum in TBS; or (6) a rat mAb specific for CD 43 (Pharmingen) diluted 1:100 with 1% rabbit serum in PBS or (7) a rat mAb specific for CD 45RA (Pharmingen) diluted 1:100 with 1% rabbit serum in PBS; or (8) a rat monoclonal Aβ specific for CD 45RB (Pharmingen) diluted 1:100 with 1% rabbit serum in PBS; or (9) a rat monoclonal Aβ specific for CD 45 (Pharmingen) diluted 1:100 with 1% rabbit serum in PBS; or (10) a biotinylated polyclonal hamster Aβ specific for CD3e (Pharmingen) diluted 1:100 with 1% rabbit serum in PBS or (11) a rat mAb specific for CD3 (Serotec) diluted 1:200 with 1% rabbit serum in PBS; or with (12) a solution of PBS lacking a primary antibody containing 1% normal horse serum.

Sections reacted with antibody solutions listed in 1,2 and 6-12 above were pretreated with 1.0% Triton X-100, 0.4% hydrogen peroxide in PBS for 20 min at RT to block endogenous peroxidase. They were next incubated overnight at 4° C. with primary antibody. Sections reacted with 3D6 or 8E5 or CD3e mAbs were then reacted for one hr at RT with a horseradish peroxidase-avidin-biotin-complex with kit components "A" and "B" diluted 1:75 in PBS (Vector Elite Standard Kit, Vector Labs, Burlingame, Calif.). Sections reacted with antibodies specific for CD 45RA, CD 45RB, CD 45, CD3 and the PBS solution devoid of primary antibody were incubated for 1 hour at RT with biotinylated anti-rat IgG (Vector) diluted 1:75 in PBS or biotinylated anti-mouse IgG (Vector) diluted 1:75 in PBS, respectively. Sections were then reacted for one hr at RT with a horseradish peroxidase-avidin-biotin-complex with kit components "A" and "B" diluted 1:75 in PBS (Vector Elite Standard Kit, Vector Labs, Burlingame, Calif.).

Sections were developed in 0.01% hydrogen peroxide, 0.05% 3,3'-diaminobenzidine (DAB) at RT. Sections destined for incubation with the GFAP-, MAC-1-AND MHC II-specific antibodies were pretreated with 0.6% hydrogen peroxide at RT to block endogenous peroxidase then incubated overnight with the primary antibody at 4° C. Sections reacted with the GFAP antibody were incubated for 1 hr at RT with biotinylated anti-mouse IgG made in horse (Vector Laboratories; Vectastain Elite ABC Kit) diluted 1:200 with TBS. The sections were next reacted for one hr with an avidin-biotin-peroxidase complex (Vector Laboratories; Vectastain Elite ABC Kit) diluted 1:1000 with TBS. Sections incubated with the MAC-1- or MHC II-specific monoclonal antibody as the primary antibody were subsequently reacted for 1 hr at RT with biotinylated anti-rat IgG made in rabbit diluted 1:200 with TBS, followed by incubation for one hr with avidin-biotin-peroxidase complex diluted 1:1000 with TBS. Sections incubated with GFAP-, MAC-1- and MHC II-specific antibodies were then visualized by treatment at RT with 0.05% DAB, 0.01% hydrogen peroxide, 0.04% nickel chloride, TBS for 4 and 11 min, respectively.

Immunolabeled sections were mounted on glass slides (VWR, Superfrost slides), air dried overnight, dipped in Propar (Anatech) and overlaid with coverslips using Permount (Fisher) as the mounting medium.

To counterstain Aβ plaques, a subset of the GFAP-positive sections were mounted on Superfrost slides and incubated in aqueous 1% Thioflavin S (Sigma) for 7 min following immunohistochemical processing. Sections were then dehydrated and cleared in Propar, then overlaid with coverslips mounted with Permount.

8. Image Analysis

A Videometric 150 Image Analysis System (Oncor, Inc., Gaithersburg, Md.) linked to a Nikon Microphot-FX microscope through a CCD video camera and a Sony Trinitron monitor was used for quantification of the immunoreactive slides. The image of the section was stored in a video buffer and a color- and saturation-based threshold was determined to select and calculate the total pixel area occupied by the immunolabeled structures. For each section, the hippocampus was manually outlined and the total pixel area occupied by the hippocampus was calculated. The percent amyloid burden was measured as: (the fraction of the hippocampal area containing Aβ deposits immunoreactive with mAb 3D6)×100. Similarly, the percent neuritic burden was measured as: (the fraction of the hippocampal area containing dystrophic neurites reactive with monoclonal antibody 8E5)×100. The C-Imaging System (Compix, Inc., Cranberry Township, Pa.) operating the Simple 32 Software Application program was linked to a Nikon Microphot-FX microscope through an Optronics camera and used to quantitate the percentage of the retrospenial cortex occupied by GFAP-positive astrocytes and MAC-1- and MHC II-positive microglia. The image of the immunoreacted section was stored in a video buffer and a monochrome-based threshold was determined to select and calculate the total pixel area occupied by immunolabeled cells. For each section, the retrosplenial cortex (RSC) was manually outlined and the total pixel area occupied by the RSC was calculated. The percent astrocytosis was defined as: (the fraction of RSC occupied by GFAP-reactive astrocytes)× 100. Similarly, percent microgliosis was defined as: (the fraction of the RSC occupied by MAC-1- or MHC II-reactive microglia)×100. For all image analyses, six sections at the level of the dorsal hippocampus, each separated by consecutive 240 µm intervals, were quantitated for each animal. In all cases, the treatment status of the animals was unknown to the observer.

Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

What is claimed is:

1. A humanized antibody that specifically binds an epitope contained within positions 13-28 of Aβ, wherein the antibody is a humanized version of monoclonal antibody 266 (ATCC accession number PTA-6123).

2. The humanized antibody of claim 1, that is an intact humanized antibody.

3. The humanized antibody of claim 1, that is a binding fragment.

4. The humanized antibody of claim 3, wherein the antibody fragment is an Fab, Fab', F(ab')2, Fabc, or Fv.

5. The humanized antibody of claim 4, which is an Fab or F(ab')$_2$ fragment.

6. The humanized antibody of claim 5, which is an F(ab')$_2$ fragment.

7. The humanized antibody of claim 5, which is an Fab fragment.

8. The humanized antibody of claim 1, which is a single chain antibody.

9. The humanized antibody of claim 1, wherein the antibody or fragment thereof is produced in a host cell selected from the group consisting of a myeloma cell and a Chinese hamster ovary cell.

10. The humanized antibody of claim 1, wherein the isotype of the antibody is human IgG1.

11. The humanized antibody of claim 1 comprising a humanized light chain comprising the light chain Kabat CDRs from monoclonal antibody 266 (ATCC accession number PTA-6123); and a humanized heavy chain comprising the heavy chain Kabat CDRs from the monoclonal antibody 266 (ATCC accession number PTA-6123).

* * * * *